(12) United States Patent
Chi et al.

(10) Patent No.: US 7,820,858 B2
(45) Date of Patent: Oct. 26, 2010

(54) CONCISE β²-AMINO ACID SYNTHESIS VIA ORGANOCATALYTIC AMINOMETHYLATION

(75) Inventors: Yonggui Chi, Berkeley, CA (US); Samuel H. Gellman, Madison, WI (US); William C. Pomerantz, Madison, WI (US); William S. Horne, Madison, WI (US); Li Guo, Madison, WI (US); Emily P. English, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 828 days.

(21) Appl. No.: 11/691,249

(22) Filed: Mar. 26, 2007

(65) Prior Publication Data

US 2008/0058548 A1    Mar. 6, 2008

Related U.S. Application Data

(60) Provisional application No. 60/786,037, filed on Mar. 25, 2006.

(51) Int. Cl.
| | |
|---|---|
| C07C 213/00 | (2006.01) |
| C07C 215/28 | (2006.01) |
| C07C 271/22 | (2006.01) |
| C07C 269/06 | (2006.01) |
| C07C 217/64 | (2006.01) |
| C07D 209/14 | (2006.01) |
| C07D 209/26 | (2006.01) |

(52) U.S. Cl. ........................ 562/553; 562/531
(58) Field of Classification Search ........................ None
See application file for complete search history.

(56) References Cited

FOREIGN PATENT DOCUMENTS

DE          542253          12/1931

OTHER PUBLICATIONS

Yokomatsu T et al., "Enzymatic Desymmetrization of Prochiral 2-Benzyl-1, 3-propanediol Derivatives: A Practical Chemoenzymatic Synthesis of Novel Phosphorylated Tryosine Analogues", Tetrahedron, Elsevier Science Publishers, Amsterdam, NL, vol. 54, No. 32, Aug. 6, 1998, pp. 9341-9356, XP004127410.

Duursma, Ate et al., "Highly Enantioselective Conjugate Addition of Dialkylzinc Reagents to Acyclic Nitroalkenes: A Catalytic Route to .beta.2-Amino Acids Aldehydes, and Alcohols", Journal of the American Chemical Society, 125(13), 3700 3701 coden: jacsat; issn: 0002-7863, 2003, XP002440652, p. 3701; compounds 5, 6.

Arend, Michael et al.,"Modern variants of the Mannich reaction", Angewandte Chemie, International Edition, 37(8), 1045-1070 coden: acief5; issn: 1433-7851, 1998, XP002440653, p. 1049, table 1, entry 2, p. 1048, paragraphs 2.3 and 2.4.

Ibrahem, Ismail et al., "Direct organocatalytic enantioselective .alpha.-aminomethylation of ketones", Tetrahedron, Volume Date 2006, 62(2-3), 357-364 coden: Tetrab; issn: 0040-4020, 2005, XP002440656, abstract, p. 360, scheme 1, p. 360, col. 2, line 3-line 10.

Chi, Yonggui et al., "Enantioselective Organocatalytic Aminomethylation of Aldehydes: A Role for Ionic Interactions and Efficient Access to .beta.2-Amino Acids", Journal of the American Chemical Society, 128(21), 6804 6805 coden, jacsat; issn: 0002-7863, 2006, XP002440654.

Ibrahem, Ismail et al., "Direct catalytic enantilioselective .alpha.-aminomethylation of aldehydes", Chemistry—A European Journal, 13(2), 683-688 coden: ceujed; issn: 0947-6539, 2007, XP002440655, abstract.

PCT/US2007/064943 International Search Report.

*Primary Examiner*—Daniel M Sullivan
*Assistant Examiner*—Yevegeny Valenrod
(74) *Attorney, Agent, or Firm*—Joseph T. Leone, Esq.; DeWitt Ross & Stevens S.C.

(57) ABSTRACT

The present invention provides a method for the synthesis of β²-amino acids. The method also provides methods yielding α-substituted β-amino aldehydes and β-substituted γ-amino alcohols. The present method according to this invention allows for increased yield and easier purification using minimal chromatography or crystallization. The methods described herein are based on an aldehyde aminomethylation which involves a Mannich reaction between an aldehyde and a formaldehyde-derived N,O-acetal (iminium precursor) and a catalyst, such as, for example, L-proline or a pyrrolidine. The invention allows for large scale, commercial preparation of β²-amino acids.

20 Claims, 76 Drawing Sheets

CONCISE β²-AMINO ACID SYNTHESIS VIA ORGANOCATALYTIC AMINOMETHYLATION

CROSS-REFERENCE TO RELATED APPLICATION

This application claims the benefit of U.S. Provisional Application No. 60/786,037, filed Mar. 25, 2006, incorporated herein by reference in its entirety for all purposes.

STATEMENT REGARDING FEDERALLY SPONSORED RESEARCH AND DEVELOPMENT

This invention was made with United States government support awarded by the following agencies: NIH GM056414 and NSF 0140621. The United States government has certain rights in this invention.

FIELD OF THE INVENTION

This invention is generally directed to methods to synthesize β²-amino acids, α-substituted β-amino aldehydes and β-substituted γ-amino alcohols that are useful as building blocks for natural and non-natural compounds.

BACKGROUND OF THE INVENTION

β²-amino acids, which bear a side chain adjacent to the carboxyl group, are valuable building blocks for non-natural oligomers that have physiological applications (e.g., specific biological functions). For example, β-peptides block human cytomegalovirus infection, contain β²-amino acid residues, as do β-peptide somatostatin mimics. These applications require that the β²-amino acid be stereochemically pure. The use of β²-amino acids is hindered by their limited availability. Many research groups, have tried to develop stereochemically controlled methods for β²-amino acid synthesis. To date these current methods have relied on non-catalytic alkylation of chiral enolates, a process that often gives very low levels for stereochemical control. In addition, most methods require five to ten chemical reactions and tedious chromatographic separations. Overall yields for these processes are commonly less than 10%.

In general, β amino acids offer a greater degree of potential conformational manipulation than do conventional α amino acids. Moreover, linkages between β amino acids are not susceptible to degradation by native enzymes that degrade proteins. There are several different types of possible β amino acid building blocks. Some of these, such as β³ amino acids are commercially available (the superscript denotes which carbon atom contains the side chain). β² amino acids, on the other hand, are difficult to synthesize and are not commercially available. β² amino acids are critical components of many β peptides, including those that block human cytomegalovirus infection, and of somatostatin mimics which are the subject of immense interest by major pharma. These applications require that the β² amino acid be stereochemically pure. The use of β² amino acids is hindered by their limited availability. Current synthesis methods provide low yield and they also result in hard to purify mixtures requiring five to ten chemical reactions and tedious chromatographic separations to purify. To date these methods have relied on non-catalytic alkylation of chiral enolates, a process that often gives very low levels of stereochemical control. Overall yields for these processes are commonly <10%. Taken together, these obstacles have precluded the development of commercial synthesis methods for these important β-peptide building blocks. There is therefore a need for new, efficient and stereoselective β² amino acid synthesis methods.

SUMMARY OF THE INVENTION

The present invention provides a method for β²-amino acid synthesis with much greater yield than present methods. In addition, the present method allows for greater and easier purification using minimal chromatography and/or crystallization. The method of the invention described herein is based on an aldehyde aminomethylation method which involves a Mannich reaction between an aldehyde and a formaldehyde-derived N,O-acetal (iminium precursor) and a catalyst such as, for example, L-proline or a pyrrolidine. In other embodiments, the invention provides methods for the synthesis of α-substituted β-amino aldehydes and β-substituted γ-amino alcohols.

This invention separately provides a method wherein the reaction is diastereoselective.

This invention separately provides a method wherein the reaction is enantioselective.

As discussed further below, the present invention is advantageous for several reasons. First current methods of β²-amino acid synthesis require long synthetic routes, have generally poor stereoselectivity, are tedious to purify, have low overall yield, require harsh synthesis conditions, provide limited side chain diversities and are difficult to scale up to commercially useful yields. In contrast, the method of the invention described herein provides for short synthetic routes, provides excellent stereoselectivity, allows for easy purification using chromatography or recrystallization methods, provides excellent yields using mild synthesis conditions, provides for a wide array of both naturally occurring and non-naturally occurring side chains and is easily scaled up to provide commercially useful yields. Thus, the present invention provides numerous advantages over current synthesis methods and greater utility for the synthesis and production of β²-amino acids that is not currently available in other described synthesis protocols.

These and other features and advantages of various exemplary embodiments of the methods according to this invention are described, or are apparent from, the following detailed description of various exemplary embodiments of the methods according to this invention.

BRIEF DESCRIPTION OF THE FIGURES

Various exemplary embodiments of the methods of this invention will be described in detail, with reference to the following figures, wherein.

DETAILED DESCRIPTION OF THE EXEMPLARY EMBODIMENTS

Figure 1:
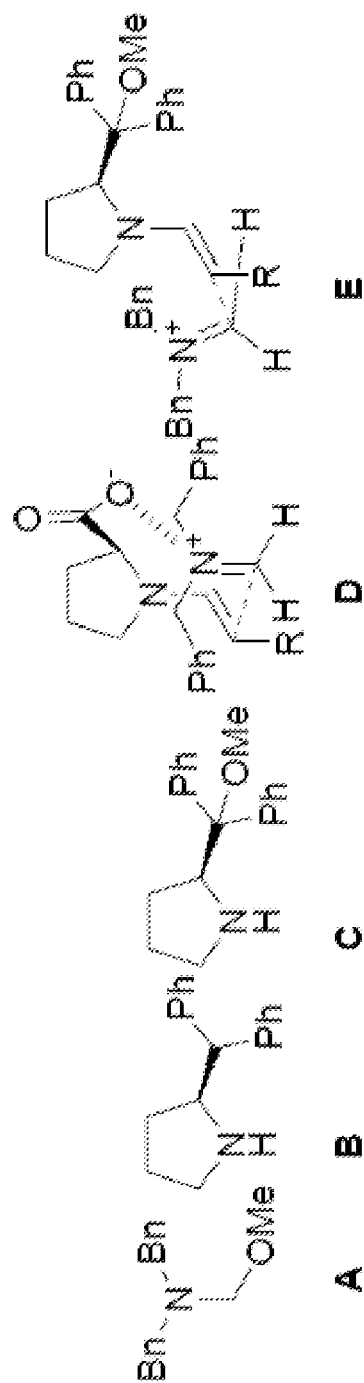
FIG. 1 shows the structures of the substrate and proposed transition states for the Mannich reaction.

Before the present methods are described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Functional groups of the present invention can be protected with a protecting group. For example, cysteine or a related compound is protected at one or more reactive moieties, such as at the amino, —SH, and/or carboxyl moieites of cysteine. As is known in the art, a protecting group reduces or eliminates the ability of a functional group to react with another functional group. For example, a thiol or an alcohol can be protected with an acyl group. Similarly, an alcohol can be protected by a tosyl or a trimethylsilyl group. An amine can, for example, be protected by an Fmoc group or a Boc group. Additional protecting groups, methods of adding a protecting group, and methods of removing a protecting group are taught in "Protective Groups in Organic Synthesis, 3$^{rd}$ Edition" by Peter G. M. Wuts and Theodora W. Greene, Wiley-Interscience, 1999, which was incorporated by reference above.

Protecting groups for basic nitrogen atoms include formyl; 4-toluenesulfonyl; tert-butoxycarbonyl group (Boc group), methoxycarbonyl group (Moc group); 9-FluorenylMethylOxyCarbonyl (Fmoc group), 2,4-dinitrophenol; benzyloxymethyl; trityl; t-butoxymethyl; 2-chlorobenzyloxy-carbonyl; allyloxycarbonyl; benzyloxycarbonyl (Z group); mesitylene-2-sulfonyl; 4-methyloxy-2,3,6-trimethyl-benzyenesulfonyl; 2,2,5,7,8-pentamethyl-chroman-6-sulfonyl; 9-xanthenyl; and 2,4,6-trimethoxybenzyl and the like.

The Mannich reaction, in which an enol or enolate attacks an imine or an iminium ion, is a powerful tool for introducing aminoalkyl fragments into organic molecules. Imines derived from aryl aldehydes have been common substrates in recent efforts to develop asymmetric organocatalytic versions of this reaction. Although many of these reactions are highly stereoselective, they result in Mannich adducts always bearing aryl groups that may not be desirable for specific applications. The inventors' attention was drawn toward formaldehyde-derived substrates to develop a method for aldehyde aminomethylation, because Mannich bases (β-amino aldehydes) produced using this method bear single substitute (side chain) at the α-position and can be used to generate β$^2$-amino acids, which are valuable building blocks for β-peptide foldamers and other targets. Current synthesis routes that rely on non-catalytic alkylation of chiral enolates to generate enantiomerically pure β$^2$-amino acids have been described, but they all require long synthetic routs and tedious chromatographic purifications and few are amenable to large-scale synthesis or side chain variety. Here the inventors disclose a new approach to optically pure Boc-protected β$^2$-amino acids that feature an enantioselective organocatalytic Mannich reaction using formaldehyde-derived iminium and its application in β$^2$-amino acid synthesis (SCHEME 1).

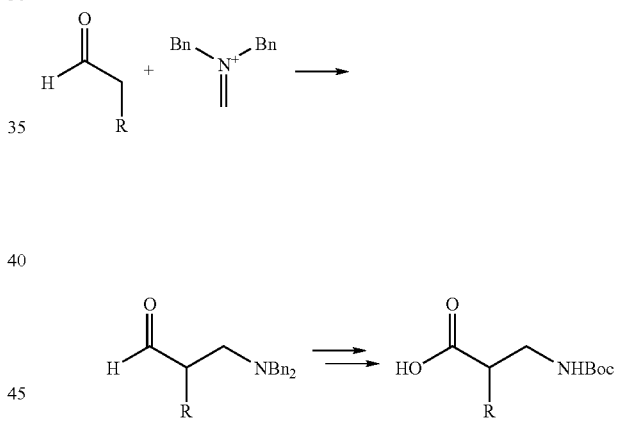

SCHEME 1

Figure 2:
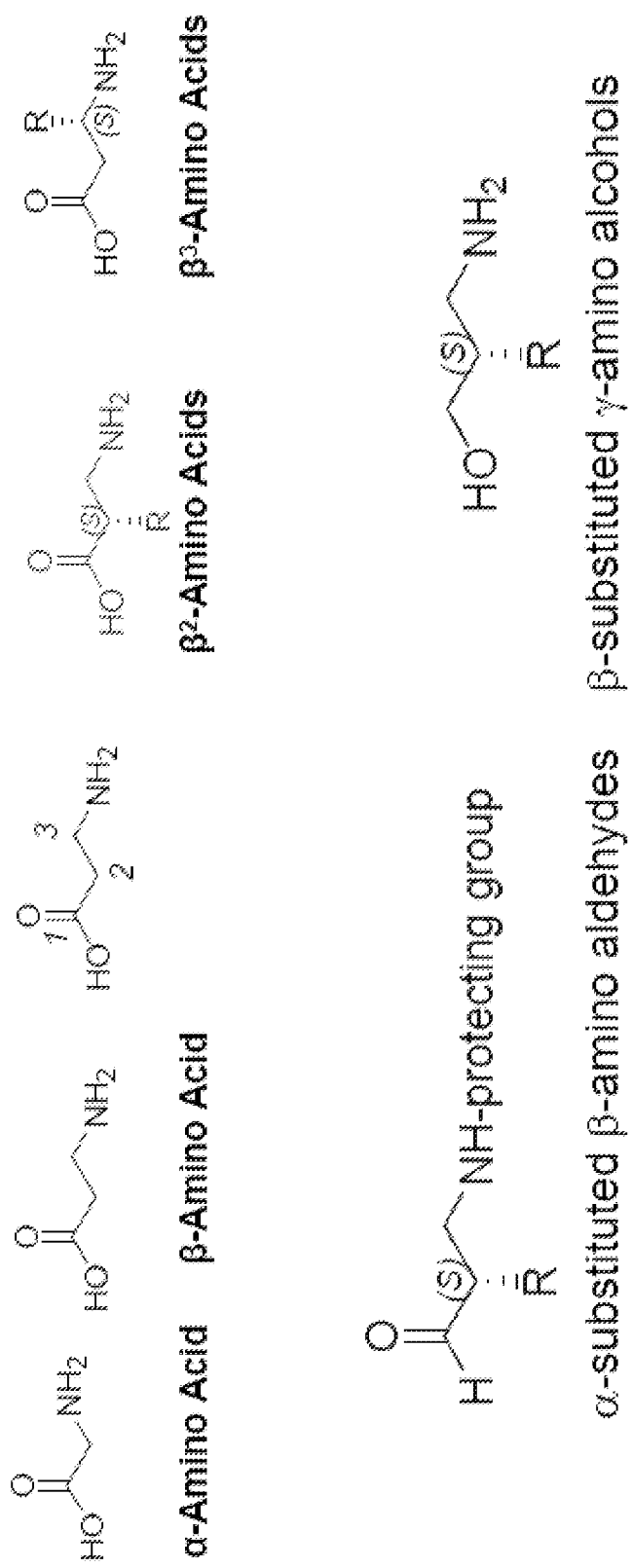
FIG. 2 shows the general structure and terminology of the α-Amino Acids, β-Amino Acids, β²-Amino Acids, β³-Amino Acids, α-Substituted β-Amino Aldehydes, and β-Substituted γ-Amino Alcohols.

As used herein, the term β$^2$-amino acid refers to an amino acid whose side-chain is attached to the second carbon atom following the carboxy carbon of the amino acid as shown in FIG. 2. While α-amino acids and β$^3$-amino acids are easy to make, β$^2$-amino acids are difficult to make using current methods. Thus, the ability to synthesize new β$^2$-peptides is extremely limited. β$^2$-amino acids are important building blocks of non-natural oligomers having applications for physiological use, for example, where the oligomer is not subject to degradation by native enzymes. β$^2$-amino acids introduce unique backbone arrangements to peptides that cannot be achieved by α-amino acids or β$^3$-amino acids, thereby introducing unique functions to peptides. Further, β-peptides containing β$^2$-residues have been shown to display useful biological activities, such as mimicry of somatostatin signaling and inhibition of viral infection. Examples of β$^2$-amino acids are shown, generally, below in SCHEME II.

SCHEME II

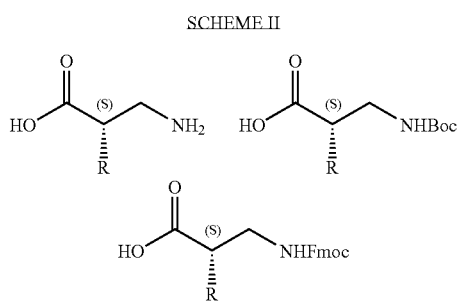

Current methods for the synthesis of β² amino acids are non-catalytic and require long synthetic routes and tedious purifications. For example, the Seebach β² amino acid synthesis strategy is shown below in SCHEME III which requires eight steps, each step providing only a 70% yield allowing for a final product yield of only approximately 10%.

gives excellent yields (>80%) and good diastereomeric excess (70-80%). Alternatively, using L-α-methyl-proline as a catalyst gave moderate yield and excellent diastereomeric excess (>70-80%). In addition, using L-α-methylproline as a catalyst gave moderate yield and excellent diastereomeric excess (>90%). The inventors have developed a three step protocol for β²-amino acid synthesis using the diastereoselective Mannich reaction with the very inexpensive L-proline as catalyst. The diastereomeric mixture of Mannich adducts, which are amino aldehydes, are reduced in situ with $NaBH_4$ to give the amino alcohol. The major diastereomer of the amino alcohol can be separated via column chromatography or recrystallization, depending on the side chain (R), resulting in a good isolated yield (50-60%). The benzyl groups are removed and the amino group is reprotected in a one-pot reaction, giving Boc-amino alcohol in excellent yield (>90%). Purification of the Boc-amino alcohol is very easy. The Boc-amino alcohol is oxidized to the corresponding carboxylic acid in good yield (>85%); this protected β²-amino

SCHEME III

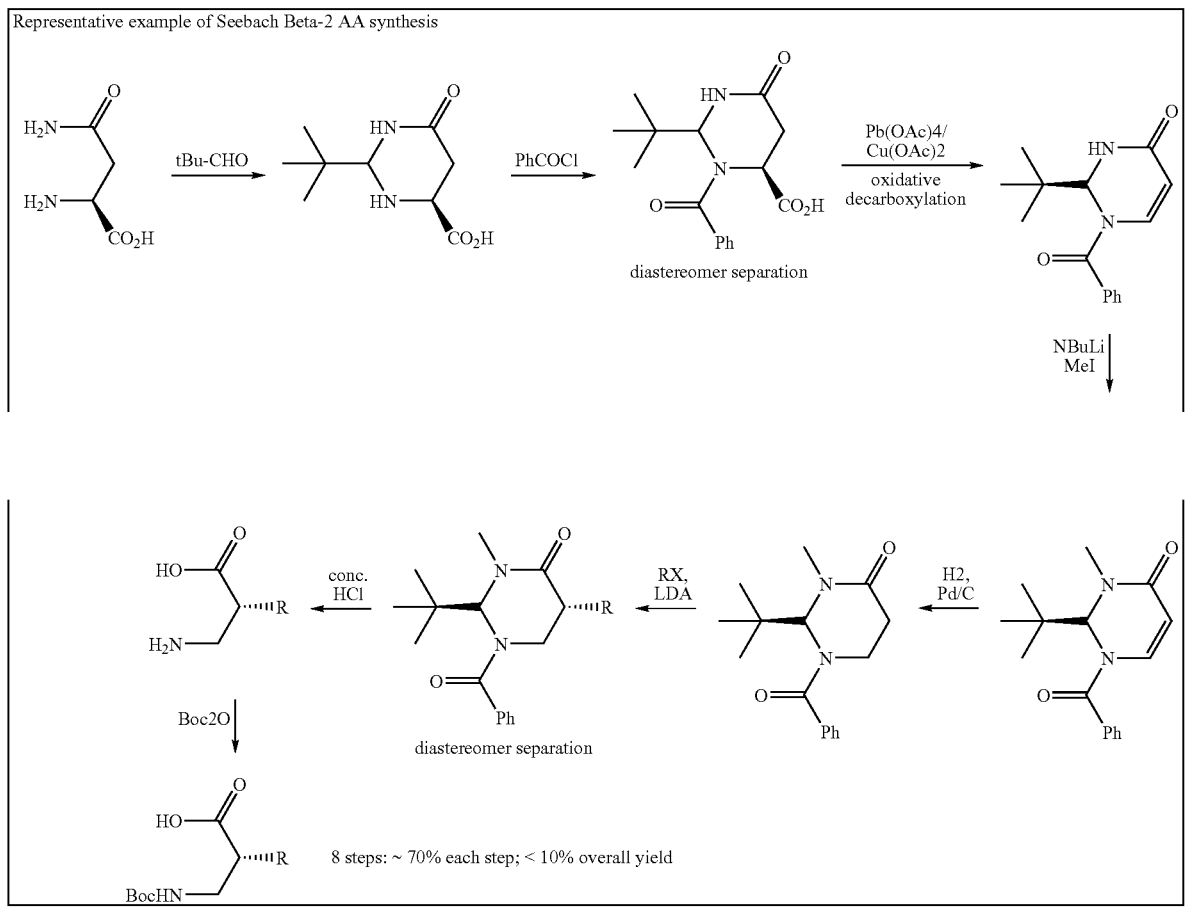

The Mannich reaction is enantioselective when an N,N-dibenzylamine-derived N,O-acetal is used or is diastereoselective when an enantiomerically pure N-benzyl-N-α-methylbenzylamine-derived N,O-acetal is used. For the reaction between aldehyde and the (S)—N-benzyl-N-α-methylbenzylamine-derived N,O-acetal, using L-proline as a catalyst acid product is analytically pure after proper work-up. Significantly, this method is amenable for large-scale synthesis. Starting materials for many desirable β²-amino acids can be inexpensively obtained from commercial sources. The strategy for stereoselective organocatalytic aldehyde aminomethylation is shown below in SCHEME IV.

SCHEME IV

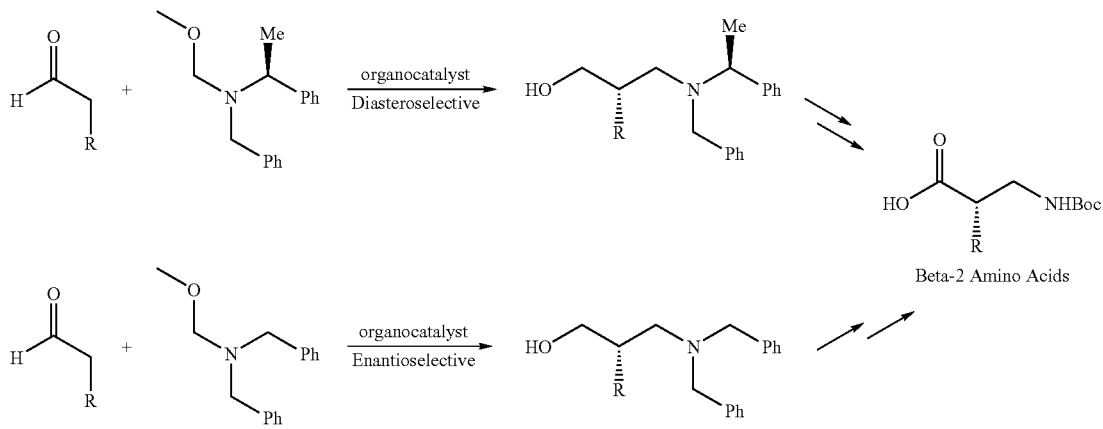

Using the strategy shown in Scheme IV, diastereomers can be easily separated and purified. As further shown in Scheme IV, some versions of the Mannich reaction are enantioselective resulting in 99% ee using recrystallization purification.

In addition, racemic mixtures can be generated using an organocatalyst such as acetic acid (HOAc) or other Lewis-acid as shown below in SCHEME V.

SCHEME V

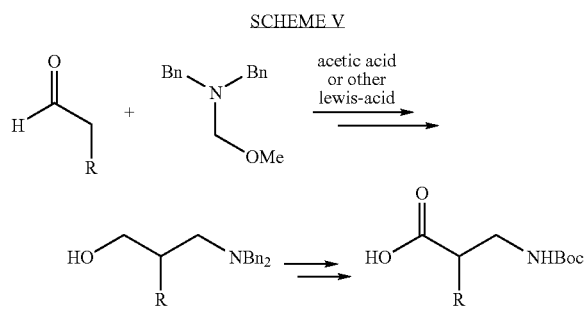

Further, the racemic compounds shown in SCHEME V can be synthesized in a one-pot multi-component reaction by mixing an aldehyde, formaldehyde, secondary amine and acetic acid or other Lewis-acid as shown below in SCHEME VI.

SCHEME VI

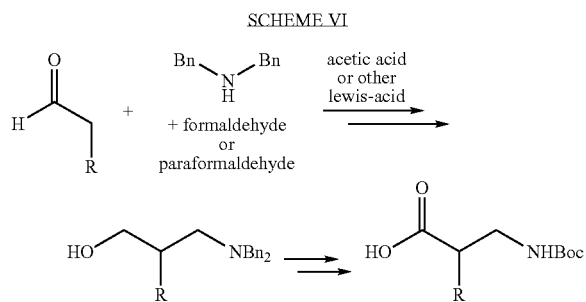

In the case of the racemic mixtures generated as shown in both SCHEMES V and VI, it should be pointed out that purification of racemic mixtures is achieved using known methods such as chromatography and crystallization as described below.

EXAMPLES

Formaldehyde does not form stable imines, so the inventors examined formaldehyde derivatives such as A (FIG. 1) that can generate a methylene iminium species in situ. The inventors examined L-proline and chiral pyrrolidines as catalysts for nucleophilic activation of aldehyde reactants. The Mannich reaction products, α-substituted β-amino aldehydes, were immediately reduced to the corresponding α-substituted β-amino alcohols to avoid epimerization and thereby facilitate stereochemical analysis and further transformations. Initial studies involving pentanal revealed modest enantioselectivity when the reactions were carried out with 20 mol % catalyst in DMF at −25° C. for 24 hr. The enantiomeric preference observed with L-proline was opposite that observed with 2-alkyl-pyrrolidines derived from L-proline, such as B or C (FIG. 1) (used with equimolar acetic acid). A comparable switch in product configuration for organocatalytic Mannich reaction involving imines and α-amination of aldehydes involving azadicarboxylate has been observed by Barbas, Jorgensen, List, Cordova and others.[2] The commonly accepted rational of this stereochemical preference switch involves hydrogen bonding: the carboxylic acid group of the L-proline-derived enamine is H-bonded to the imine or azodicarboxylate electrophile at the transition state, while the substituent of a 2-alkyl-pyrrolidine sterically repels the electrophile, forcing it to approach the enamine from the opposite face. This hypothesis is reasonable, but it cannot explain the inventors' results with L-proline since the electrophile, an iminium ion, cannot accept a hydrogen bond. In light of this new evidence, the inventors instead investigated whether the electrophile to the proline-derived enamine is controlled by an electrostatic attraction of iminium to carboxylate (FIG. 1D); the carboxylate is presumably generated by the methoxide liberated upon iminium formation. Without being held to any particular theory, it is possible to invoke steric repulsion to rationalize the stereochemical preference displayed by 2-alkyl-pyrrolidines such as FIG. 1B and FIG. 1C (FIG. 1E).

In brief a comparison of current methods to produce β²-amino acids vs. those of the present invention is shown in Table 1.

TABLE 1

| Entry | Current Method | Present Invention |
|---|---|---|
| Overall yield | <10% | >40-50% |
| Synthetic Route | Very long routes | Short routes |
| Purification | Tedious chromatography | Minimal chromatography |
| Scale | Limited | Amendable for large scale |
| Condition | Involve harsh condition | Very mild condition |
| Side chain variety | Generally narrow | Wide |
| Strategy | Non-catalytic | Organocatalytic |
| Stereoselectivity | Mostly low or no | High |
| | | Novel Aldehyde aminomethylation |
| | | Future generation of catalytic system can be developed based on our invention |

Example 1

Diastereoselective Strategy

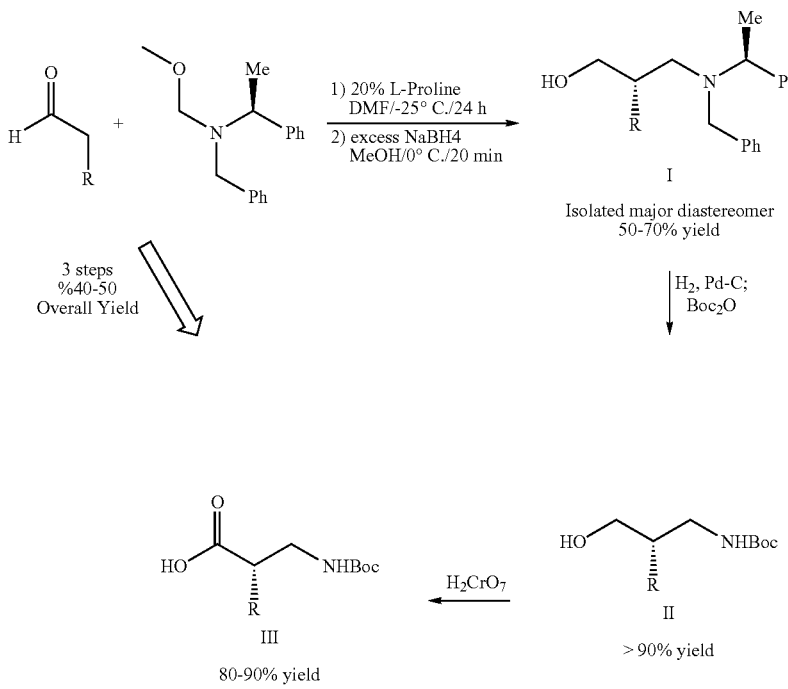

SCHEME VII

An overview of the diastereoselective strategy for β2-amino acid synthesis is shown above in SCHEME VII. As shown, the three-step procedure results in an overall yield of 40-50% with an up to 90% yield in steps II and III. Examples of the products and yield for a variety of representative reactions are shown in Table 2.

TABLE 2
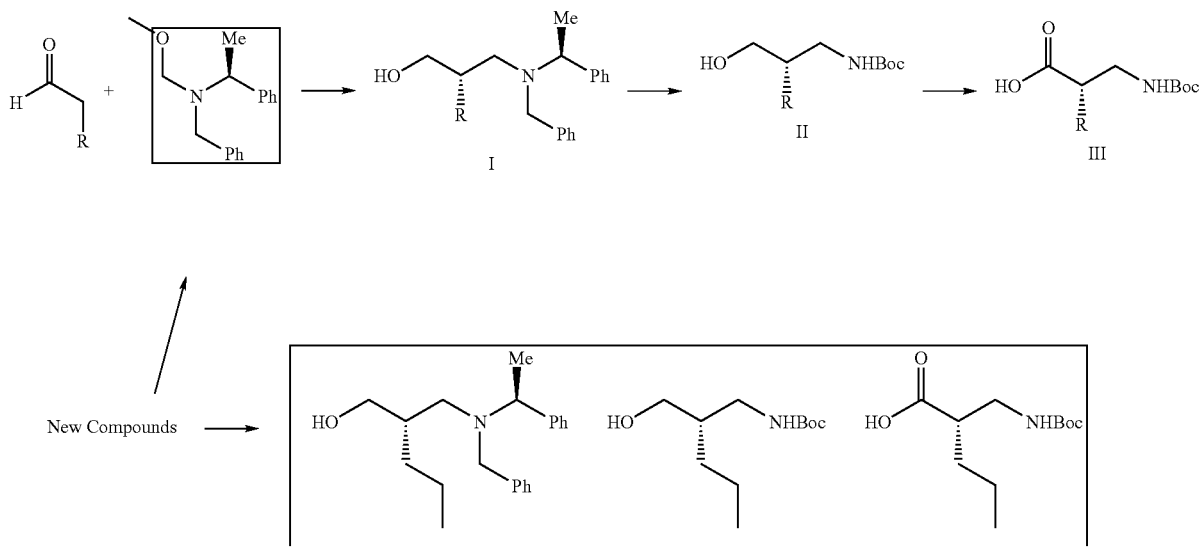
| entry | R | rxn dr | I[a] | II | III |
|---|---|---|---|---|---|
| 1 | Pr | 86:14 | 62[b] | 92 | 85 |
| 2 | nHex | 89:11 | 51[c] | 92 | 89 |
| 3 | Bn | 88:12 | 62[b] | 99 | 92 |
| 4 | iPr | 85:15 | 49[c] | 95 | 91 |
| 5 | CH2iPr | 83:17 | 51[c] | 96 | 90 |
| 6 | CH2C6H12 | 84:16 | 52[c] | 91 | 95 |
isolated yield % (major diastereomer)
Using this strategy, a variety of new compounds have been synthesized. These compounds include those illustrated below where the 'R' groups of the new compounds are shown in the box in SCHEME VIII.

-continued
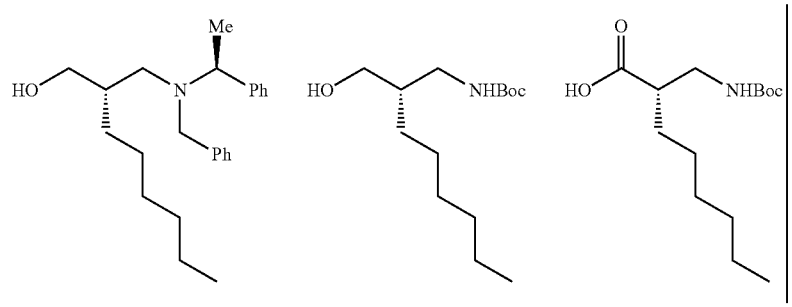
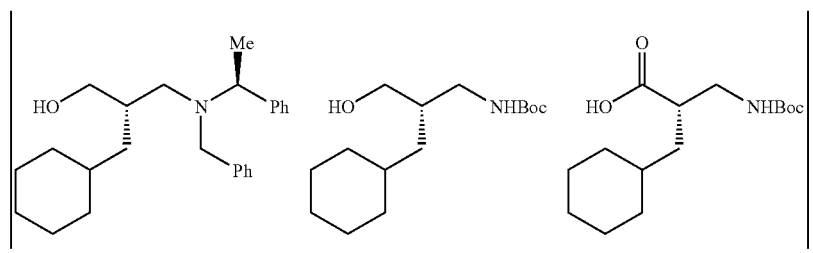
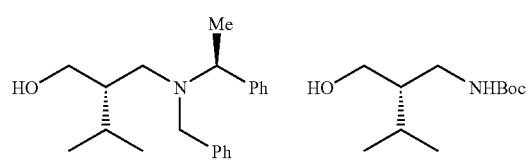
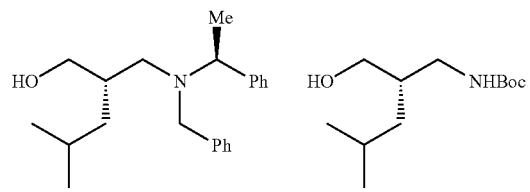
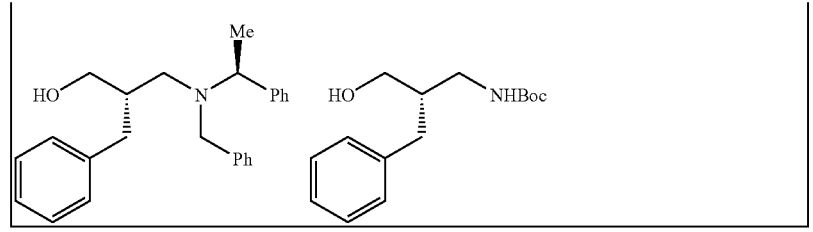

Example 2

Enantioselective Strategy: Aldehyde Aminomethylation

The second strategy identified by the inventors to produce β²-amino acids is the enantioselective aldehyde aminomethylation strategy summarized in Table 3, below. As illustrated this strategy utilizes as a catalyst and results in between a 65-90% yield that has an ee of greater than 90%.

TABLE 3

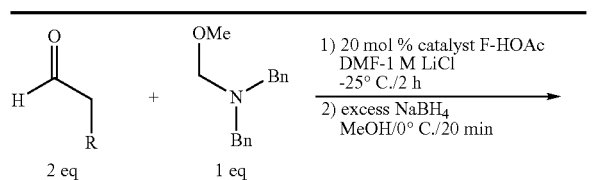

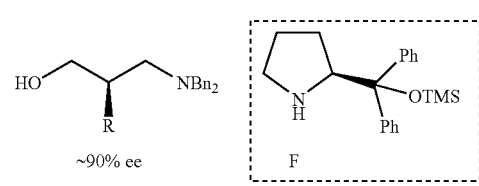

| entry | R | isolated yield (%) | ee (%) |
|---|---|---|---|
| 1 | Et | 84 | 90 |
| 2 | Pr | 87 | 92 |
| 3 | i-Pr | 86 | 91 |
| 4 | Bn | 81 | 92 |
| 5 | (Boc₂)N(CH₂)₃ | 82 | n.d. |

TABLE 3-continued

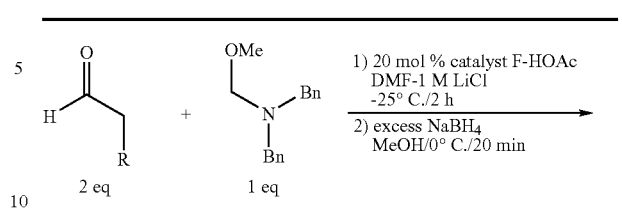

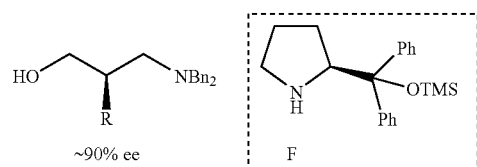

| entry | R | isolated yield (%) | ee (%) |
|---|---|---|---|
| 6 | MeO₂CCH₂ | 65 | 93 |
| 7 | CH₂=HC(CH₂)₇ | 89 | n.d. |

Use of this strategy has provided the following new compounds where those compounds in the box represent the 'R' group in SCHEME IX below.

SCHEME IX

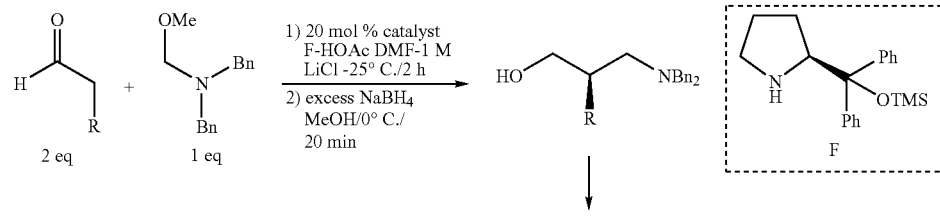

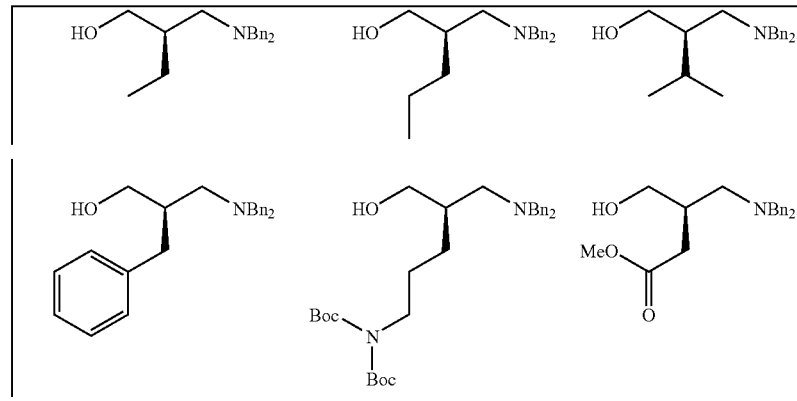

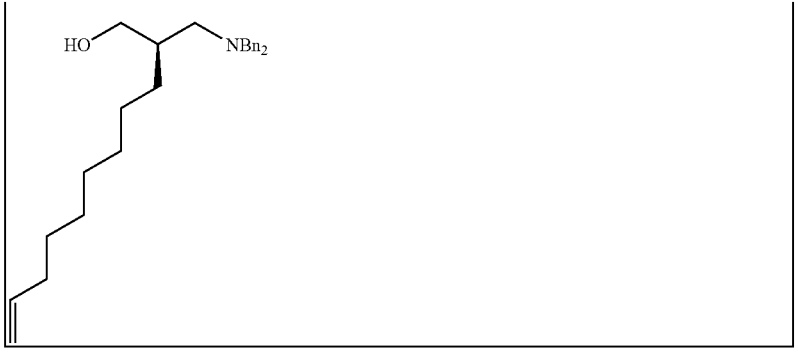

The compounds shown above, in SCHEME IX are representative species of β²-amino acids produced by the enantioselective strategy shown below in SCHEME X. In Scheme X, the exemplary catalyst is F from Scheme IX above.

α-substituted β-amino aldehydes and β-substituted γ-amino alcohols both of which can serve as small chiral building blocks for complex molecules (e.g., natural product) synthesis as shown in SCHEME XI.

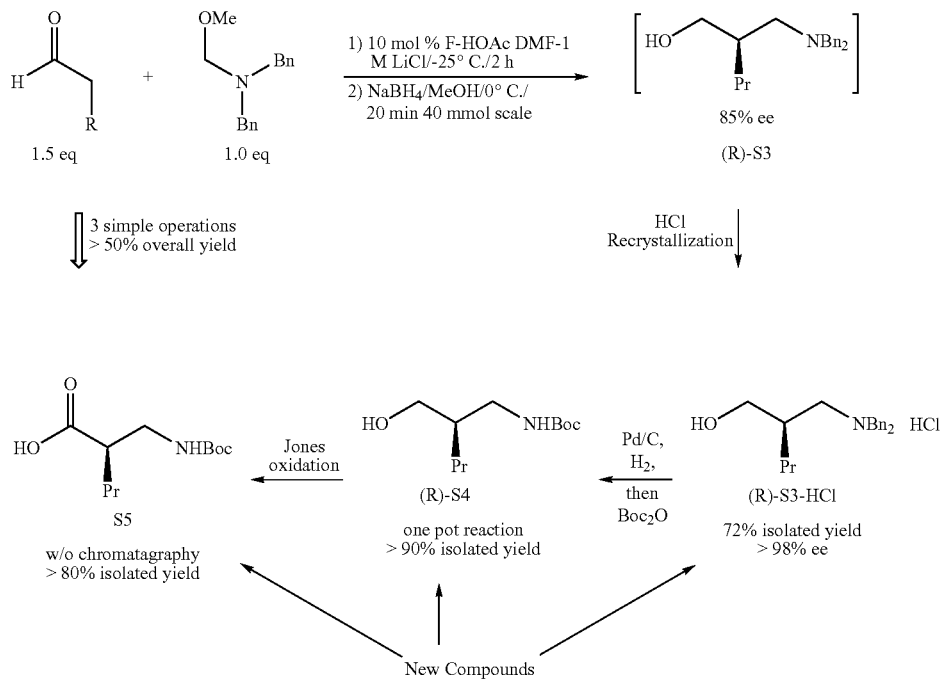

As illustrated above, in Scheme X, not only does the invention provide a simple synthesis scheme by which to produce β²-amino acids, it also provides three different points in the synthesis at which new compounds can be isolated with good yields and high purities. Further, compared to previous synthesis methods, the synthesis conditions used require mild reaction conditions and the percent yield shown represents the product prior to purification using chromatography.

In addition to the β²-amino acids synthesized by the strategies discussed above, other useful molecules are also products of the disclosed methods. The molecules include both

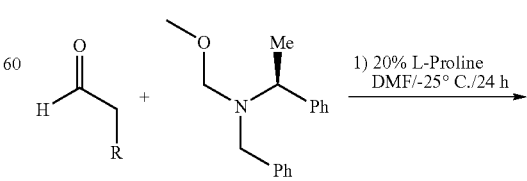

-continued

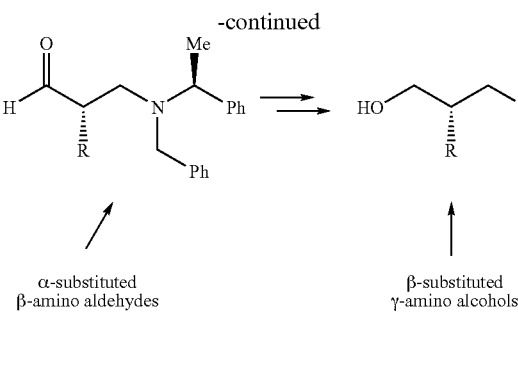

α-substituted
β-amino aldehydes

β-substituted
γ-amino alcohols

Example 3

General Laboratory Procedures

Analytical thin-layer chromatography (TLC) was carried out on Whatman TLC plates precoated with silica gel 60 (250 μm thickness). Visualization was performed using a UV lamp or potassium permanganate stain. Column chromatography was performed on EM Science silica gel (230-400 mesh).

(S)-Diphenylmethyl pyrrolidine (FIG. 1B) was purchased from Acros Organics; other commercial reagents were purchased from Sigma-Aldrich. DMF is biotech grade from Sigma-Aldrich. All commercial reagents were used as received. N,O-acetal (FIG. 1A) was prepared using literature procedures.

General Laboratory Instrumentation: Proton nuclear magnetic resonance ($^1$H NMR) spectra were recorded on Bruker AC-300 (300 MHz) spectrometers. Chemical shifts were recorded in parts per million (ppm, δ) relative to tetramethylsilane (δ 0.00). $^1$H NMR splitting patterns are designated as singlet (s), doublet (d), triplet (t), or quartet (q). All first-order splitting patterns were assigned on the basis of the appearance of the multiplet. Splitting patterns that could not be easily interpreted are designated as multiplet (m) or broad (br). Carbon nuclear magnetic resonance ($^{13}$C NMR) spectra were recorded on a Bruker AC-300 (75 MHz) spectrometer. Mass spectra (MS) were obtained using an electrospray ionization (ESI) mass spectrometer. Chromatographic enantiomeric excess (ee) determinations were performed on a Shimadzu 10A HPLC using a Chiracel OD or ODH analytical column (detection at 254 nm). Optical rotations were measured using a 5 mL cell with a 1 dm path length on a Perkin-Elmer 241 digital polarimeter and are reported as follows: $[\alpha]^{rt}_D$ (c in g per 100 mL solvent).

Example 4

Stereochemistry Determination

Scheme XII shows the synthesis of β$^2$ amino acid using the enantioselective strategy utilizing catalytic reduction (top synthesis) and the diastereoselective strategy, using L-proline as a catalyst. Absolute configuration of compound S1 was obtained by X-ray diffraction analysis. Absolute configuration of β-propyl γ-dibenzylamino alcohol (S3) was assigned by comparing the optical rotation of S4 and S2. The absolute configuration of other β-substituted γ-dibenzylamino alcohols from the Mannich reaction was assigned by analogy to S3.

SCHEME XII

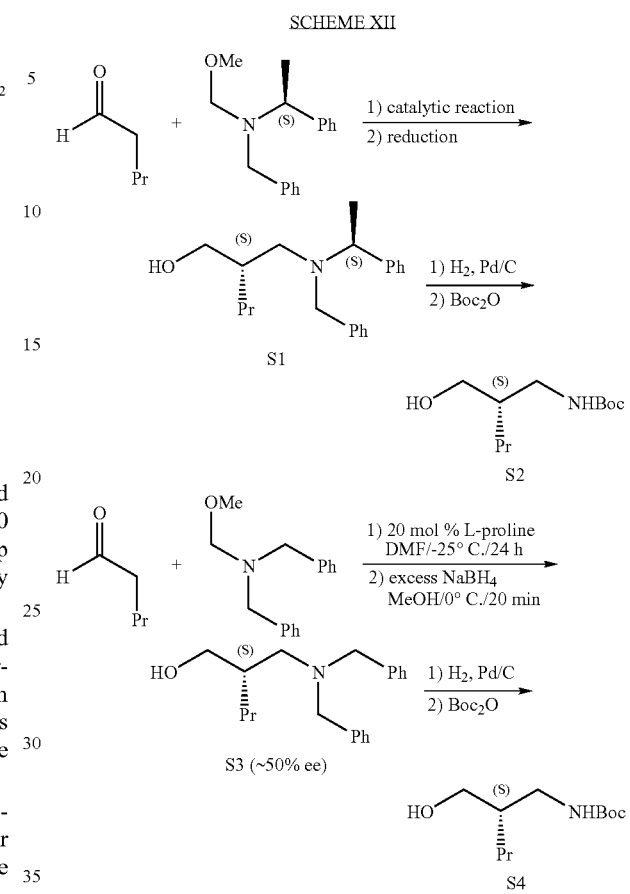

Example 5

(S)-β-Propyl-γ-(S)—N-benzyl-α-methylbenzylamino alcohol (S1)

Figure 5:
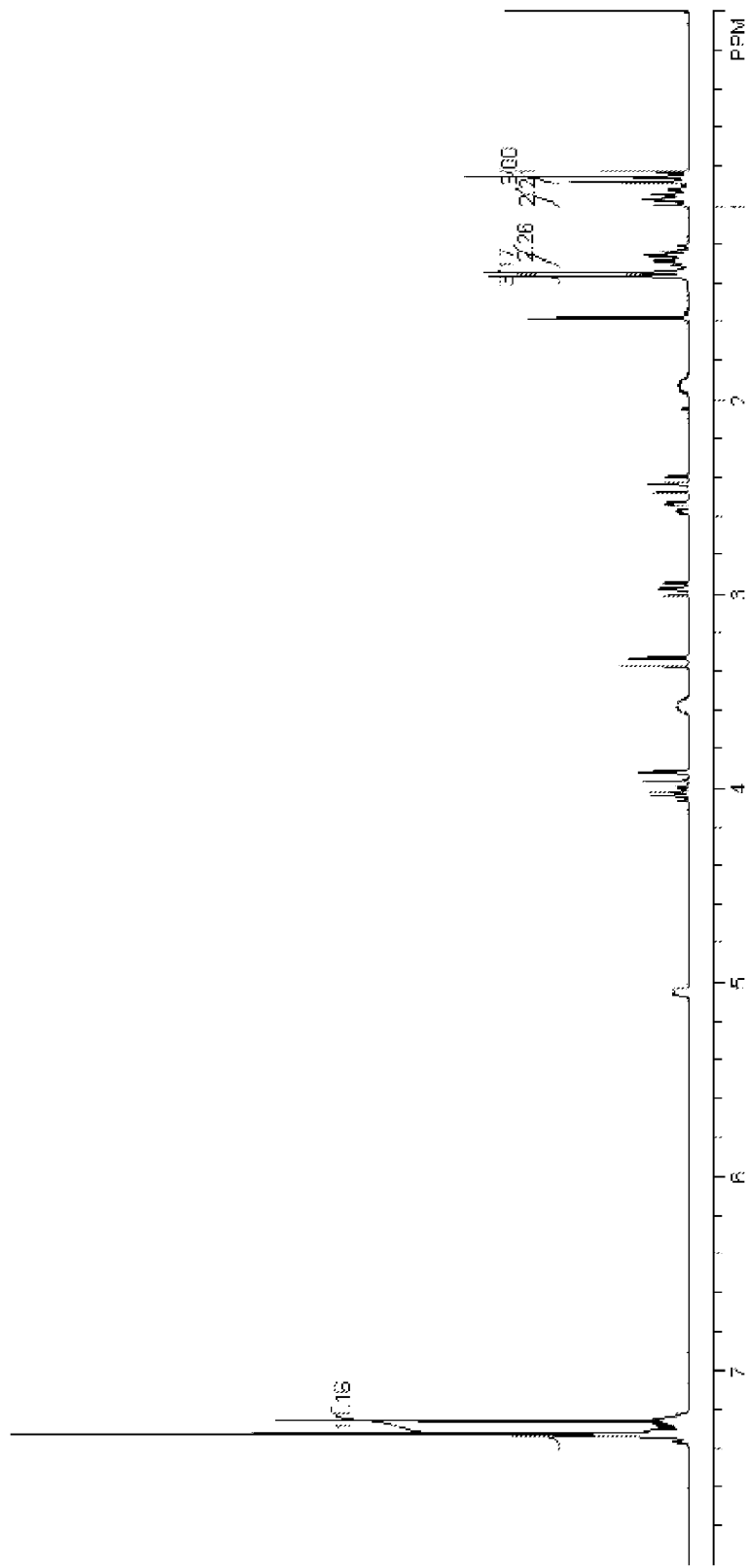
FIG. 5 is an $^1$H NMR spectrum for compound S1 shown in Scheme XI.
Figure 6:
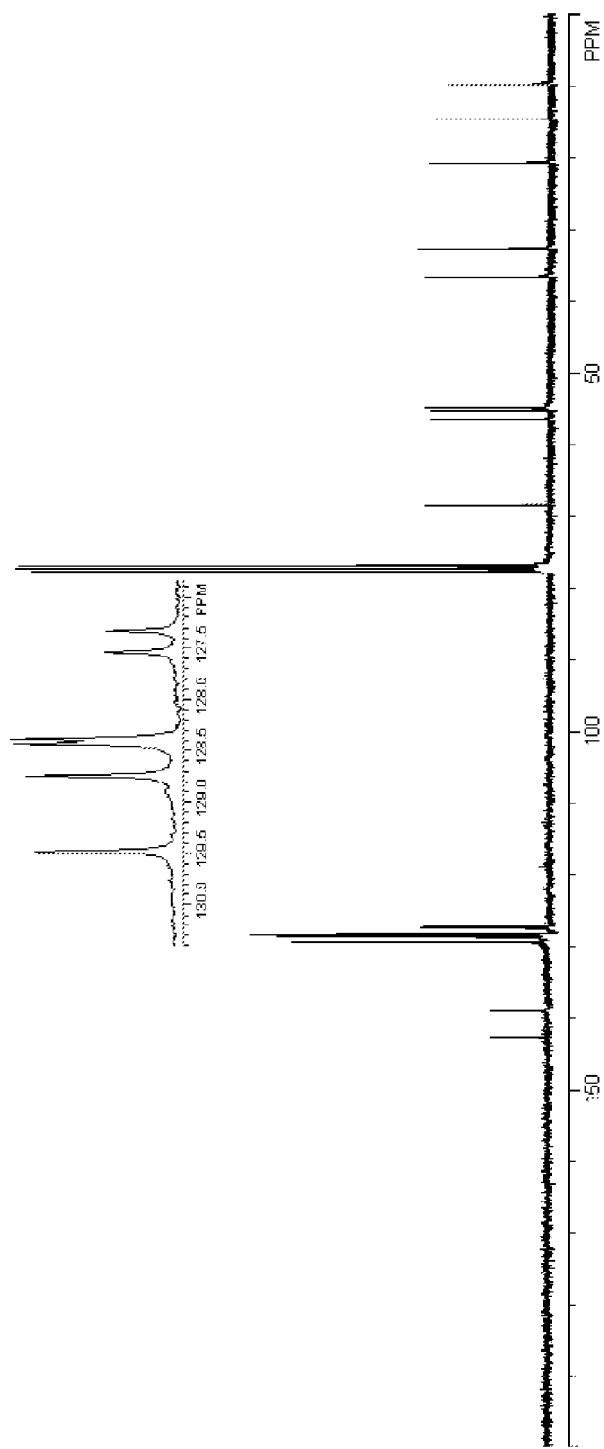
FIG. 6 is a $^{13}$C NMR spectrum for compound S1 shown in Scheme XI.

An NMR analysis of (S)-β-Propyl-γ-(S)—N-benzyl-α-methylbenzylamino alcohol (S1) was performed: $^1$H NMR (300 MHz, CDCl$_3$) δ 7.24-7.35 (m, 10H), 5.05 (br, 1H), 4.03 (q, J=6.9 Hz, 1H), 3.92 &3.97 (s, 1H), 3.58 (m, 1H), 3.33 &3.38 (s, 1H), 2.94-2.98 (m, 1H), 2.53-2.59 (m, 1H), 2.40-2.48 (m, 1H), 1.89-1.96 (m, 1H), 1.35 (d, J=6.9, 3H), 1.21-1.31 (m, 2H), 0.91-0.99 (m, 3H), 0.85 (t, J=7.5, 3H). $^{13}$C NMR (75 MHz, CDCl$_3$): 142.8, 140.0, 129.5, 128.7, 128.4, 128.3, 127.5, 127.3, 68.5, 56.5, 55.2, 54.9, 36.5, 32.5, 20.6, 14.5, 9.5. TOF-MS-ESI: [M+H]$^+$ calculated 312.2, found 312.4. X-ray quality crystals were obtained via slow evaporation of a hexane solution. Spectra for S1 are shown in FIGS. 5 and 6.

Example 6

(S)-β-Propyl-γ-Bocamino alcohol (S2)

Figure 7:
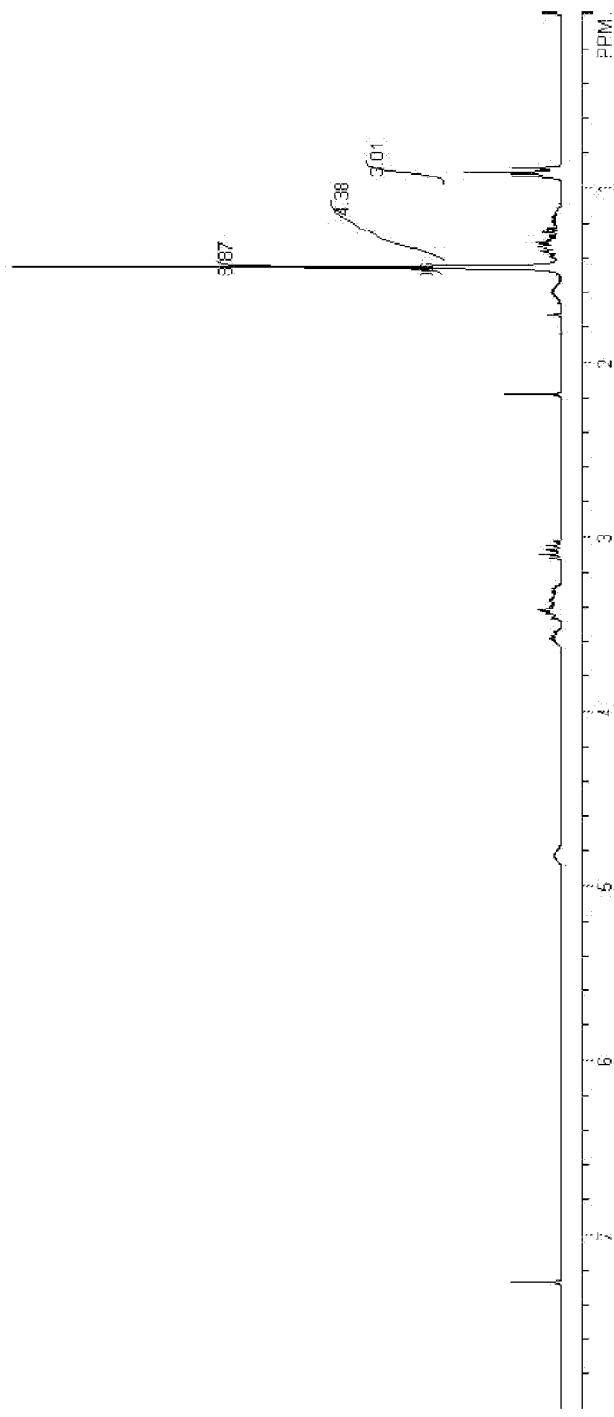
FIG. 7 is an $^1$H NMR spectrum for compound S2 shown in Scheme XI.
Figure 8:
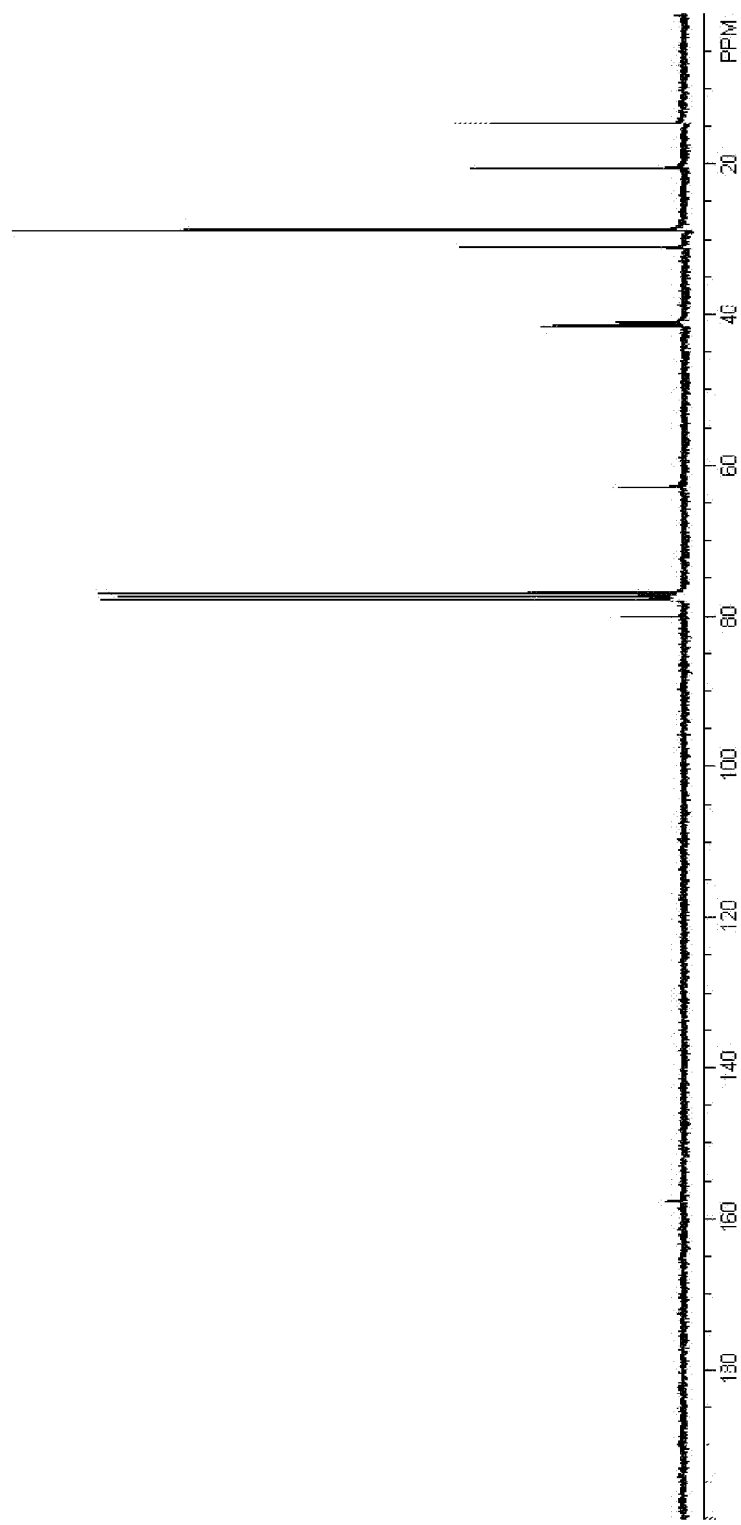
FIG. 8 is a $^{13}$C NMR spectrum for compound S2 shown in Scheme XI.

An NMR analysis of (S)-β-Propyl-γ-Bocamino alcohol (S2) was performed: NMR (300 MHz, CDCl$_3$) δ 4.82 (br, 1H), 3.48-3.64 (m, 1H), 3.29-3.44 (m, 3H), 3.04-3.13 (m, 1H), 1.54-1.66 (m, 1H), 1.45 (s, 9H), 1.09-1.41 (m, 4H), 0.91 (t, J=7.2 Hz, 3H). $^{13}$C NMR (75 MHz, CDCl$_3$): 157.7, 80.0, 62.8, 41.5, 41.0, 31.1, 28.6, 20.5, 14.5. TOF-MS-ESI:

[M+H]+ calculated 218.2, found 218.4; [M+Na]+ calculated 240.2, found 240.4; [2M+Na]+ calculated 457.4, found 457.8. Optical rotation: $[\alpha]^{rt}_D$=+7.0° (c=0.20, MeOH). Spectra for S2 are shown in FIGS. 7 and 8.

Example 7

(S)-β-Propyl-γ-dibenzylamino alcohol (S3)

An NMR analysis of (S)-β-Propyl-γ-dibenzylamino alcohol (S3) was performed: $^1$H NMR (300 MHz, CDCl$_3$) δ 7.24-7.37 (m, 10H), 5.60 (br, 1H), 4.04 & 4.00 (s, 2H), 3.66-3.70 (m, 1H), 3.20-3.26 (m, 1H), 3.16 & 3.11 (s, 2H), 2.50-2.58 (m, 1H), 2.44-2.46 (m, 1H), 1.99-2.10 (m, 1H), 1.25-1.33 (m, 1H), 0.96-1.02 (m, 1H), 0.84-0.89 (t, J=7.2 Hz, 3H). $^{13}$C NMR (75 MHz, CDCl$_3$): 138.2, 129.5, 128.8, 127.6, 69.3, 60.4, 59.4, 36.4, 32.5, 20.6, 14.6. TOF-MS-ESI: [M+H]+ calculated 298.2, found 298.5, [M+Na]+ calculated 320.2, found 320.5; [2M+Na]+ calculated 617.4, found 618.1. Optical rotation: $[\alpha]^{rt}_D$=+18.0° (c=0.25, MeOH; as HCl salt). 49% ee [Chiracel OD column; 95/5 hexane/isopropanol; flow rate=1 ml/min; T$_R$ 1: 7.8 min (minor), T$_R$ 2: 8.9 (major)]. Spectra not shown.

Example 8

(S)-β-Propyl-γ-Boc amino alcohol (S4)

(S)-β-Propyl-γ-Boc amino alcohol (S4): Optical rotation: $[\alpha]^{rt}_D$=+3.4° (c=0.20, MeOH). Spectra not shown.

Example 9

Determination of Salt Effect

An investigation into the effect of salt on the formation of the enantiomeric product was performed as illustrated in Table 4.

TABLE 4

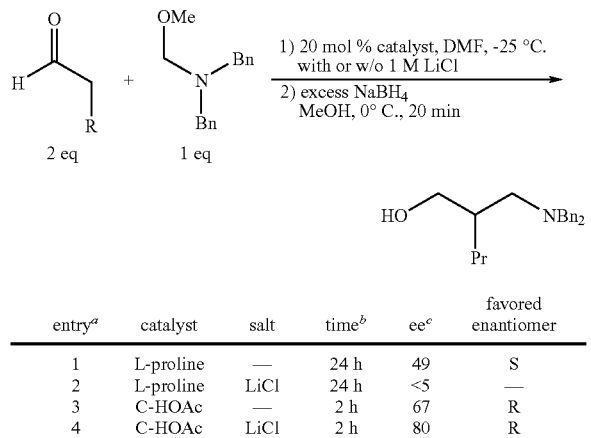

| entry[a] | catalyst | salt | time[b] | ee[c] | favored enantiomer |
|---|---|---|---|---|---|
| 1 | L-proline | — | 24 h | 49 | S |
| 2 | L-proline | LiCl | 24 h | <5 | — |
| 3 | C-HOAc | — | 2 h | 67 | R |
| 4 | C-HOAc | LiCl | 2 h | 80 | R |

[a]Reactions were repeated more than twice.
[b]Yield of all reactions >80% as determined by $^1$H NMR.
[c]Determined by chiral phase HPLC.

Figure 3:
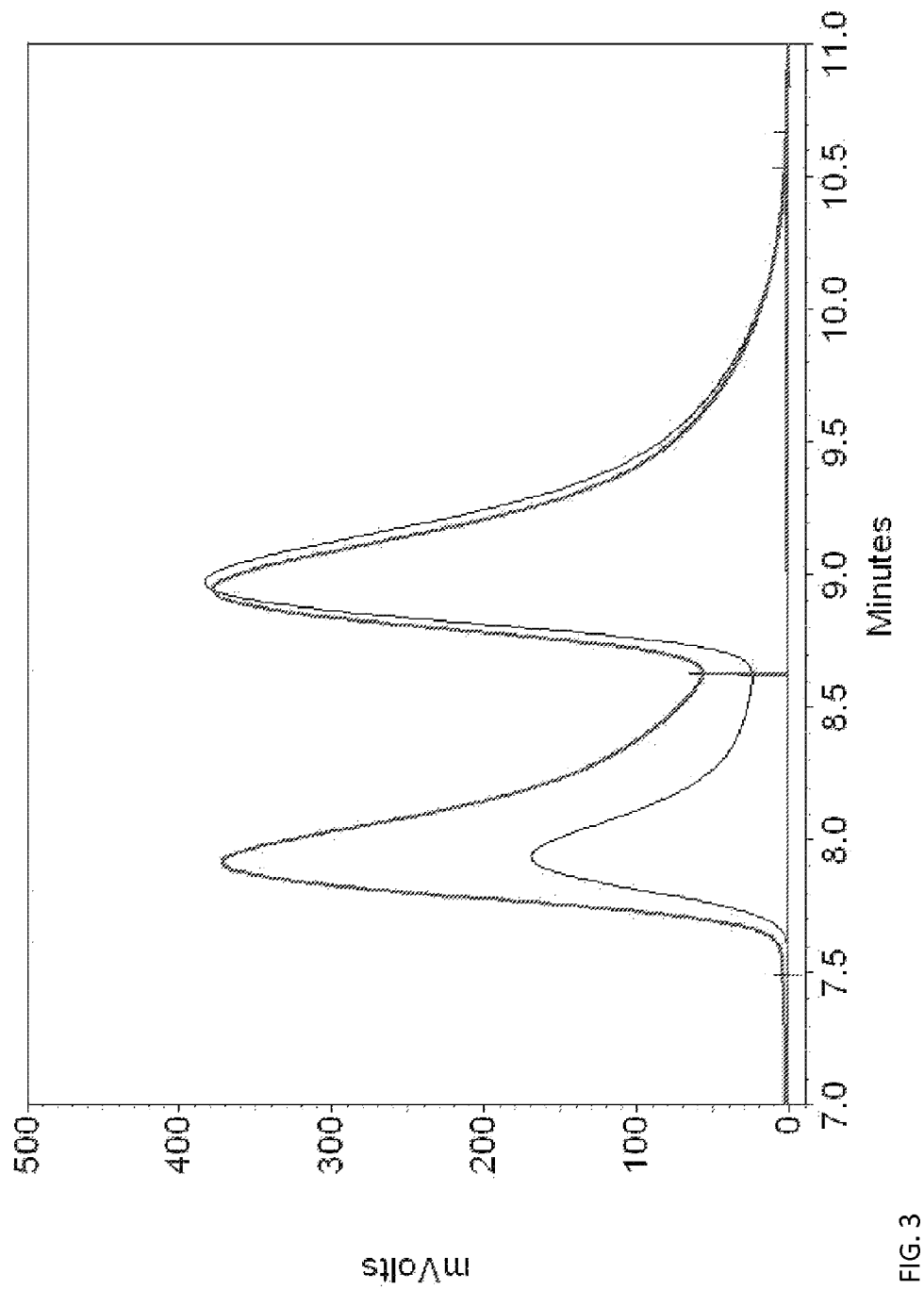
FIG. 3 is an HPLC chromatogram for the compounds shown in entries 1 and 2 of Table 4, illustrating the Salt Effect when using L-Proline as a catalyst.
Figure 4:
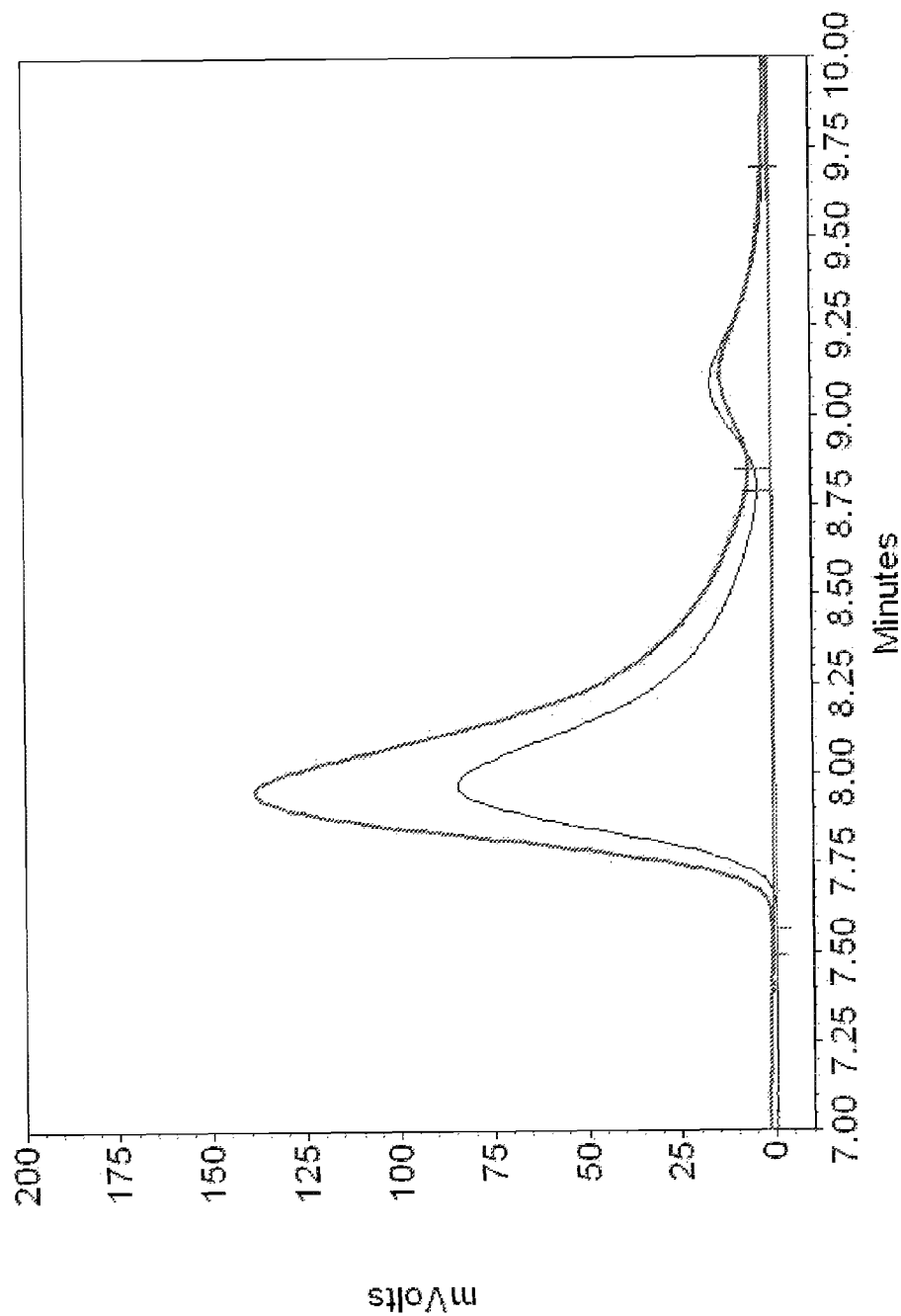
FIG. 4 is an HPLC chromatogram for the compounds shown in entries 3 and 4 of Table 4, illustrating the Salt Effect when using C—HOAc as a catalyst.

General Procedures: To 0.1 mmol catalyst dissolved in 1 ml biotech grade DMF (or 1 M LiCl DMF solution) in an 8 ml vial at −25° C. was added 110 μL (1 mmol) pentanal. The mixture was stirred for a few minutes, and 127 μL (0.5 mmol) N,O-acetal A was added. The vial was capped and the mixture was stirred at −25° C. for 2 or 24 hours. Yield of the reaction was determined by $^1$H NMR analysis of the crude reaction mixture. Excess NaBH$_4$ (0.06 g, 1.5 mmol) was added, followed by the addition of 1 ml MeOH, and the mixture was stirred for a few minutes. The −25° C. cooling bath was replaced by an ice bath, and the mixture was stirred for another 20 minutes. The mixture was then slowly poured into a 24 ml vial containing 5 ml saturated NH$_4$Cl at 0° C. and extracted with 10 ml Et$_2$O. The Et$_2$O layer was collected, washed with 5 ml water and then 5 ml brine, dried over MgSO$_4$, filtered and concentrated to give a colorless oil. The oil was dissolved in a mixture of hexane/isopropanol (v/v; 90/10) and used for ee determination without further purification. The corresponding racemic Mannich product was obtained by using D,L-proline as catalyst for ee assay development. The ee determination was performed on a Shimadzu 10A HPLC using a Chiracel OD column. Mobile phase: hexane/isopropanol (v/v: 95/5, premixed); flow rate=1 ml/min; retention time: ~7.8 minutes and ~8.9 minutes. FIGS. 3 and 4 are the HPLC chromatograms.

Example 10

Enantioselective Aminomethylation of Aldehydes

Table 5 shows the representative schema for the enantioselective aminomethylation of aldehydes and their yield and enantiomer excess (ee) value.

TABLE 5

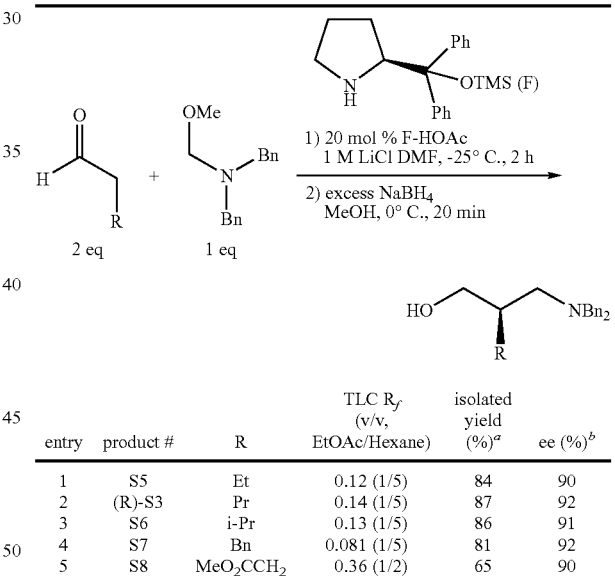

| entry | product # | R | TLC R$_f$ (v/v, EtOAc/Hexane) | isolated yield (%)[a] | ee (%)[b] |
|---|---|---|---|---|---|
| 1 | S5 | Et | 0.12 (1/5) | 84 | 90 |
| 2 | (R)-S3 | Pr | 0.14 (1/5) | 87 | 92 |
| 3 | S6 | i-Pr | 0.13 (1/5) | 86 | 91 |
| 4 | S7 | Bn | 0.081 (1/5) | 81 | 92 |
| 5 | S8 | MeO$_2$CCH$_2$ | 0.36 (1/2) | 65 | 90 |

General Procedures: To 0.33 g (1 mmol) catalyst F dissolved in 9 ml 1 M LiCl DMF in a 100 ml round bottom flask at −25° C. was added 57 μL (1 mmol) HOAc (in 1 ml 1M LiCl DMF). Aldehyde (neat, 10 mmol) was added, and the mixture was stirred for a few minutes. N,O-acetal A (neat, 1.27 mL, 5 mmol) was added. The flask was capped, and the mixture was stirred at −25° C. for 2 hours. Excess NaBH$_4$ (0.57 g, 15 mmol) was added, followed by the addition of 10 ml MeOH, and the mixture was stirred for a few minutes. The −25° C. cooling bath was replaced by an ice bath, and the mixture was stirred for another 20 minutes. The mixture was then slowly poured into a 250 ml beaker containing 50 ml saturated NH$_4$Cl at 0° and extracted with Et$_2$O (about 3×100 ml). Complete extraction of the product to the organic phases was monitored by TLC analysis. The Et$_2$O layers were collected, washed with 50 ml water and then 50 ml brine, dried over MgSO₄, filtered and concentrated to give crude β-substituted γ-amino alcohols, which were purified via flash column chromatography eluted with EtOAc/Hexane (1:10; v/v) to give the desired products as colorless viscous oils. Characterization and ee determination were then performed.

Example 11

(R)-β-Ethyl-γ-Dibenzylamino Alcohol (S5)

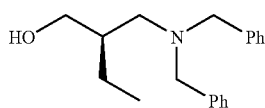

S5

Figure 13:
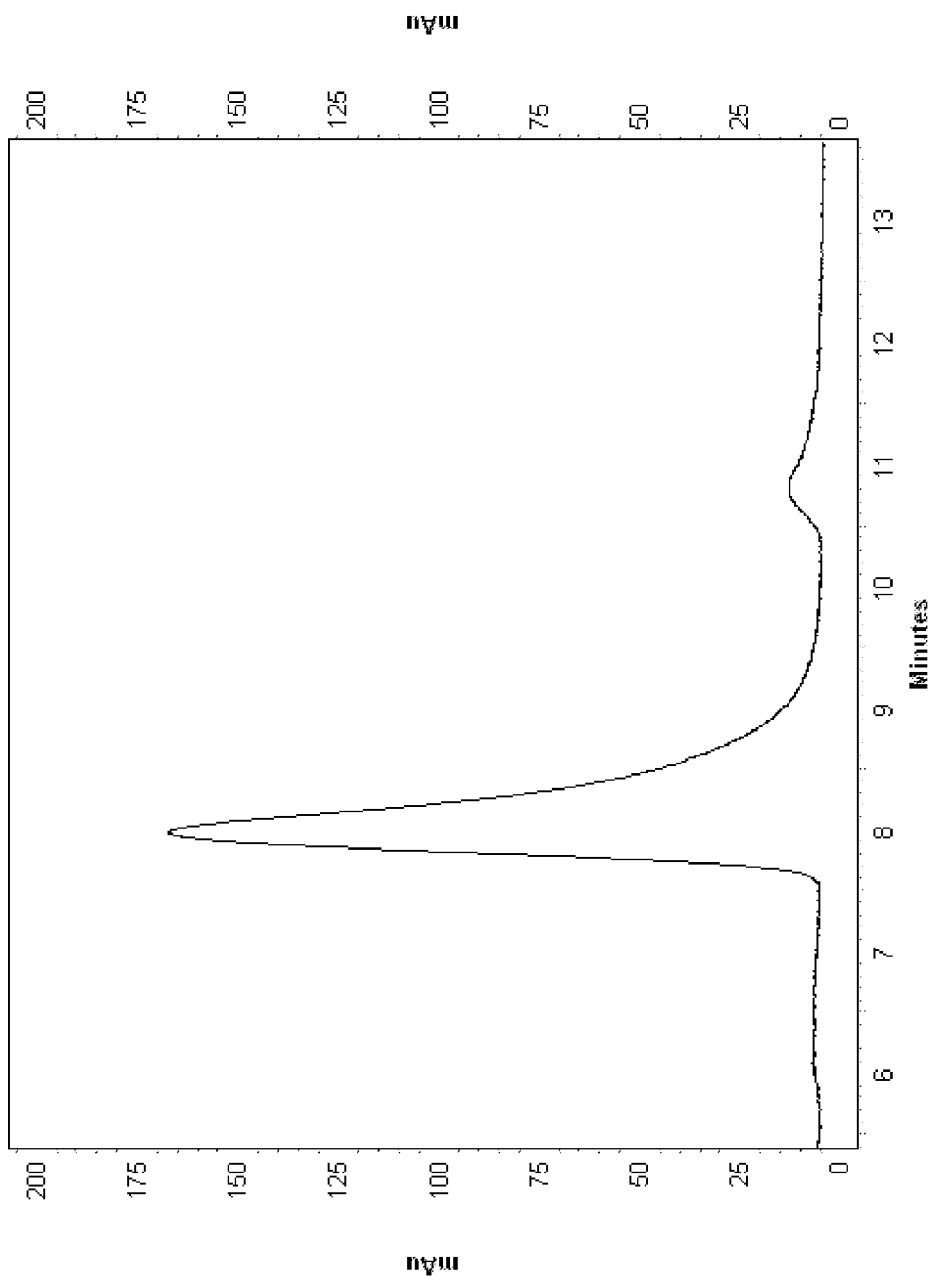
FIG. 13 is an HPLC chromatograph of ee determination for compound S5 shown in Table 5 and recrystallized.

An NMR analysis of (R)-β-Ethyl-γ-dibenzylamino alcohol (S5) (Table 5 entry 1) was performed: ¹H NMR (300 MHz, CDCl₃) δ 7.25-7.37 (m, 10H), 5.59 (br, 1H), 4.05 & 4.00 (s, 2H), 3.68-3.74 (m, 1H), 3.21-3.28 (m, 1H), 3.13 & 3.17 (s, 2H), 2.51-2.59 (m, 1H), 2.43-2.48 (m, 1H), 1.98 (m, 1H), 1.06 (td, J=6.3, 7.5 Hz, 2H), 0.88 (t, J=7.5 Hz, 3H). ¹³C NMR (75 MHz, CDCl₃): 138.1, 129.5, 128.7, 127.6, 68.9, 60.1, 59.3, 38.4, 23.1, 12.1. TOF-MS-ESI: [M+H]⁺ calculated 284.2, found 284.5; [M+Na]⁺ calculated 306.2, found 306.5; [2M+Na]⁺ calculated 589.4, found 590.0. Optical rotation: $[\alpha]^{rt}_D$=+16.8° (c=0.13, MeOH; as HCl salt). 90% ee [Chiracel OD column; 95/5 hexane/isopropanol; flow rate=1 ml/min; $T_R$ 1: 8.0 min (major), $T_R$ 2: 10.8 min (minor)]. FIG. 13 is a chromatograph showing the determination of ee by HPLC.

Example 12

(R)-β-Ppropyl-γ-dibenzylamino alcohol [(R)—S3]

Figure 9:
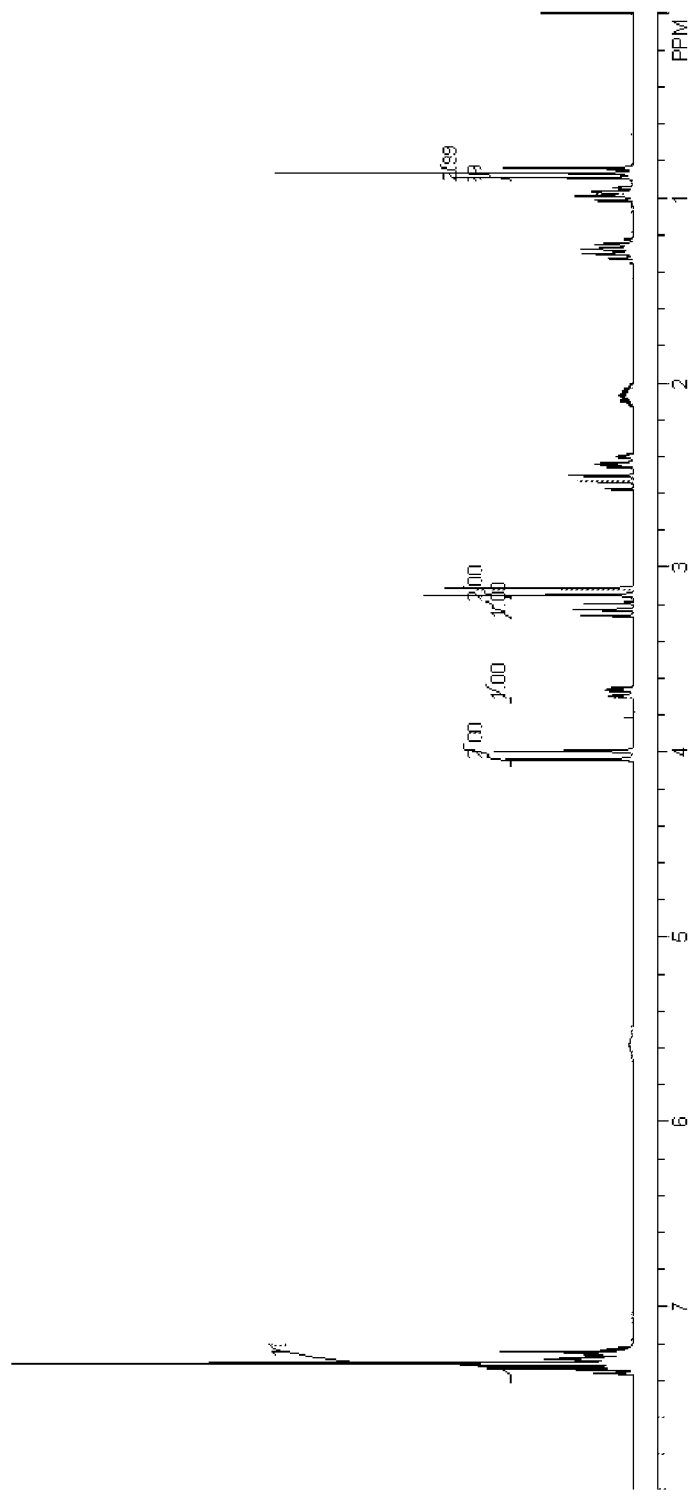
FIG. 9 is an $^1$H NMR spectrum for compound S3 shown in Scheme XI.
Figure 10:
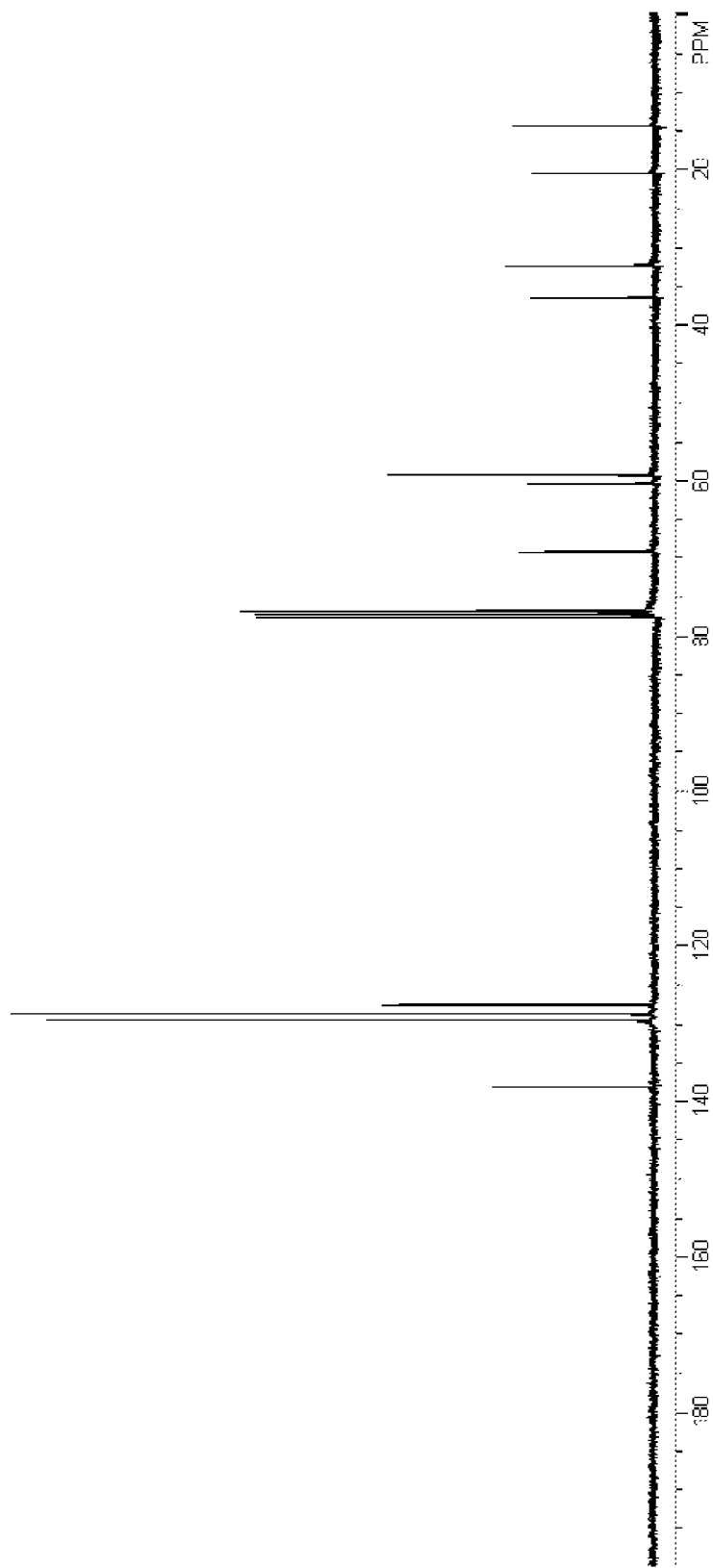
FIG. 10 is a $^{13}$C NMR spectrum for compound S3 shown in Scheme XI.
Figure 14:
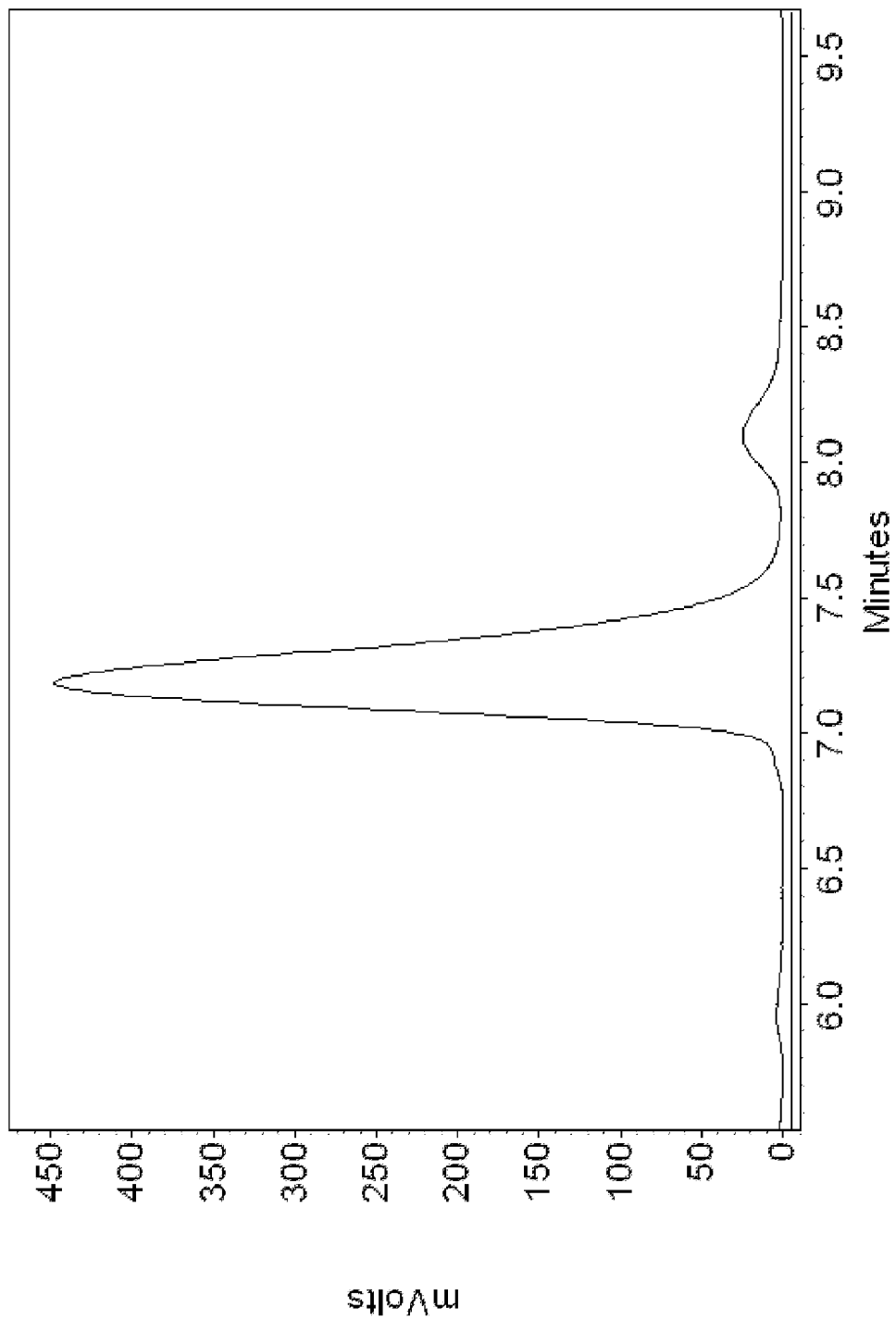
FIG. 14 is an HPLC chromatograph of ee determination compound (R)—S3 shown in Table 5, entry 2 and illustrated in Scheme VII.
Figure 15:
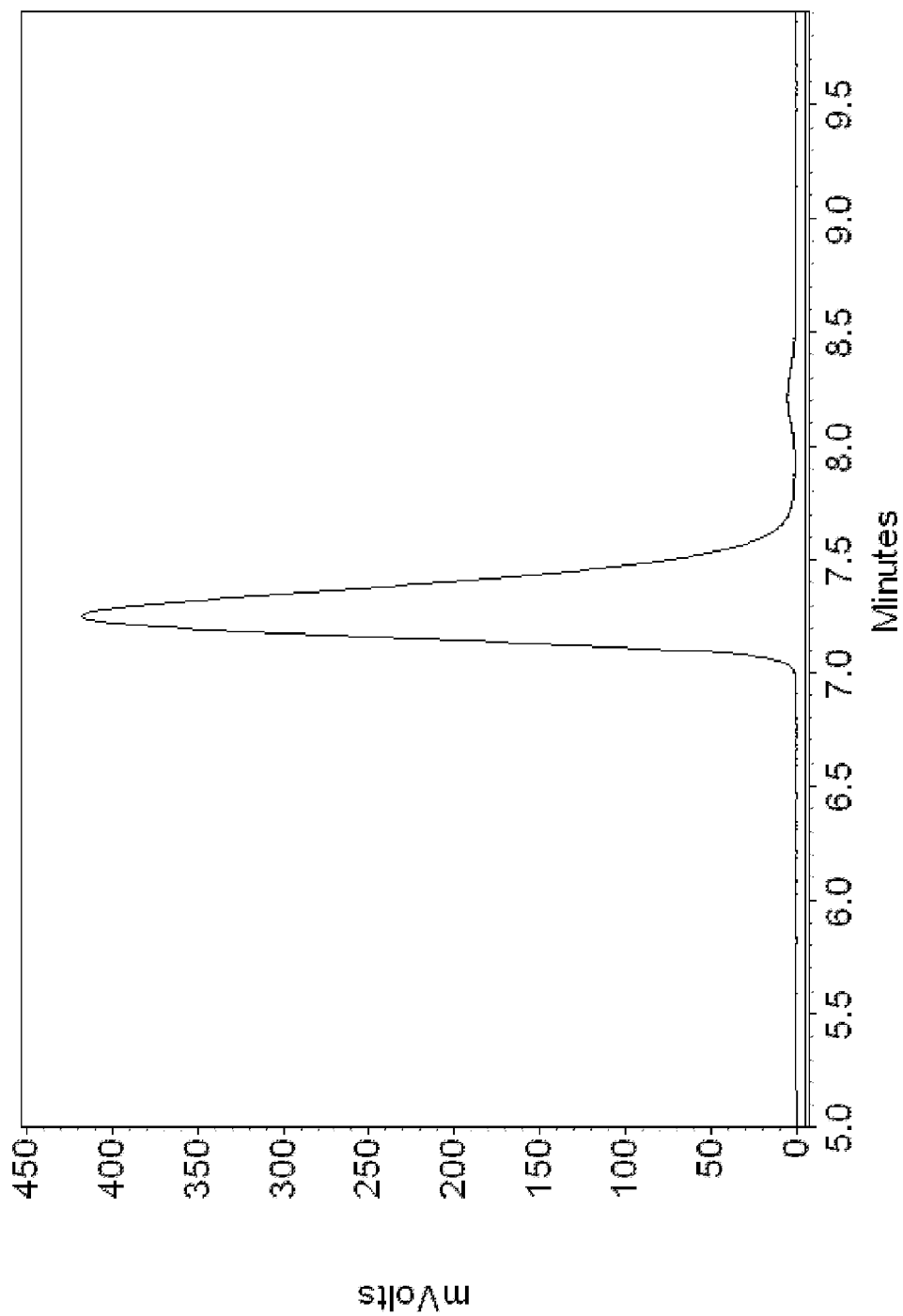
FIG. 15 is an HPLC chromatograph of an ee determination of compound (R)—S3 recrystallized, shown in Table 5, entry 2, illustrated in Scheme VII.

An NMR analysis of (R)-β-Ppropyl-γ-dibenzylamino alcohol [(R)—S3] (Table 5 entry 2) was performed: Optical rotation: $[\alpha]^{rt}_D$=−32.4° (c=0.25, MeOH; as HCl salt). 92% ee [Chiracel ODH column; 95/5 hexane/isopropanol; flow rate=1 ml/min; $T_R$ 1: 7.26 min (major), $T_R$ 2: 8.20 min (minor)]. NMR spectra for (R)—S3 are shown in FIGS. 9 and 10. FIGS. 14 and 15 are determinations of ee by HPLC before and after recrystallization respectively.

Example 13

(R)-β-Isopropyl-γ-dibenzylamino alcohol (S6)

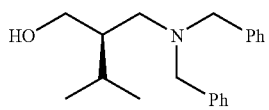

S6

Figure 16:
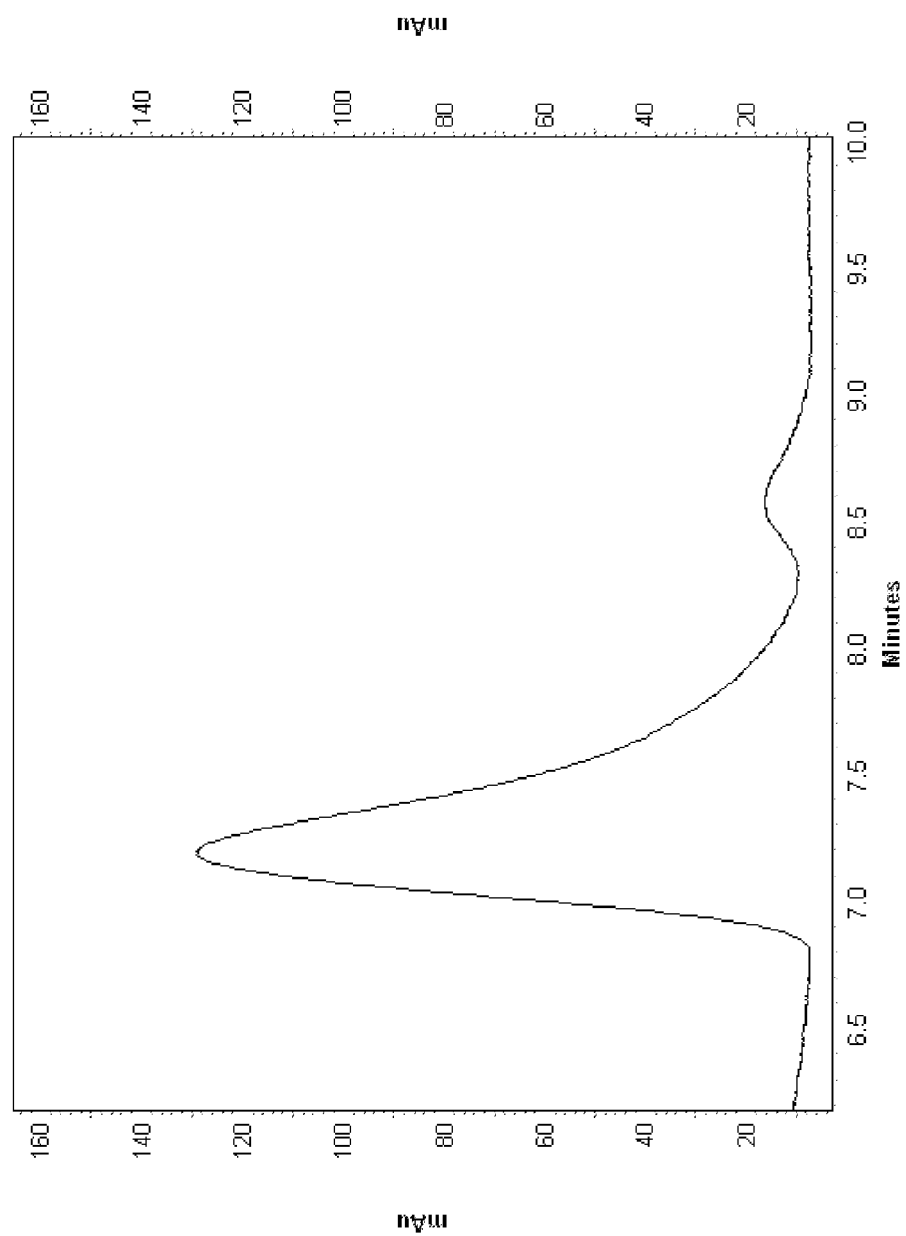
FIG. 16 is an HPLC chromatograph of an ee determination of compound S6 illustrated in Table 5.

An NMR analysis of (R)-β-Isopropyl-γ-dibenzylamino alcohol (S6) (Table 5 entry 3): ¹H NMR (300 MHz, CDCl₃) δ 7.24-7.36 (m, 10H), 5.62 (m, 1H), 4.04 & 4.00 (s, 2H), 3.69-3.74 (m, 1H), 3.30-3.34 (m, 1H), 3.17 & 3.13 (s, 2H), 2.64-2.72 (m, 1H), 2.44-2.50 (m, 1H), 1.88-1.94 (m, 1H), 1.44-1.51 (m, 1H), 0.83 & 0.81 (diastereotopic, d, J=6.7 Hz, 6H). ¹³C NMR (75 MHz, CDCl₃): δ 138.1, 129.5, 128.7, 127.6, 67.2, 59.3, 57.9, 42.1, 28.8, 20.4, 20.0. TOF-MS-ESI: [M+H]⁺ calculated 298.2, found 298.5; [M+Na]⁺ calculated 320.2, found 320.5; [2M+Na]⁺ calculated 617.4, found 618.1. Optical rotation: $[\alpha]^{rt}_D$=−29.5° (c=0.20, MeOH; as HCl salt). 91% ee [Chiracel OD column; 95/5 hexane/isopropanol; flow rate=1 ml/min; $T_R$ 1: 7.2 min (major), $T_R$ 2: 8.6 min (minor)]. FIG. 16 is a determination of ee using HPLC.

Example 14

(R)-β-Benzyl-γ-dibenzylamino alcohol (S7)

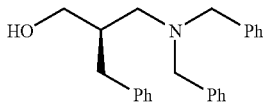

S7

Figure 17:
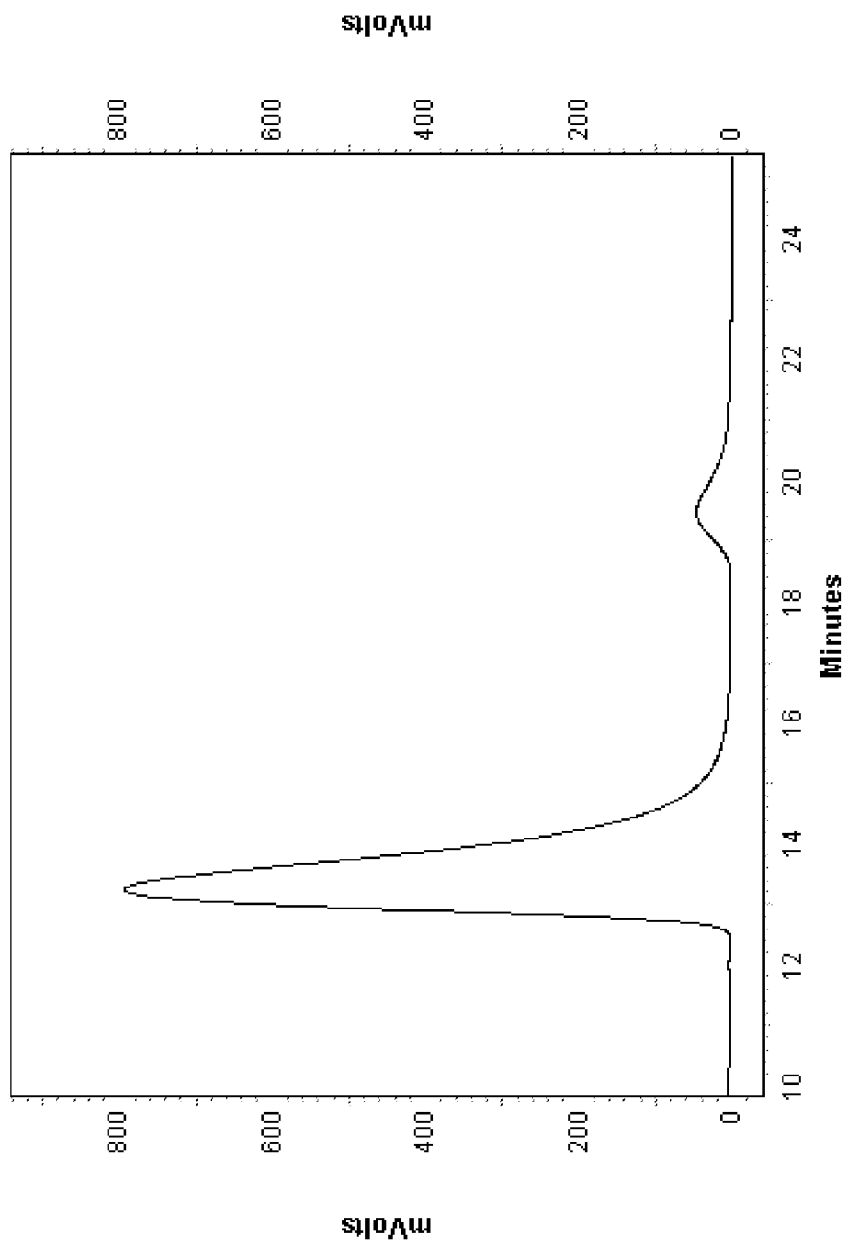
FIG. 17 is an HPLC chromatograph of an ee determination of compound S7 described in Table 5.

An NMR analysis of (R)-β-Benzyl-γ-dibenzylamino alcohol (S7) (Table 5 entry 4) was performed: ¹H NMR (300 MHz, CDCl₃) δ 7.09-7.35 (m, 15H), 3.95 & 3.90 (s, 2H), 3.64-3.69 (m, 1H), 3.13-3.34 (m, 1H), 3.18 & 3.13 (s, 2H), 2.28-2.58 (m, 5H). ¹³C NMR (75 MHz, CDCl₃): δ 140.1, 138.0, 129.5, 129.1, 128.7, 128.6, 127.6, 126.3, 68.5, 59.2, 59.0, 38.7, 36.6. TOF-MS-ESI: [M+H]⁺ calculated 346.2, found 346.6. Optical rotation: $[\alpha]^{rt}_D$=−44.1° (c=0.14, MeOH; as HCl salt). 92% ee [Chiracel OD column; 95/5 hexane/isopropanol; flow rate=1 ml/min; $T_R$ 1: 13.2 min (major), $T_R$ 2: 19.5 min (minor)]. FIG. 17 is a determination of ee using HPLC.

Example 15

(R)-methyl 4-(dibenzylamino)-3-(hydroxymethyl) butanoate (S8)

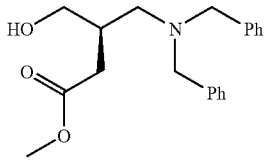

S8

Figure 18:
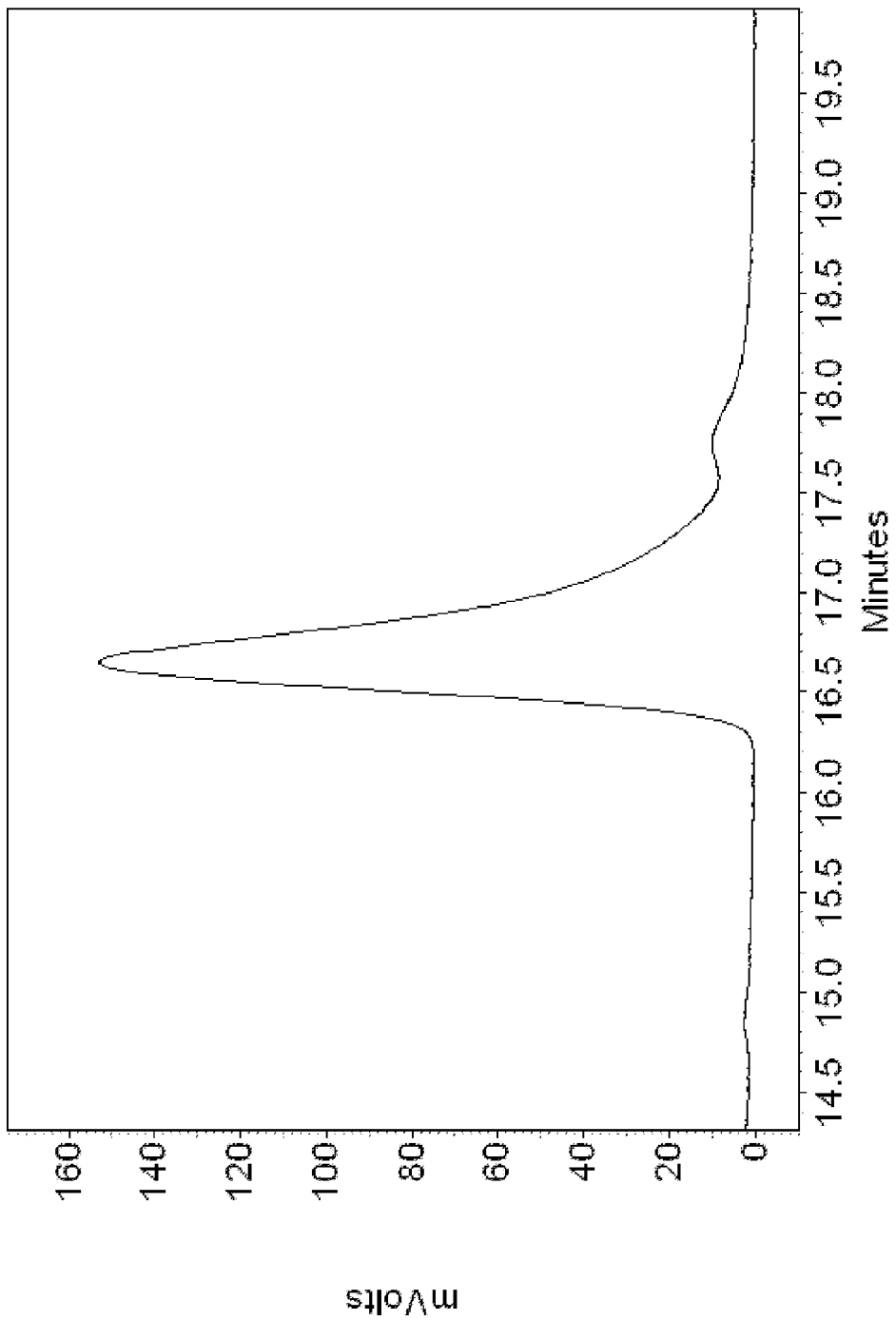
FIG. 18 is an HPLC chromatogram of an ee determination of compound S8 described in Table 5.

An NMR analysis of (R)-methyl 4-(dibenzylamino)-3-(hydroxymethyl) butanoate 8 (Table 5 entry 6) was performed: ¹H NMR (300 MHz, CDCl₃) δ 7.25-7.36 (m, 10H), 4.64 (br, 1H), 4.14 & 4.16 (s, 2H), 3.65 (s, 3H), 3.63-3.69 (m, 1H), 3.33-3.39 (m, 1H), 3.26 & 3.22 (s, 2H), 2.42-2.58 (m, 3H), 2.11 (d, 6.0 Hz, 2H). ¹³C NMR (75 MHz, CDCl₃): δ 137.1, 128.3, 129.4, 128.7, 127.6, 67.4, 59.1, 57.9, 51.9, 34.9, 34.4. TOF-MS-ESI: [M+H]⁺ calculated 328.2, found 328.5. Optical rotation: $[\alpha]^{rt}_D$=−24.7° (c=0.20, MeOH; as HCl salt). ~90% ee [Chiracel OD column; 95/5 hexane/isopropanol; flow rate=1 ml/min; $T_R$ 1: 16.4 min (major), $T_R$ 2: 19.6 min (minor)]. FIG. 18 is a determination of ee using HPLC.

Example 16

Enantioselective Aldehyde Aminomethylations

To the inventors' knowledge, non-H-bonded ionic attractions such as that proposed in FIG. 1 have not been invoked to explain the stereochemical outcome of organocatalytic reactions, although they are frequently invoked to rationalize enzymatic catalysis. This hypothesis was tested by conducting the L-proline-catalyzed reaction in the presence of LiCl. If the putative iminium/carboxylate attraction determines the direction of iminium approach to the enamine, then the ionic additive should diminish enantioselectivity because lithium cation will compete with the iminium and chloride will compete with the carboxylate for ion pairing. Indeed, the L-proline-catalyzed Mannich reaction carried out in the presence of 1 M LiCl showed little or no enantioselectivity (Table 4), which supports the transition state model shown in FIG. 1. However, 1 M LiCl leads to a moderate but reproducible enantioselectivity enhancement for the reaction catalyzed by 2-alkyl-pyrrolidine C; a similar result was observed for B. The origin of this enhancement is unclear.

Without being held to any specific theory, the inventors attribute the improved enantioselectivity of catalyst C relative to B to the increased steric bulk of the 2-substituent in C. Jorgensen et al. and Hayashi et al. have recently reported nucleophilic activation of aldehydes by pyrrolidine F, in which the trimethylsilyl group provides a further increase in steric bulk relative to the methyl group in C. It was found that F leads to an improvement in Mannich reaction enantioselectivity, relative to C. Table 6 shows that Mannich reactions of six aldehydes proceeded with ≧90% ee when catalyzed by 20 mol % F (with an equivalent amount of acetic acid) in DMF containing 1 M LiCl. The reaction condition is mild enough to introduce various functional groups through the aldehyde: e.g. amino or ester groups (entry 5, 6).

TABLE 6

Enantioselective aldehyde aminomethylations

| entry | R | isolated yield (%) | ee (%)[a] |
|---|---|---|---|
| 1 | Et | 84 | 90 |
| 2 | Pr | 87 | 92 |
| 3 | i-Pr | 86 | 91 |
| 4 | Bn | 81 | 92 |
| 5 | $(Boc)_2N(CH_2)_3$ | 82 | n.d.[b] |
| 6 | $MeO_2CCH_2$ | 65 | 93 |

[a]Determined by chiral phase HPLC.
[b]Not determined

Example 17

Concise Synthesis of β²-Amino Acids

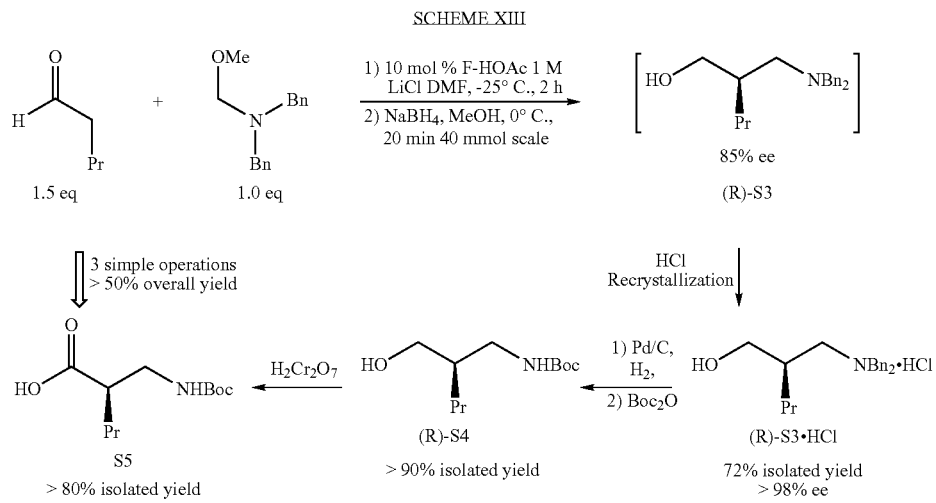

SCHEME XIII

The β-substituted γ-amino alcohols generated via the Mannich/reduction sequence could be converted in a straight forward manner to appropriately protected β²-amino acids, as illustrated in SCHEME XIII for the synthesis of Boc-β²-norvaline and Fmoc-β²-Lysine analog. The benzyl groups were removed from the amino group via hydrogenolysis and replaced by Boc or Fmoc in an efficient one-pot operation. Jones oxidation then provided the desired products. The reaction conditions are mild enough to tolerate properly protected side chain functional groups such as ester and amines. The work-up and purifications are simple therefore this protocol is amendable for large scale synthesis as demonstrated by a 3-step protocol resulting in multi-gram Boc-β²-norvaline with >50% overall yield. It is worth to notice that the β-substituted γ-amino alcohols can be crystallized as the corresponding salt (e.g., HCl salt). A single recrystallization of β-propyl γ-amino alcohol HCl salt boosts the ee >98% with excellent yield (Scheme X).

Example 18

Synthesis of (R)—S3-HCl

The Mannich reaction/reduction sequence followed the general procedures described above for Table 5 to give (R)—S3 as a viscous oil in quantitative yield. (R)—S3 was dissolved in 50 ml $Et_2O$, followed by the slow addition of 50 ml 4N HCl in dioxane. The resulting mixture was stirred for a few minutes and the solvent was removed under reduced pressure to give a viscous oil. To this viscous oil in a 150 ml flask, was added 50 ml EtOAc. The flask was shaken with heating (with a heat gun) until the oil solidified in ethyl acetate to give a milky mixture with white solid. A few drops of MeOH were added to the milky mixture until the solid was just completely dissolved to give a clear solution. The open flask with the EtOAc-MeOH hot solution was then kept in a glass container containing hot $Et_2O$. The container was sealed and stayed at room temperature for crystallization. Crystals from this procedures were filtered, washed with EtOAc and dried in vacuo to afford 9.6 g (72% yield) (R)—S3-HCl as white crystals with >98% ee (determined using the free amino alcohol after a base wash of the HCl salt). Melting point: 135-137° C. Optical rotation: $[\alpha]^{rt}_D = -36.30°$ (c=0.25, MeOH; as HCl salt).

Example 19

Synthesis of (R)—S4

(R)—S3-HCl (5.0 g, 15 mmol) and wet 10% Pd/C (1.0 g) were added to 50 ml MeOH in a hydrogenation flask. The heterogeneous mixture was put under 40-60 psi $H_2$ at room temperature overnight. After the hydrogenolysis was completed as indicted by TLC analysis, the mixture was diluted by 50 ml $CH_2Cl_2$, and DIEA (26 mmol, 6.4 ml) and $Boc_2O$ (18 mmol, 4.0 g) were added. The mixture was stirred at room temperature overnight and filtered through a pad of celite to remove Pd/C, and the celite washed with MeOH extensively. The filtrate was collected, concentrated and applied to a silica chromatography column eluted with EtOAc/Hexane (⅕, v/v, TLC $R_f$=0.07) to give 3.1 g (96% yield) (R)—S4 as a colorless oil. Optical rotation: $[\alpha]^{rt}_D = -7.0°$ (c=0.20, MeOH).

Example 20

Synthesis of (R)-Boc-β²-Homonovaline-OH(S9)

Figure 11:
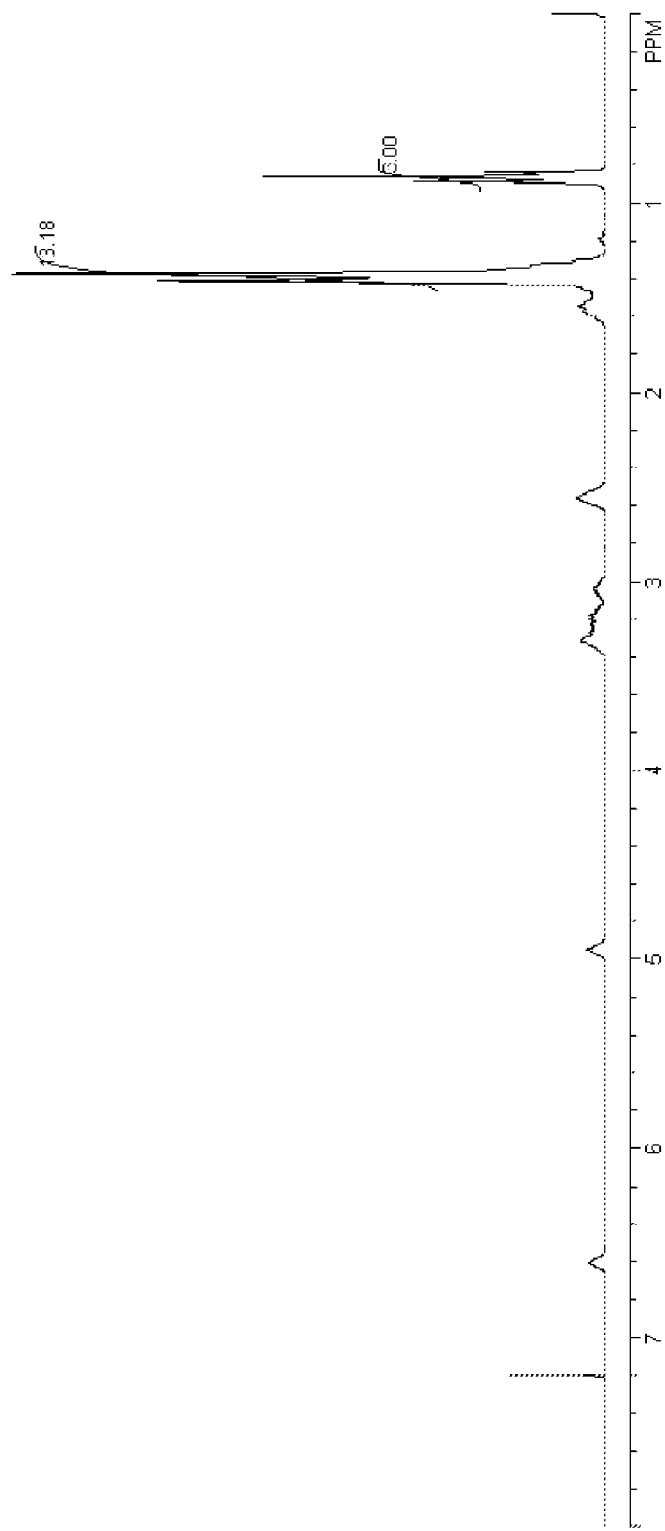
FIG. 11 is an $^1$H NMR spectrum for compound S9 described in Example 20.
Figure 12:
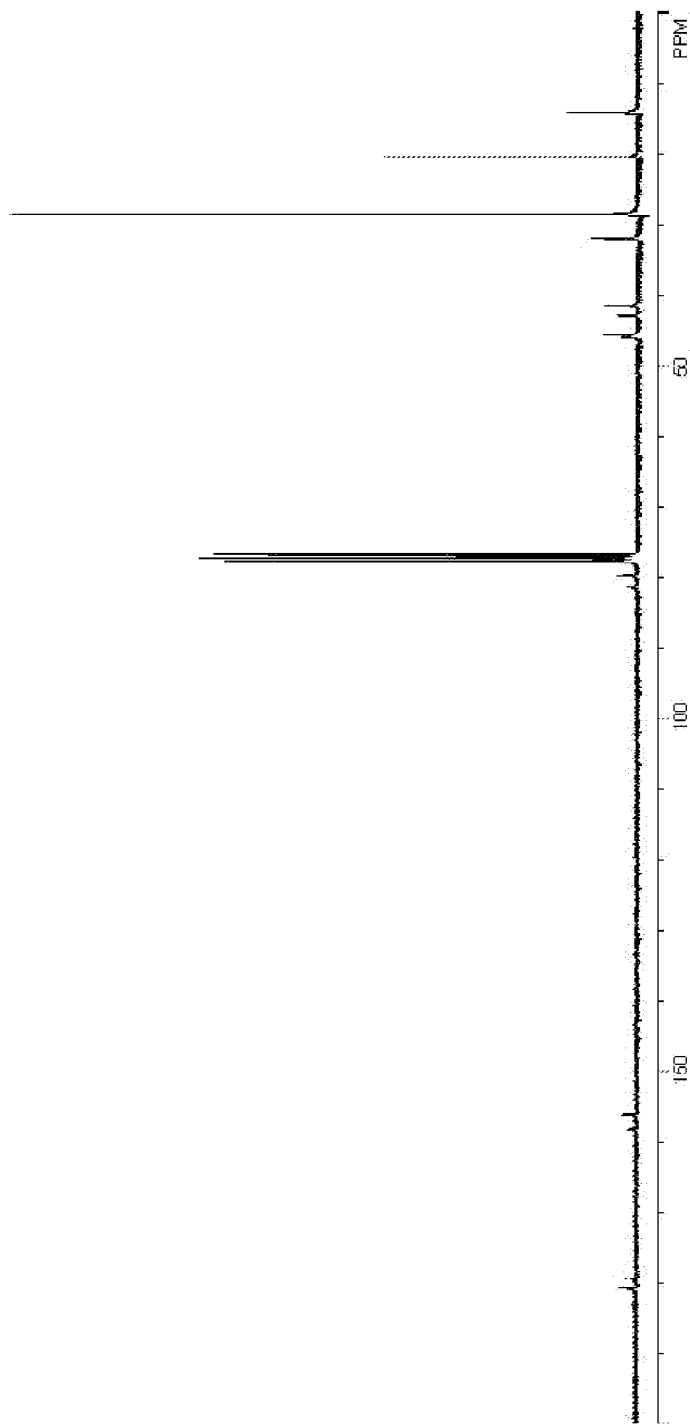
FIG. 12 is a $^{13}$C NMR spectrum for compound S9 described in Example 20.

To 2.8 g (13 mmol) (R)—S4 dissolved in 130 ml acetone at 0° C. was added 19.5 mmol $H_2Cr_2O_7$ (39 ml Jones reagent). The mixture was stirred for 12 h, during which time the mixture warmed to room temperature. Excess isopropanol was added, and the mixture was stirred overnight. The mixture was filtered, and the solution was concentrated to about 20 ml under reduced pressure at room temperature. The concentrated mixture was diluted with 20 ml 2 N HCl and extracted with $Et_2O$. Complete extraction of the product into the $Et_2O$ phase was monitored by TLC. The $Et_2O$ layers were collected, combined and concentrated to about 50 ml. This concentrated $Et_2O$ solution was extracted with 2 M NaOH (monitored by TLC). The basic aqueous extracts were collected, combined and washed with 2×10 ml $Et_2O$. The basic aqueous solution was then acidified with 2 N HCl and extracted with $Et_2O$ (monitored by TLC). The $Et_2O$ layers were combined, washed with saturated NaCl, dried over $MgSO_4$, filtered and concentrated under reduced pressure to give Boc-β²-Homonovaline-OH as a viscous colorless oil that is pure by TLC and NMR analysis (present as rotamers on the NMR time scale). $^1H$ NMR (300 MHz, $CDCl_3$) δ 10.10 (br, 1H), 6.61 & 4.95 (br, 1H), 3.16-3.36 (m, 2H), 2.54-2.56 (m, 1H), 1.18-1.57 (m, 13H), 0.86 (t, J=6.9 Hz, 3H); $^{13}C$ NMR (75 MHz, $CDCl_3$): δ 180.7 & 179.3, 158.2 & 156.2, 81.3 & 79.8, 45.9 & 45.6, 42.9 & 41.6, 31.9, 28.6, 20.5, 14.1. TOF-MS-ESI: [M−H]⁻ calculated 230.2, found 230.5; [2M−H]⁻ calculated 461.3, found 462.0. Optical rotation: $[\alpha]^{rt}_D = -17.5°$ (c=0.33, MeOH). Spectra for S9 are shown in FIGS. 11 and 12.

The inventors have described catalytic asymmetric Mannich reactions involving a formaldehyde-derived iminium electrophile and aldehydes as the formal nucleophiles. Mechanistic analysis of the proline-catalyzed versions suggests that non-H-bonded ionic interactions can be used as a stereochemistry-determining feature in organocatalytic reactions. The new organocatalytic process constitutes the key step in an efficient synthesis of diverse β²-amino acids. This contribution is significant because β²-amino acid residues are essential for the formation of certain β-peptide secondary structures (the 14-helix, 12/10-helix and the β³/β² reverse turn). Peptides containing β²-residues have been reported to display potentially useful biological activities, such as mimicry of somatostatin signaling and inhibition of viral infection; these activities require β²-residues at specific positions within the β-peptide sequence. To date, utilization β²-amino acid building blocks has been limited by the cumbersome routes that are generally required to prepare them. Few β²-amino acids are commercially available. In contrast, many β³-amino acids (side chain adjacent to nitrogen) are commercially available, and such building blocks are readily prepared from the analogous α-amino acids. The disclosed catalytic route offers large-scale access to protected β²-amino acids with a range of side chains, as well as to other chiral molecules (α-substituted β-amino aldehydes, β-substituted γ-amino alcohols) of potential value.

Example 21

Organocatalytic Aldehyde Aminomethylation: A Three Step Protocol

The inventors report the first simple catalytic aldehyde aminomethylation method using formaldehyde derived iminium salts as electrophiles and proline (and proline derivatives) as catalysts; and the first organocatalytic method for concise β²-amino acid synthesis using this method. The stereochemistry outcome of the Mannich reaction is opposite using L-proline and L-diphenylprolinol methyl ether (B, Table 7) as catalyst respectively, indicating two different transition states of the reaction. Giving the fact that the iminium salts are not favorable hydrogen bond acceptor (as opposite to imines, which are good hydrogen bond acceptor as shown in proline-mediated Mannich reactions) for the acidic proton of proline, the stereochemistry outcome of the proline-catalyzed reaction must be controlled by a different non-covalent interaction other than hydrogen bonding. This new mechanistic insights will lead to better understanding of weak interactions in catalytic controls therefore inspiring novel strategies for catalyst development. The reaction is diastereoselective when chiral iminium was used and the major diastereomer can be separated in good yield. The optically pure Mannich adducts (β²-amino aldehydes) were converted to β²-amino acids. The overall yield of the synthesis is higher than 40% via a short reaction path (three steps) from readily available starting materials. To the best of inventors' knowledge, this strategy provides the most efficient way for β² amino acids synthesis.

For a reaction between aldehyde and iminium catalyzed by proline and its derivatives, initial studies using preformed iminium salts gave no stereoselectivity at various conditions. When iminium intermediate was generated in situ from aqueous formaldehyde, dibenzylamine and acetic acid in DMF, the reaction catalyzed by proline gave Mannich adduct with significant stereoselectivity, along with side products from self-aldol reaction of aldehyde and cross-aldol reaction between aldehyde and formaldehyde. Significant reaction was also observed with the absence of proline catalyst, resulting in low stereoselectivity. Further studies found that by using N,O-acetal as iminium precursor, the reaction gave exclusively the Mannich adduct with good stereoselectivity in DMF at −25° C.

TABLE 7

Enantioselective Aminomethylation of Aldehyde

| entry | catalyst | conversion[b] (%) | ee[c] (%) | favored enantiomer[d] |
|---|---|---|---|---|
| 1 | L-proline | >89 | 50 | S |
| 2 | L-α-m-proline | ~15 | 56 | S |
| 3 | L-pro-NH₂[a] | >86 | 33 | S |
| 4 | L-pro-NHMe[a] | >79 | 19 | S |
| 5 | L-pro-NMe₂[a] | >92 | 44 | S |

TABLE 7-continued

Enantioselective Aminomethylation of Aldehyde

| entry | catalyst | conversion[b] (%) | ee[c] (%) | favored enantiomer[d] |
|---|---|---|---|---|
| 6 | L-pro-OMe[a] | >83 | <5 | — |
| 7 | A[a] | >87 | 19 | R |
| 8 | B[a] | >72 | 65 | R |

[a]With 20 mol % HOAc.
[b]Determined by 1H NMR of the crude reaction mixture before reduction; reduction is quantitative.
[c]Determined by chiral phase HPLC.
[d]Determined by optical rotation comparison, see supporting information for details.

Shown in Table 7 is an enantioselective Mannich reaction between aldehyde and N,O-acetal. The reaction is very efficient (except entry 2), giving excellent conversions, albeit moderate enantioselectivity. The reaction catalyzed by proline and proline amide favored S-enantiomer (entry 1-5) with 19-56% ee, while proline ester gave almost no ee. Simple chiral pyrrolidine (Table 7 A & B) favored R-enantiomer, with 19% and 65% ee respectively.

Figure 19:
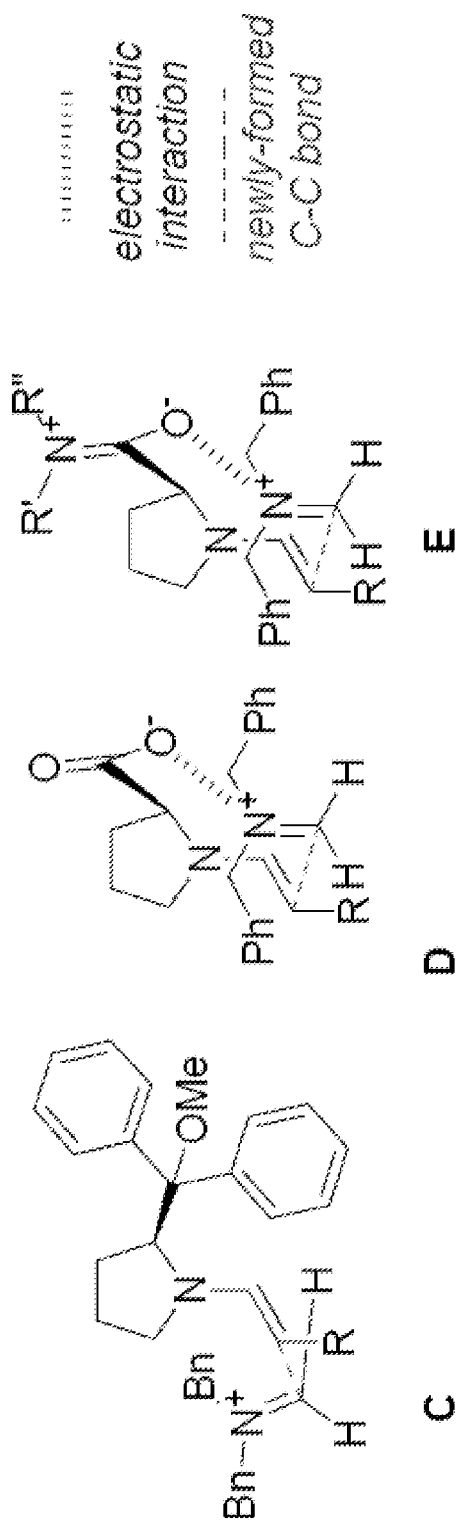
FIG. 19 are hypothetical structures of the proposed transition states of the 3-step protocol according to the invention.
Figure 20:
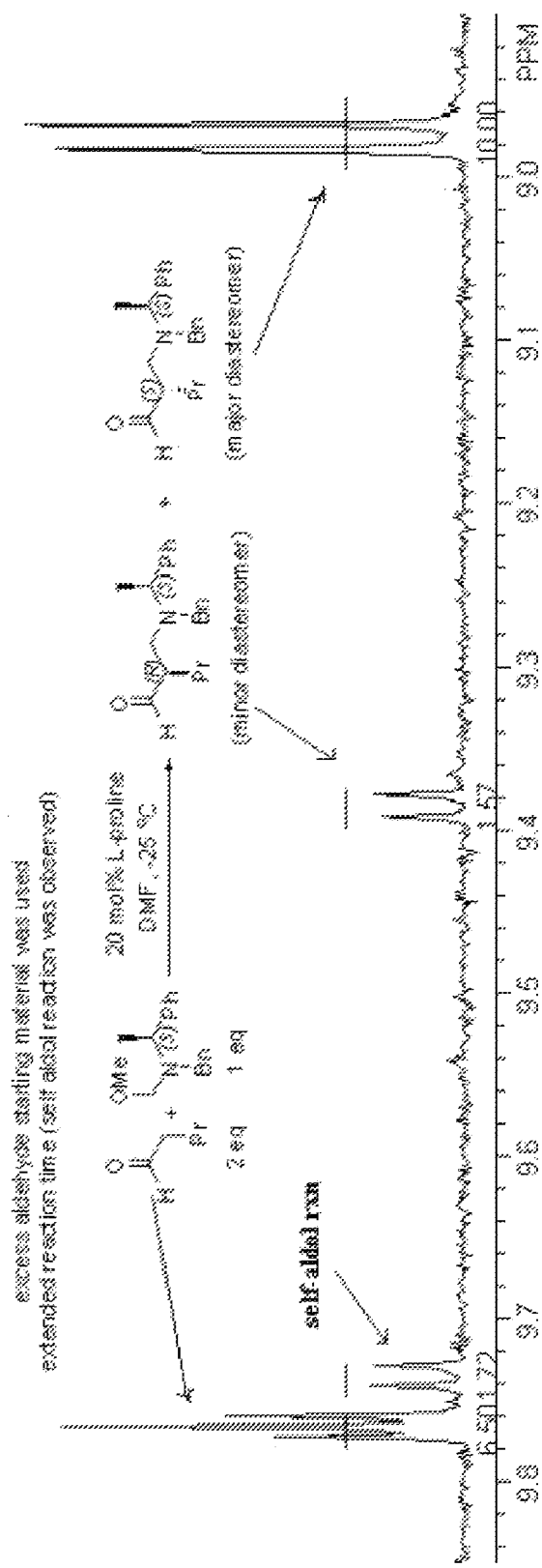
FIG. 20 is an $^1$H NMR spectrum for a Mannich reaction having an extended reaction time.

Without being held to any specific theory, it is believed that the reaction proceeds via an enamine intermediate (from condensation of aldehyde and catalyst) and a positively charged iminium generated in situ (from N,O-acetal). A hydrogen bonding interaction between the enamine and the iminium ion is not expected in this situation since iminium nitrogen is already electron deficient. It is possible to speculate that a different non-covalent interaction, an electrostatic interaction, between proline (and proline amide) and iminium, giving a stereochemical preference different from that of simple chiral pyrrolidines is responsible. In all cases, the enamine preferentially adopts E-conformation (FIG. 19). Then simple chiral pyrrolidine is the catalyst, the iminium approaches the enamine from the Si-face (favoring R-enantiomer) because of the steric repulsion between the pyrrolidine side chain and the iminium (FIG. 19C). When proline is the catalyst, a favorable electrostatic interaction between the positively charged iminium nitrogen and the negatively charged proline carboxylate ion brings the iminium to the Re-face of the enamine (favoring S-enantiomer) (FIG. 19D). For proline amide as catalyst, electron delocalization of the amide bond will make the amide oxygen electron-rich, therefore, a favorable electrostatic interaction between the iminium nitrogen and the amide oxygen (FIG. 19E) may be responsible.

The salt effect study previously described (Example 9, Table 4) agrees with such an electrostatic interaction. For the proline-catalyzed Mannich reaction at room temperature, <5% ee was observed when 1M LiCl DMF solution was used, as comparing to 35% ee in blank DMF solution. When simple chiral pyrrolidine (B) was the catalyst, LiCl has no significant effect on reaction ee (both gave ~20% ee).

The Mannich adducts ($\beta^2$-amino aldehyde) can be easily transformed to $\beta^2$-amino alcohol and $\beta^2$-amino acids. $\beta^2$-Amino acids are an important type of building blocks for non-natural foldamers that show promising applications (e.g., specific biological functions). The use of $\beta^2$-amino acids is hindered by their limited availability. Many groups, including ours, have tried to develop stereochemically controlled methods for $\beta^2$-amino acid synthesis.[7] To date these methods have relied on non-catalytic alkylation of chiral enolates, a process that often gives very low levels of stereochemical control. In addition, most methods require five to ten chemical reactions and tedious chromatographic separations. Overall yields for these processes are commonly <10%. There is an immediate need for new, efficient and stereoselective $\beta^2$-amino acid synthesis methods.

While the inventors are developing highly enantioselective catalysts for the Mannich reaction, the aldehyde aminomethylation strategy was applied for $\beta^2$-amino acids synthesis by employing catalytic diastereoselective Mannich reaction using chiral N,O-acetal as iminium precursor (Table 8). There is some effect of the "match" and "mis-match" of the chirality of the catalyst and the N,O-acetal on the diastereoselectivity of the reaction. When N,O-acetal has S-configuration, using L-proline as catalyst gave ~70% de, while using D-proline as catalyst gave ~50% de. For the conditions shown in Table 9, the Mannich reaction gave excellent conversion and good diastereoselectivity (70-80%) using proline as catalyst. Alternatively, catalyst L-α-methyl-proline gave moderate conversion (<30%) and excellent diastereomeric excess (>90%).

The inventors developed the three-step protocol for $\beta^2$-amino acid synthesis using the diastereoselective Mannich reaction with the very inexpensive L-proline as catalyst. It was further encouraging to find that the major diastereomer (I, amino alcohol after in situ reduction) can be separated either through column chromatography or recrystallization with reasonable yield (>50% in most cases). The benzyl group was removed and the amine was protected in a one-pot reaction to give II with excellent yield (>90%). The Boc protected amino alcohol (II) was oxidized to the corresponding $\beta^2$-amino acids (III) with decent yield. Purification of II is very easy, and III is analytically pure after proper work-up in most cases. The overall yield of the synthesis is larger than 40% after three step transformations starting from readily available materials, and the synthesis is amendable for large scale synthesis.

TABLE 8

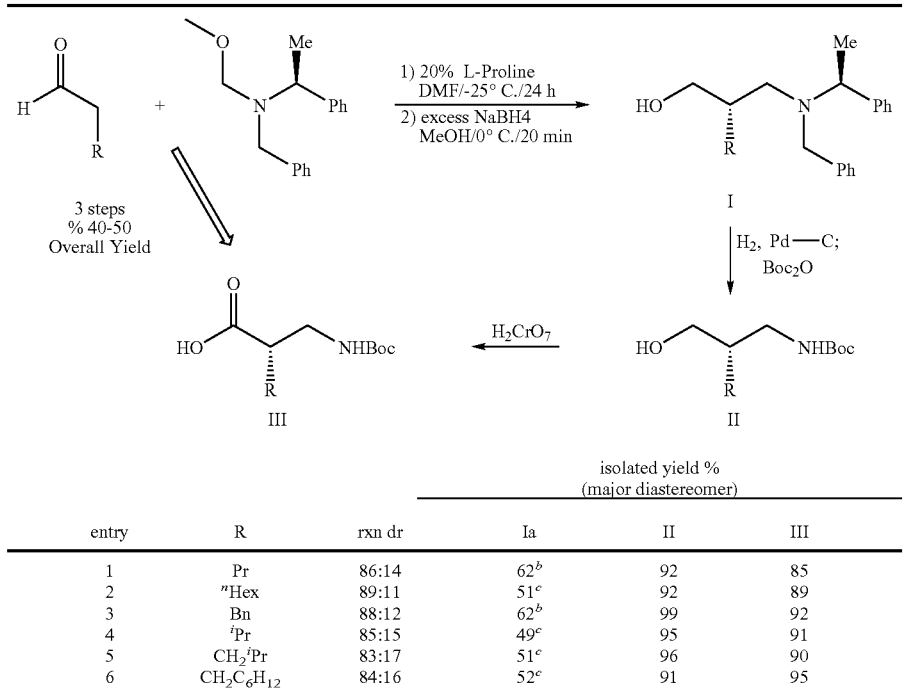

| entry | R | rxn dr | Ia | II | III |
|---|---|---|---|---|---|
| 1 | Pr | 86:14 | 62[b] | 92 | 85 |
| 2 | $^n$Hex | 89:11 | 51[c] | 92 | 89 |
| 3 | Bn | 88:12 | 62[b] | 99 | 92 |
| 4 | $^i$Pr | 85:15 | 49[c] | 95 | 91 |
| 5 | CH$_2$$^i$Pr | 83:17 | 51[c] | 96 | 90 |
| 6 | CH$_2$C$_6$H$_{12}$ | 84:16 | 52[c] | 91 | 95 | isolated yield % (major diastereomer)

[a]Conversion (sum of tow diastereomers) of the Mannich reaction was >80% as determined by $^1$H NMR of the crude reaction mixture before reduction; reduction is quantitative.
[b]Purified through recrystallization.
[a]Purified by column chromatography.

As can be appreciated, the inventors have developed a novel simple organocatalytic aminomethylation of aldehydes method for the production of $\beta^2$-amino derivatives. The Mannich products, chiral $\beta^2$-amino aldehydes, can be easily incorporated into molecules of biological interests such as the O$_2$ somatostatin mimics earlier reported or converted to readily useful chiral amino alcohols and $\beta^2$-amino acids. Further, the inventors developed a very short method for $\beta^2$-amino acid synthesis based on this strategy employing diastereoselective aldehyde aminomethylations. An unexpected non-covalent electrostatic interaction, was observed in organocatalytic stereochemical controls. Hydrogen bonding has long been the dominated non-covalent interaction observed in organocatalytic reactions, and organocatalysts have been developed based on this weak interaction. Not only does the present invention provide more rapid and more commercially usable methods for the rapid synthesis of $\beta^2$ amino acids, it also furthers the understanding of non-covalent interactions in catalytic controls, therefore inspiring novel strategies for catalyst development.

Example 22

Synthesis of Enantiomerically Pure $\beta^2$-Amino Acids via Proline-Catalyzed Diastereoselective Aminomethylation of Aldehydes

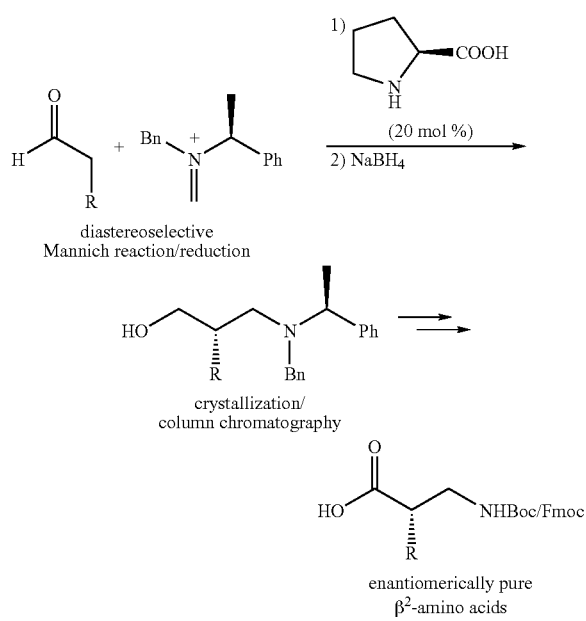

Proline-catalyzed diastereoselective aminomethylation of aldehydes using a chiral iminium ion, generated from a readily prepared precursor, provides α-substituted-β-amino aldehydes with 85:15 to 90:10 dr. The α-substituted-β-amino aldehydes can be reduced to β-substituted-γ-amino alcohols, the major diastereomer of which can be isolated via crystallization or column chromatography. The amino alcohols are efficiently transformed to protected $\beta^2$-amino acids, which are valuable building blocks for β-peptides, natural products and interesting other molecules. Because conditions for the aminomethylation and subsequent reactions are mild, $\beta^2$-amino acid derivatives with protected functional groups in the side chain, such as $\beta^2$-homoglutamic acid, $\beta^2$-homotyrosine and $\beta^2$-homolysine, can be prepared in this way. The synthetic route is short, and purifications are simple; therefore, this method enables the preparation of protected $\beta^2$-amino acids in useful quantities.

$\beta^2$-Amino acids are 3-aminopropanoic acids bearing a single substituent adjacent to the carboxylic acid group. $\beta^2$-Amino acid residues can be found embedded within natural products that exhibit interesting biological activities. (Shih, C.; Gossett, L. S.; Gruber, J. M.; Grossman, C. S.; Andis, S. L.; Schultz, R. M.; Worzalla, J. F.; Corbett, T. H. and Metz, J. T. *Bioorg. Med. Chem. Lett.* 1999, 9, 69.) In addition, $\beta^2$-residues are essential for the formation of specific β-peptide secondary structures ((a) Cheng, R. P.; Gellman, S. H.; DeGrado, W. F. *Chem. Rev.* 2001, 101, 3219. (b) Gellman, S. H. *Acc. Chem. Res.* 1998, 31, 173. (c) Cheng, R. P. *Curr. Opin. Struct. Biol.* 2004, 14, 512) (e.g., 12/10-helix, $\beta^2/\beta^3$ reverse turn ((a) Hintermann, T.; Seebach, D. *Synlett* 1997, 437. (b) Seebach, D.; Abele, S.; Gademann, K.; Jaun, B. *Angew. Chem., Int. Ed.* 1999, 38, 1595. (c) Seebach, D.; Abele, S.; Gademann, K.; Jaun, B. *Angew. Chem., Int. Ed.* 1999, 38, 1595)). Designed β-peptides containing $\beta^2$-residues display useful functions including mimicry of somatostatin signaling (Gademann, K.; Kimmerlin, T.; Hoyer, D.; Seebach, D. *J. Med. Chem.* 2001, 44, 2460) and inhibition of viral infection. (English, E. P.; Chumanov, R. S.; Gellman, S. H.; Compton, T. *J. Biol. Chem.* 2006, 281, 2661) Many routes to enantio-enriched $\beta^2$-amino acids or protected derivatives have been described; however, most of these routes involve tedious chromatographic purifications (e.g., isolation of diastereomers from alkylation of chiral enolates), and few of these synthetic approaches are amenable to large-scale synthesis or diversity in side chain functionality. (Lelais, G.; Seebach, D. *Biopolymers*, 2004, 76, 206).

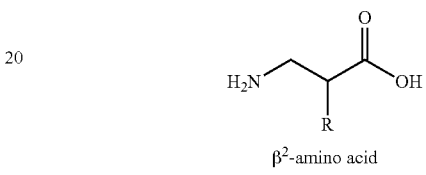

$\beta^2$-amino acid

The inventors recently reported a new route to protected $\beta^2$-amino acids (Ch, Y.; Gellman, S. H. *J. Am. Chem. Soc.* 2006, 128, 6804), the general structure of which is represented above, that is based on enantioselective aminomethylation of aldehydes (via an organocatalytic Mannich reaction. The Mannich reaction involves diphenylprolinol TMS ether 1 as catalyst and a formaldehyde-derived iminium generated in situ from N,O-acetal 2 as the electrophile. This route to protected $\beta^2$-amino acids is efficient, as illustrated by a multi-gram synthesis of Boc-$\beta^2$-homonovaline. This synthetic approach has been very valuable in the inventors exploration of structure and function among β-peptides and (α/β-peptides; however, some drawbacks have become apparent as the inventors have tried to expand the scope of this new route, i.e., to generate protected $\beta^2$-amino acids with diverse side chains. The use of achiral iminium precursor 2 leads to γ-amino alcohols with ~90% ee under the optimal conditions; this level of enantioselectivity is excellent for an organocatalytic reaction but inadequate for some applications. Multiple crystallizations of γ-amino alcohol salts provide material with >99% ee in a number of cases, but not all derivatives are readily crystallized, and not all crystallization attempts lead to improvement of ee. Thus, in the inventors hands this approach is very effective for generating substantial quantities of some protected $\beta^2$-amino acids in enantio-pure form, but other protected $\beta^2$-amino acids are difficult to prepare in this way.

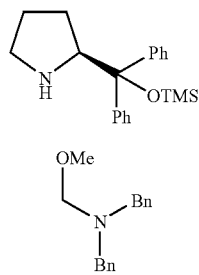

-continued

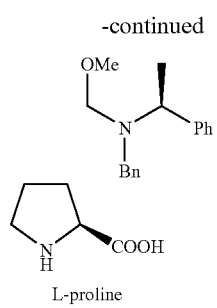

L-proline

The inventors turned their attention to a diastereoselective version of the Mannich reaction (SCHEME XVIII), since the major stereoisomer from such a reaction should be readily isolated via column chromatography or crystallization. The inventors experience suggested that such a process would be very valuable in rapid preparation of a diverse set of $\beta^2$-amino acids, including those bearing protected functional groups in the side chain. The inventors had previously disclosed an example of a diastereoselective Mannich reaction; (Ch, Y.; Gellman, S. H. *J. Am. Chem. Soc.* 2006, 128, 6804.) this reaction was used to establish the stereochemical outcome of an enantioselective Mannich reaction. Herein is disclosed the development of a general approach to diastereoselective $\beta^2$-amino acid synthesis. The inventors have focused on substrates and catalysts that are commercially available or easily prepared in large quantity and at low cost so that this approach will be attractive to other chemists.

SCHEME XVIII

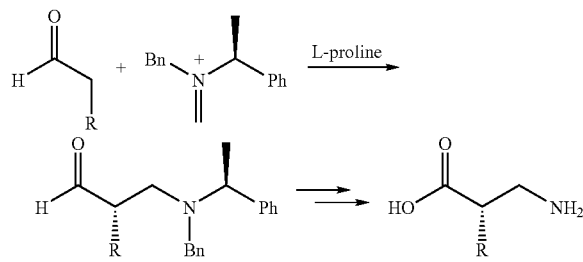

Development of a diastereoselective Mannich Reaction: N,O-acetal 3 was prepared by allowing enantiomerically pure N-benzyl-α-methylbenzylamine to react with paraformaldehyde in anhydrous methanol. Since both enantiomers of N-benzyl-α-methylbenzylamine are commercially available, both enantiomers of 3 are easily accessible. Compound 3 is a chiral analogue of 2, the iminium precursor used in the disclosed enantioselective route to protected $\beta^2$-amino acids. N,O-Acetal 3 can be isolated from the reaction mixture in >100 g quantities via simple distillation.

The inventors used the aminomethylation of pentanal (4) for initial investigation of diastereoselective Mannich reaction protocols involving 3 (Table 1). No reaction could be detected when 3 and 4 were combined in DMF and allowed to stand for 24 h at room temperature. Addition of acetic acid to the DMF solution, to promote iminium ion formation from 3, caused nearly complete conversion of 3 to Mannich product 5, albeit with virtually no diastereoselectivity (Table 9, entry 2). The low stereoselectivity under these conditions suggests that Mannich reaction between the chiral iminium electrophile and the enol of aldehyde 4 (or enamine derived from 4 and N-benzyl-α-methylbenzylamine) proceeds with little stereoinduction. In contrast to these results obtained at room temperature, no reaction occurs when 3, 4 and acetic acid are combined in DMF at −25° C. In addition to this suppression of the "background" Mannich reaction, low temperature minimizes other undesired processes, such as self-aldol reaction of aldehyde 4, epimerization of the Mannich adduct 5, and retro-Michael reaction of the Mannich adduct (SCHEME XIX).

TABLE 9

Diastereoselective Mannich Reaction

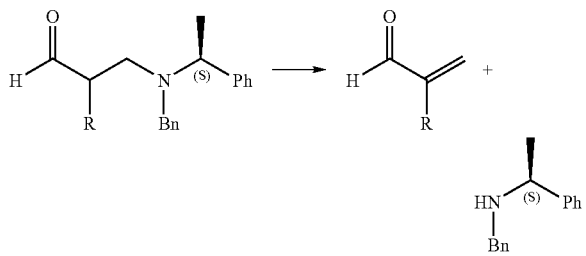

| entry[a] | catalyst | T | yield[c] | dr[c] | favored diastereomer[d] |
|---|---|---|---|---|---|
| 1 | — | rt | <1 | — | — |
| 2 | HOAc | rt | >90 | 57:43 | S, S |
| 3 | HOAc | −25° C. | <1 | — | — |
| 4 | L-proline | −25° C. | >90 | 86:14 | S, S |
| 5[b] | L-proline | −25° C. | >90 | 76:24 | R, S |
| 6 | D-proline | −25° C. | >90 | 23:77 | R, S |
| 7[b] | (R)-1-HOAc | −25° C. | >90 | ~95:5 | S, S |

[a]2.0 eq aldehyde was used; reaction for 24 h except entry 7 (2 h).
[b]Reaction with 1M LiCl DMF as solvent.
[c]Yield% (sum of two diastereomers) was measured by $^1$H NMR of the crude reaction mixture.
[d]See supporting information for details.

SCHEME XIX. Retro-Michael Reaction of the Mannich Product

Figure 21:
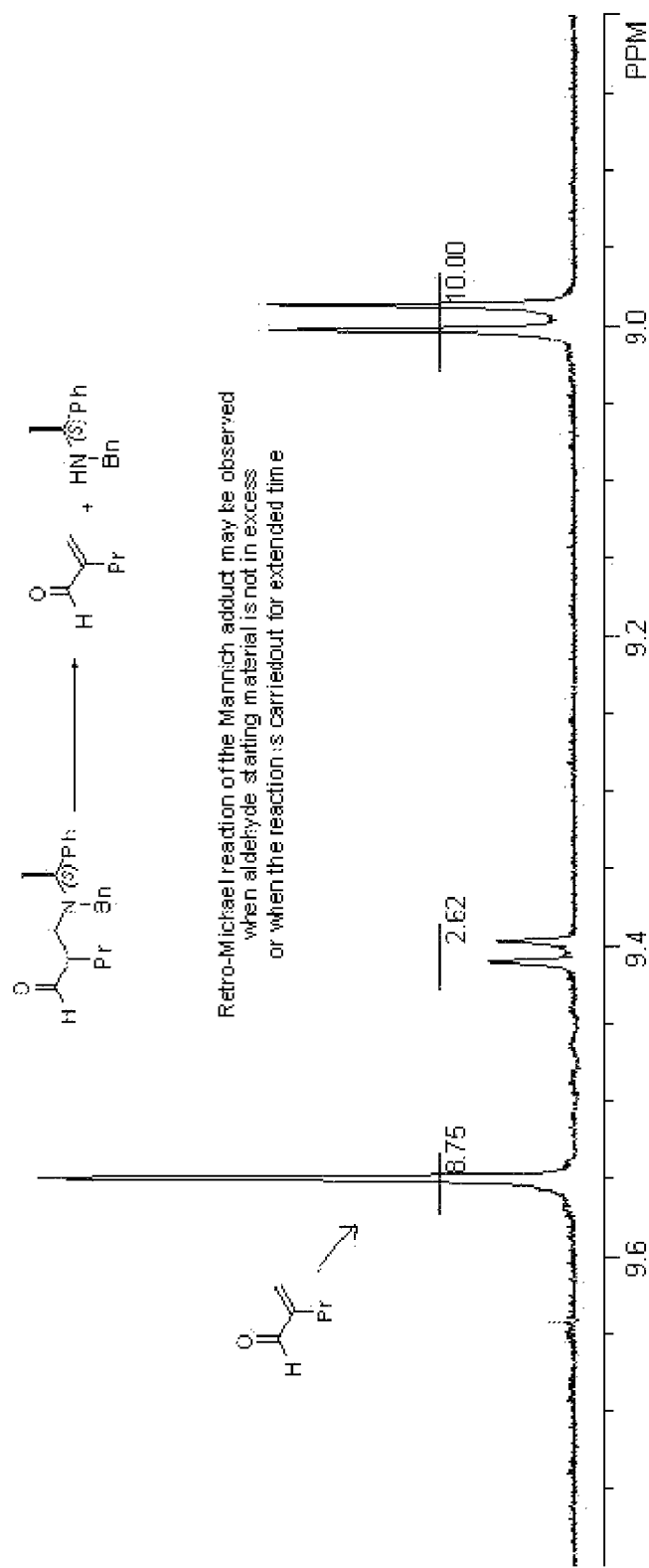
FIG. 21 is an $^1$H NMR spectrum for a Retro-Michael reaction of the Mannich products as shown.

The Mannich reaction occurs at −25° C. in DMF when 3, 4 and L-proline are combined in 1:2:0.2 ratio (i.e., L-proline is present in a catalytic amount, 20 mol % relative to iminium precursor 3). This reaction generates desired product 5 with 86:14 dr (Table 9, entry 4). Optimal results for the proline-mediated Mannich reaction require the use of excess (≧1.5 eq) aldehyde, relative to N,O-acetal 3. The presence of excess aldehyde slows two undesired reactions of the Mannich product, epimerization and retro-Michael reaction, processes that are promoted by L-proline and by N-benzyl-α-methylbenzylamine. When the proline-catalyzed Mannich reaction carried out in the presence of 1 M LiCl, the diastereoselectivity declined somewhat, to 76:24 dr (Table 9, entry 5). This diminution in stereoselectivity in the presence of salt is consistent with the inventors previously reported observations regarding salt effects on the enantioselective Mannich reaction catalyzed by L-proline. This salt effect suggests that non-hydrogen-bonded ionic interactions in the transition state influence the stereochemical outcome of the reaction. An NMR spectra of the products is shown in FIG. 21.

Switching chirality of the catalyst (D-proline) had little impact on the yield of product 5 but altered and diminished the stereoselectivity of the Mannich reaction. The reaction catalyzed by D-proline favored the diastereomer of 5 with R configuration at the newly formed stereocenter, while L-proline favored S configuration at this center. With D-proline, the dr was 23:77, while L-proline gave a product with 86:14 dr. This difference stereoselectivity likely arises from a matched/mismatched relationship between the chirality of the iminium ion and the chirality of the proline-derived enamine in the transition state for the Mannich reaction. Diphenylprolinol TMS ether (R)-1 gave improved diastereoselectivity (a 95:5 dr; Table 9, entry 7) relative to L-proline in the matched case; however, the inventors decided to develop the $\beta^2$-amino acid synthesis with L-proline rather than 1 as the Mannich reaction catalyst because proline is very inexpensive.

Synthesis of Boc-protected $\beta^2$-Amino Acids: If the diastereoselective Mannich reaction is to be useful for the synthesis of enantio-enriched $\beta^2$-amino acid derivatives, then isolation of the major diastereomer from the aminomethylation reaction must be straightforward. In order to avoid epimerization at the newly created stereocenter during reaction workup and purification, the inventors immediately reduced the aldehydes to the corresponding alcohols with NaBH$_4$. For all the substrates described here the major γ-amino alcohol diastereomer was readily isolated via column chromatography. Furthermore, a number of the derivatives could be easily isolated by crystallization, either as the γ-amino alcohol itself or as the corresponding HCl salt. Isolation via crystallization is very attractive for large-scale synthesis. In addition, the availability of crystalline, enantio-pure γ-amino alcohols or salts thereof allowed confirmation of product configuration through X-ray diffraction analysis for 7a, 7c, 7e and 7f (see below).

In order to establish the generality of this synthetic approach to protected $\beta^2$-amino acids, the inventors carried out multi-gram syntheses of six compounds bearing hydrophobic side chains (Table 10). Four commercially available aldehydes (6a-d) and two aldehydes prepared in one step from commercially available alcohols via PCC oxidation (6e and 6f) (The aldehyde prepared from PCC oxidation was filtered through a silica pad; the filtrates were collected, concentrated, and subjected to Mannich reaction without further purification.) were subjected to the optimized L-proline-catalyzed Mannich reaction/reduction sequence. In each case, the major diastereomer of the γ-amino alcohol (7a-f) was isolated in 50-60% yield. Hydrogenolytic removal of the benzyl groups followed by Boc-protection of the resulting primary amine yielded Boc-protected γ-amino alcohols 8a-f. Subsequent Jones oxidation (Oxidation of chiral α-substituted aldehydes and alcohols to carboxylic acid without epimerization: ((a) Rangaishenvi, M. V.; Singaram, B.; Brown, H. C. *J. Org. Chem.* 1991, 56, 3286; (b) Peelen, T. J.; Chi, Y.; Gellman, S. H. *J Am. Chem. Soc.* 2005, 127, 11598) provided the protected $\beta^2$-amino acids 9a-f after extractive work-up. The complete synthetic routes involve only three or four simple operations and provide the enantio-pure $\beta^2$-amino acid derivatives in >40% overall yield.

Synthesis of Fmoc-protected $\beta^2$-Amino Acids with Functionalized Side Chains: A major limitation of most synthetic approaches to $\beta^2$-amino acids is the difficulty of introducing sensitive functional groups, such as protected carboxylic acid or amino groups, into the side chain. The method disclosed herein does not involve strongly acidic or basic conditions, which should make this route well-suited for synthesis of $\beta^2$-amino acids bearing side chain functionality. The inventors demonstrated this utility through the synthesis of Fmoc-protected derivatives of $\beta^2$-homoglutamic acid, $\beta^2$-homotyrosine and $\beta^2$-homolysine with orthogonally protected side chains (SCHEME XX). Aldehydes 10a-c, each prepared in a few steps from commercially available materials (see Supporting Information), were used in the L-proline-catalyzed Mannich reaction, with subsequent NaBH$_4$ reduction, to yield γ-amino alcohols 11a-c. The yields for these Mannich/reduction sequences were a little lower than those observed for the analogous processes involving hydrocarbon side chains (Table 10); however, the diastereoselectivites were comparable to those in Table 10. Moreover, the subsequent transformations leading to Fmoc-$\beta^2$-amino acid derivatives 13a-c proceeded efficiently. Careful workup of the Jones oxidation reactions that generate 13a-c was necessary in order to avoid loss of acid-sensitive side chain protecting groups. Alternatively, oxidation can be achieved with NaIO$_4$/RuCl$_3$ under neutral conditions.

TABLE 10

Synthesis of Boc-$\beta^2$-Amino Acids with Hydrophobic Side Chains.

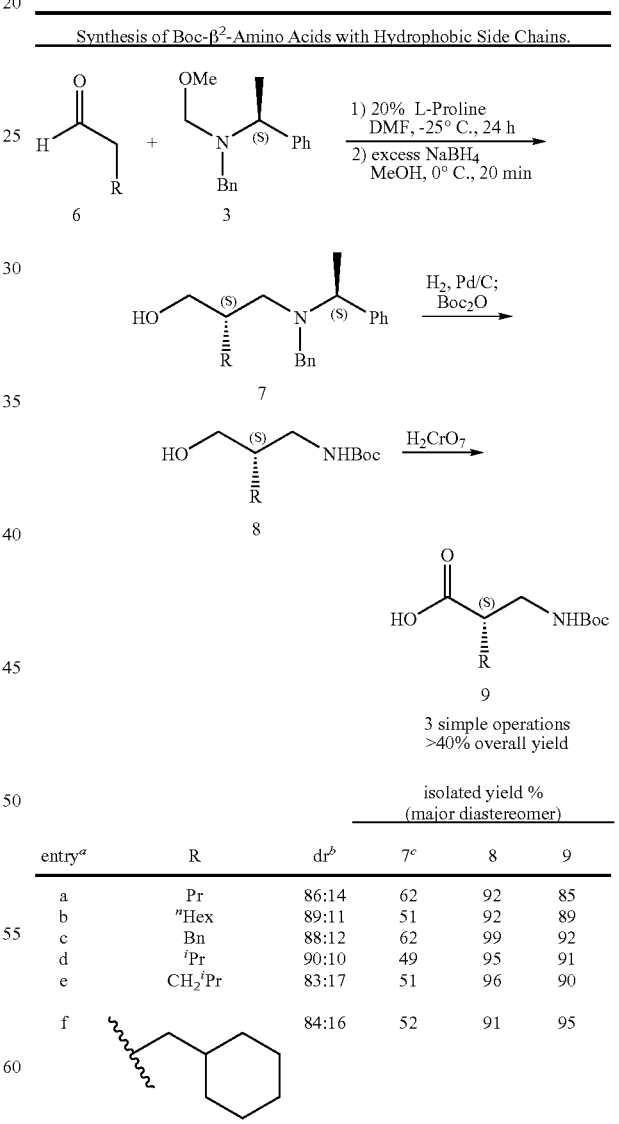

| entry[a] | R | dr[b] | 7[c] | 8 | 9 |
|---|---|---|---|---|---|
| a | Pr | 86:14 | 62 | 92 | 85 |
| b | $^n$Hex | 89:11 | 51 | 92 | 89 |
| c | Bn | 88:12 | 62 | 99 | 92 |
| d | $^i$Pr | 90:10 | 49 | 95 | 91 |
| e | CH$_2$$^i$Pr | 83:17 | 51 | 96 | 90 |
| f | cyclohexylmethyl | 84:16 | 52 | 91 | 95 |

[a] 2.0 eq (entry a-d) or 1.5 eq (entry e-f) aldehyde was used; yield % (sum of two diastereomers) of the Mannich reaction was >90% as determined by $^1$H NMR of the crude reaction mixture before reduction; the reduction is quantitative.
[b] Determined by $^1$H NMR of the crude reaction mixture before reduction.
[c] Isolated via crystallization or column chromatography.

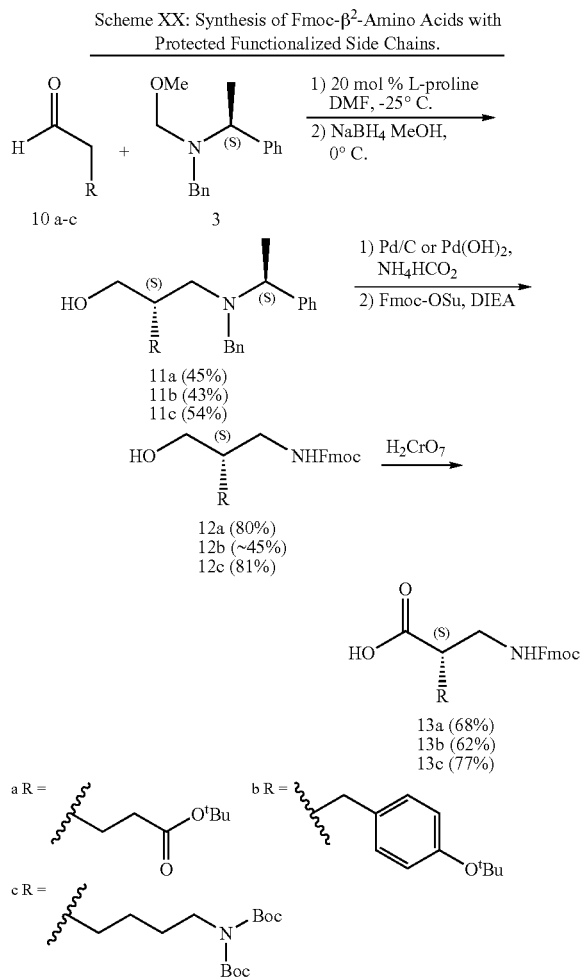

Scheme XX: Synthesis of Fmoc-β²-Amino Acids with Protected Functionalized Side Chains.

The inventors were unsuccessful in their attempts to prepare Fmoc-β²-homolysine with a single Boc protecting group on the side chain, starting from aldehyde 14. No Mannich reaction product could be obtained. Moreover, the synthesis of 14 from the corresponding mono-Boc-protected aminohexanol gave only low yields, perhaps because the urethane adds intramolecularly to the carbonyl carbon.

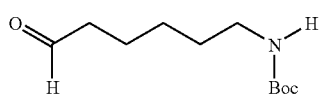

Experimental Section

Materials: Fmoc-OSu was purchased from Advanced ChemTech; other commercially available materials were purchased from Sigma-Aldrich and used as received. Catalyst 1 was prepared from diphenylmethyl prolinol according to a literature procedure.

N,O-acetal (3) was prepared by using procedures analogous to those previously described for the synthesis of 2. To 150 ml (0.70 mol) (S)—N-benzyl-α-methylbenzylamine dissolved in ~500 ml anhydrous MeOH in a 1000 ml round bottom flask at room temperature was added 53 g (2.5 eq) paraformaldehyde, followed by 100 g anhydrous $K_2CO_3$ and 100 g anhydrous $Na_2SO_4$. The reaction proceeded immediately upon the addition of all reactants; and $^1H$ NMR analysis indicated complete conversion of the amine to N,O-acetal 3 within 1 h (typically within 5 min). The heterogeneous mixture was stirred for another 12 h (overnight) to ensure that $H_2O$ produced during the reaction was completed absorbed by the anhydrous $Na_2SO_4$ and anhydrous $K_2CO_3$. The mixture was filtered through a pad of anhydrous $Na_2SO_4$ (~50 g) to remove solid materials, and the remaining solids were washed with about 300 ml anhydrous MeOH and filtered. All filtrates were combined to give a light milky mixture. The mixture was concentrated to give a mixture of oil and white solid (the white solid is mainly paraformaldehyde). This mixture was mixed with about 150 ml anhydrous $Et_2O$ (paraformaldehyde remains as a solid in the $Et_2O$ solution) and filtered through a pad of anhydrous $Na_2SO_4$. The remaining solid in the flask washed with another 150 ml anhydrous $Et_2O$ and filtered. All filtrates were collected, combined and concentrated to give a clear oil (181 g, 98% yield). $^1H$ NMR analysis of this oil indicated >95% purity of the N,O-acetal; this oil can be used for the Mannich reaction without further purification. From the above oil, pure N,O-acetal 3 was obtained via vacuum distillation (168-170° C. at 36-37 mm Hg) as a colorless oil (168 g, 92% yield). This material can be stored at 4° C. for several months without observable decomposition. $^1H$ NMR (300 MHz, $CDCl_3$): δ 7.22-7.45 (m, 10H), 4.18 & 4.21 (s, 1H), 4.08 (q, J=6.6 Hz, 1H), 3.93 & 3.97 (s, 1H), 3.70-3.78 (m, 2H), 3.17 (s, 3H), 1.46 (d, J=6.6 Hz, 3H). $^{13}C$ NMR (75 MHz, $CDCl_3$): δ 145.3, 140.0 129.0, 128.5, 128.3, 127.7, 127.1, 127.0, 82.8, 59.5, 55.2, 52.9, 20.0. TOF-MS-ESI: the compound decomposes to amine under the conditions of this analysis; however, a trace amount of N,O-acetal was detected at 278.5 ([M+Na]$^+$ calculated 278.2). Optical rotation: $[α]^{rt}_D$=−6.5° (c=2.0, MeOH).

Figure 22:
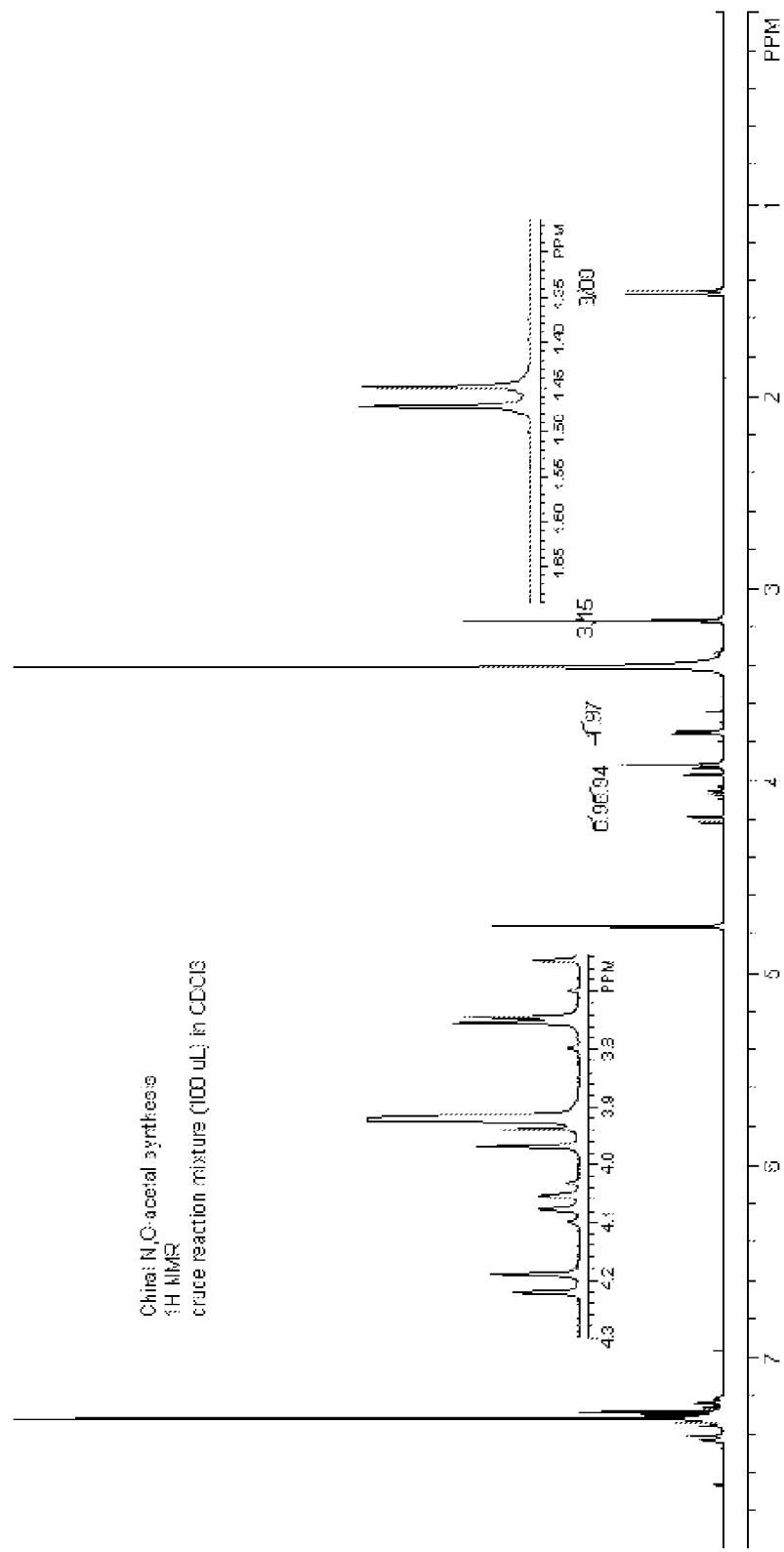
FIG. 22 is an $^1$H NMR spectrum of the crude reaction mixture of compound (S)—N,O-acetal (3) before work-up.

General procedure for the diastereoselective Mannich reaction (Table 9). To 0.1 mmol catalyst in 1 ml HPLC grade DMF (or 1 M LiCl in DMF) in an 8 ml vial cooled to −25° C. was added 1 mmol (110 μL) aldehyde. The mixture was stirred for a few minutes, and then 0.5 mmol (130 μL) N,O-acetal 3 was added. The mixture was stirred at −25° C. for 2 h or 24 h, as indicated in Table 1. Yield and dr of the reaction were determined by $^1H$ NMR analysis of the crude reaction mixture (FIG. 22).

Figure 23:
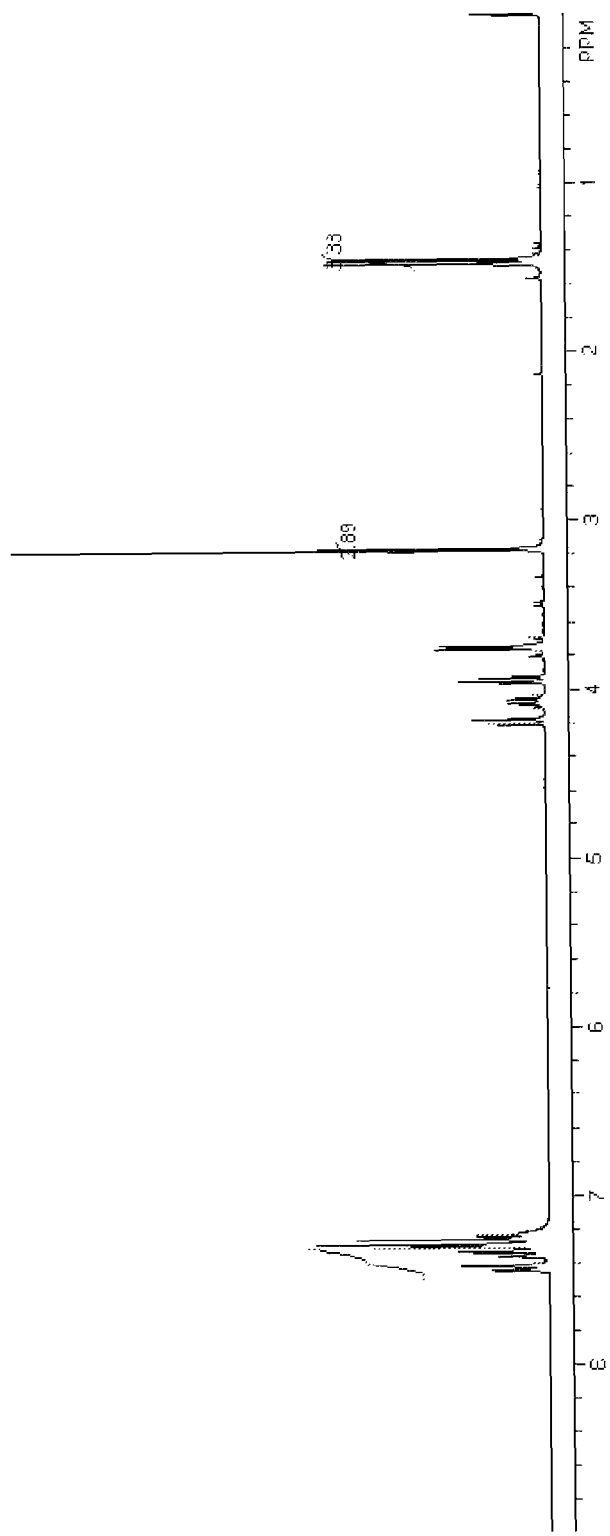
FIG. 23 is an $^1$H NMR spectrum of the reaction mixture of compound (S)—N,O-acetal (3) after work-up.
Figure 24:
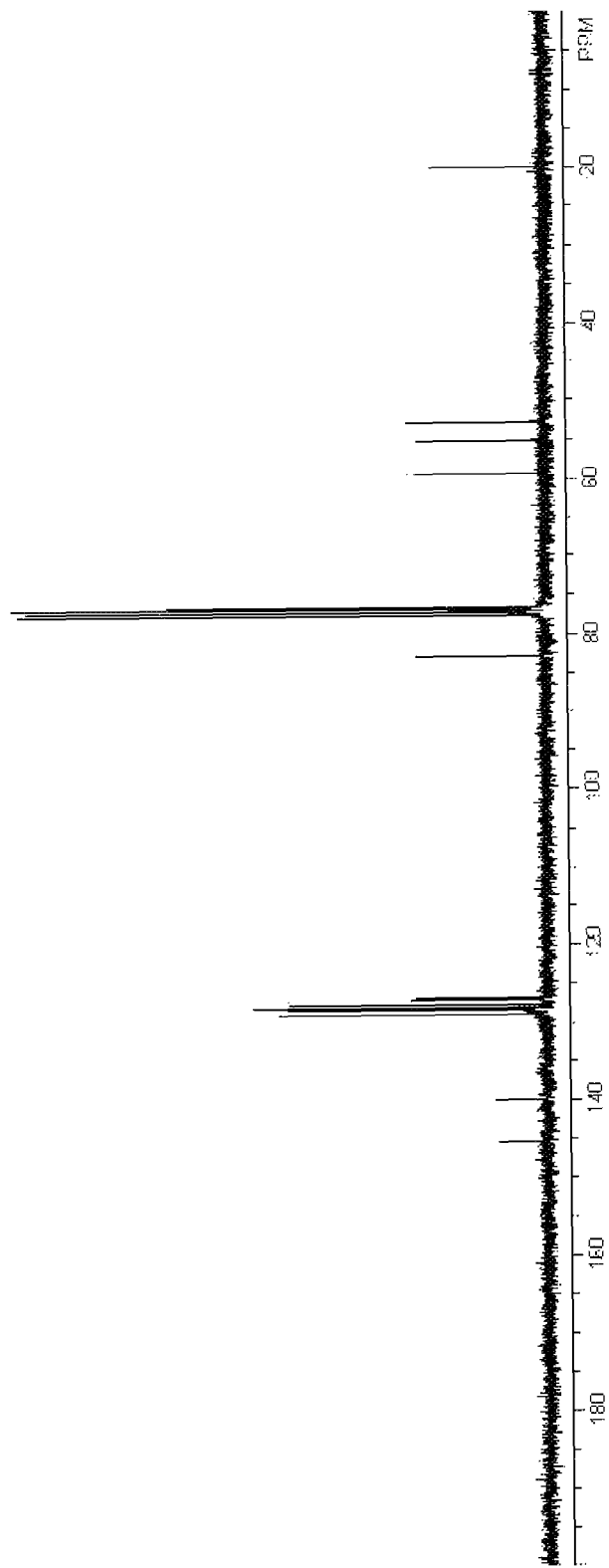
FIG. 24 is an $^{13}$C NMR spectrum of the reaction mixture of compound (S)—N,O-acetal (3) after work-up.

General procedure for Mannich reaction/reduction (Table 10): A mixture of 6 mmol (0.69 g) L-proline in 60 ml HPLC grade DMF was stirred at room temperature for several hours, and then this mixture was cooled to −25° C. To the cooled catalyst mixture was added aldehyde (60 mmol, neat), and the mixture was stirred for a few minutes. N,O-acetal 3 (30 mmol, 7.8 ml) was then added, and the mixture was stirred at −5° C. for 24 h. $^1H$ NMR analysis of the crude reaction mixture at this point revealed complete conversion of the limiting reagent, 3 The product diastereomer ratio was determined by $^1H$ NMR (FIG. 22). Excess $NaBH_4$ (90 mmol, 3.4 g) was added, followed by ~20 ml MeOH. The mixture was stirred for a few minutes; the −25° C. bath was then replaced by an ice bath, and the mixture was stirred for an additional 20 min. The mixture was then slowly poured into a 1000 mL beaker containing 50-100 mL saturated $NH_4Cl$ at 0° C. to quench excess $NaBH_4$. The resulting mixture was extracted several times with $Et_2O$, until TLC indicated that all product had been removed into the organic phase. The $Et_2O$ layers were combined, washed with water and then brine, dried over $MgSO_4$, filtered and concentrated to give crude β-substituted γ-amino alcohols (the remaining DMF was removed under vacuum). NMR spectra for the washed product is given in FIGS. 23 and 24. The major diastereomer (Table 10, 7a-f) was isolated via column chromatography or crystallization as described below.

Isolation of the major diastereomer via crystallization (Table 10): In some cases the major diastereomer from the Mannich reaction/reduction sequence could be directly crystallized by evaporation of a hexane solution (Table 10, entry 1 & 3). A more general protocol for crystallization was realized via vapor diffusion of Et$_2$O into a EtOAc-MeOH solution of the amino alcohol-HCl salt as described in detail below. The crude amino alcohol (or the diastereomeric mixture of the amino alcohols obtained after preliminary column chromatographic purification, if the crude sample could not be directly crystallized) was dissolved in Et$_2$O in an 150 flask at 0° C. To this solution was added 4 N HCl in dioxane with stirring until the solution turned acidic as indicated by pH paper. The resulting mixture was stirred for a few minutes, and the solvent was removed under reduced pressure to give a viscous oil (or solid depending on the substrate and initial purity). To this viscous oil, was added 50 ml EtOAc. The flask was shaken with heating (heat gun) until the oil solidified to give a milky mixture. A minimal amount (a few drops) of MeOH was added until a clear solution was obtained. The open flask with the hot EtOAc-MeOH solution was then placed in a large glass gar containing hot Et$_2$O. The container was sealed and left to stand at room temperature for crystallization, which took from minutes to days. White crystals from this procedure were isolated by filtration, washed with EtOAc and dried in vacuo to afford the major diastereomer; no minor diastereomer was detected by $^1$H NMR analysis. This crystallization protocol generally gave the major diastereomer in 40-60% overall yield for the Mannich reaction/reduction sequence. X-ray crystal structures of several amino alcohols (7a, 7c, 7e and 7f) were determined (see below).

One-pot hydrogenolysis and Boc protection (Table 10): To about 1.0 g wet 10% Pd/C in 50 ml MeOH in a hydrogenation flask was added 15 mmol amino alcohol (as either the free base or the HCl salt) (Table 10, 7a-f). The heterogeneous mixture was placed under 40-60 psi H$_2$ at room temperature overnight. After the hydrogenolysis was complete, as indicated by TLC and $^1$H NMR analysis, the mixture was diluted with 50 mL CH$_2$Cl$_2$, and DIEA (18 mmol, 3.2 mL for free amino alcohol; or 36 mmol, 6.4 ml for HCl salt of the amino alcohol) and Boc$_2$O (18 mmol, 4.0 g) were added. The mixture was stirred at room temperature overnight and then filtered through a pad of celite to remove Pd/C, and the celite washed with MeOH extensively. The combined filtrate was concentrated and applied to a silica chromatography column eluted with EtOAc/Hexane to give Boc protected β-substituted γ-amino alcohols (Table 10, 8a-f) in excellent yield.

Jones oxidation of Boc protected β-substituted γ-amino alcohols to Boc-β$^2$-amino acids (Table 10): To 10 mmol Boc protected β-substituted γ-amino alcohol (Table 2, 8a-f) dissolved in 100 mL acetone at 0° C. was added 15 mmol H$_2$Cr$_2$O$_7$ (30 mL Jones reagent). The mixture was stirred for 12 h, during which time the mixture warmed to room temperature. Excess isopropanol was then added, and the mixture was stirred overnight. The mixture was filtered, and the filtrate was concentrated to about 20 mL under reduced pressure at room temperature. The concentrate was diluted with 20 mL 2 N aqueous HCl and extracted with Et$_2$O until TLC indicated that all product had been removed from the aqueous phase. The combined Et$_2$O layers were concentrated to about 50 mL. Except in the case of 9b, the concentrated Et$_2$O solution was extracted with 2 M aqueous NaOH (monitored by TLC). The combined basic aqueous extracts were washed with 2×10 mL Et$_2$O, and the organic layers were discarded. The basic aqueous solution was then acidified with 2 N aqueous HCl and extracted with Et$_2$O (monitored by TLC). The combined Et$_2$O layers were washed with saturated NaCl, dried over MgSO$_4$, and filtered. The filtrate was concentrated under reduced pressure to give Boc-β-amino acid that was pure by TLC and NMR analysis.

For 9b, the Et$_2$O layers from the first extraction washed with saturated NaCl, dried over MgSO$_4$, filtered and concentrated to give a viscous oil, from which the desired compound was purified via column chromatography eluted with MeOH/CH$_2$Cl$_2$ (1/10, v/v; TLC R$_f$=0.29) to give pure product in 89% yield.

Synthesis of β$^2$-homoglutamic acid, β$^2$-homotyrosine, and β$^2$-homolysine: The synthesis of the above three β$^2$-amino acids, with acid- or base-sensitive functional groups in the side chain, involved procedures analogous to those described above for making β$^2$-amino acids with hydrocarbon side chains (Table 10). Detailed procedures are provided below.

General Procedures: Analytical thin-layer chromatography (TLC) was carried out on Whatman TLC plates precoated with silica gel 60 (250 μm thickness). Visualization was performed using a UV lamp or potassium permanganate stain. Column chromatography was performed on EM Science silica gel (230-400 mesh) or Biotage flash column chromatography system.

Instrumentation: Proton nuclear magnetic resonance ($^1$H NMR) spectra were recorded on Bruker AC-300 (300 MHz) spectrometers. Chemical shifts were recorded in parts per million (ppm, δ) relative to tetramethylsilane (δ 0.00). $^1$H NMR splitting patterns are designated as singlet (s), doublet (d), triplet (t), or quartet (q). All first-order splitting patterns were assigned on the basis of the appearance of the multiplet. Splitting patterns that could not be easily interpreted are designated as multiplet (m) or broad (br). Carbon nuclear magnetic resonance ($^{13}$C NMR) spectra were recorded on a Bruker AC-300 (75 MHz) spectrometer. Mass spectra (MS) were obtained using an electrospray ionization (ESI) mass spectrometer. Optical rotations were measured using a 1 mL cell with a 1 dm path length on a Perkin-Elmer 241 digital polarimeter and are reported as follows: [α]$^{rt}_D$ (c in g per 100 mL solvent).

Monitoring the Mannich reaction by $^1$H NMR: A small aliquot (e.g., 50 μL via a micropipettor) of the reaction mixture from the reaction flask at −25° C. was immediately injected to a NMR tube with 650 μL CDCl$_3$ pre-cooled at −25° C. The reaction solution and NMR solvent was mixed at −25° C., and then warmed to ambient temperature for $^1$H NMR analysis. It is important to prepare the NMR solution at low temperature in order to measure the accurate conversion and diastereoselectivity of the Mannich reaction. NMR parameter: RG (gain)=1; NS=32 (or more scans). Examples of the $^1$H NMR and $^{13}$C NMR spectra for the compounds described above are shown in FIGS. 25-54.

Example 23

(S)-β-″Hexyl-γ-(S)—N-benzyl-α-methylbenzylamino alcohol (7b)

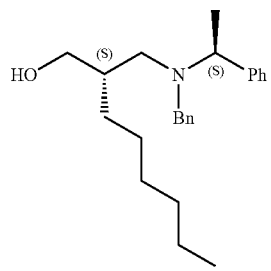

7b

Figure 25:
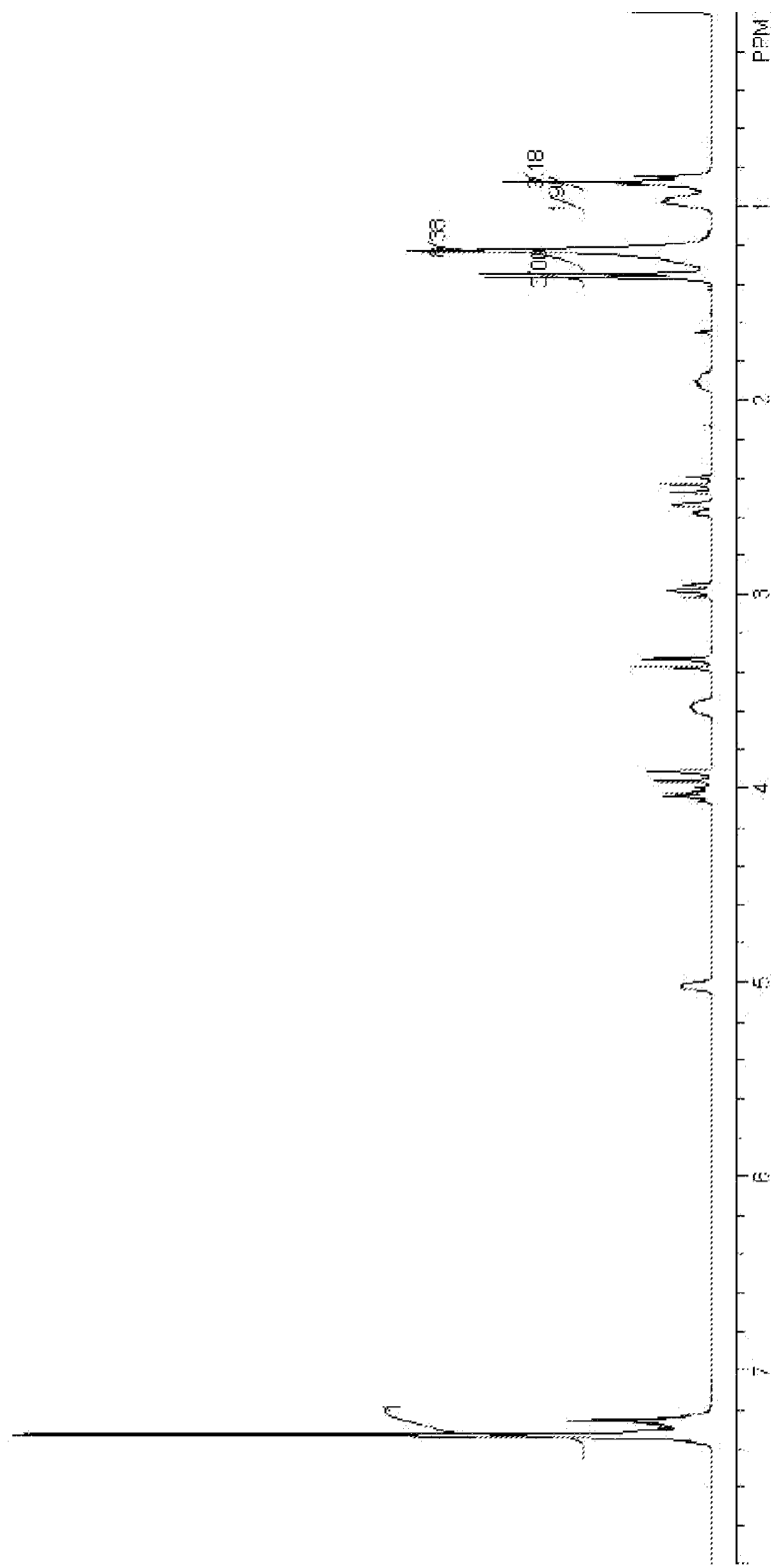
FIG. 25 is an $^1$H NMR spectrum of compound 7b shown in Table 10.
Figure 26:
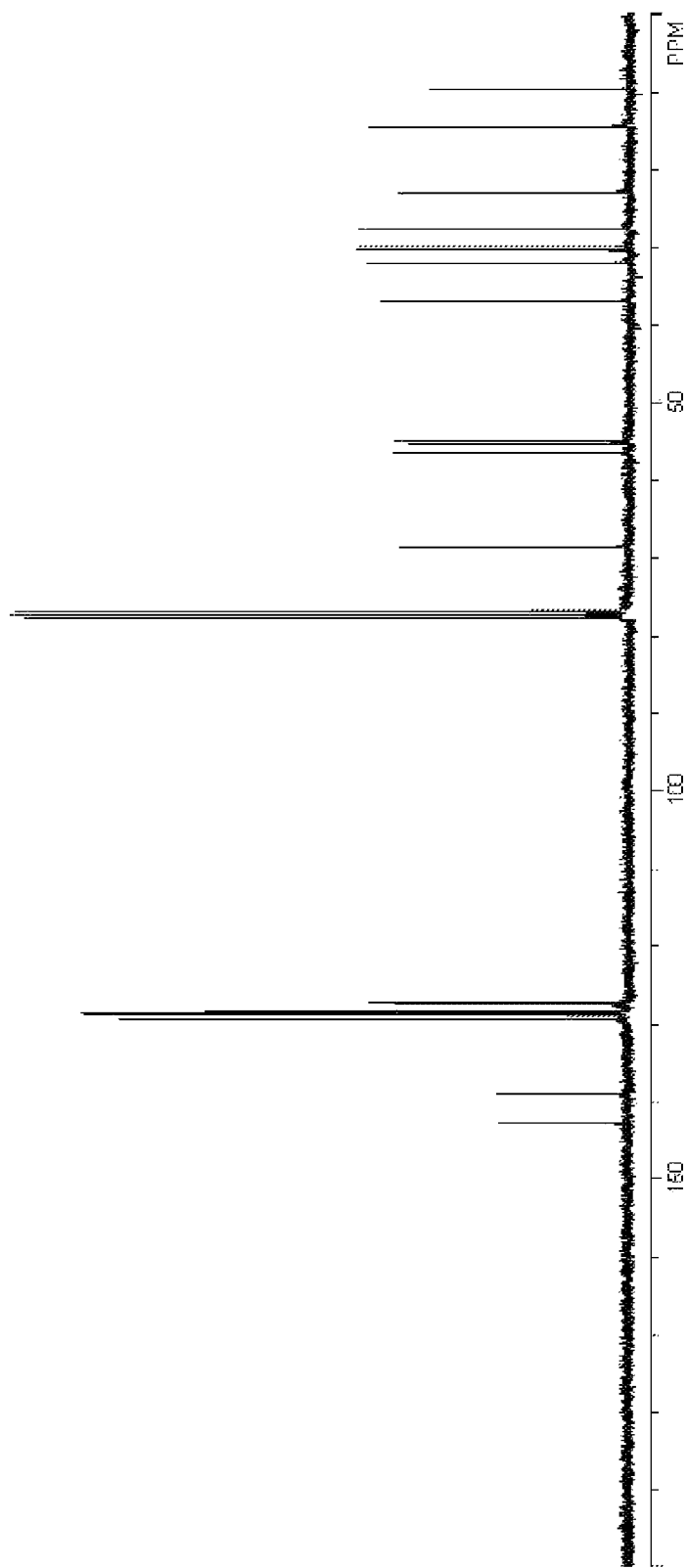
FIG. 26 is an $^{13}$C NMR spectrum of compound 7b shown in Table 10.

The NMR data for 7b are as follows: colorless oil. TLC R$_f$=0.28 (EtOAc/Hexanes, v/v, 1:5). $^1$H NMR (300 MHz, CDCl$_3$) δ 7.23-7.37 (m, 10H), 5.01 (br, 1H), 4.03 (q, J=6.6 Hz, 1H), 3.92 & 3.96 (s, 1H), 3.58 (m, 1H), 3.33 & 3.38 (s, 1H), 2.95-3.01 (m, 1H), 2.53-2.54 (m, 1H), 2.39-2.47 (m, 1H), 1.86-1.4 (m, 1H), 1.35 (d, J=6.6 Hz, 3H), 1.22-1.28 (m, 8H), 0.94-0.98 (m, 2H), 0.87 (t, J=6.6 Hz, 3H). $^{13}$C NMR (75 MHz, CDCl$_3$): δ 142.8, 140.0, 129.5, 128.7, 128.42, 128.38, 127.5, 127.3, 68.5, 56.5, 55.2, 54.9, 36.8, 31.9, 30.3, 29.8, 27.5, 22.8, 14.3, 9.6. TOF-MS-ESI: [M+H]$^+$ calculated 354.3, found 354.6. Optical rotation: $[\alpha]^{rt}_D$=+9.4° (c=0.50, MeOH). FIGS. 25 and 26.

Example 24

(S)-β-$^n$Hexyl-γ-Boc-amino alcohol (8b)

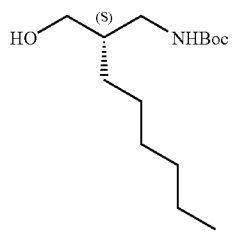

Figure 27:
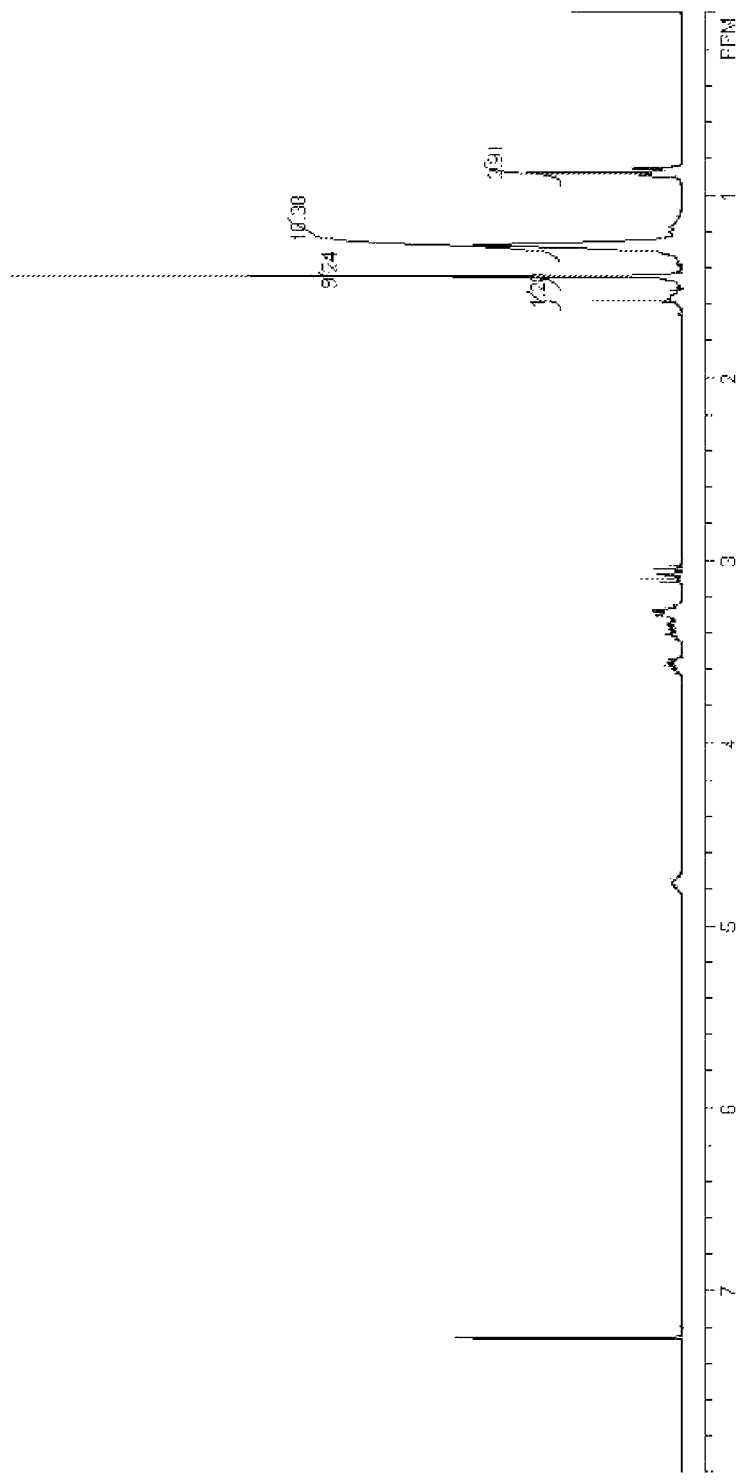
FIG. 27 is an $^1$H NMR spectrum of compound 8b shown in Table 10.
Figure 28:
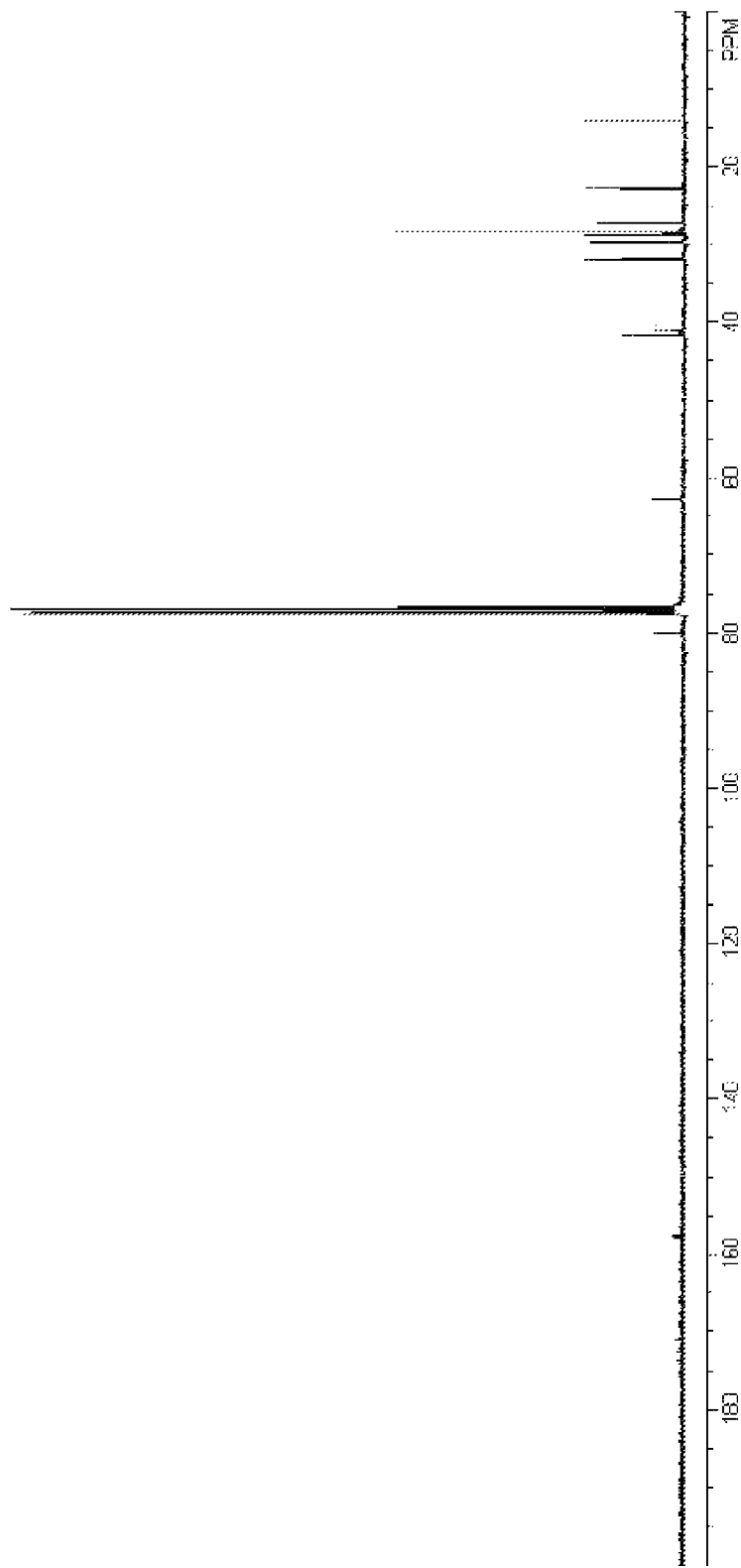
FIG. 28 is an $^{13}$C NMR spectrum of compound 8b shown in Table 10.

The NMR data for 8b are as follows: colorless oil (may solidify upon staying at rt). TLC R$_f$=0.07 (EtOAc/Hexanes, v/v, 1:5). $^1$H NMR (300 MHz, CDCl$_3$) δ 4.77 (br, 1H), 3.55-3.58 (m, 1H), 3.28-3.41 (m, 3H), 3.03-3.12 (m, 1H), 1.53-1.58 (m, 1H), 1.45 (s, 9H), 1.18-1.32 (m, br, 10H), 0.88 (t, J=6.9 Hz, 3H). $^{13}$C NMR (75 MHz, CDCl$_3$): δ 157.9, 80.1, 62.8, 41.8, 41.1, 32.0, 29.7, 28.9, 28.6, 27.3, 22.9, 14.3. TOF-MS-ESI: [M+H]$^+$ calculated 260.2, found 260.5; [M+Na]$^+$ calculated 282.2, found 282.5; [2M+Na]$^+$ calculated 541.4, found 542.0. Optical rotation: $[\alpha]^{rt}_D$=+5.0° (c=0.50, MeOH). FIGS. 27 and 28.

Example 25

(S)-α-$^n$Hexyl-β$^2$-Boc-amino acid (9b)

Figure 29:
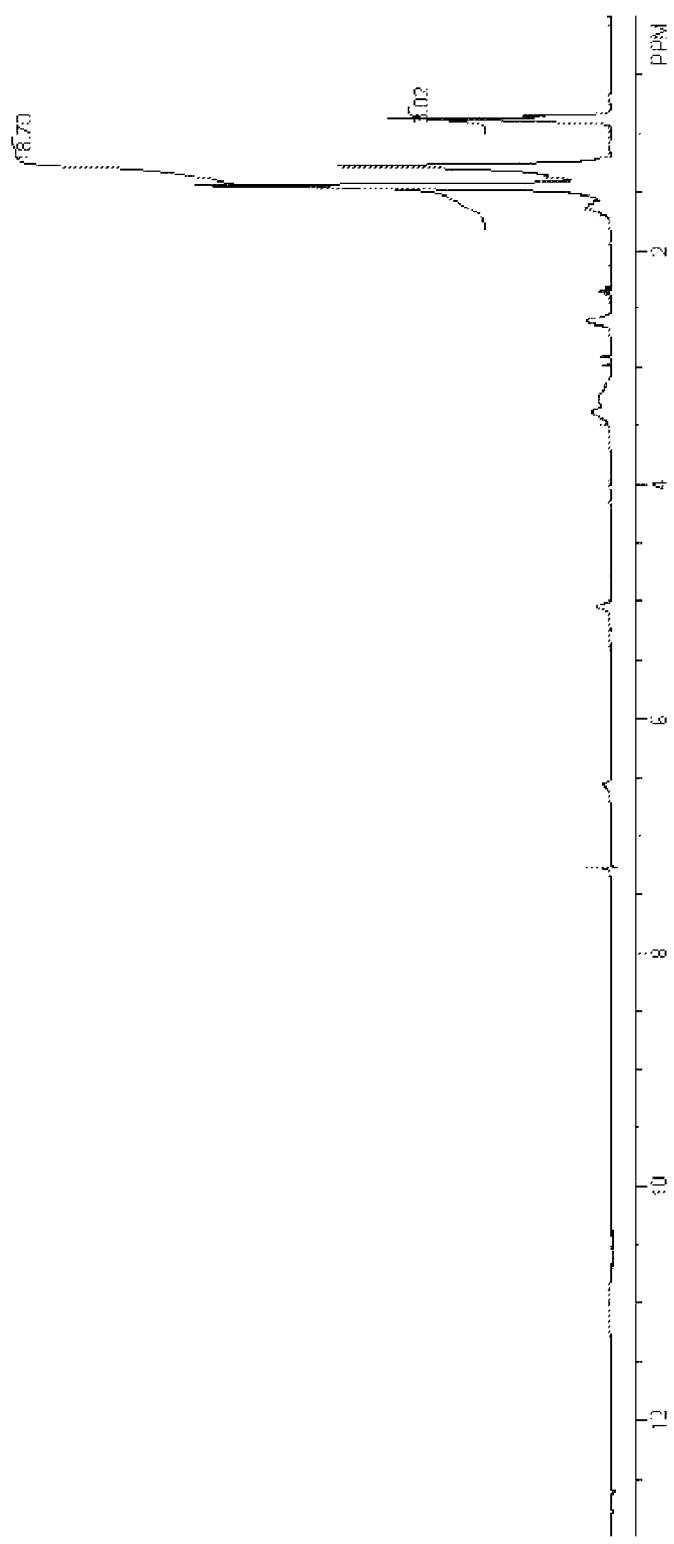
FIG. 29 is an $^1$H NMR spectrum of compound 9b shown in Table 10.
Figure 30:
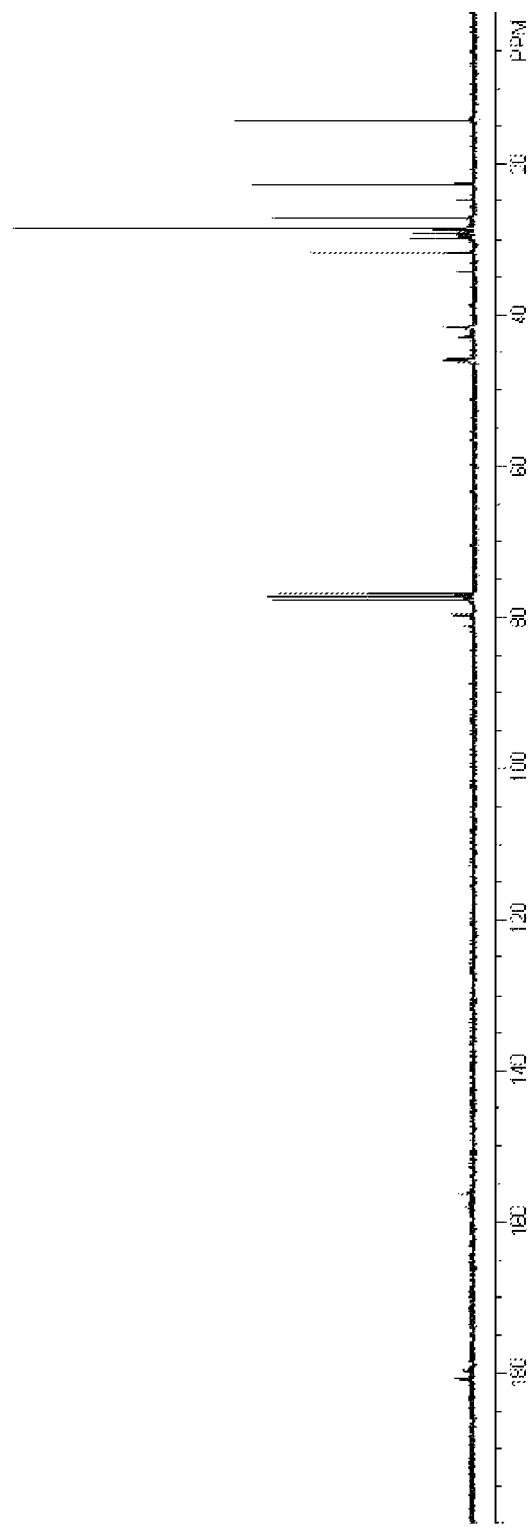
FIG. 30 is an $^{13}$C NMR spectrum of compound 9b shown in Table 10.

The NMR data for 9b are as follows: colorless viscous oil. TLC R$_f$=0.32 (MeOH/CH$_2$Cl$_2$, v/v, 1:10). $^1$H NMR (300 MHz, CDCl$_3$) δ 10.91 (br, 1H), 5.05 & 6.57 (br, 1H), 3.16-3.49 (m, 2H), 2.61 (br, 1H), 1.28-1.68 (m, 18H), 0.88 (t, J=6.9 Hz, 3H). $^{13}$C NMR (75 MHz, CDCl$_3$): δ 180.9 & 179.4, 158.1 & 156.2, 81.2 & 79.8, 46.2 & 45.9, 42.9 & 41.6, 31.7, 29.9, 29.3, 28.5, 27.1, 22.8, 14.2. TOF-MS-ESI: [M−H]$^-$ calculated 272.2, found 272.6; [2M−H]-calculated 545.4, found 546.2. Optical rotation: $[\alpha]^{rt}_D$=+6.0° (c=0.50, MeOH). FIGS. 29 and 30.

Example 26

(S)-β-Benzyl-γ-(S)—N-benzyl-α-methylbenzylamino alcohol (7c)

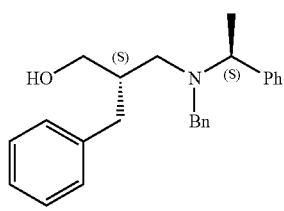

Figure 31:
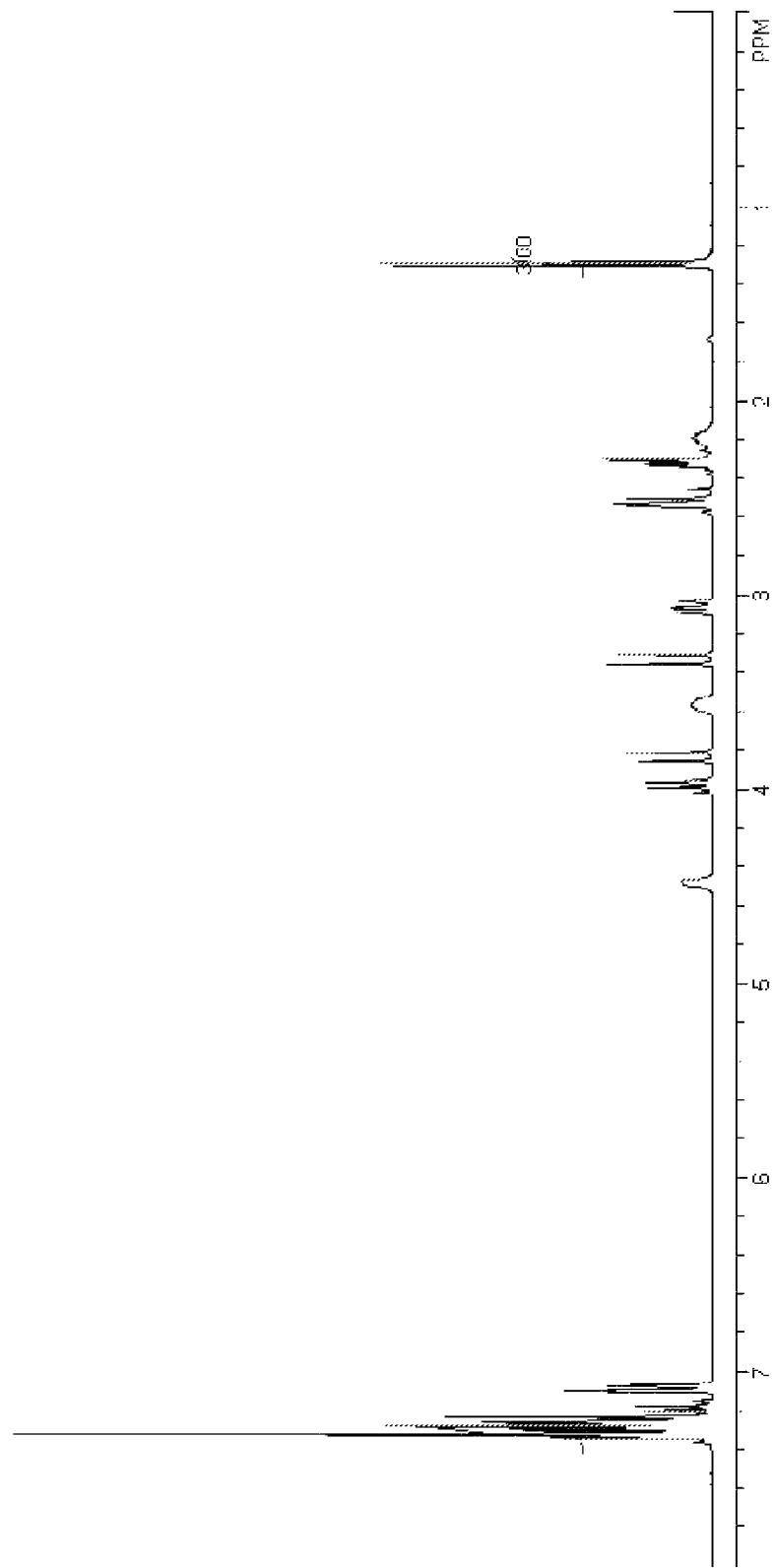
FIG. 31 is an $^1$H NMR spectrum of compound 7c shown in Table 10.
Figure 32:
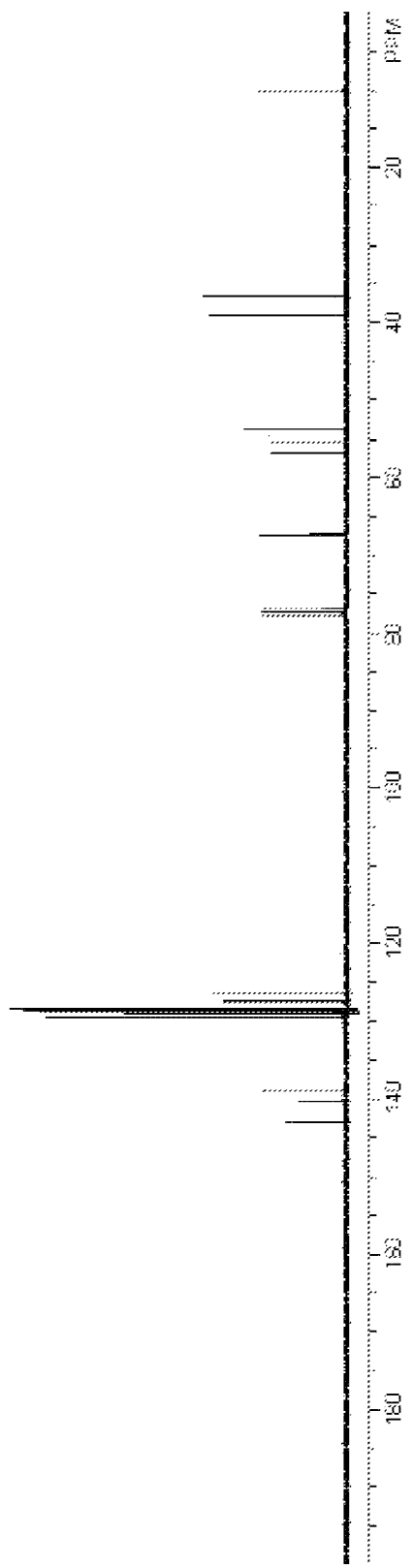
FIG. 32 is an $^{13}$C NMR spectrum of compound 7c shown in Table 10.

White solid; mp=96-97° C.; TLC R$_f$=0.22 (EtOAc/Hexanes, v/v, 1:5). $^1$H NMR (300 MHz, CDCl$_3$) δ 7.07-7.37 (m, 15H), 4.48-4.49 (br, 1H), 3.98 (q, J=6.6 Hz, 1H), 3.81 & 3.86 (s, 1H), 3.57 (br, 1H), 3.32 & 3.36 (s, 1H), 3.03-3.10 (m, 1H), 2.46-2.54 (m, 2H), 2.31-2.34 (m, 2H), 2.17-2.23 (m, 1H), 1.90 (d, J=6.6 Hz, 3H). $^{13}$C NMR (75 MHz, CDCl$_3$): δ 142.9, 140.3, 140.0, 129.5, 129.1, 128.7, 128.6, 128.4, 18.45, 128.35, 127.5, 127.3, 126.2, 67.3, 56.8, 55.2, 53.8, 39.0, 36.7, 10.2. TOF-MS-ESI: [M+H]$^+$ calculated 360.2, found 360.6. FIGS. 31 and 32. Optical rotation: $[\alpha]^{rt}_D$=+31.4° (c=0.50, MeOH).

Example 27

(S)-β-Benzyl-γ-Boc-amino alcohol (8c)

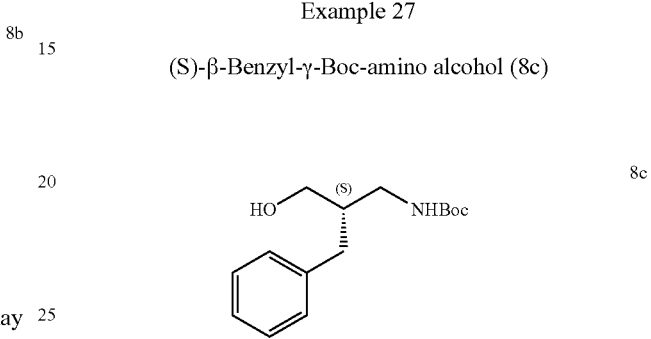

Figure 33:
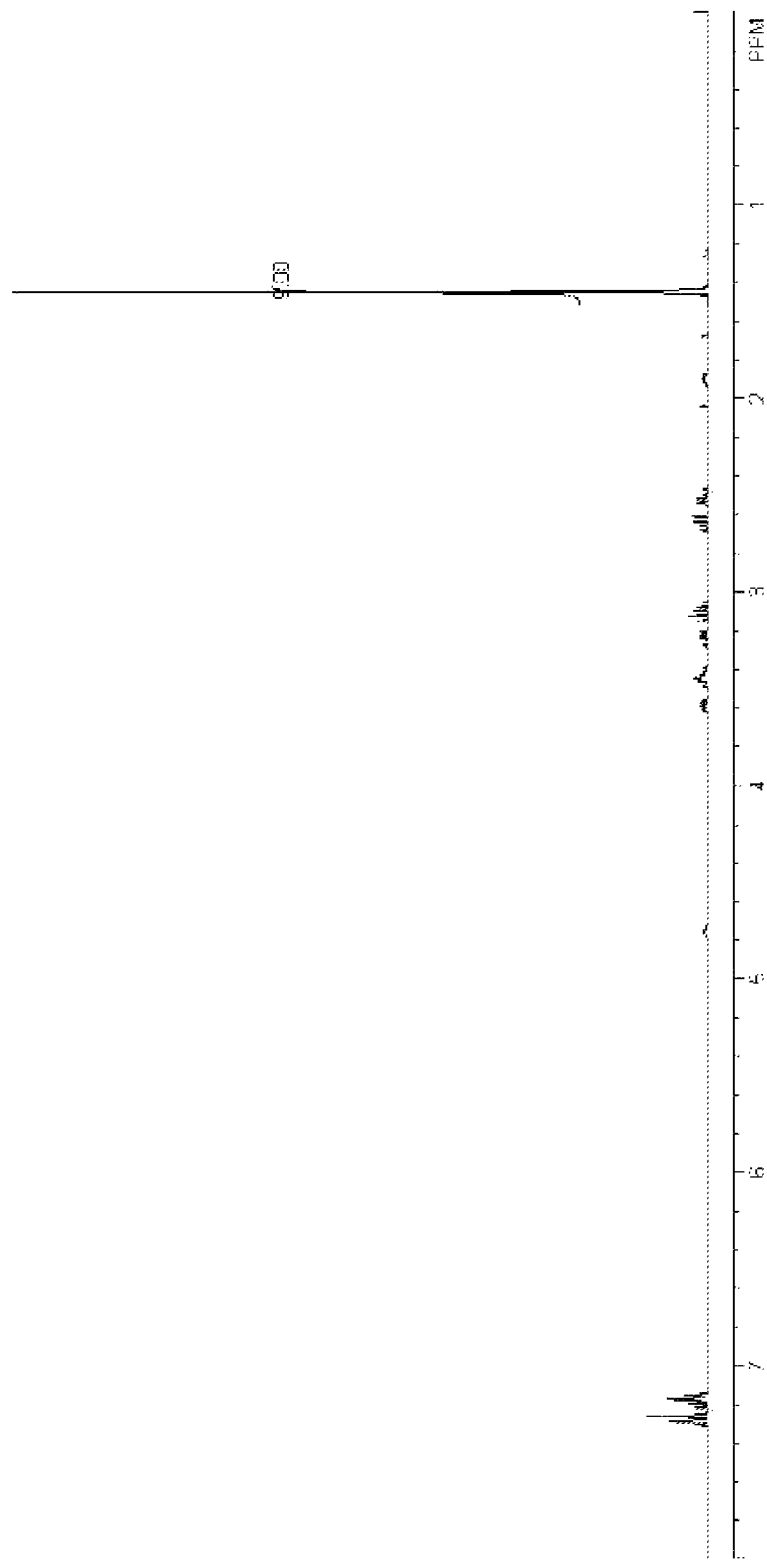
FIG. 33 is an $^1$H NMR spectrum of compound 8c shown in Table 10.
Figure 34:
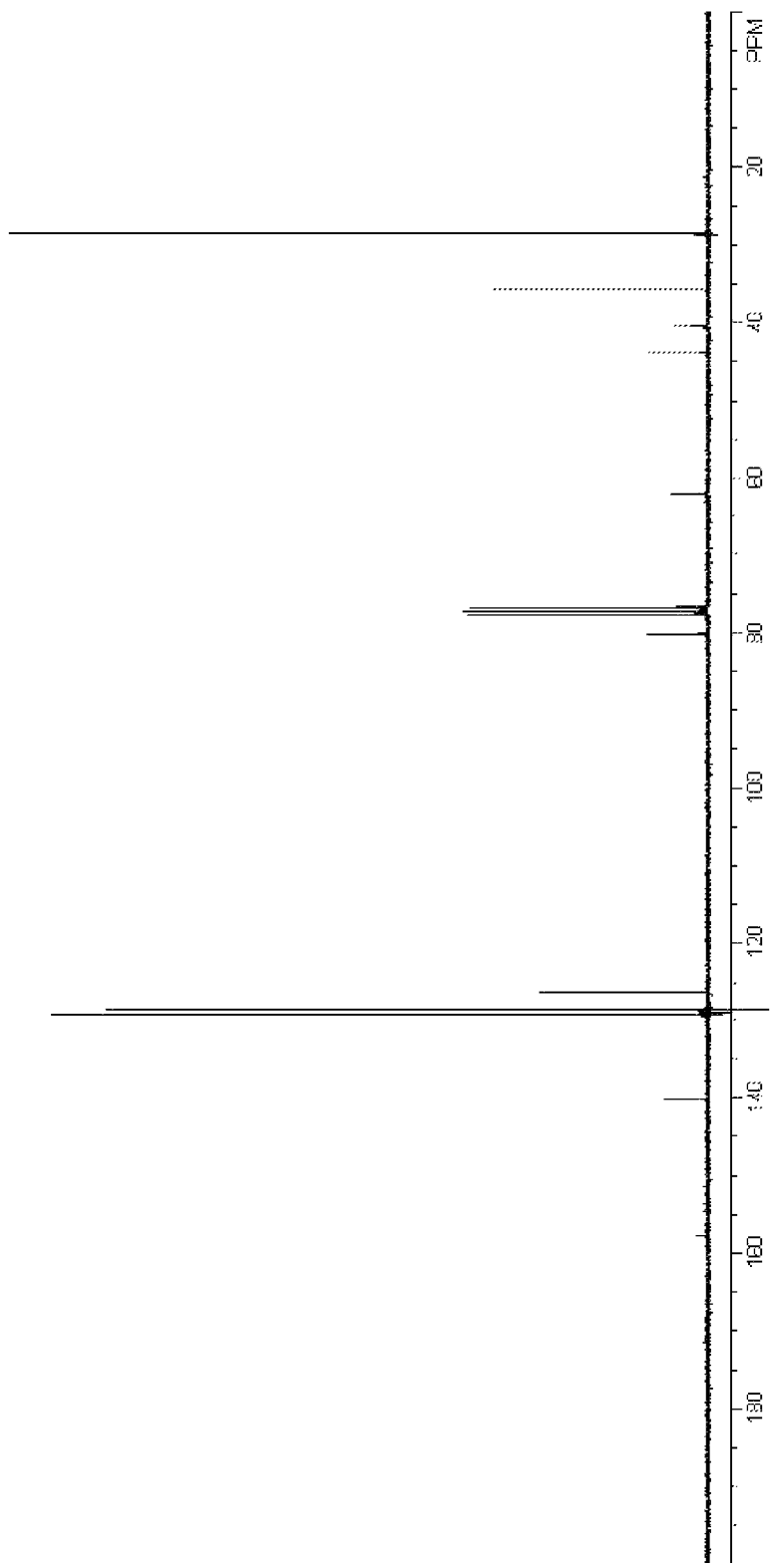
FIG. 34 is an $^{13}$C NMR spectrum of compound 8c shown in Table 10.

An NMR analysis of (S)-β-Benzyl-γ-Boc-amino alcohol (8c) was performed. Pale yellow solid; mp=70-71° C.; TLC R$_f$=0.03 (EtOAc/Hexanes, v/v, 1:5). $^1$H NMR (300 MHz, CDCl$_3$) δ 7.31-7.15 (m, 5H), 4.76 (m, 1H), 3.61-3.56 (m, 1H), 3.48-3.39 (m, 2H), 3.29-3.20 (m, 1H), 3.15-3.05 (m, 1H), 2.68-2.61 (m, 1H), 2.54-2.47 (m, 1H), 1.92-1.87 (m, 1H), 1.45 (s, 9H). $^{13}$C NMR (75 MHz, CDCl$_3$): δ 157.9, 140.1, 129.18, 129.15, 128.7, 126.4, 80.2, 62.2, 43.8, 40.5, 35.6, 28.6. TOF-MS-ESI: [M+H]$^+$ calculated 266.2, found 266.5; [M+Na]$^+$ calculated 288.2, found 288.5; [2M+Na]$^+$ calculated 553.4, found 553.9. FIGS. 33 and 34. Optical rotation: $[\alpha]^{rt}_D$=+12.6° (c=1.0, MeOH).

Example 28

(S)-Boc-β$^2$-Homophenylanaline-OH (9c)

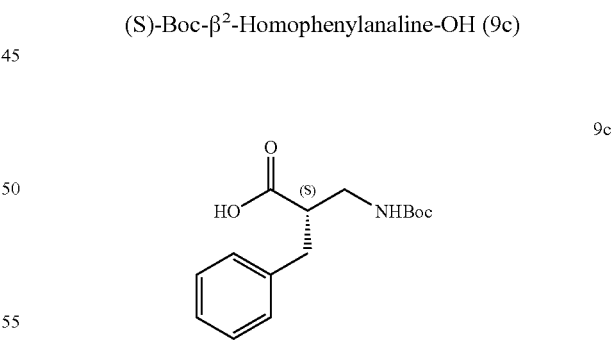

Figure 35:
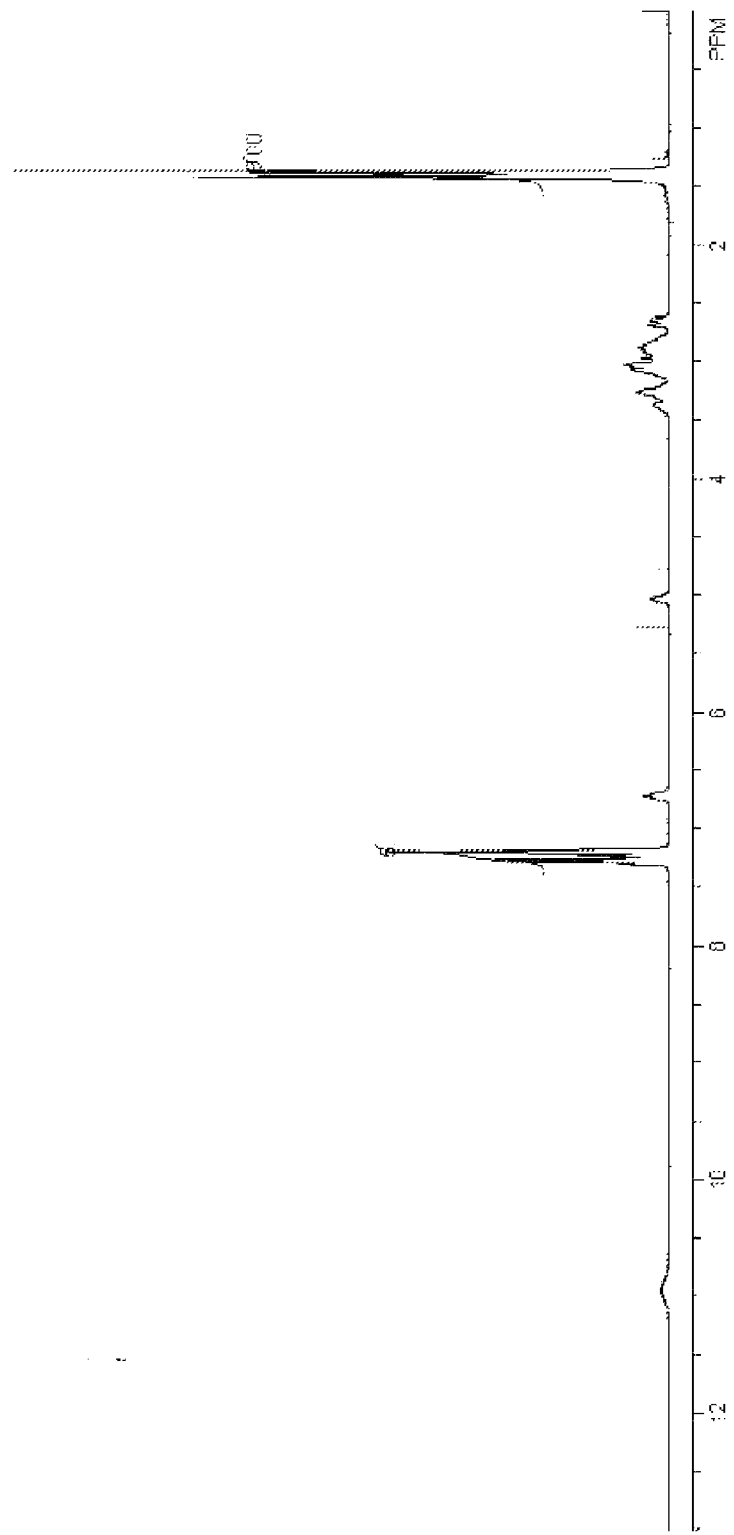
FIG. 35 is an $^1$H NMR spectrum of compound 9c shown in Table 10.
Figure 36:
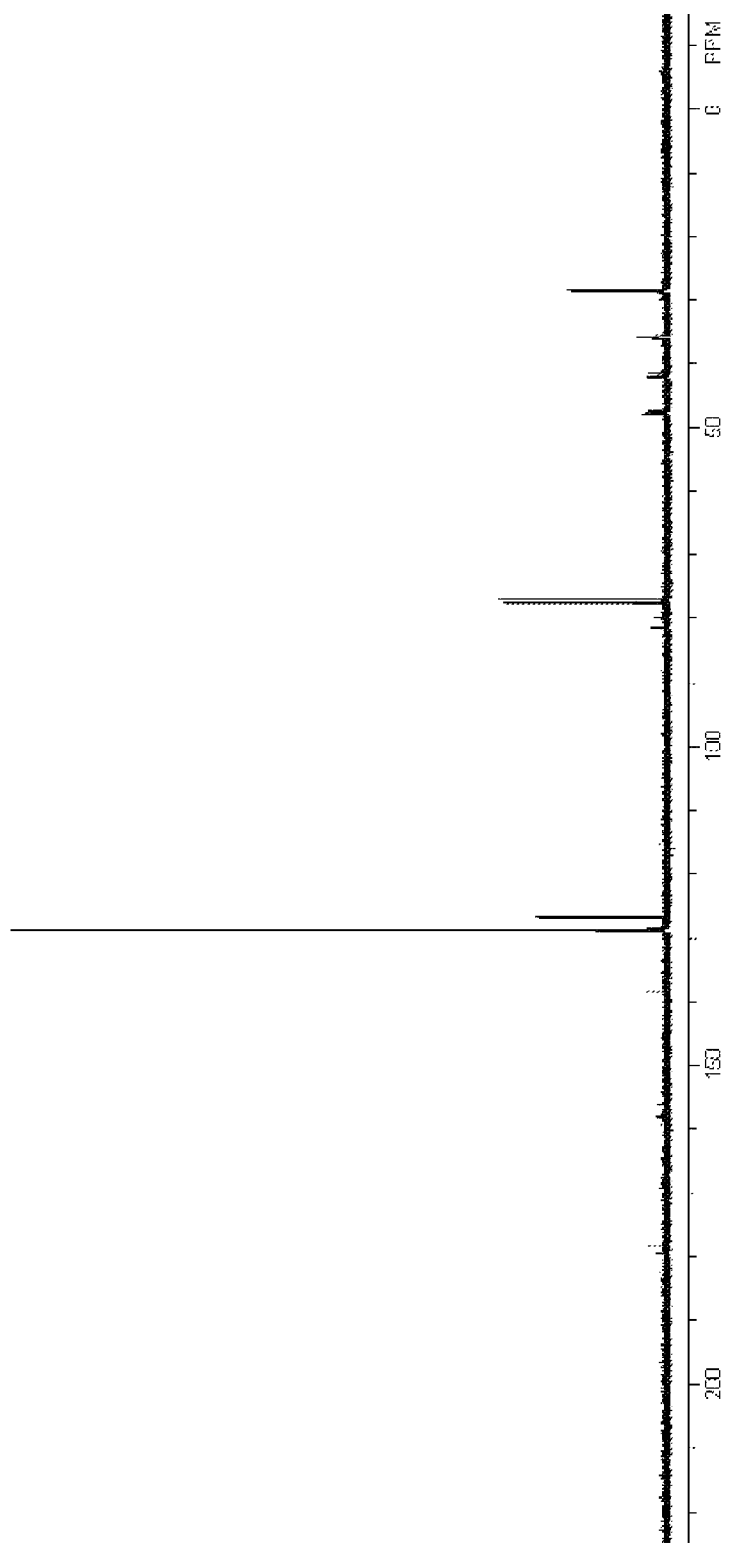
FIG. 36 is an $^{13}$C NMR spectrum of compound 9c shown in Table 10.

An NMR analysis of (S)-Boc-β$^2$-Homophenylanaline-OH (9c) was performed. White solid; mp=82-83° C.; TLC R$_f$=0.33 (MeOH/CH$_2$Cl$_2$, v/v, 1:10). $^1$H NMR (300 MHz, CDCl$_3$) δ 10.93 (br, 1H), 7.31-7.20 (m, 5H), 6.72 & 5.02 (br, 1H), 3.44-2.58 (m, 5H), 1.42-1.37 (m, 9H). $^{13}$C NMR (75 MHz, CDCl$_3$): δ 179.4 & 179.3, 158.1 & 156.1, 138.4, 129.0, 128.8, 126.8, 81.4 & 79.9, 47.7 & 47.4, 42.3 & 41.5, 36.0 & 35.9, 28.5 & 28.4. TOF-MS-ESI: [M−H]$^-$ calculated 278.3, found 278.5; [2M−H]$^-$ calculated 557.6, found 558.0. FIGS. 35 and 36. Optical rotation: $[\alpha]^{rt}_D$=−45.0° (c=1.0, CH$_2$Cl$_2$).

Example 29

(S)-β-Isopropyl-γ-(S)—N-benzyl-α-methylbenzylamino alcohol (7d)

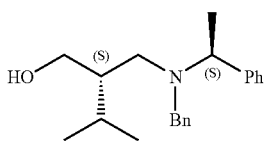

7d

Figure 37:
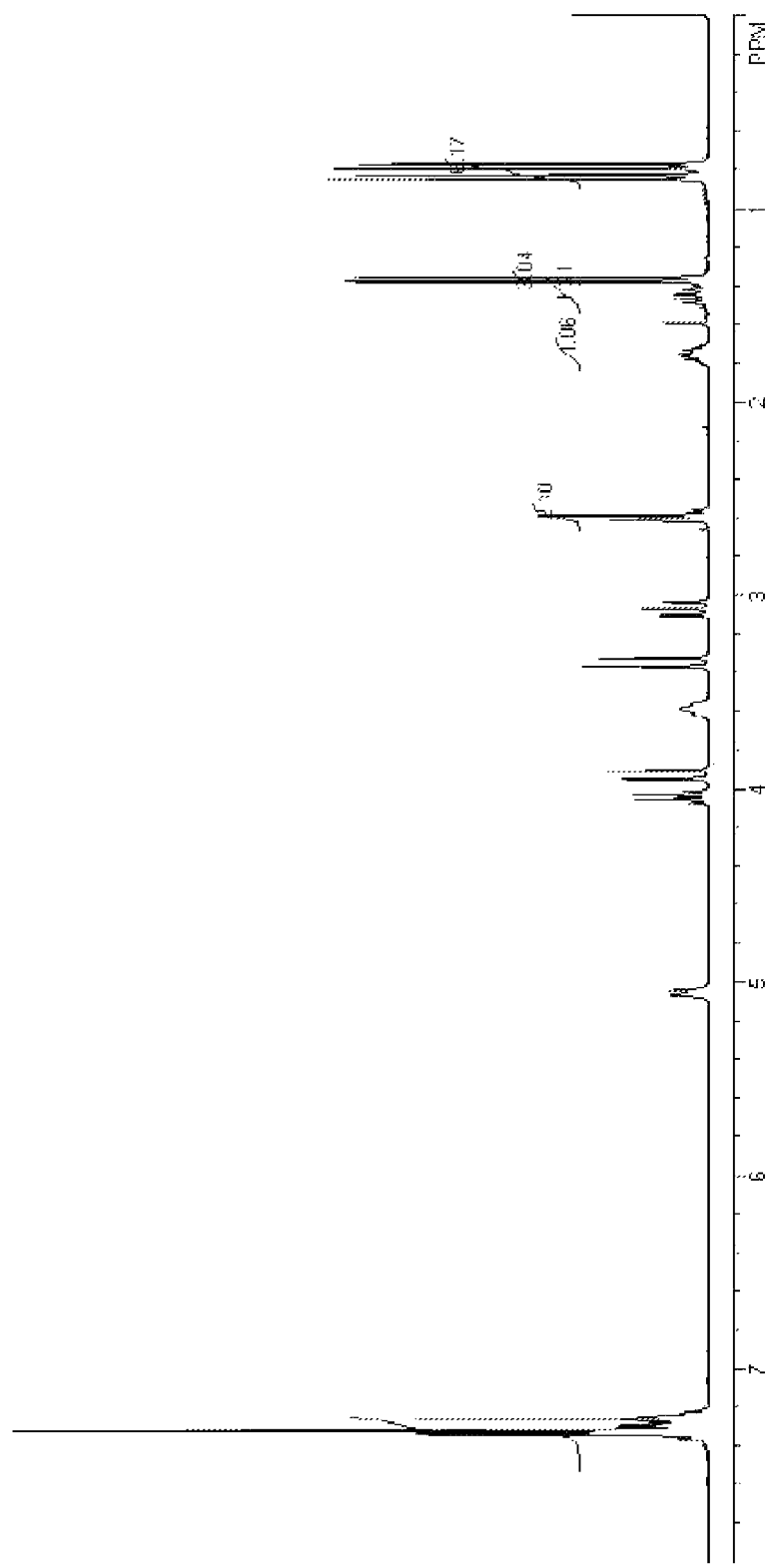
FIG. 37 is an $^1$H NMR spectrum of compound 7d shown in Table 10.
Figure 38:
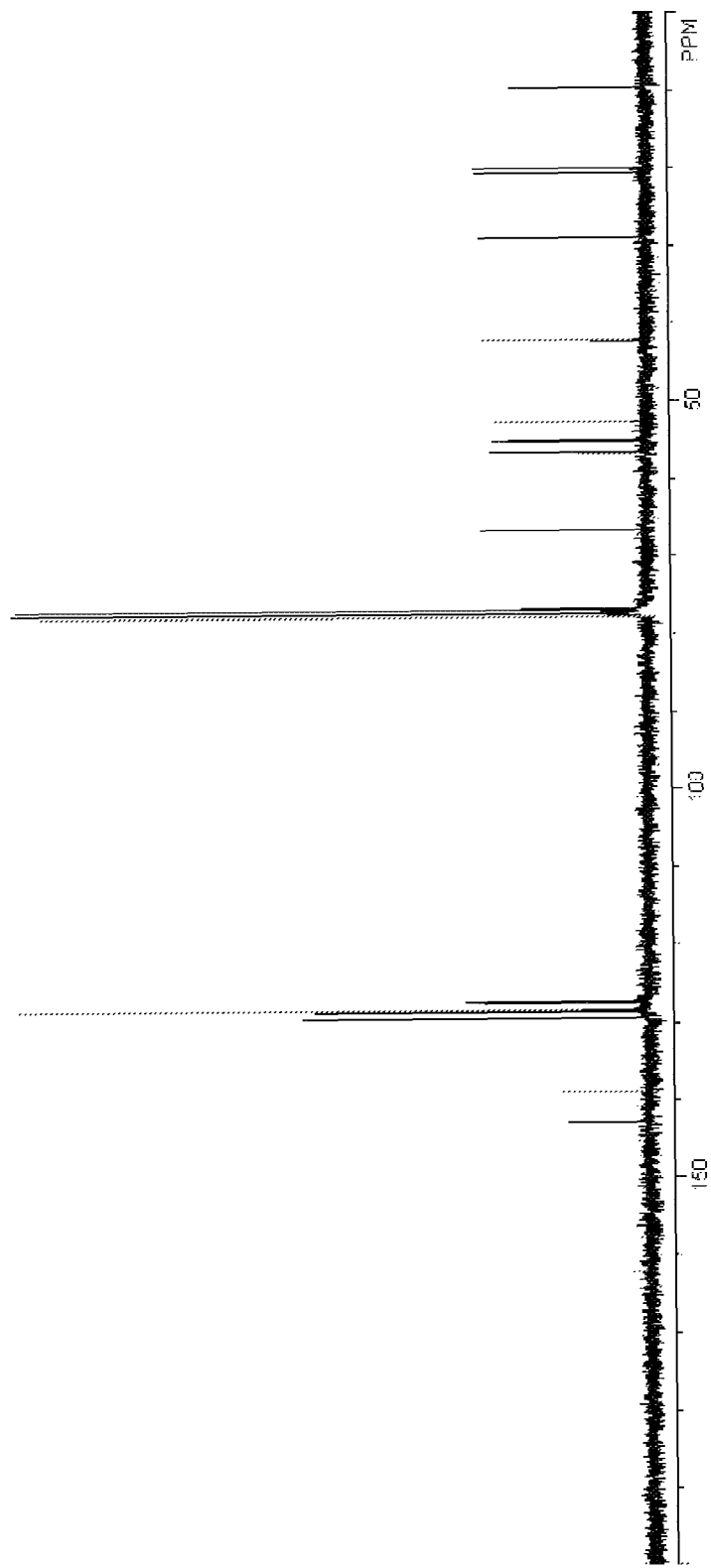
FIG. 38 is an $^{13}$C NMR spectrum of compound 7d shown in Table 10.

An NMR analysis of (S)-β-Isopropyl-γ-(S)—N-benzyl-α-methylbenzylamino alcohol (7d) was performed. Colorless oil; TLC $R_f$=0.19 (EtOAc/Hexanes, v/v, 1:5). $^1$H NMR (300 MHz, CDCl$_3$) δ 7.37-7.23 (m, 10H), 5.07-5.04 (br, 1H), 4.05 (q, J=6.6 Hz, 1H), 3.95 & 3.91 (s, 1H), 3.62-3.56 (br, 1H), 3.37 & 3.33 (s, 1H), 3.10-3.04 (m, 1H), 2.62-2.59 (m, 2H), 1.78-1.73 (m, 1H), 1.49-1.42 (m, 1H), 1.37 (d, J=6.6 Hz, 3H), 0.84 & 0.78 (diastereotopic, d, J=6.9 Hz). $^{13}$C NMR (75 MHz, CDCl$_3$): δ 142.7, 138.9, 129.5, 128.7, 128.4, 127.5, 127.4, 66.5, 56.5, 56.1, 52.5, 42.2, 28.8, 20.5, 20.0, 9.5. TOF-MS-ESI: [M+H]$^+$ calculated 312.2, found 312.5. FIGS. 37 and 38. Optical rotation: $[α]^{rt}_D$=+19.20° (c=0.50, MeOH).

Example 30

(S)-β-Isopropyl-γ-Boc-amino alcohol (8d)

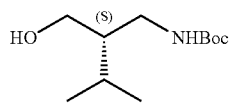

Figure 39:
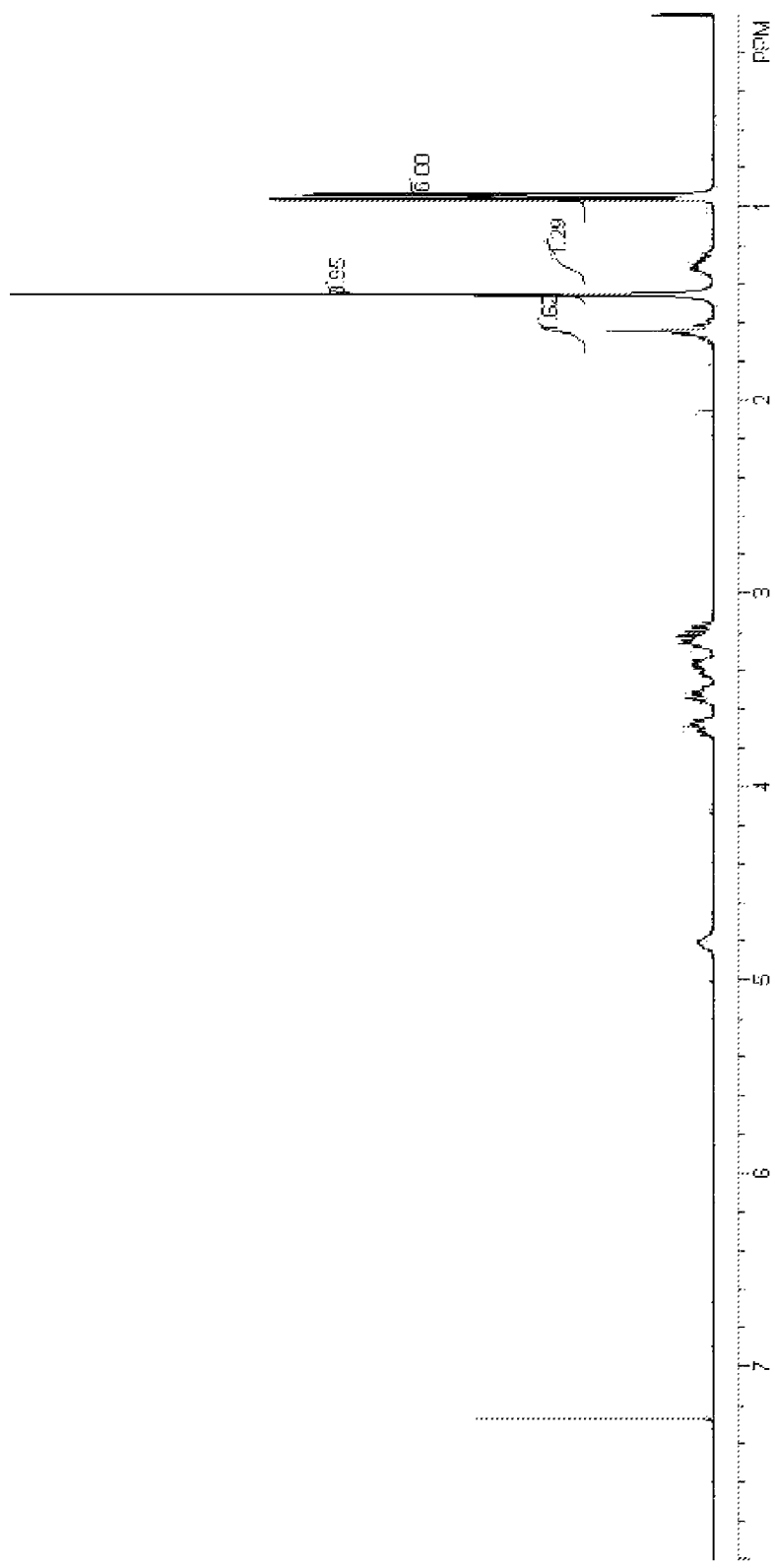
FIG. 39 is an $^1$H NMR spectrum of compound 8d shown in Table 10.
Figure 40:
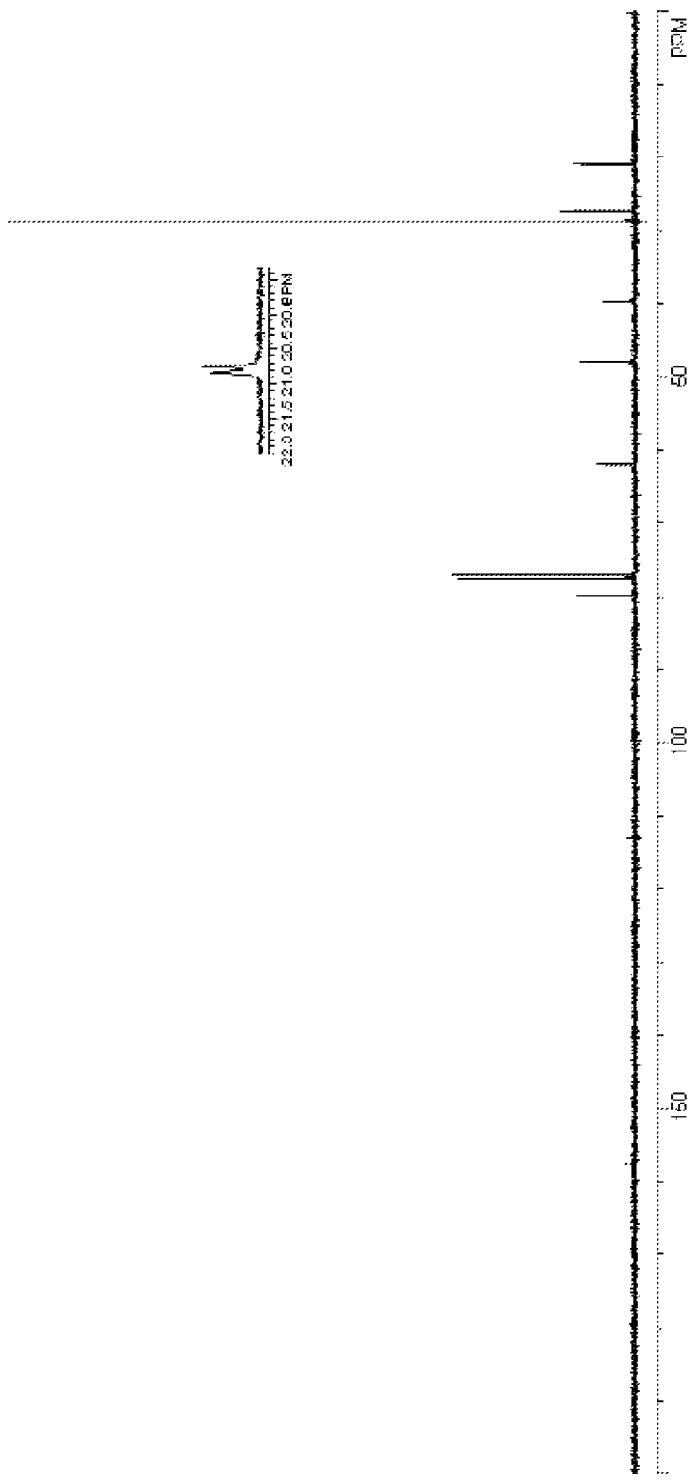
FIG. 40 is an $^{13}$C NMR spectrum of compound 8d shown in Table 10.

8d (S)-β-Isopropyl-γ-Boc-amino alcohol (8d): Pale yellow solid; mp=68-69° C.; TLC $R_f$=0.05 (EtOAc/Hexanes, v/v, 1:5). $^1$H NMR (300 MHz, CDCl$_3$) δ 4.80 (br, 1H), 3.69-3.66 (m, 1H), 3.55-3.51 (m, 1H), 3.38-3.35 (m, 1H), 3.28-3.17 (m, 2H), 1.66-1.61 (m, 1H), 1.32-1.30 (m, 1H), 0.95 & 0.94 (diastereotopic, d, J=7.2 Hz, 6H). $^{13}$C NMR (75 MHz, CDCl$_3$): δ 157.9, 79.9, 61.9, 47.9, 39.7, 28.6, 27.3, 20.8, 20.7. TOF-MS-ESI: [M+H]$^+$ calculated 218.2, found 218.4; [M+Na]$^+$ calculated 240.2, found 240.4; [2M+Na]$^+$ calculated 457.4, found 457.8. FIGS. 39 and 40. Optical rotation: $[α]^{rt}_D$=+11.40° (c=0.50, MeOH).

Example 31

(S)-Boc-β$^2$-Homovaline-OH (9d)

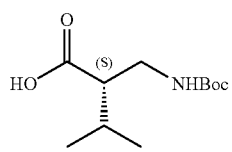

Figure 41:
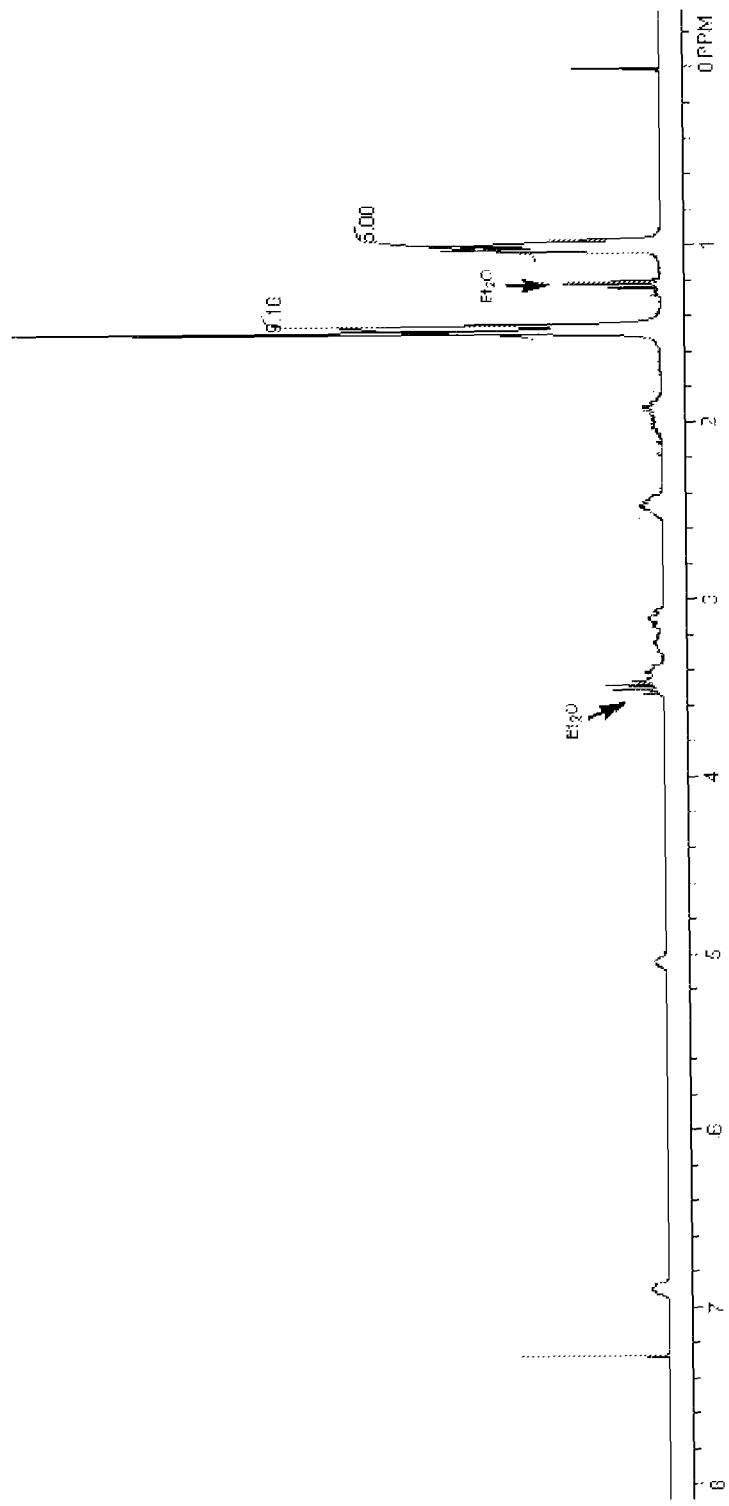
FIG. 41 is an $^1$H NMR spectrum of compound 9d shown in Table 10.
Figure 42:
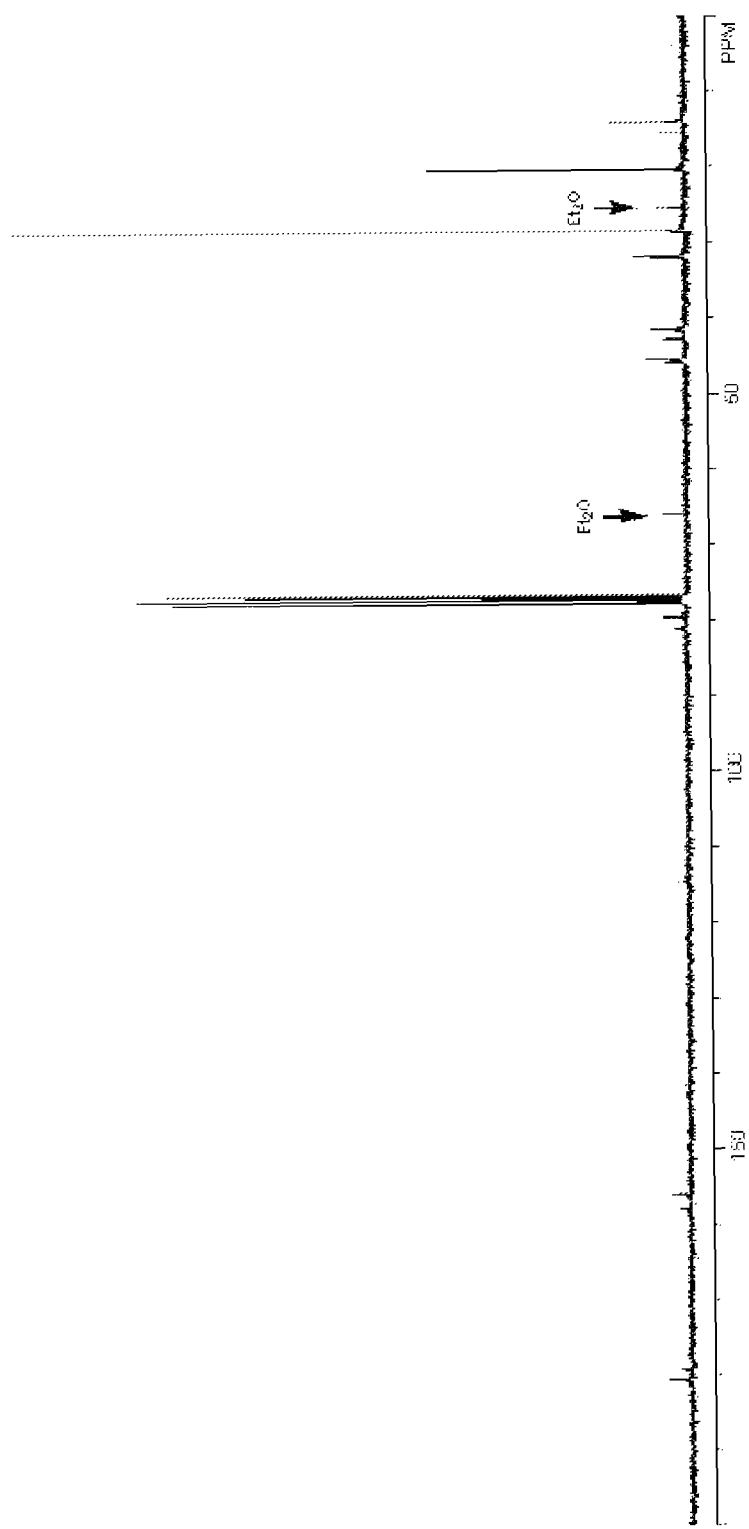
FIG. 42 is an $^{13}$C NMR spectrum of compound 9d shown in Table 10.

9d (S)-Boc-β$^2$-Homovaline-OH (9d): White solid; mp=70-71° C.; TLC $R_f$=0.28 (MeOH/CH$_2$Cl$_2$, v/v, 1:10). $^1$H NMR (300 MHz, CDCl$_3$) δ 6.90 & 5.05 (br, 1H), 3.53-3.38 (m, 1H), 3.29-3.10 (m, 1H), 2.50-2.41 (m, 1H), 2.05-1.89 (m, 1H), 1.49-1.45 (m, 9H), 1.02-0.96 (m, 6H). $^{13}$C NMR (75 MHz, CDCl$_3$): δ 180.6 & 179.3, 158.1 & 156.2, 81.2 & 79.8, 45.9 & 45.6, 42.9 & 41.6, 31.9, 28.6, 20.4, 14.1. TOF-MS-ESI: [M−H]$^-$ calculated 230.2, found 230.5; [2M−H]$^-$ calculated 461.3, found 462.0. FIGS. 41 and 42. Optical rotation: $[α]^{rt}_D$=+35.4° (c=0.50, MeOH).

Example 32

(S)-β-2-Methylpropyl-γ-(S)—N-benzyl-α-methylbenzylamino alcohol (7e)

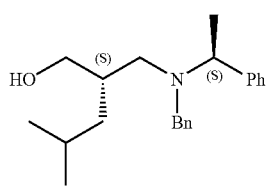

Figure 43:
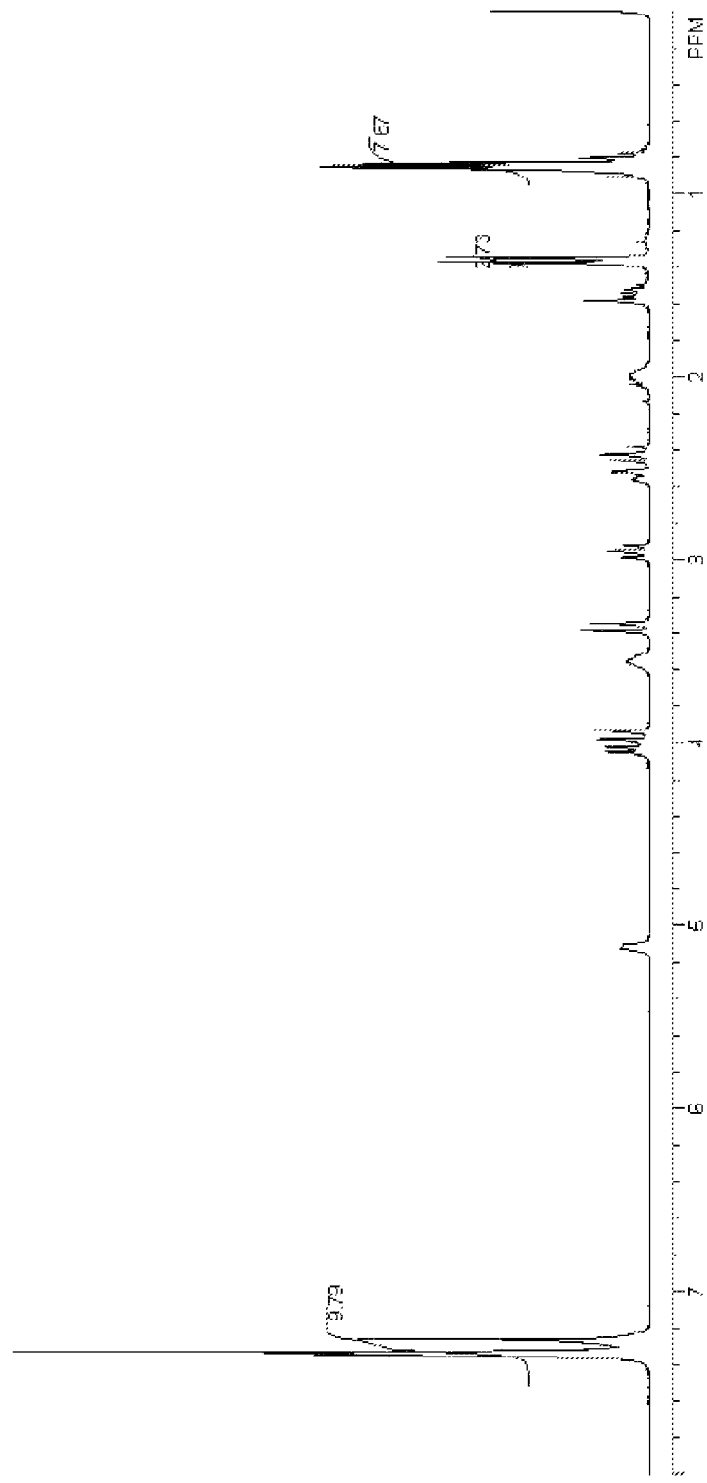
FIG. 43 is an $^1$H NMR spectrum of compound 7e shown in Table 10.
Figure 44:
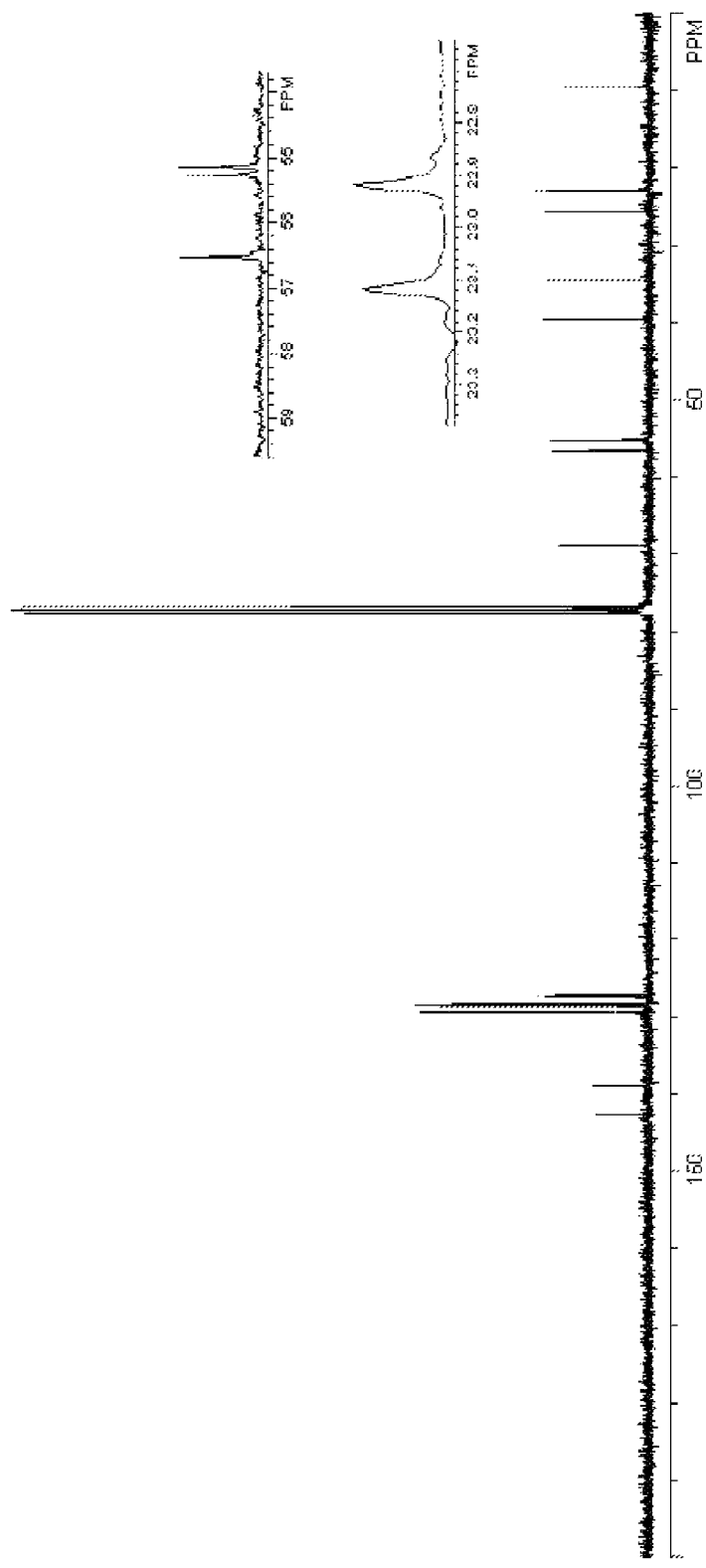
FIG. 44 is an $^{13}$C NMR spectrum of compound 7e shown in Table 10.

7e (S)-β-2-Methylpropyl-γ-(S)—N-benzyl-α-methylbenzylamino alcohol (7e): Colorless oil; TLC $R_f$=0.22 (EtOAc/Hexanes, v/v, 1:5). $^1$H NMR (300 MHz, CDCl$_3$) δ 7.34-7.26 (m, 10H), 5.12 (br, 1H), 4.03 (q, J=6.9 Hz, 1H), 3.98 & 3.93 (s, 1H), 3.54 (br, 1H), 3.39 & 3.35 (s, 1H), 2.98-2.92 (m, 1H), 2.56-2.52 (m, 1H), 2.46-2.38 (m, 1H), 2.08-1.93 (br, 1H), 1.58-1.54 (m, 1H), 1.35 (d, J=6.9 Hz, 3H), 0.90-0.78 (m, 6H). $^{13}$C NMR (75 MHz, CDCl$_3$): δ 142.8, 138.9, 129.5, 128.7, 128.4, 128.3, 127.5, 127.3, 68.8, 56.5, 55.3, 55.1, 39.5, 34.5, 25.6, 23.1, 22.9, 9.5. TOF-MS-ESI: [M+H]$^+$ calculated 326.2, found 326.6. Optical rotation: $[α]^{rt}_D$=+13.8° (c=0.50, MeOH). FIGS. 43 and 44. X-ray quality crystals were obtained via vapor diffusion of Et$_2$O to a MeOH-EtOAc solution of 7e HCl salt.

Example 33

(S)-β-2-Methylpropyl-γ-Boc-amino alcohol (8e)

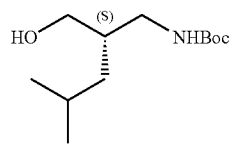

Figure 45:
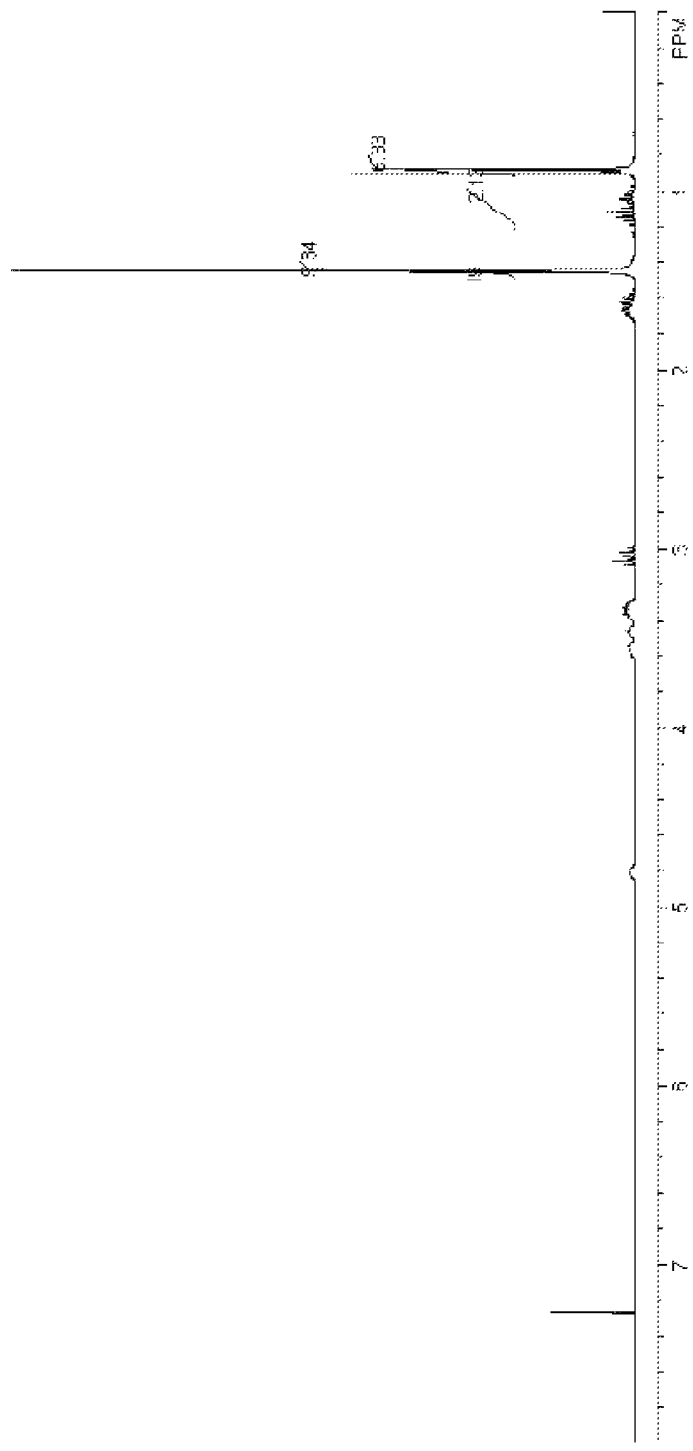
FIG. 45 is an $^1$H NMR spectrum of compound 8e shown in Table 10.
Figure 46:
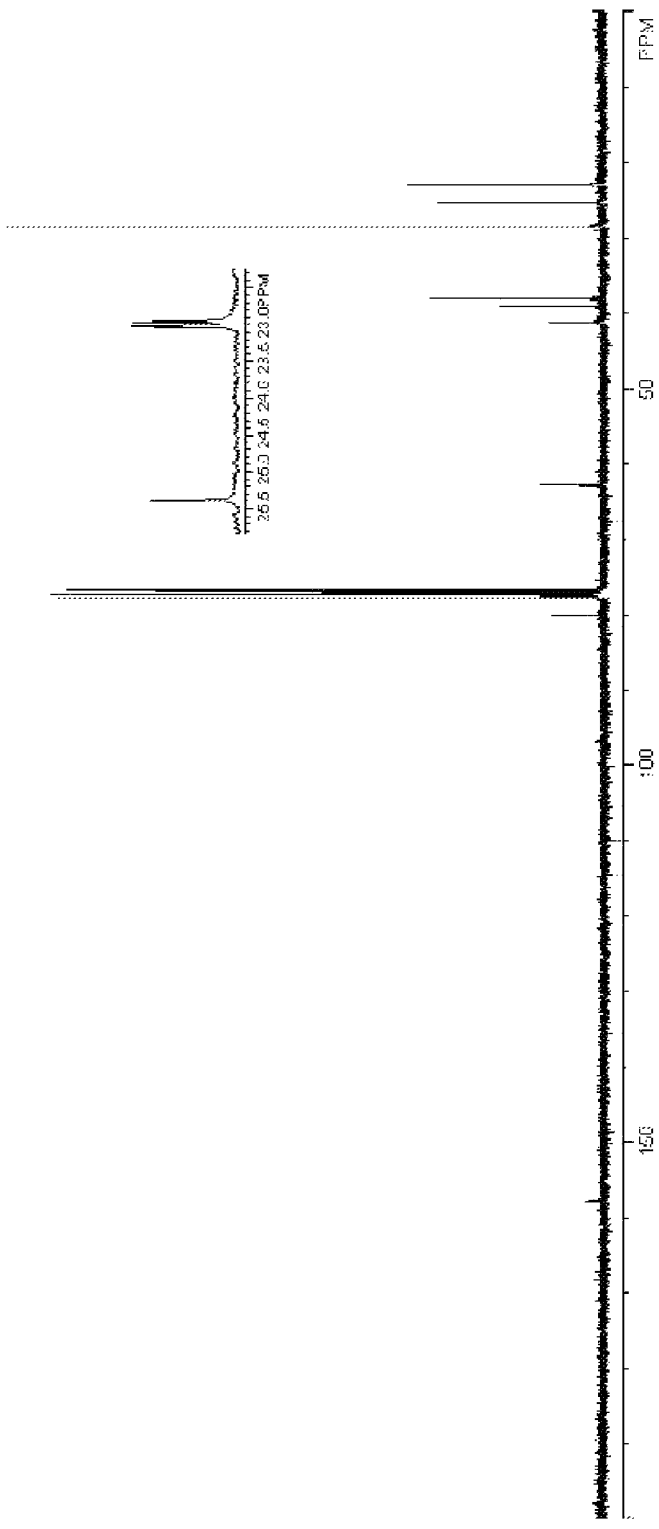
FIG. 46 is an $^{13}$C NMR spectrum of compound 8e shown in Table 10.

8e (S)-β-2-Methylpropyl-γ-Boc-amino alcohol (8e): White solid; mp=54-55° C.; TLC $R_f$=0.07 (EtOAc/Hexanes, v/v, 1:5). $^1$H NMR (300 MHz, CDCl$_3$) δ 4.81 (br, 1H), 3.60-3.53 (m, 1H), 3.48-3.44 (m, 1H), 3.37-3.31 (m, 1H), 3.09-3.02 (m, 1H), 1.72-1.58 (m, 2H), 1.45 (s, 9H), 1.19-0.98 (m, 2H), 0.89 (d, J=6.9 Hz, 6H). $^{13}$C NMR (75 MHz, CDCl$_3$): δ 157.9, 80.0, 62.9, 41.2, 39.3, 28.6, 25.4, 23.0, 22.9. TOF-MS-ESI: [M+Na]$^+$ calculated 254.2, found 254.4; [2M+Na]$^+$ calculated 485.4, found 485.9. FIGS. 45 and 46. Optical rotation: $[α]^{rt}_D$=+5.60° (c=0.50, MeOH).

Example 34

(S)-Boc-β²-Homoleucine-OH (9e)

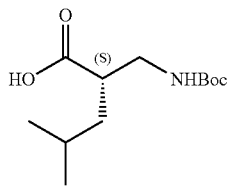

Figure 47:
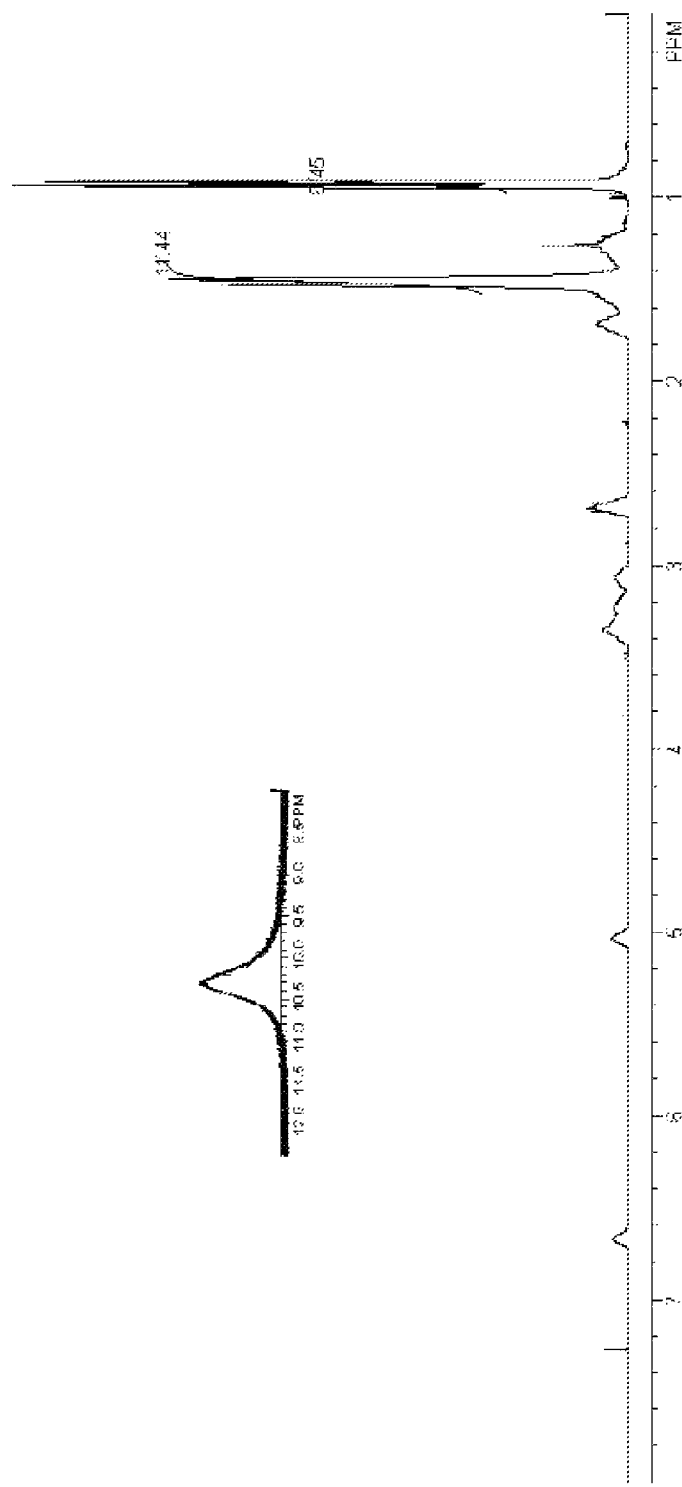
FIG. 47 is an $^1$H NMR spectrum of compound 9e shown in Table 10.
Figure 48:
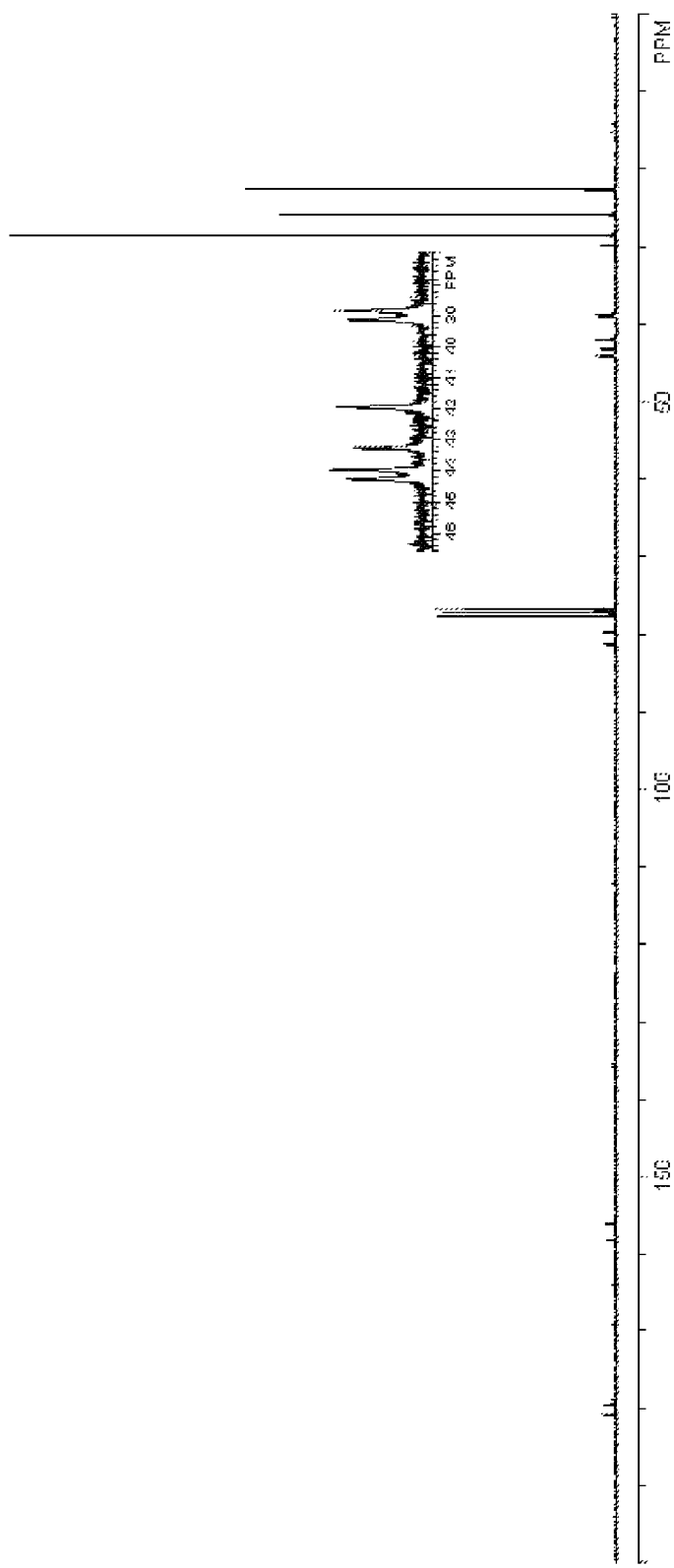
FIG. 48 is an $^{13}$C NMR spectrum of compound 9e shown in Table 10.

9e (S)-Boc-β²-Homoleucine-OH (9e): White solid; mp=56-57° C.; TLC $R_f$=0.28 (MeOH/CH$_2$Cl$_2$, v/v, 1:10). $^1$H NMR (300 MHz, CDCl$_3$) δ 10.26 (br, 1H), 6.68 & 5.04 (br, 1H), 3.44-2.98 (m, 2H), 2.73-2.61 (m, 1H), 1.75-1.65 (m, 1H), 1.54-1.44 (m, 11H), 0.94-0.91 (m, 6H). $^{13}$C NMR (75 MHz, CDCl$_3$): δ 181.0 & 179.6, 158.1 & 156.1, 81.3 & 79.8, 44.3 & 44.0, 43.3 & 42.0, 39.1 & 38.8, 29.9, 20.5, 26.0, 22.60 & 22.56. TOF-MS-ESI: [M–H]⁻ calculated 244.2, found 244.5; [2M–H]⁻ calculated 489.4, found 490.1. FIGS. 47 and 48. Optical rotation: $[\alpha]^{rt}_D$=+12.40° (c=0.50, MeOH).

Example 35

(S)-β-Cyclohexlmethyl-γ-(S)—N-benzyl-α-methyl-benzylamino alcohol (7f)

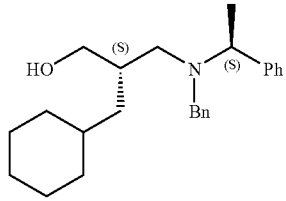

Figure 49:
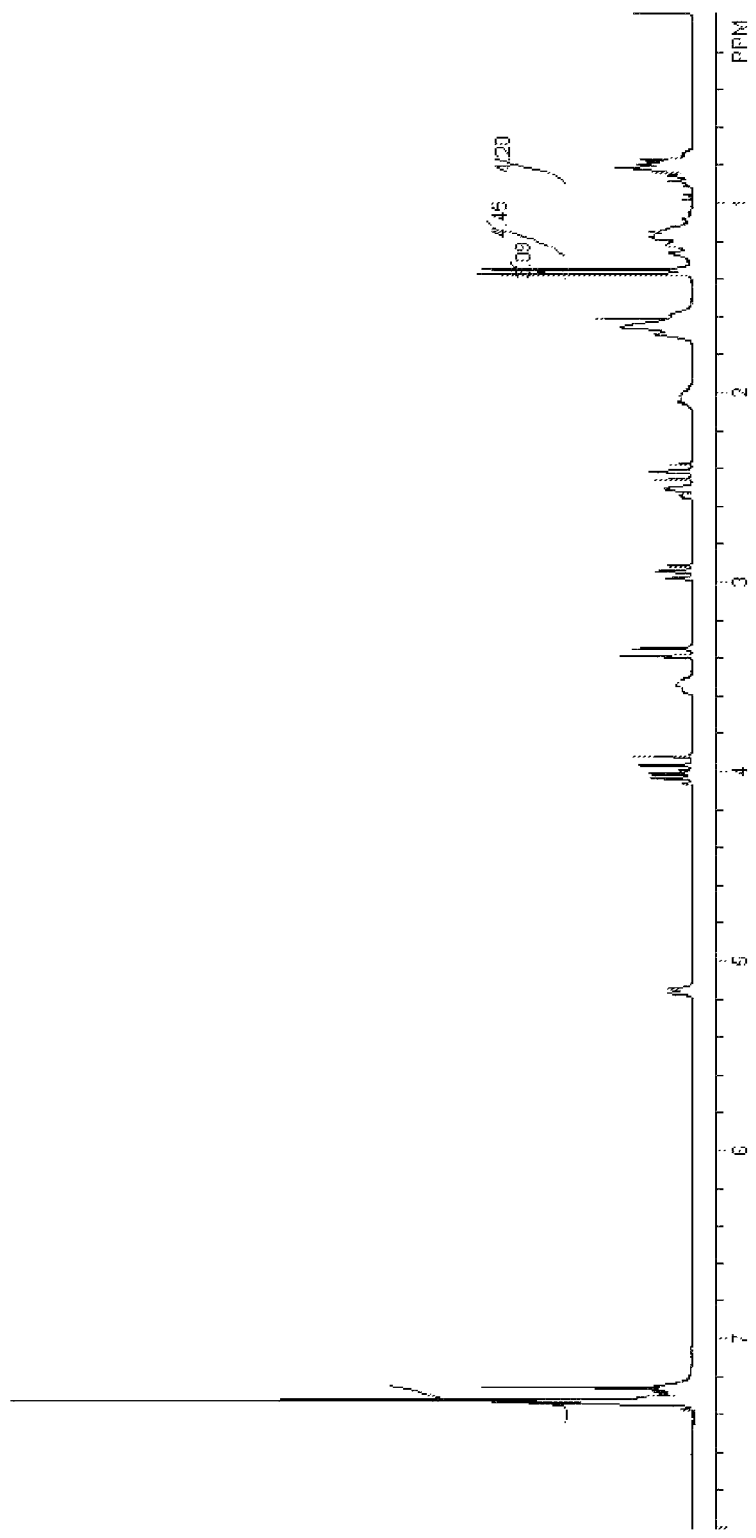
FIG. 49 is an $^1$H NMR spectrum of compound 7f shown in Table 10.
Figure 50:
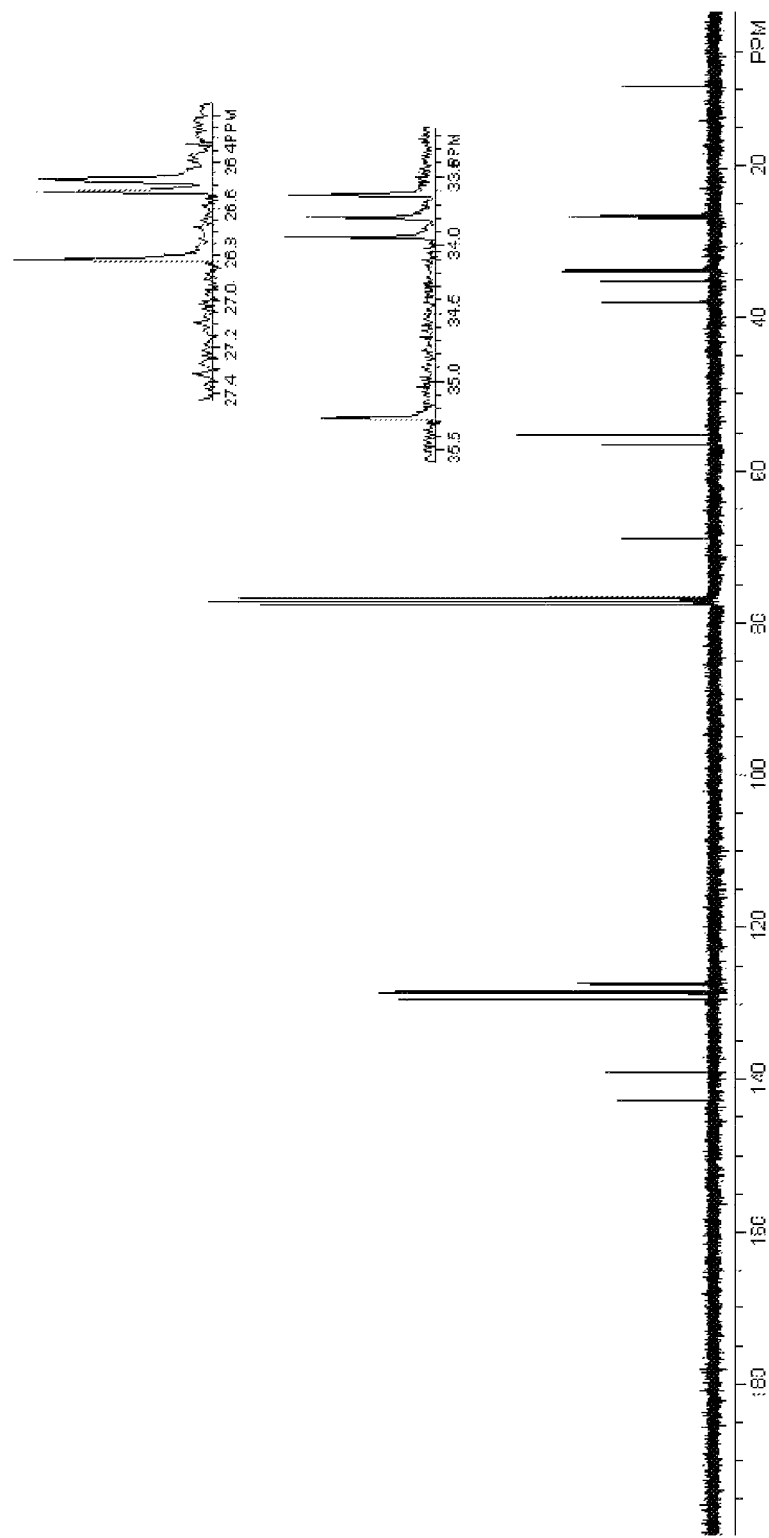
FIG. 50 is an $^{13}$C NMR spectrum of compound 7f shown in Table 10.

7f (S)-β-Cyclohexlmethyl-γ-(S)—N-benzyl-α-methylbenzylamino alcohol (7f): Colorless oil (may solidify upon staying at rt). TLC $R_f$=0.28 (EtOAc/Hexanes, v/v, 1:5). $^1$H NMR (300 MHz, CDCl$_3$) δ 7.34-7.25 (m, 10H), 5.15 (d, J=7.8 Hz), 4.03 (q, J=7.5 Hz, 1H), 3.97 & 3.92 (s, 1H), 3.57-3.54 (m, 1H), 3.39 & 3.35 (s, 1H), 2.98-2.91 (m, 1H), 2.55-2.51 (m, 1H), 2.45-2.37 (m, 1H), 2.02 (br, 1H), 1.70-1.61 (m, 4H), 1.36 (d, J=7.5 Hz, 3H), 1.22-1.13 (m, 4H), 0.84-0.78 (m, 4H). $^{13}$C NMR (75 MHz, CDCl$_3$): δ 142.8, 138.9, 129.5, 128.7, 128.42, 128.39, 127.5, 127.3, 68.9, 56.6, 55.3, 38.0, 35.3, 33.9, 33.8, 33.6, 26.8, 26.53, 26.47, 9.7. TOF-MS-ESI: [M+H]⁺ calculated 366.3, found 366.7. FIGS. 49 and 50. Optical rotation: $[\alpha]^{rt}_D$=+17.2° (c=0.50, MeOH). X-ray quality crystals were obtained via vapor diffusion of Et$_2$O to a MeOH-EtOAc solution of 7f-HCl salt.

Example 36

(S)-β-Cyclohexylmethyl-γ-Boc-amino alcohol (8f)

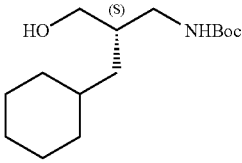

Figure 51:
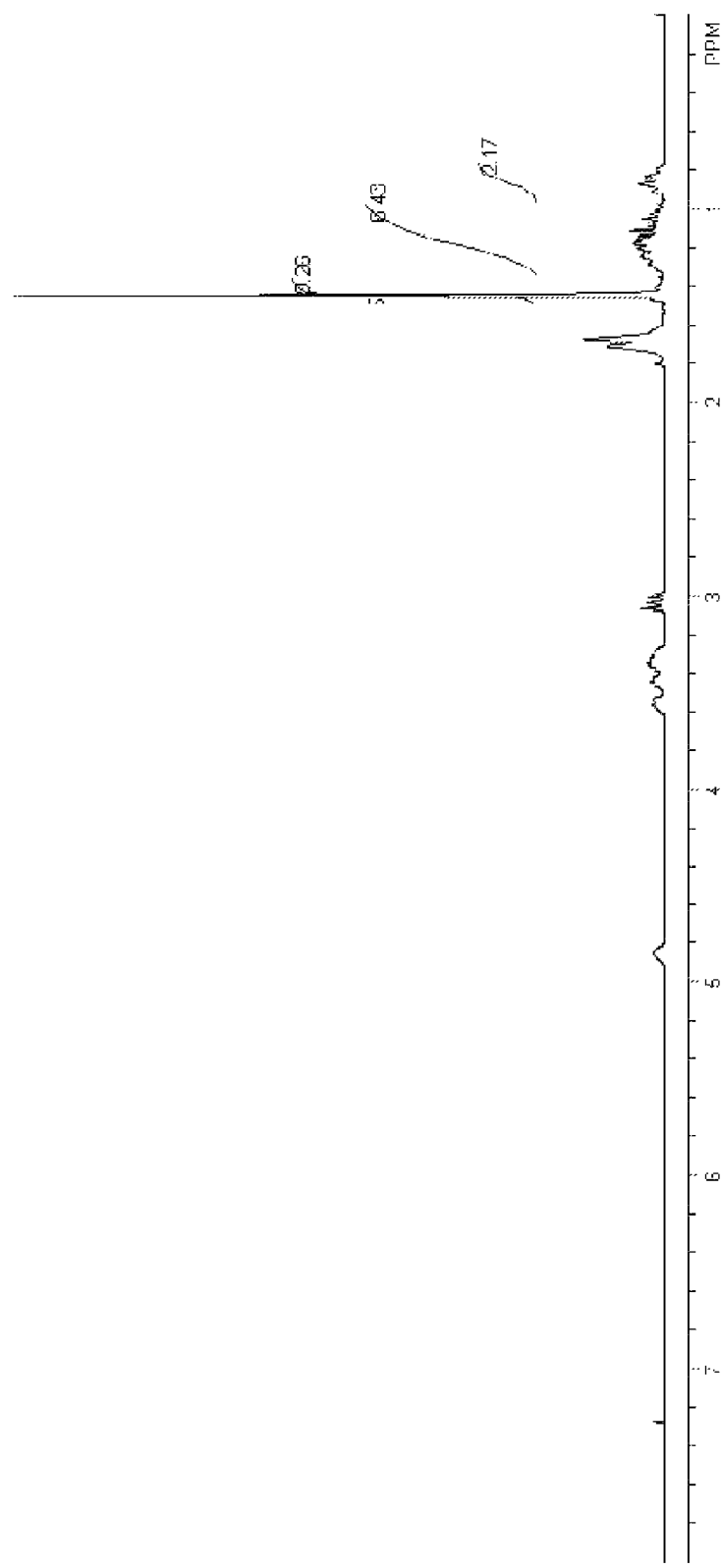
FIG. 51 is an $^1$H NMR spectrum of compound 8f shown in Table 10.
Figure 52:
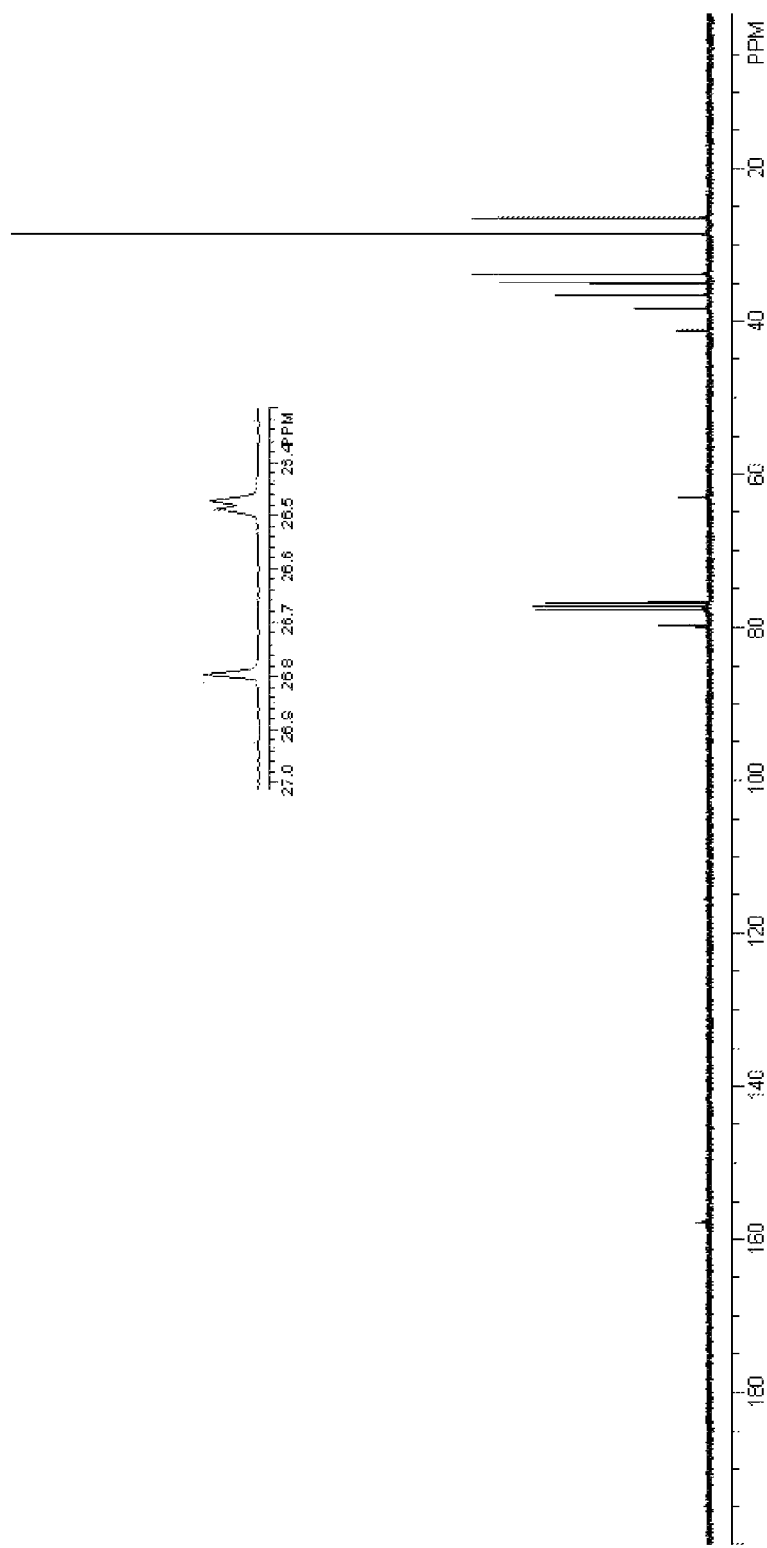
FIG. 52 is an $^{13}$C NMR spectrum of compound 8f shown in Table 10.

8f (S)-β-Cyclohexylmethyl-γ-Boc-amino alcohol (8f): White solid; mp=69-71° C.; TLC $R_f$=0.08 (EtOAc/Hexanes, v/v, 1:5). $^1$H NMR (300 MHz, CDCl$_3$) δ 4.86 (br, 1H), 3.56-3.29 (m, 4H), 3.08-3.01 (m, 1H), 1.80-1.67 (m, 6H), 1.45 (s, 9H), 1.28-1.03 (m, 6H), 0.91-0.84 (m, 2H). $^{13}$C NMR (75 MHz, CDCl$_3$): δ 157.8, 79.9, 63.0, 41.3, 38.4, 36.6, 34.9, 33.8, 28.6, 26.8, 26.49, 26.47. TOF-MS-ESI: [M+H]⁺ calculated 272.2, found 272.5; [M+Na]⁺ calculated 294.2, found 294.5, [2M+Na]⁺ calculated 565.4, found 566.0. FIGS. 51 and 52. Optical rotation: $[\alpha]^{rt}_D$=+23.0° (c=0.50, CH$_2$Cl$_2$).

Example 37

(S)-α-Cyclohexylmethyl-β²-Boc-amino acid (9f)

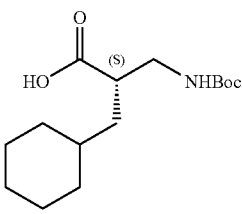

Figure 53:
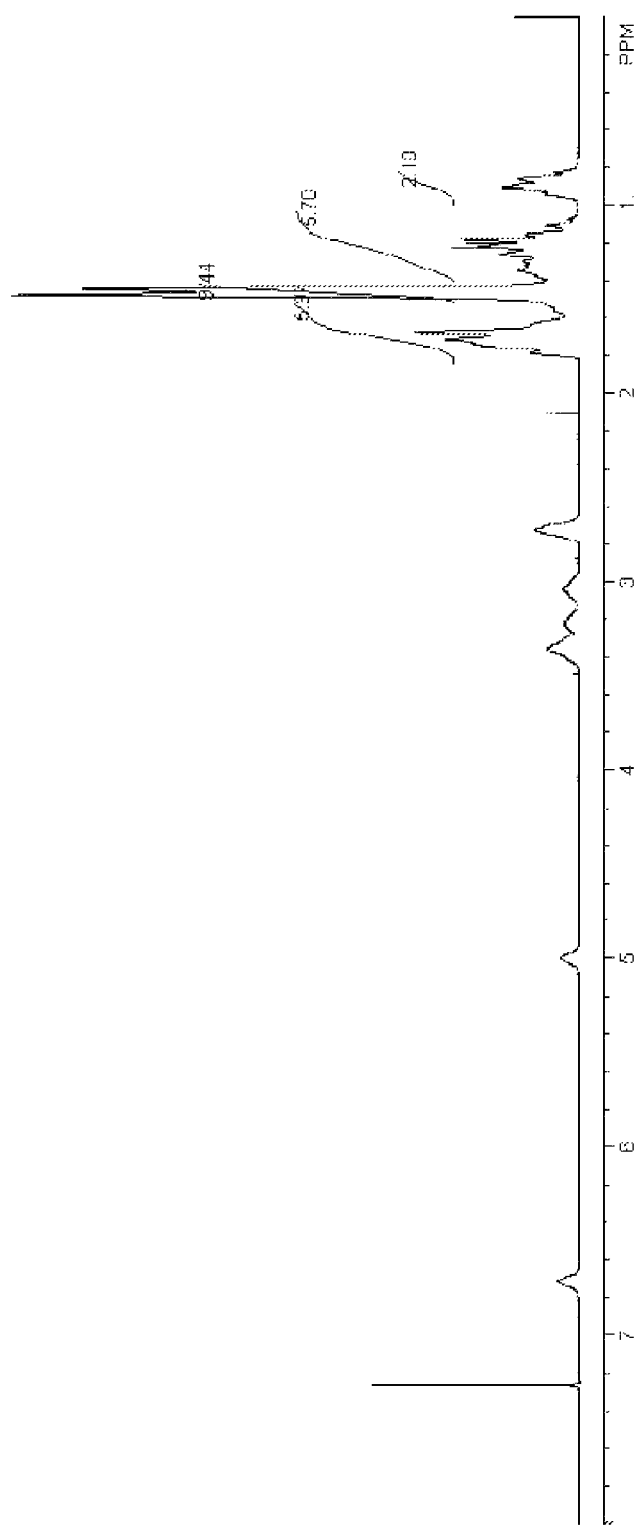
FIG. 53 is an $^1$H NMR spectrum of compound 9f shown in Table 10.
Figure 54:
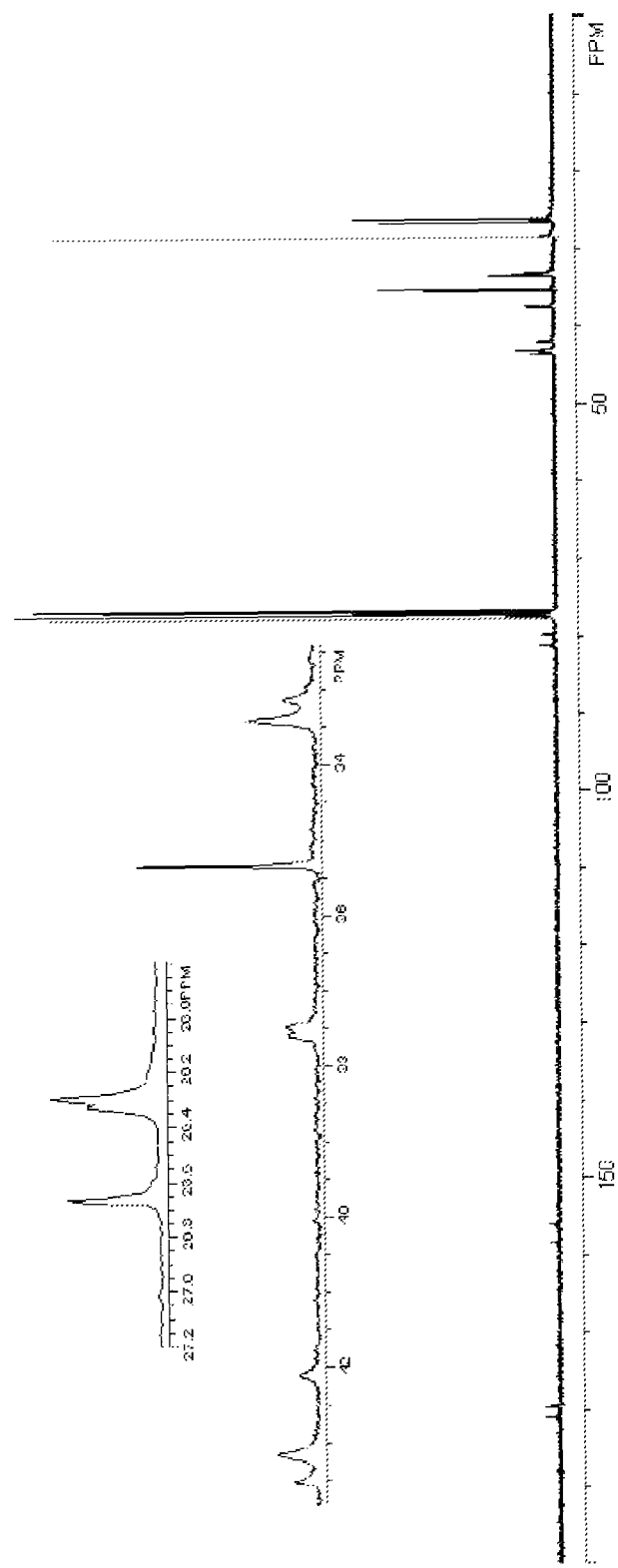
FIG. 54 is an $^{13}$C NMR spectrum of compound 9f shown in Table 10.

9f (S)-α-Cyclohexylmethyl-β²-Boc-amino acid (9f): White solid; mp=98-99° C.; TLC $R_f$=0.35 (MeOH/CH$_2$Cl$_2$, v/v, 1:10). $^1$H NMR (300 MHz, CDCl$_3$) δ 6.71 & 5.00 (br, 1H), 3.43-2.95 (m, 2H), 2.73 (br, 1H), 1.79-1.57 (m, 6H), 1.48-1.44 (m, 9H), 1.35-1.18 (m, 6H), 0.94-0.86 (m, 2H). $^{13}$C NMR (75 MHz, CDCl$_3$): δ 180.8 & 179.6, 81.3 & 79.8, 43.5 & 43.2, 42.1, 37.6 & 37.5, 35.3, 33.4 & 33.1, 28.6, 26.7, 26.32 & 26.29. TOF-MS-ESI: [M–H]⁻ calculated 284.2, found 284.6; [2M–H]⁻ calculated 569.4, found 570.2. FIGS. 53 and 54. Optical rotation: $[\alpha]^{rt}_D$=−27.1° (c=1.0, CH$_2$Cl$_2$). (Optical rotation of this compound in MeOH is weak ($[\alpha]^{rt}_D$=~+1.0° (c=5.0, MeOH)), and such a small reading is not reliable).

Example 38

β²-Homoglutamic Acid (13a)

β²-Homoglutamic Acid (13a): The aldehyde precursor used for the synthesis of Fmoc-β²-Glu(t-Bu) was prepared by modification of a previously reported method. (Lelais, G.; Campo, M. A.; Kopp, S.; Seebach, D. *Helv. Chim. Acta* 2004, 87, 1545-1560). Briefly, glutaric anhydride was allowed to react with t-butanol to yield mono t-butyl glutarate S1. The carboxylic acid was converted to the corresponding Weinreb amide (S2) and subsequently reduced with DIBAL-H to yield aldehyde 10a. Aldehyde 10a was subjected to the diastereoselective Mannich reaction conditions to afford N,N-disubstituted amino alcohol 11a. Hydrogenolysis followed by Fmoc-protection and oxidation yielded Fmoc-β²-Glu(t-Bu) 13a, which suitable for use in solid phase peptide synthesis Example 39

Carboxylic Acid S1

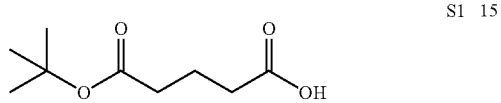

S1

Figure 55:
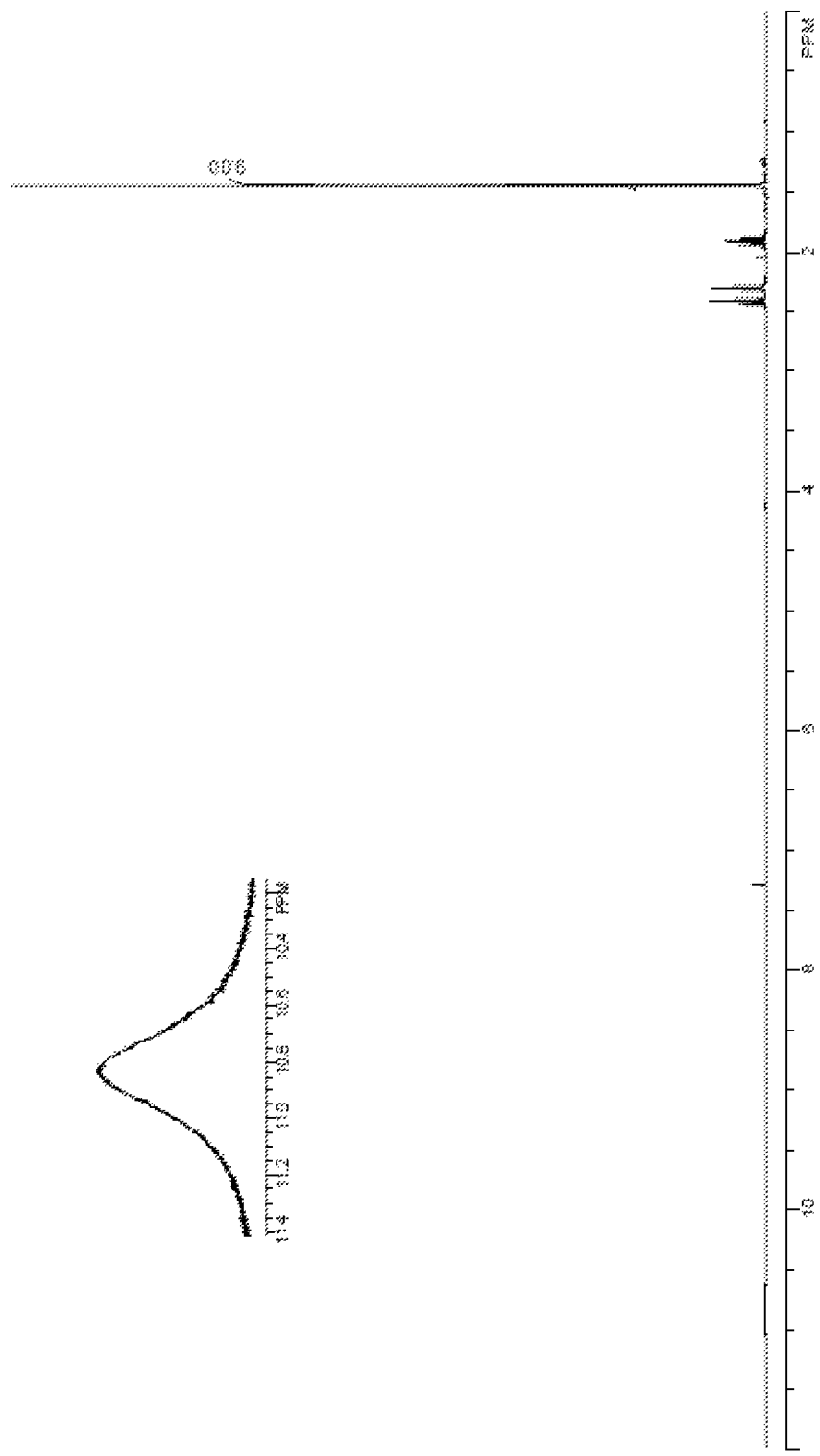
FIG. 55 is an $^1$H NMR spectrum of compound S1 used in the synthesis of β2-Homoglutamic Acid.
Figure 56:
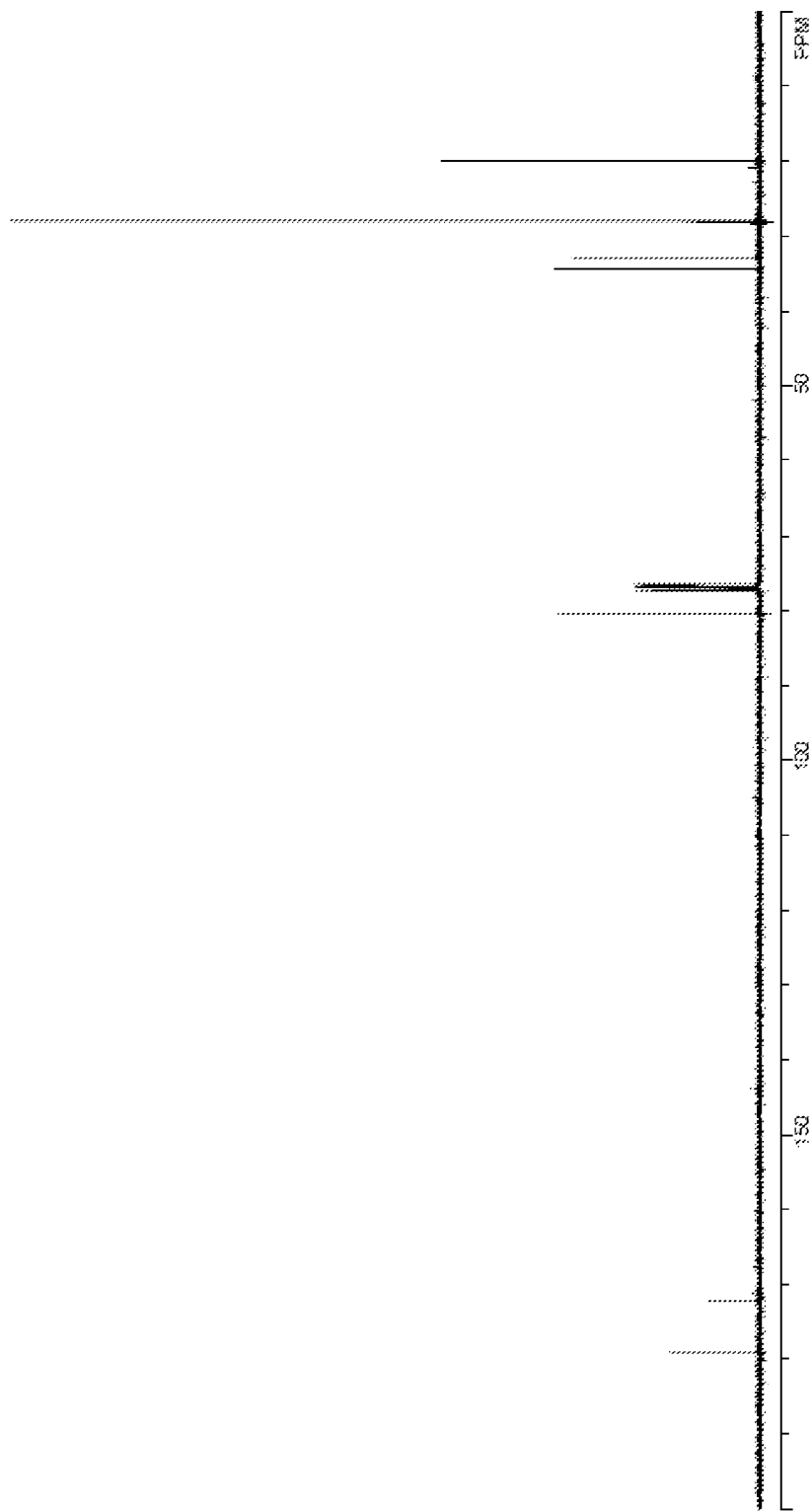
FIG. 56 is an $^{13}$C NMR spectrum of compound S1 used in the synthesis of β2-Homoglutamic Acid.

Carboxylic acid S1: Prepared as previously described in the literature. Glutaric anhydride (10.0 g, 87.6 mmol) was weighed into a dry flask and purged with N₂. Dry toluene (50 mL) was added followed by N-hydroxysuccinimide (3.0 g, 26.1 mmol), 4-dimethylaminopyridine (1.07 g, 8.8 mmol), anhydrous tert-butanol (24.3 mL, 262.3 mmol), and triethylamine (3.6 ml, 25.8 mmol). The flask was fitted with a reflux condenser, heated to 115° C., and allowed to stir for 16 h under N₂. The solution was cooled to room temperature, diluted with 300 mL EtOAc, and washed with 5% aqueous NaHSO₄ (3×) followed by brine. The organic layer was dried over MgSO₄, filtered and concentrated. The crude material was purified by chromatography eluting with 1:1 hexanes/EtOAc to yield 4.48 g (27% yield) of the product as a colorless oil. TLC R$_f$=0.34 (EtOAc/hexanes, v/v, 1:1). ¹HNMR (300 MHz, CDCl₃): δ 10.83 (br s, 1H), 2.42 (t, J=7.4 Hz, 2H), 2.31 (t, J=2.31 Hz, 2H), 1.92 (m, 2H), 1.45 (s, 9H). FIG. 55. ¹³CNMR (75 MHz, CDCl₃): δ 179.2, 172.3, 80.5, 34.4, 33.0, 28.0, 20.0. FIG. 56. ESI-TOF-MS: [M–H]⁻ calculated 187.1, found 187.4.

Example 40

Weinreb Amide S2

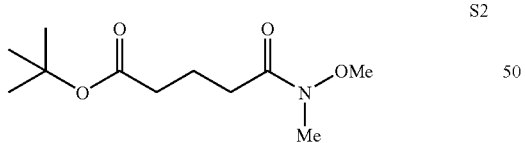

S2

Figure 57:
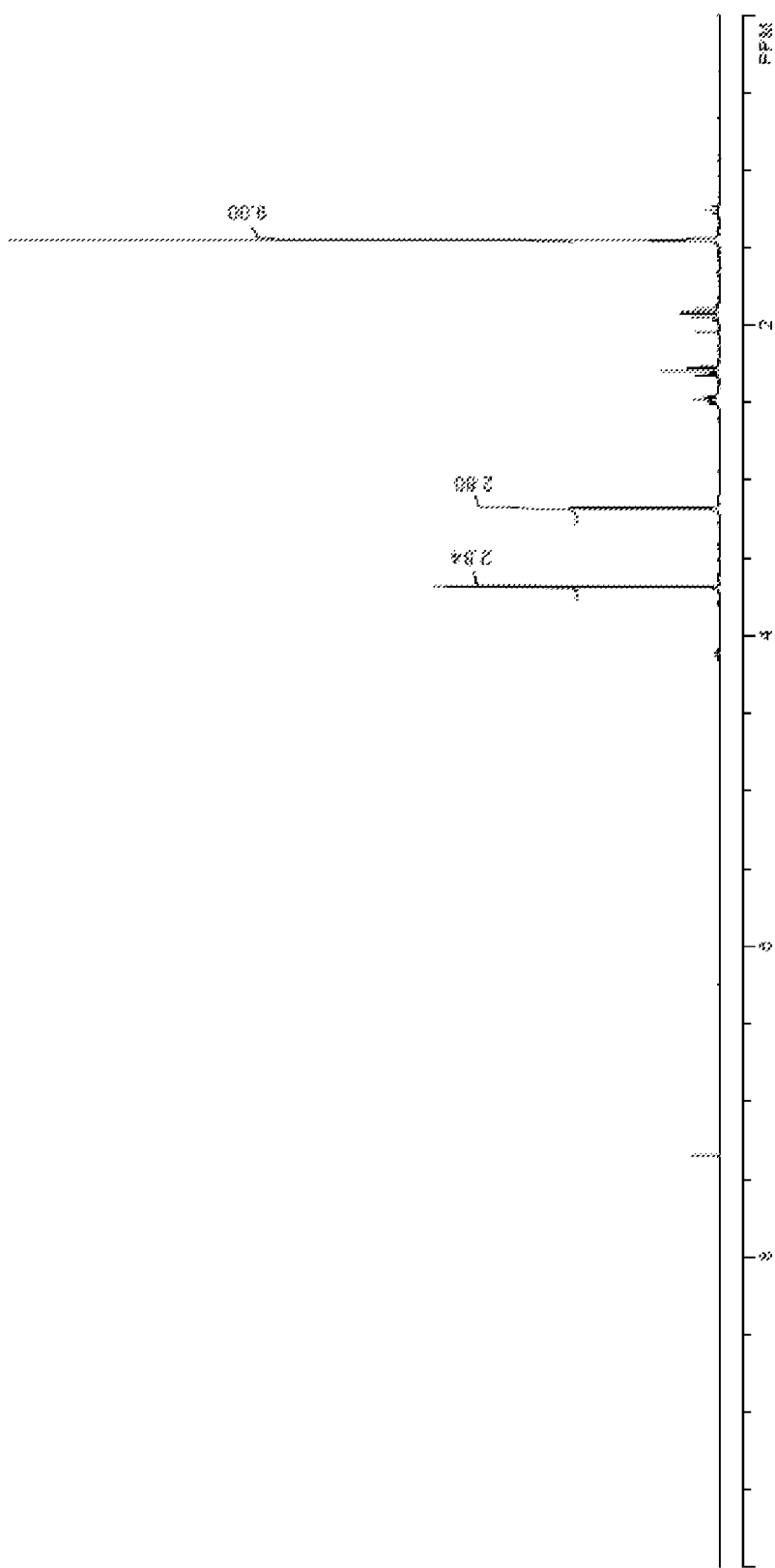
FIG. 57 is an $^1$H NMR spectrum of Weinreb amide S2 used in the synthesis of β2-Homoglutamic Acid
Figure 58:
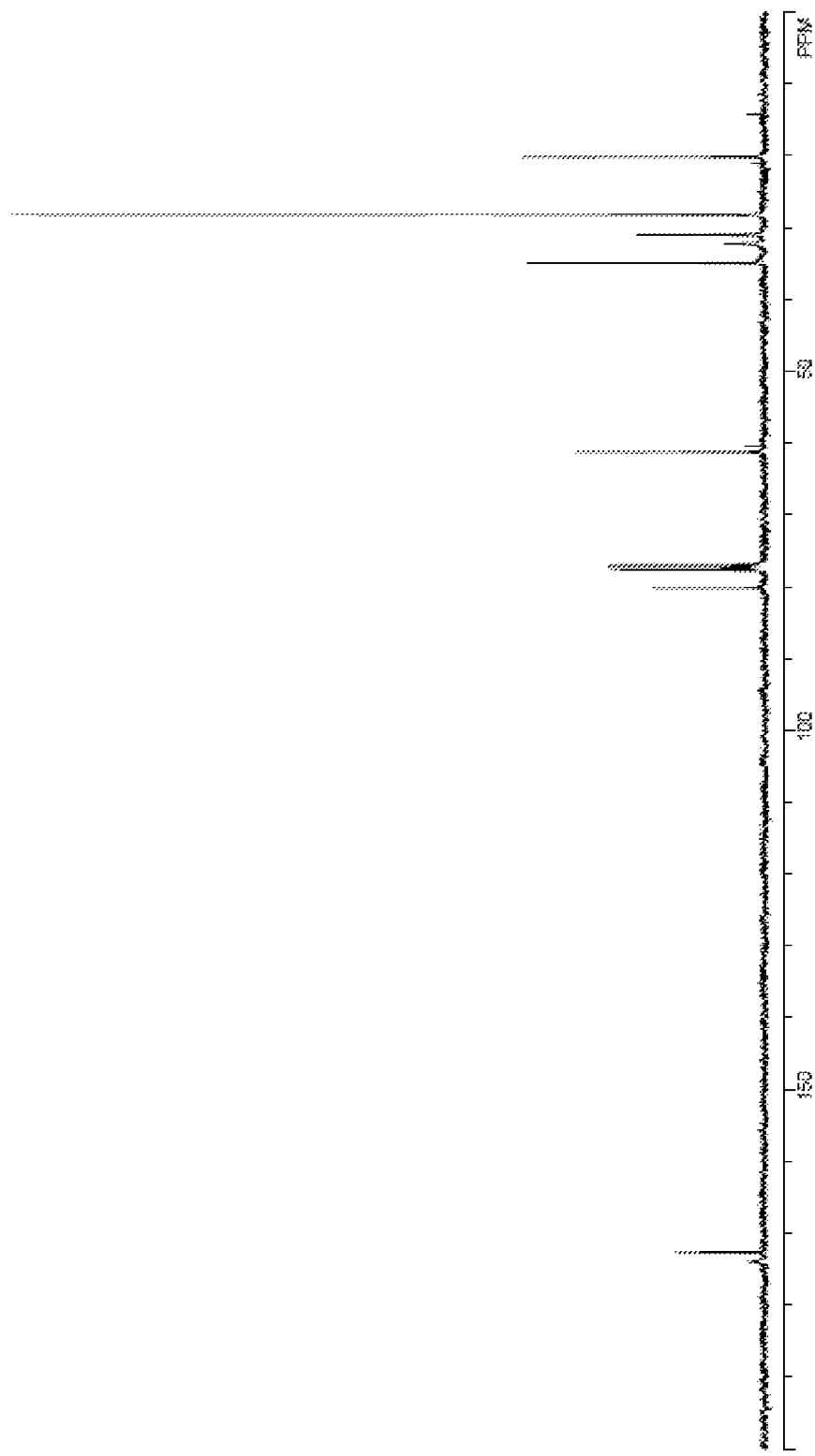
FIG. 58 is an $^{13}$C NMR spectrum of Weinreb amide S2 used in the synthesis of β2-Homoglutamic Acid.

Weinreb amide S2: Prepared by a modification of a literature method. The starting carboxylic acid S1 (4.4 g, 23.4 mmol) was dissolved in CH₂Cl₂ (100 mL). N,O-dimethylhydroxylamine.HCl (2.51 g, 25.7 mmol), 1-hydroxybenzotriazole hydrate (3.93 g, 25.7 mmol), diisopropylethylamine (9.0 mL, 51.7 mmol), and EDC.HCl (4.93 g, 25.7 mmol) were added sequentially to the reaction mixture. The solution was allowed to stir at room temperature for 2 h and then concentrated under vacuum to remove most of the CH₂Cl₂. The crude material was diluted with EtOAc (300 mL), and washed successively with 5% aqueous NaHSO₄ (3×), 5% aqueous NaHCO₃ (3×), and brine. The organic layer was dried over MgSO₄, filtered and concentrated to afford 5.14 g (95% yield) of the product as a pale yellow oil which was used without further purification. TLC R$_f$=0.44 (EtOAc/hexanes, v/v, 1:2). ¹HNMR (300 MHz, CDCl₃) δ 3.68 (s, 3H), 3.18 (s, 3H), 2.48 (t, J=7.4 Hz, 2H), 2.30 (t, J=7.4 Hz, 2H), 1.92 (m, 2H), 1.45 (s, 9H), FIG. 57. ¹³CNMR (75 MHz, CDCl₃) δ 174.0, 172.7, 80.2, 77.5, 61.3, 35.0, 32.3, 31.0, 28.2, 20.2, FIG. 58. ESI-TOF-MS: [M+H]⁺ calculated 232.2, found 232.4.

Example 40

Aldehyde 10a

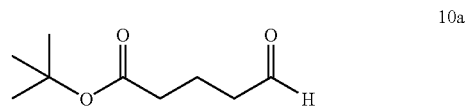

10a

Figure 59:
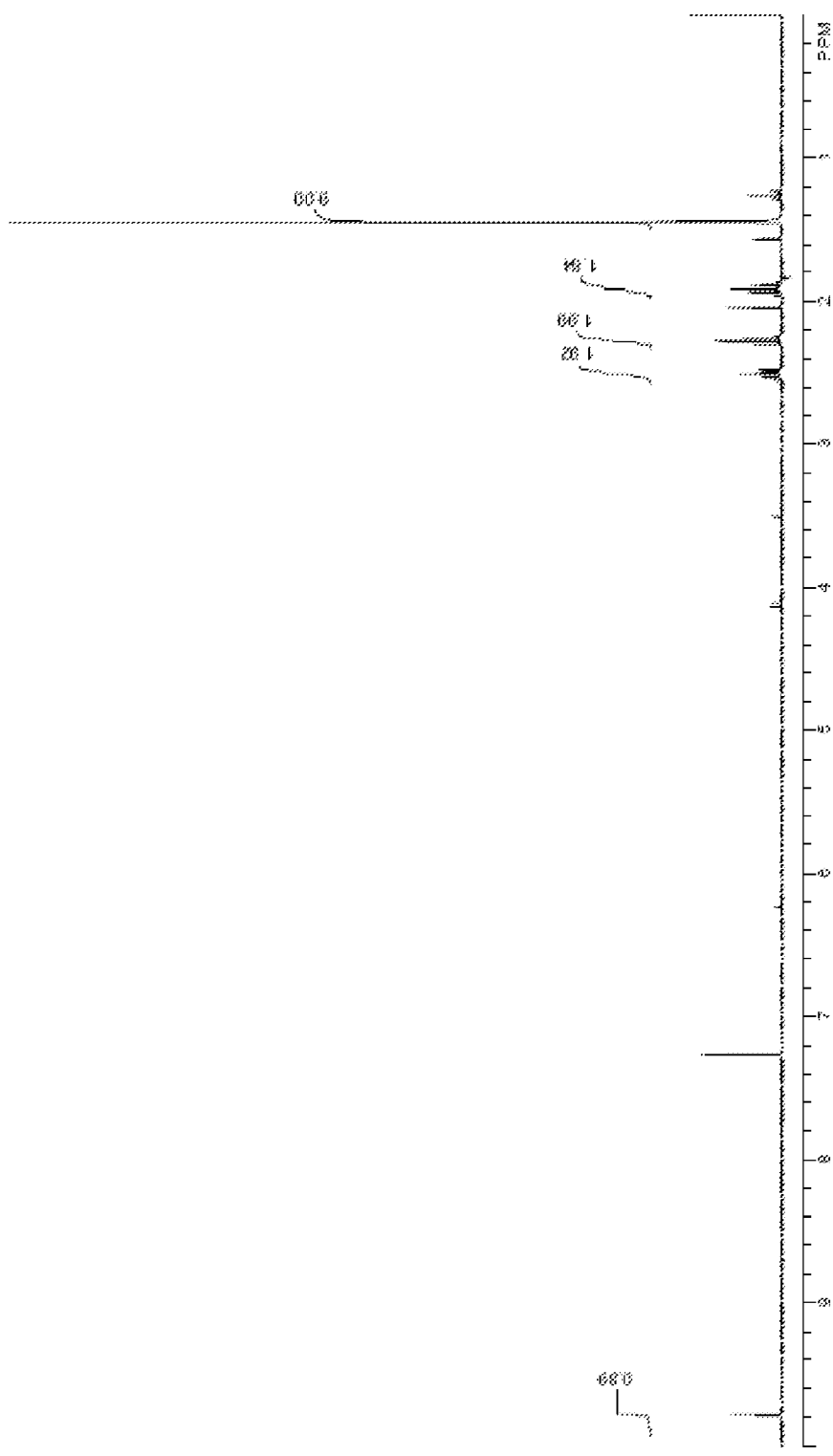
FIG. 59 is an $^1$H NMR spectrum of Aldehyde 10a used in the synthesis of β2-Homoglutamic Acid.
Figure 60:
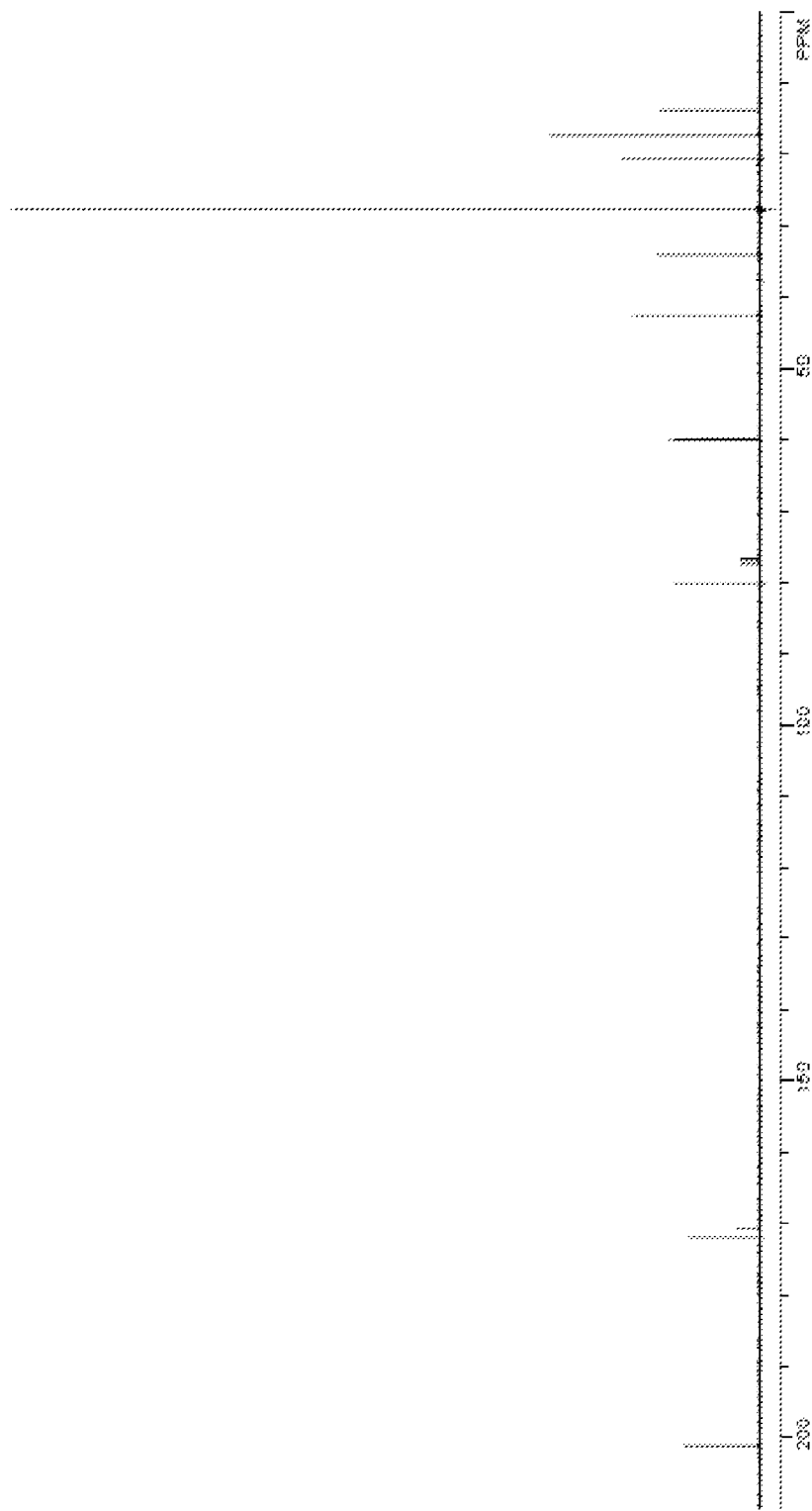
FIG. 60 is an $^{13}$C NMR spectrum of Weinreb amide S2 used in the synthesis of β2-Homoglutamic Acid.

Aldehyde 10a: Weinreb amide S2 (5.0 g, 21.6 mmol) was dissolved in dry THF (100 mL) and the solution was cooled to 0° C. under N₂. Diisobutylaluminum hydride (43 mL of a 1.0 M solution in CH₂Cl₂, 43 mmol) was added over 5 min. The reaction mixture was allowed to stir at 0° C. for 30 min and then quenched by slow addition of EtOAc (50 mL). The solution was poured into water (200 mL) and extracted with EtOAc (2×400 mL). The combined organic layers were washed successively with satd. NaHCO₃ (100 mL) and brine (100 mL), dried over MgSO₄, filtered and concentrated. The crude material was purified by chromatography eluting with 3:1 hexanes/EtOAc to yield 2.2 g (59% yield) of the product as a colorless oil. TLC R$_f$=0.76 (EtOAc/hexanes, v/v, 1:2). ¹HNMR (300 MHz, CDCl₃) δ 9.78 (t, J=1.4 Hz, 1H), 2.51 (td, J=7.3 Hz, 1.4 Hz, 2H), 2.28 (t, J=7.3 Hz, 2H), 1.92 (m, 2H), 1.45 (s, 9H), FIG. 59. ¹³CNMR (75 MHz, CDCl₃) δ 201.2, 171.9, 80.0, 42.7, 34.1, 27.8, 17.3, FIG. 60. ESI-TOF-MS: [M+Na]⁺ calculated 195.1, found 195.1.

Example 41

(S)-β-Carboxyethyl-tert-butyl ester-γ-(S)—N-benzyl-α-methylbenzyl amino alcohol (11a)

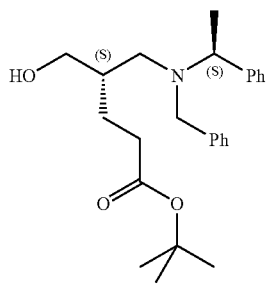

Figure 61:
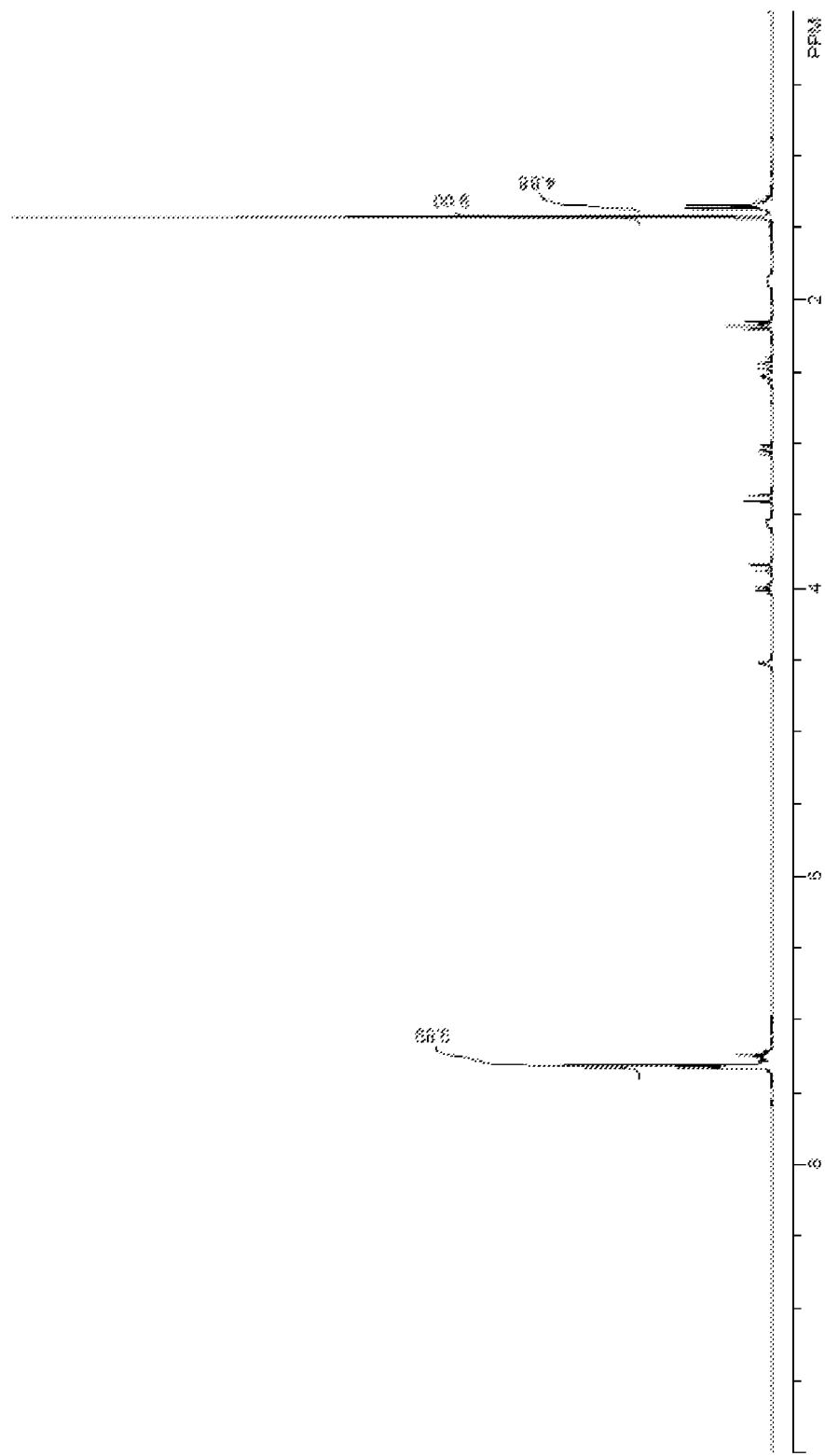
FIG. 61 is an $^1$H NMR spectrum of compound 11a used in the synthesis of β2-Homoglutamic Acid.
Figure 62:
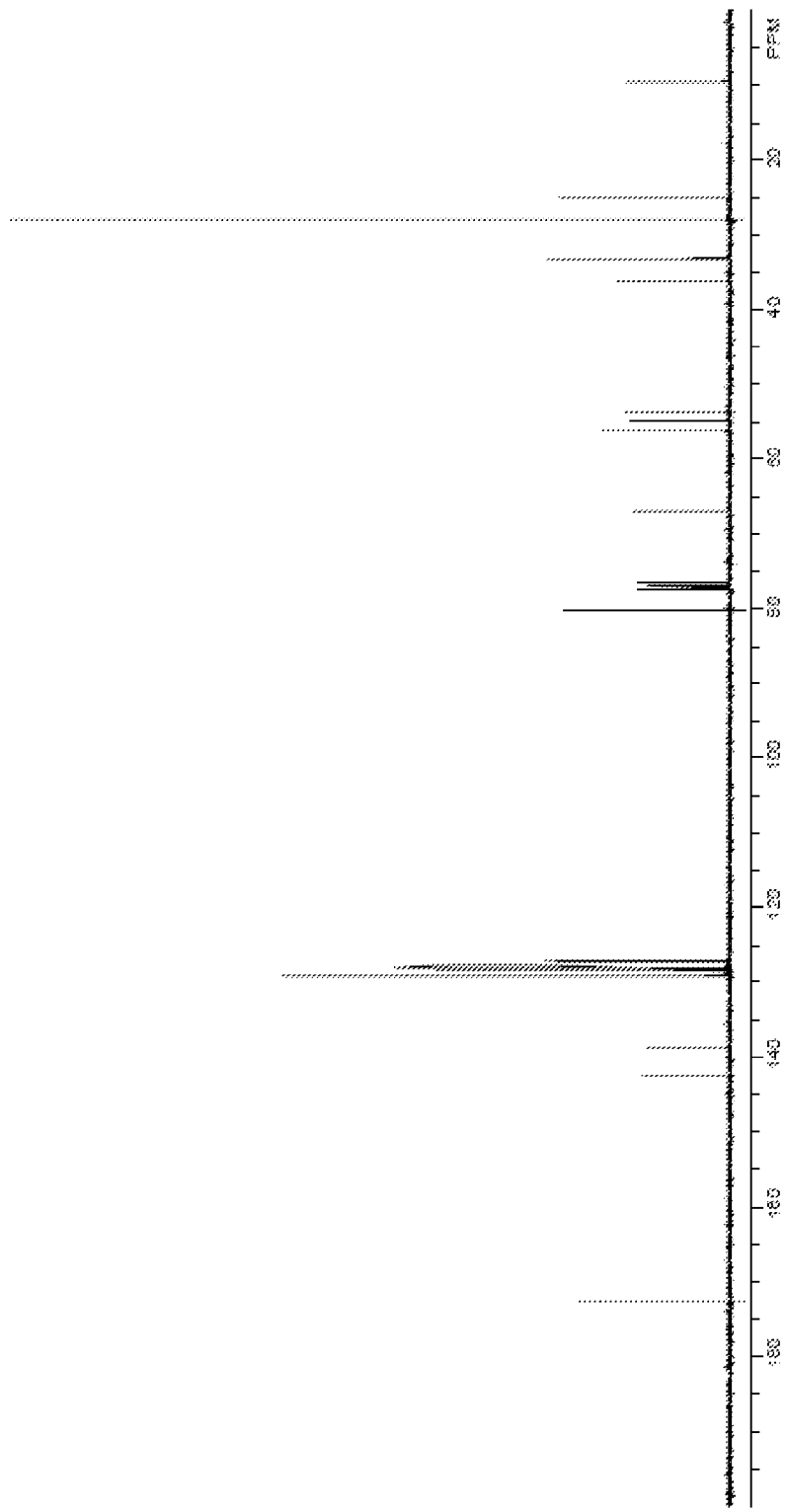
FIG. 62 is an $^{13}$C NMR spectrum of compound 11a used in the synthesis of β2-Homoglutamic Acid.

11a (S)-β-Carboxyethyl-tert-butyl ester-γ-(S)—N-benzyl-α-methylbenzyl amino alcohol (11a): L-Proline (40 mg, 0.35 mmol) was suspended in DMF (2 ml) and allowed to stir at room temperature overnight. The mixture was then cooled to −25° C. in a temperature-regulated cooling bath. Aldehyde 10a (300 mg, 1.74 mmol) in DMF (0.5 mL) was added followed by N,O-acetal 3 (296 mg, 1.16 mmol) in DMF (0.5 mL). The reaction mixture was allowed to stir at −25° C. for 2 h, ¹H NMR analysis indicated complete conversion of the limiting reagent, and then warmed to 0° C. (Addition of NaBH$_4$ (and MeOH) at −25° C., and then replacement of the −25° C. bath with an ice bath was used in the synthesis shown in Table 10 and for β$^2$-homolysine. Although no studies were performed to compare the difference of these two procedures, addition of NaBH$_4$ at −25° C. before the switch to an ice bath is recommended). NaBH$_4$ (174 mg, 4.6 mmol) was added followed by MeOH (1 mL). The reaction mixture was allowed to stir at 0° C. for 20 min. and then transferred slowly into a solution of saturated aqueous. NH$_4$Cl (10 mL). The resulting milky suspension was extracted with Et$_2$O (3×30 mL). The organic extracts were combined, washed with brine, dried over MgSO$_4$, filtered and concentrated. The crude material was purified by chromatography eluting with 4:1 hexanes/EtOAc to yield 207 mg (45% yield) of the desired product (the major diastereomer) as a colorless oil. TLC R$_f$=0.58 (EtOAc/hexanes, v/v, 1:2). $^1$HNMR (300 MHz, CDCl$_3$) δ 7.40-7.20 (m, 10H), 4.52 (br s, 1H), 4.01 (q, J=6.9 Hz, 1H), 3.86 (d, J=13.2 Hz, 1H), 3.55 (m, 1H), 3.38 (d, J=13.2 Hz, 1H), 3.04 (dd, J=10.8 Hz, 8.0 Hz, 1H), 2.55 (m, 1H), 2.44 (dd, J=12.8, 10.8 Hz, 1H), 2.18 (t, J=7.7 Hz, 2H), 1.88 (m, 1H), 1.42 (s, 9H), 1.35 (d, J=6.9 Hz, 3H), 1.40-1.30 (m, 2H), FIG. 61. $^{13}$CNMR (75 MHz, CDCl$_3$) δ 172.1, 142.4, 138.7, 129.1, 128.4, 128.1, 128.0, 127.2, 127.0, 80.2, 66.9, 56.2, 54.8, 53.7, 36.3, 33.1, 28.0, 25.0, 9.5, FIG. 62. ESI-TOF-HRMS: [M+H]$^+$ calculated 398.2695, found 398.2693. Optical rotation: [α]$^{rt}_D$=+38.0° (c=0.5, CHCl$_3$).

Example 42

(S)-β-Carboxyethyl-tert-butyl ester-γ-Fmoc-amino alcohol (12a)

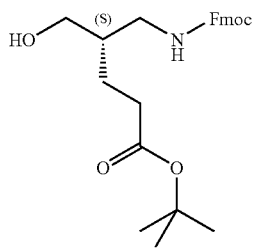

Figure 63:
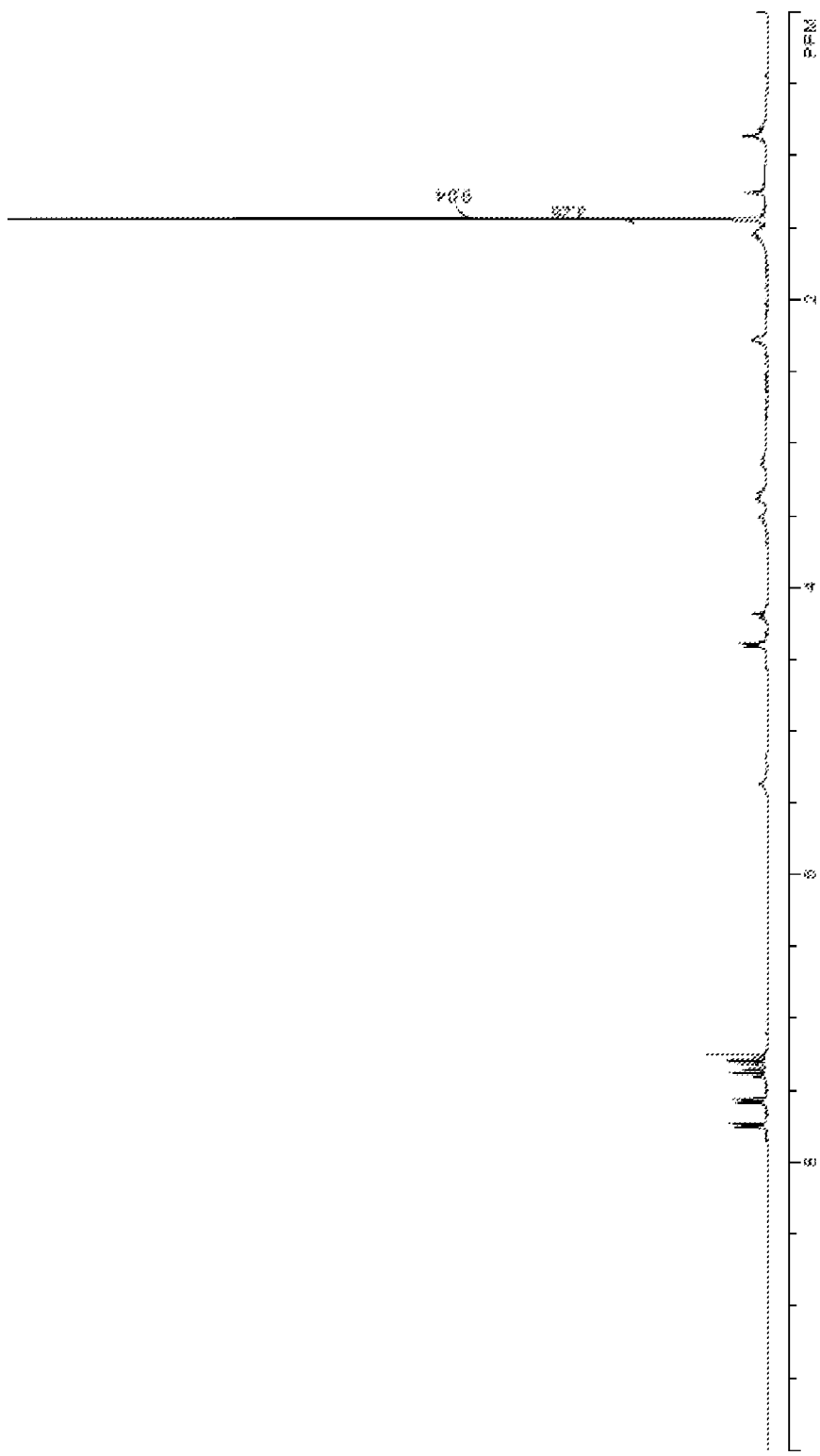
FIG. 63 is an $^1$H NMR spectrum of compound 12a used in the synthesis of β2-Homoglutamic Acid.
Figure 64:
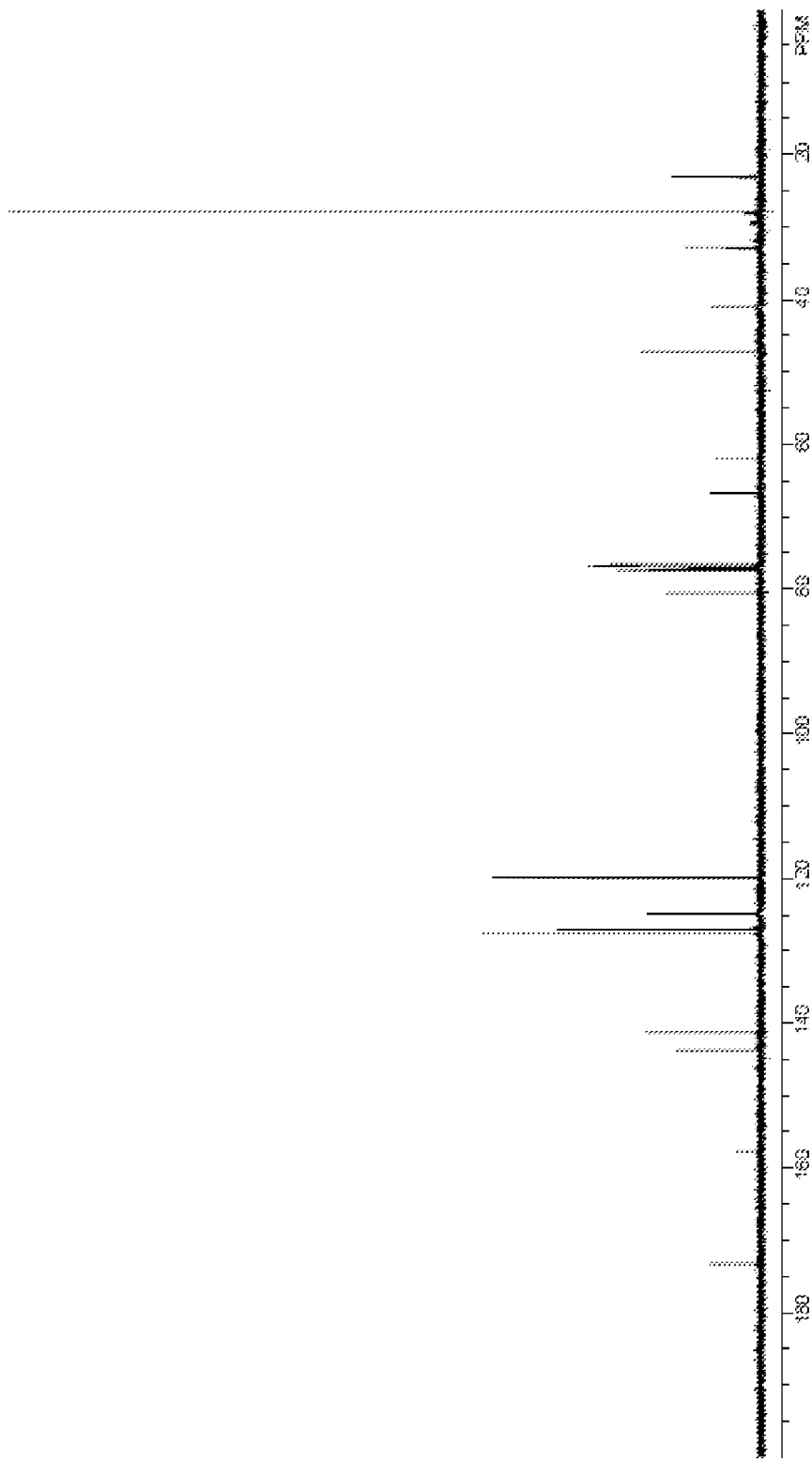
FIG. 64 is an $^{13}$C NMR spectrum of compound 12a used in the synthesis of β2-Homoglutamic Acid.

12a (S)-β-Carboxyethyl-tert-butyl ester-γ-Fmoc-amino alcohol (12a): Benzyl protected amino alcohol 11a (282 mg, 0.71 mmol) was dissolved in MeOH (10 mL) under N$_2$. Ammonium formate (448 mg, 7.10 mmol) was added followed by Pd/C (282 mg of 10 wt. % on activated carbon, wet). The reaction mixture was refluxed overnight. The mixture was cooled to room temperature and filtered over celite with thorough MeOH washes of the filter agent to recover all product. The filtrate was concentrated to a residue to which CH$_2$Cl$_2$ (7 mL) was added followed by diisopropylethylamine (123 µL, 0.71 mmol) and Fmoc N-hydroxysuccinimide ester (239 mg, 0.71 mmol). The reaction mixture was allowed to stir at room temperature for 1 h. The solution was diluted with EtOAc (70 mL) and washed successively with 5% aqueous NaHSO$_4$, 5% aqueous NaHCO$_3$, and brine. The organic layer was dried over MgSO$_4$, filtered and concentrated. The crude material was purified by chromatography eluting with 2:1 to 1:1 hexanes/EtOAc to yield 240 mg (80% yield) of the product as a colorless oil. TLC R$_f$=0.43 (EtOAc/hexanes, v/v, 1:1). $^1$HNMR (300 MHz, CDCl$_3$) δ 7.74 (d, J=7.6 Hz, 2H), 7.58 (d, J=7.6 Hz, 2H), 7.38 (t, J=7.6 Hz, 2H), 7.29 (td, J=7.6 Hz, 1.3 Hz, 2H), 5.37 (t, J=7.2 Hz, 1H), 4.41 (d, J=6.9 Hz, 2H), 4.19 (t, J=6.9 Hz, 1H), 3.6-3.0 (m, 5H), 2.28 (m, 2H), 1.55 (m, 3H), 1.44 (s, 9H), FIG. 63. $^{13}$CNMR (75 MHz, CDCl$_3$) δ 173.3, 157.6, 143.80, 143.78, 141.3, 127.6, 127.0, 124.9, 119.9, 80.6, 77.2, 66.7, 62.1, 47.2, 41.03, 40.99, 32.9, 28.0, 23.1, FIG. 64. ESI-TOF-HRMS: [M+Na]$^+$ calculated 448.2100, found 448.2101. Optical rotation: [α]$^{rt}_D$=+8.8° (c=0.5, CH$_2$Cl$_2$).

Example 43

(S)-Fmoc-β$^2$-Homoglutamic Acid Tert-Butyl Ester (13a)

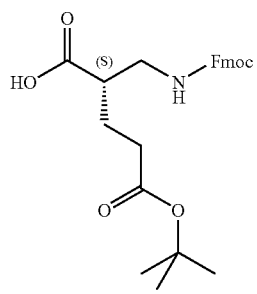

Figure 65:
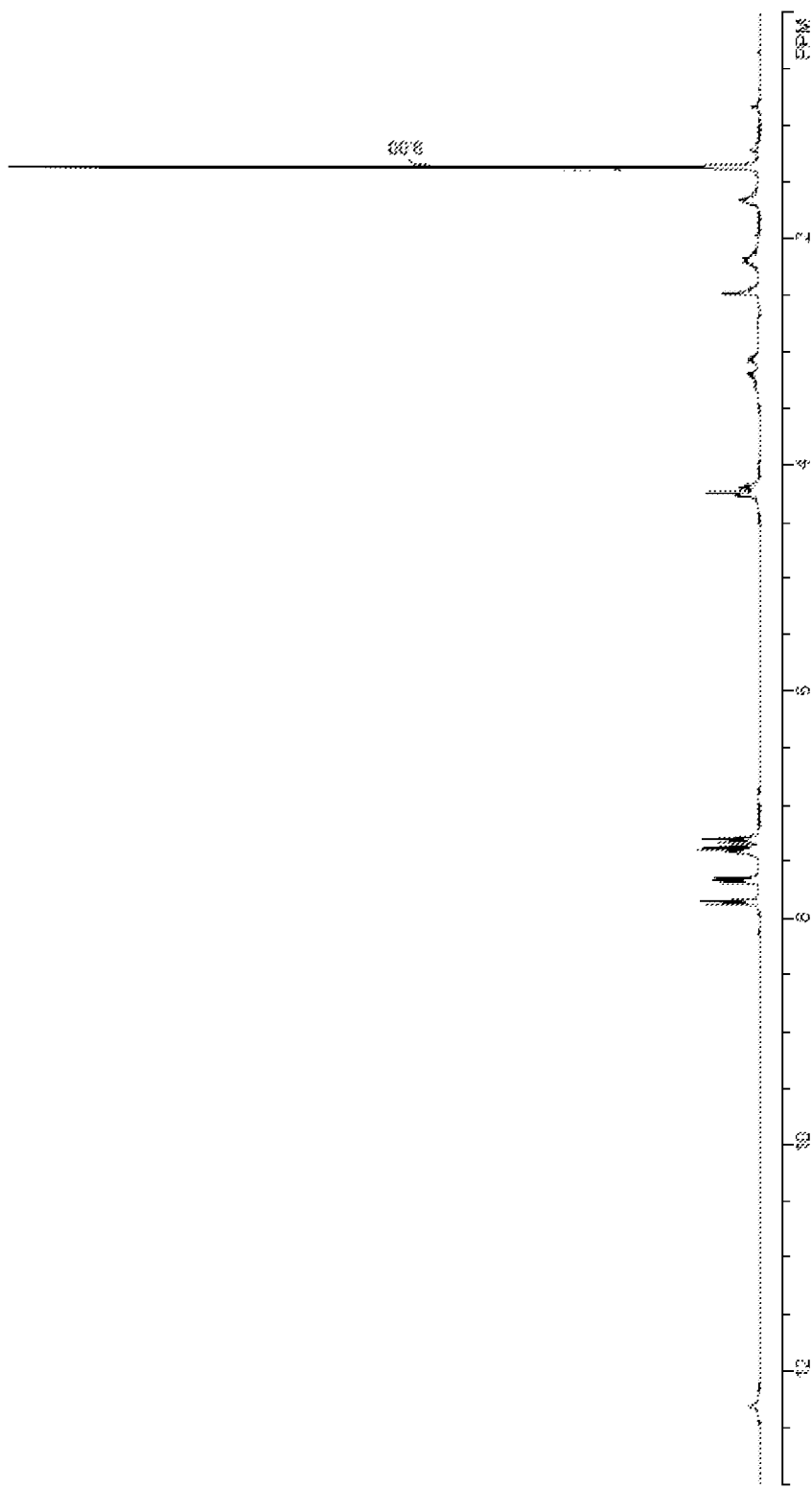
FIG. 65 is an $^1$H NMR spectrum of compound 13a used in the synthesis of β2-Homoglutamic Acid.
Figure 66:
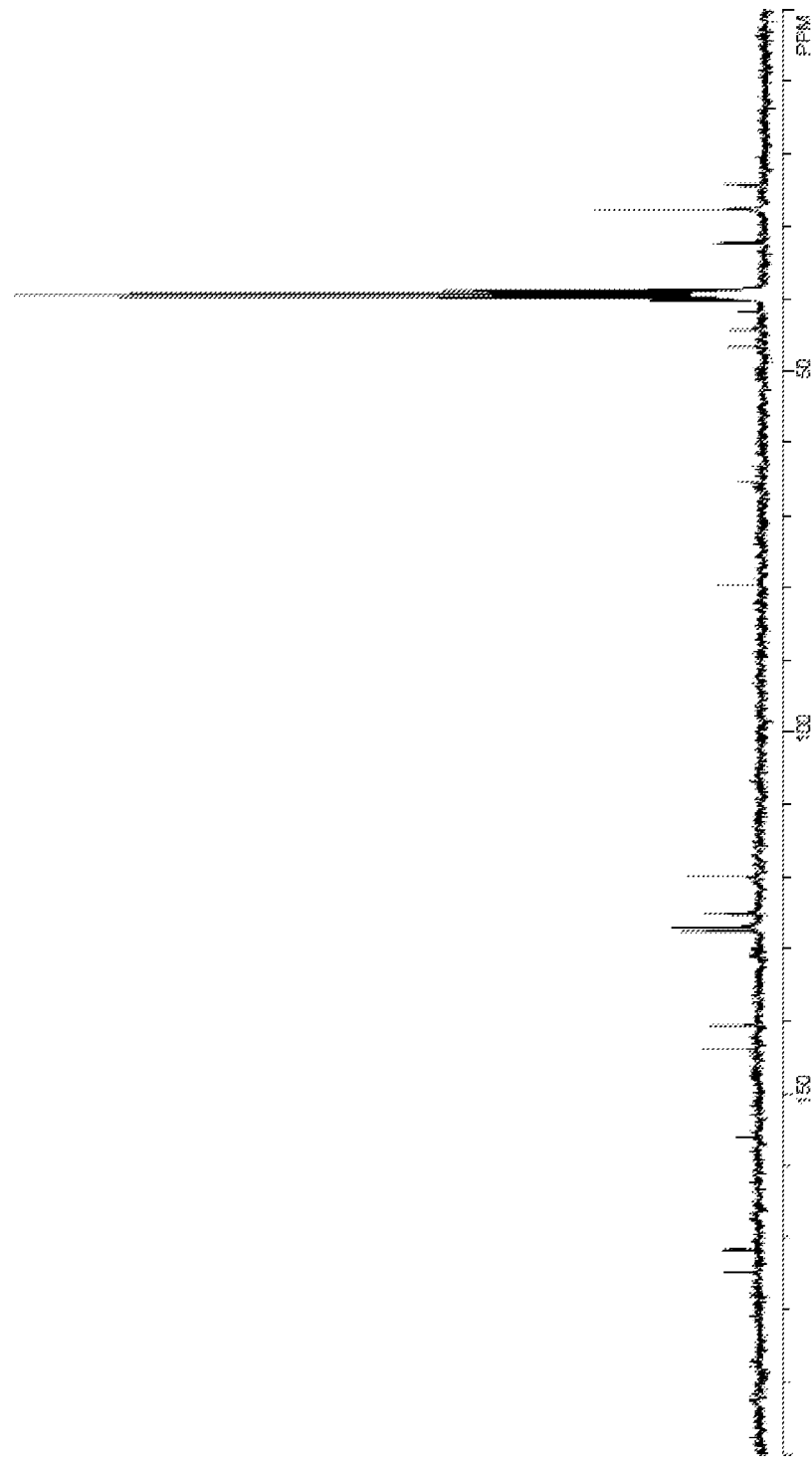
FIG. 66 is an $^{13}$C NMR spectrum of compound 13a used in the synthesis of β2-Homoglutamic Acid.

13a (S)-Fmoc-β$^2$-homoglutamic acid tert-butyl ester (13a): Fmoc-amino alcohol 12a (185 mg, 0.44 mmol) was dissolved in acetone (4 mL) and cooled to 0° C. Jones reagent (1.75 mL of a 0.5 M H$_2$Cr$_2$O$_7$ solution in H$_2$O, 0.88 mmol) was added dropwise. The reaction mixture was warmed to room temperature and allowed to stir for 2 h. i-PrOH (1 mL) was added, and the reaction mixture was allowed to stir for an additional 15 min. to quench the remaining Jones reagent. The reaction mixture was partitioned between H$_2$O (50 mL) and EtOAc (150 mL). The organic layer was separated, dried over MgSO$_4$, filtered and concentrated. The crude material was purified by chromatography eluting with 60:40:1 hexanes/EtOAc/AcOH to yield 129 mg (68% yield) of the product as a colorless oil. The product could be obtained as a solid by dissolving the oil in minimal EtOAc followed by dilution with heptane, overnight refrigeration, and filtration to collect the product as a white solid. mp=1118-120° C. TLC R$_f$=0.47 (MeOH/CH$_2$Cl$_2$, v/v, 1:9). $^1$HNMR (300 MHz, DMSO-d$_6$) δ 12.32 (br s, 1H), 7.86 (d, J=7.3 Hz, 2H), 7.67 (d, J=7.4 Hz, 2H), 7.50-7.35 (m, 3H), 7.31 (t, J=7.4 Hz, 2H), 4.35-4.15 (m, 3H), 3.21 (m, 1H), 3.06 (m, 1H), 2.45 (m, 1H), 2.21 (m, 2H), 1.66 (m, 2H), 1.36 (s, 9H), FIG. 65. $^{13}$CNMR (75 MHz, DMSO-d$_6$) δ 175.6, 172.3, 156.8, 144.6, 141.4, 128.3, 127.7, 125.9, 120.8, 80.3, 66.1, 47.4, 45.0, 42.6, 33.1, 28.4, 25.0, FIG. 66. ESI-TOF HRMS (m/z) [M−H]$^−$ obsd.=438.1904 (calc.=438.1917). Optical rotation: [α]$^{rt}_D$=+1.0° (c=1.0, CHCl$_3$).

β$^2$-Homotyrosine (13b): The aldehyde precursor 10b used for the synthesis of β$^2$-homotyrosine (13b) was prepared from p-cresol as outlined below.

Example 44

1-tert-Butoxy-4-methylbenzene (S3)

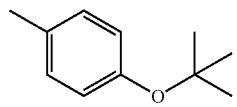

S3

Figure 67:
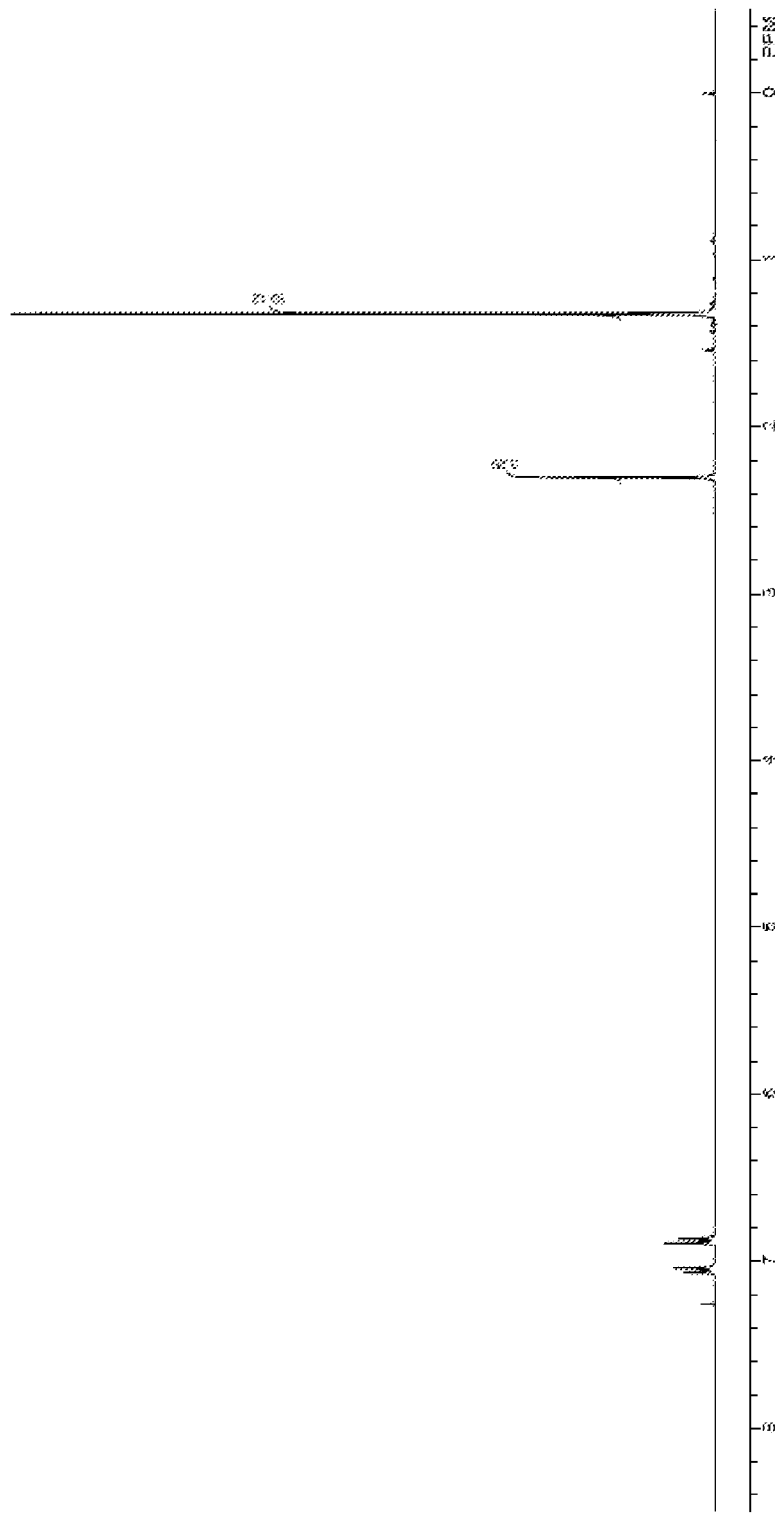
FIG. 67 is an $^1$H NMR spectrum of compound S3 used in the synthesis of β2-Homotyrosine.
Figure 68:
FIG. 68 is an $^{13}$C NMR spectrum of compound S3 used in the synthesis of β2-Homotyrosine.

1-tert-Butoxy-4-methylbenzene (S3): A solution of p-cresol (20 g, 185 mmol) in anhydrous $CH_2Cl_2$ (370 mL) was cooled to −15° C. Catalytic conc. $H_2SO_4$ (1 mL) was added to the stirred solution. Isobutene gas was bubbled through the reaction mixture for 15 min. The reaction mixture was stirred under $N_2$ at −15° C. for an additional 20 min. Saturated aqueous $NaHCO_3$ was added to the reaction flask until reaction mixture was neutralized. [Caution: The reaction must be kept cold until the acid is completely quenched. Warmer temperatures result in extensive Friedel-Crafts alkylation side products. Under these conditions, the major side product is Friedel-Crafts alkylation ortho to the hydroxyl group.] The layers were separated, and the organic layer was collected and washed with 1 M aqueous NaOH. The combined aqueous layers were further extracted with $CH_2Cl_2$, and all the organic layers were combined, dried over $MgSO_4$, filtered and concentrated to give a crude product, from which the product was isolated via chromatography (19:1 Hexanes: EtOAc) as a clear oil (13.3 g, 44% yield); TLC $R_f$=0.64 (Hexanes/EtOAc, v/v, 7:3). $^1H$ NMR (300 MHz, CDCl3): 7.05 (m, 2H), 6.88 (m, 2H), 2.31 (s, 3H), 1.32 (s, 9H), FIG. 67. $^{13}C$ NMR (75 MHz, CDCl3): 153.1, 132.9, 129.5, 124.3, 78.2, 29.0, 20.9, FIG. 68. TOF-MS-ESI: [M+Na]$^+$ calculated 187.23, found 187.3.

Example 45

3-(4-tert-Butoxyphenyl)-propan-1-ol (S4)

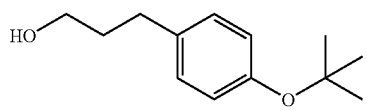

S4

Figure 69:
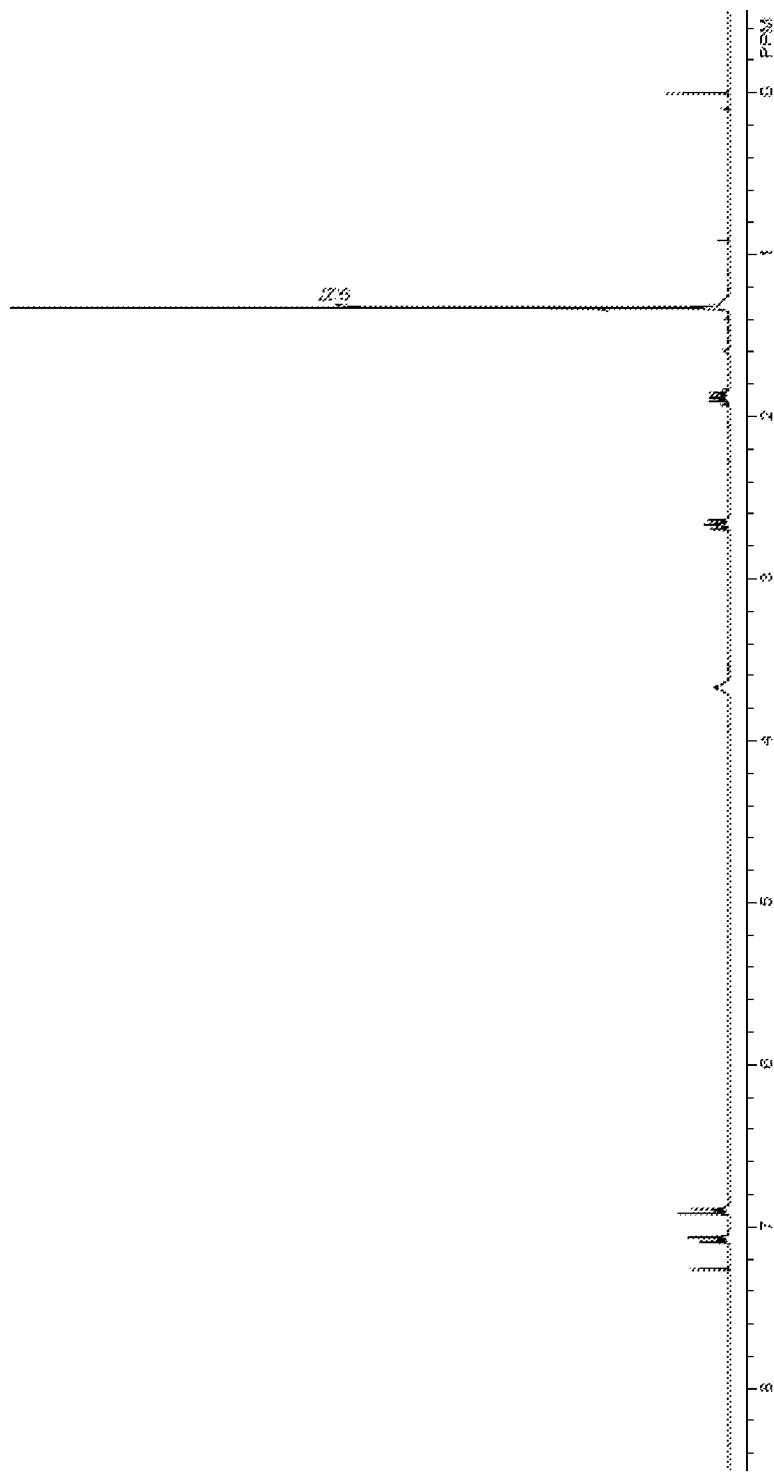
FIG. 69 is an $^1$H NMR spectrum of compound S4 used in the synthesis of β2-Homotyrosine.
Figure 70:
FIG. 70 is an $^{13}$C NMR spectrum of compound S4 used in the synthesis of β2-Homotyrosine.

3-(4-tert-Butoxyphenyl)-propan-1-ol (S4): A solution of 1-tert-Butoxy-4-methylbenzene (S3) (8.81 g, 53.7 mmol) in anhydrous THF (165 mL) was cooled to −15° C. under $N_2$. KO$^t$Bu (80.6 mL, 1 M in THF, 80.6 mmol) and n-BuLi (32.2 mL, 2.5 M in hexane, 80.6 mmol) were added; upon addition the reaction mixture turned a deep red color. After 1 h, (2-Bromoethoxy)-tert-butyl-dimethylsilane (17.3 mL, 80.6 mmol) was added by a syringe to the cold solution. The red color began to dissipate, and the reaction mixture was gradually warmed to room temperature and was stirred overnight under $N_2$. The reaction mixture was poured into a separation funnel containing 400 mL $H_2O$. The layers were separated, and the aqueous layer was extracted with EtOAc (3×200 mL). The extraction was monitored by TLC. The combined organic layers were dried over $MgSO_4$, filtered and concentrated to give an oil. The crude oil was filtered through a silica gel plug with excess EtOAc. The filtrates were collected and concentrated to give a yellow oil. The yellow oil was dissolved in anhydrous THF (85 mL). TBAF (85 mL, 1M in THF, 80.6 mmol) was added, and the reaction mixture was stirred at room temperature under $N_2$. After complete conversion of the silyl ether, the reaction was diluted with $H_2O$ (200 mL). The layers were separated, and the aqueous layer was extracted with EtOAc (3×100 mL). The combined organic layers were dried over $MgSO_4$, filtered and concentrated to give an oil. The crude oil was purified by chromatography (7:3 Hex: EtOAc) to yield 6.60 g product (59% yield) as a clear oil; TLC $R_f$=0.25 (Hex/EtOAc, v/v, 7:3). $^1H$ NMR (300 MHz, CDCl$_3$): 7.08 (m, 2H), 6.91 (m, 2H), 3.68 (m, 2H), 2.67 (m, 2H), 1.88 (m, 2H), 1.33 (s, 9H), FIG. 69. $^{13}C$ NMR (75 MHz, CDCl3): 153.6, 136.8, 128.9, 124.4, 78.3, 62.5, 34.5, 31.6, 29.0, FIG. 70. TOF-MS-ESI: [M+H]$^+$ calculated 209.30, found 209.1; [M+Na]$^+$ calculated 231.1, found 231.1; [2M+Na]$^+$ calculated 439.6, found 439.3.

Example 46

3-(4-tert-Butoxyphenyl)propionaldehyde (10b)

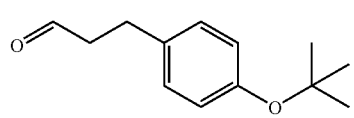

Figure 71:
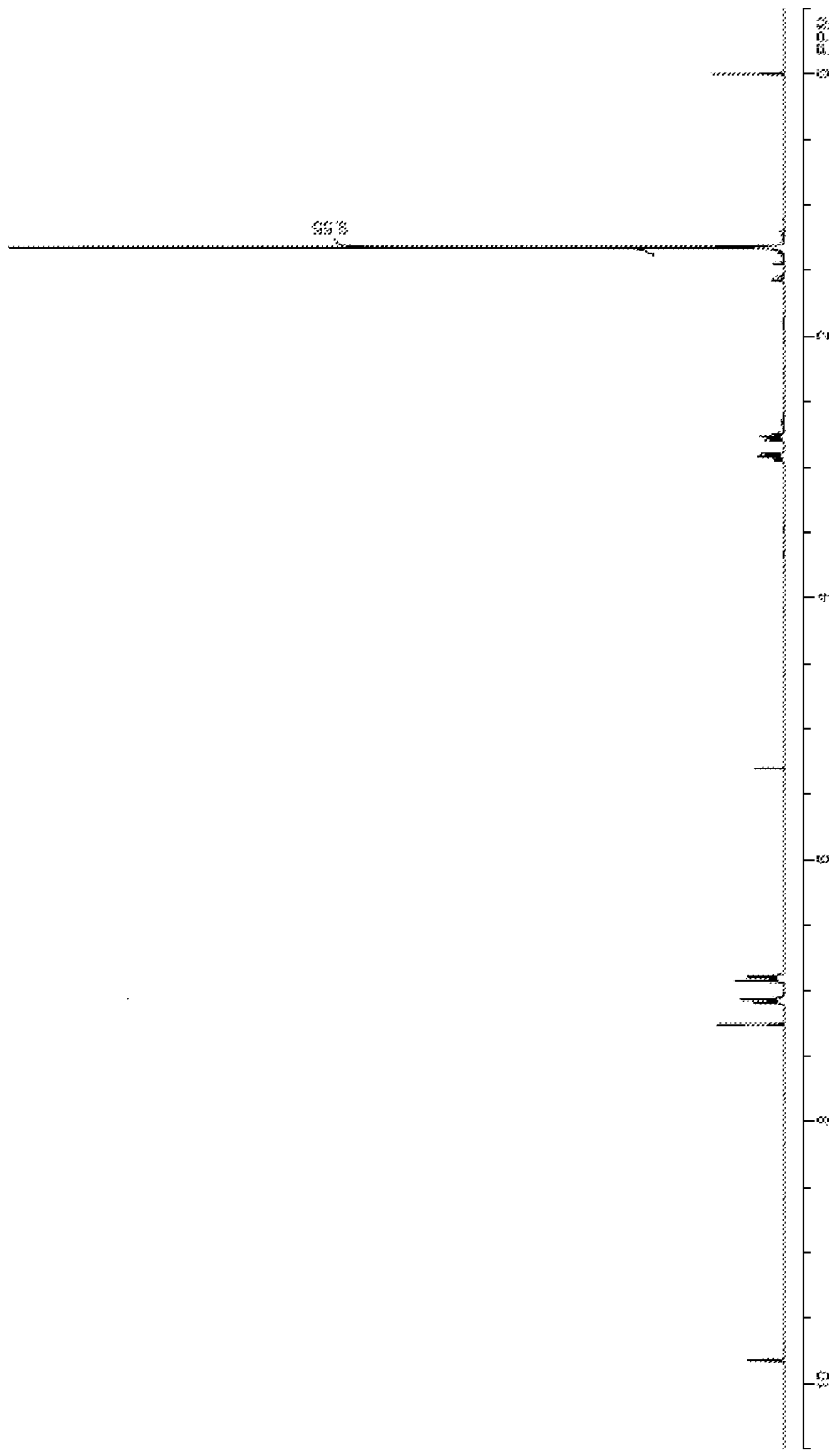
FIG. 71 is an $^1$H NMR spectrum of compound 10b used in the synthesis of β2-Homotyrosine.
Figure 72:
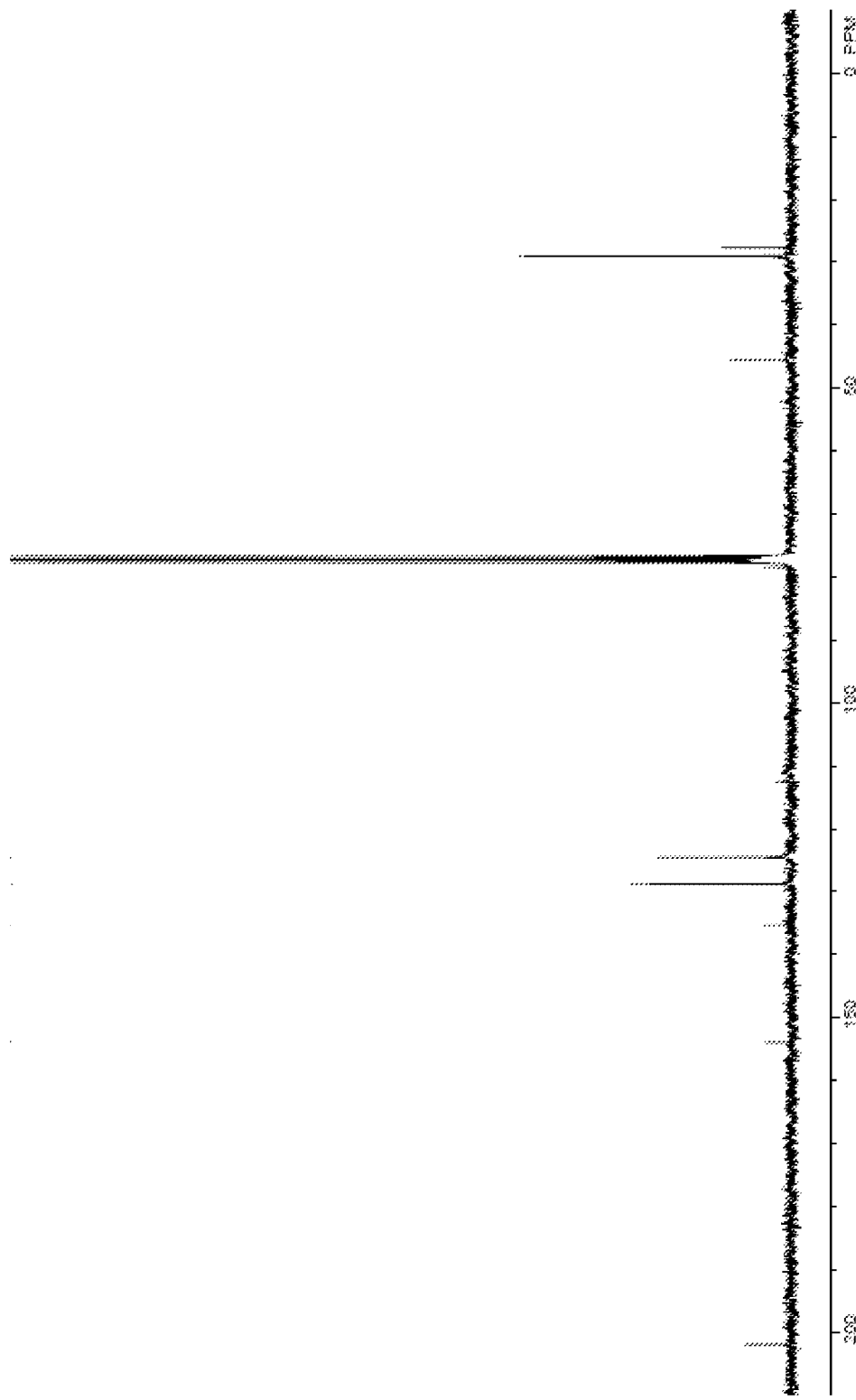
FIG. 72 is an $^{13}$C NMR spectrum of compound 10b used in the synthesis of β2-Homotyrosine.
Figure 73:
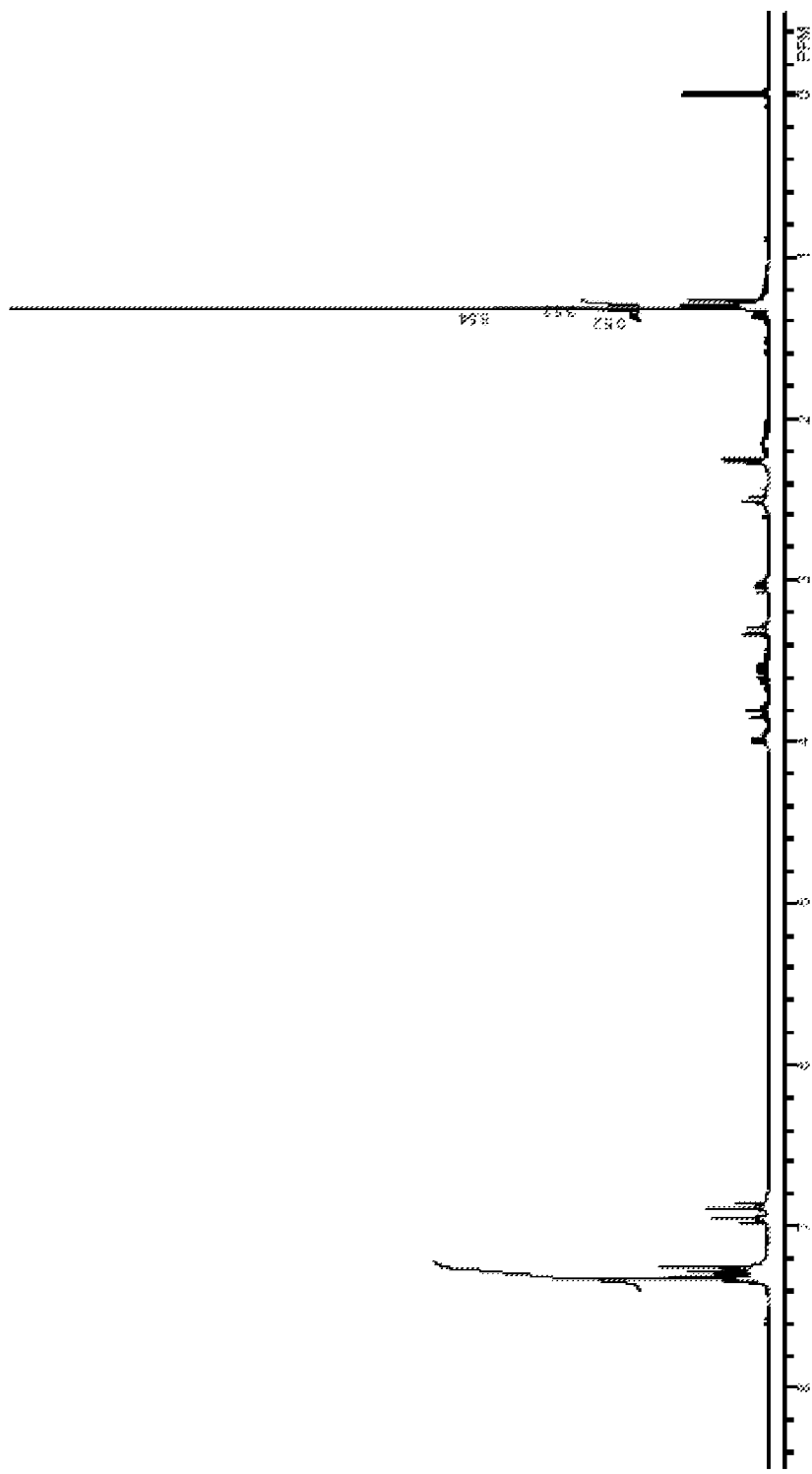
FIG. 73 is an $^1$H NMR spectrum of compound 11b used in the synthesis of β2-Homotyrosine.
Figure 74:
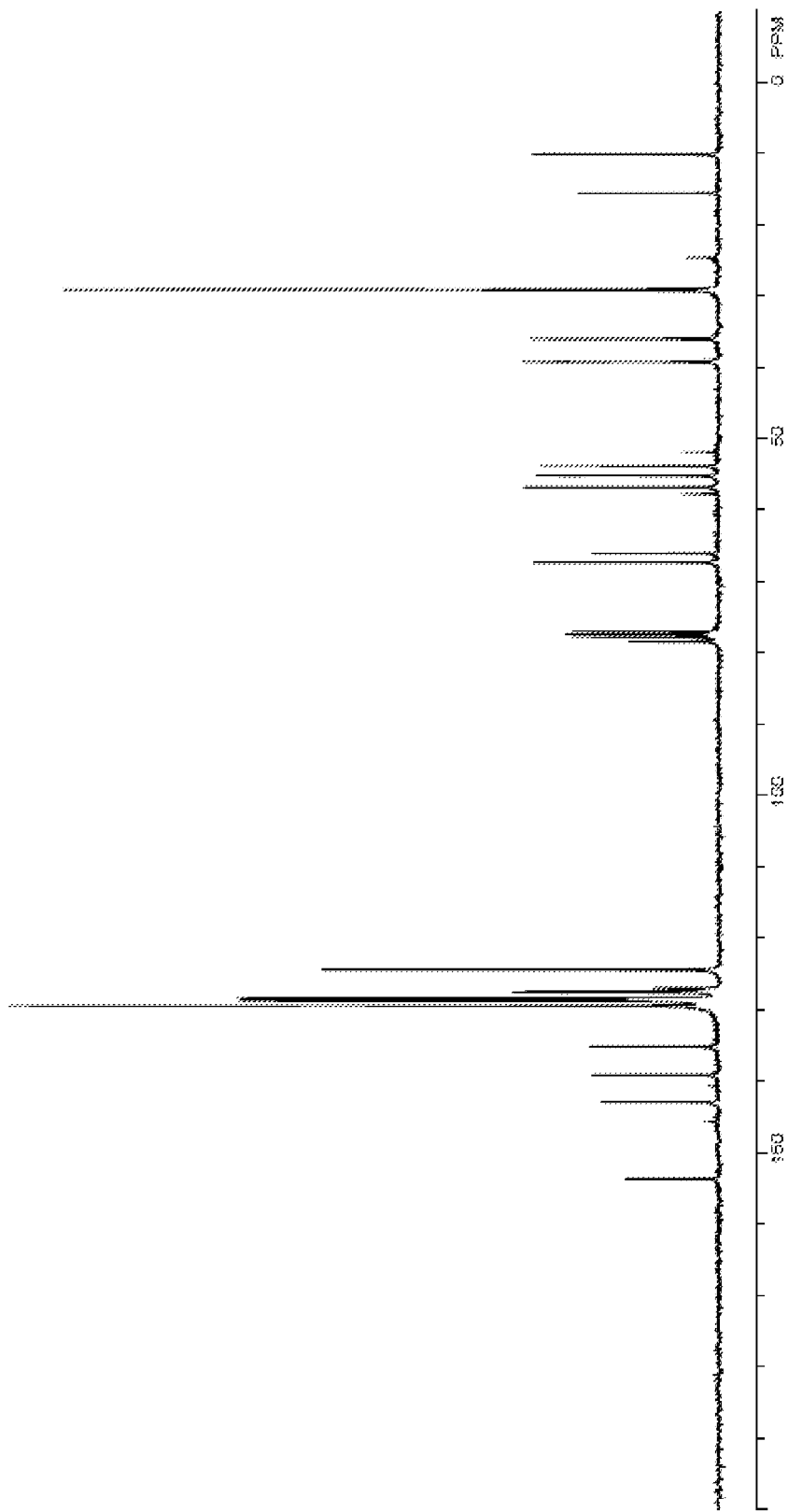
FIG. 74 is an $^{13}$C NMR spectrum of compound 11b used in the synthesis of β2-Homotyrosine.
Figure 75:
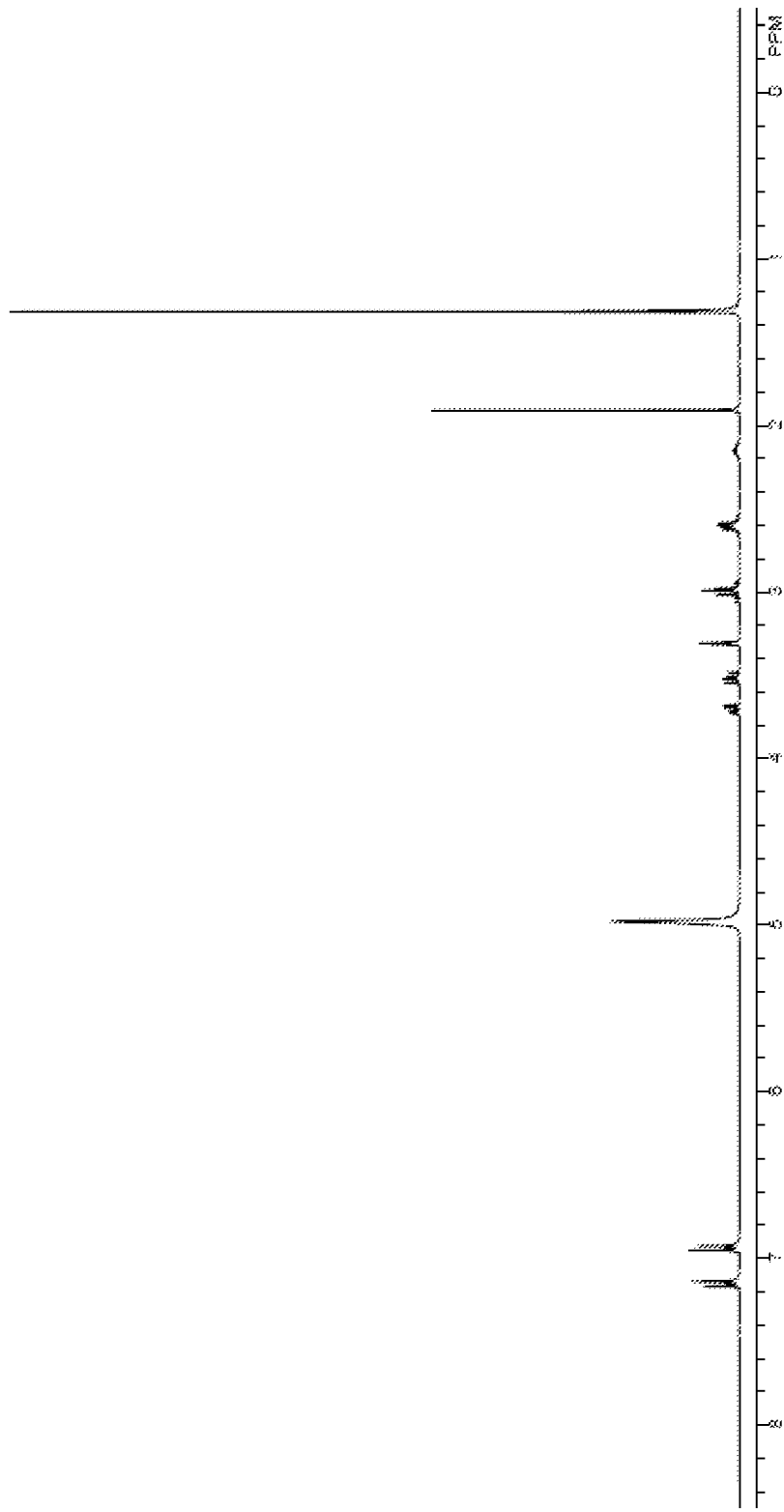
FIG. 75 is an $^1$H NMR spectrum of the amino alcohol of compound 12b used in the synthesis of β2-Homotyrosine.
Figure 76:
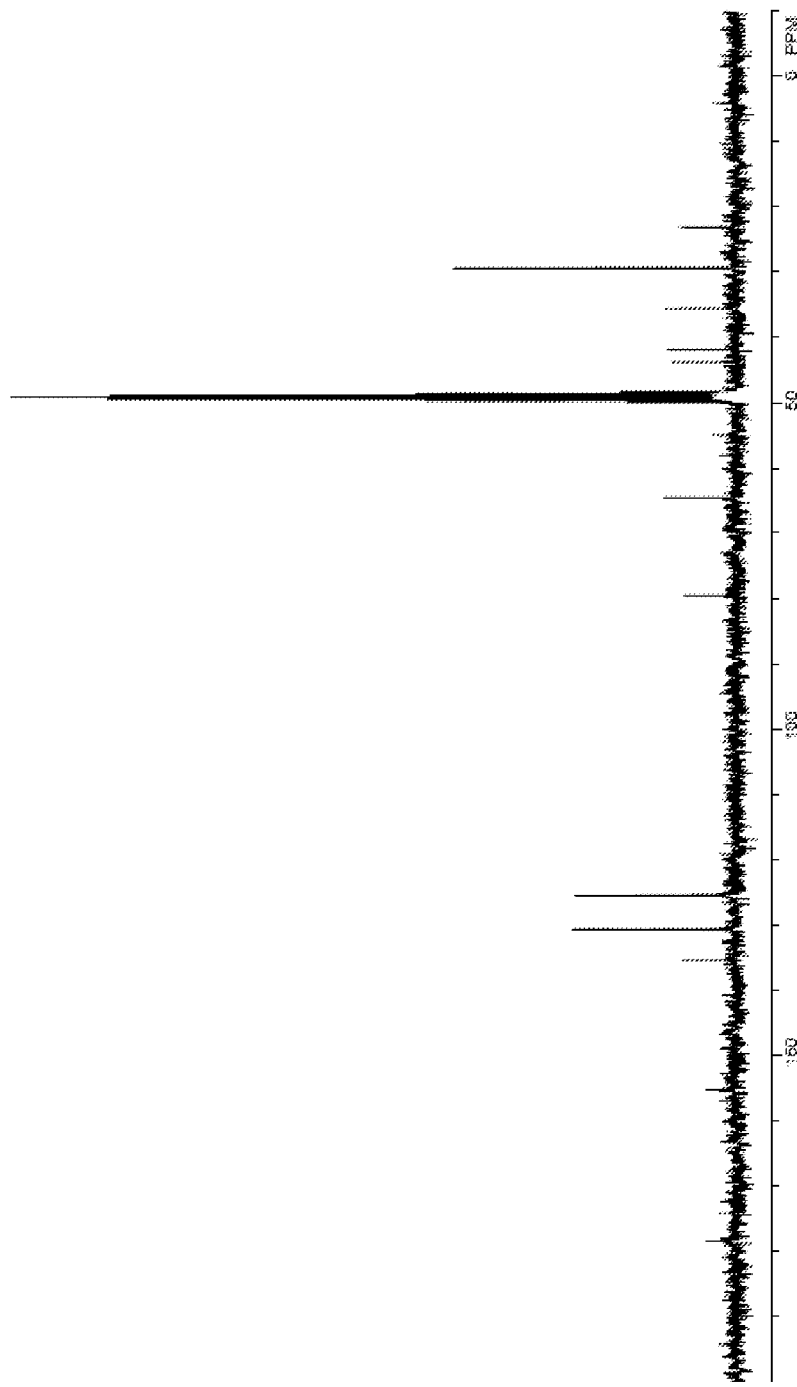
FIG. 76 is an $^{13}$C NMR spectrum of the amino alcohol of compound 12b used in the synthesis of β2-Homotyrosine.

10b 3-(4-tert-Butoxyphenyl)propionaldehyde (10b): To a solution of 3-(4-tert-butoxyphenyl)-propan-1-ol S4 (2.39 g, 11.5 mmol) in anhydrous $CH_2Cl_2$ (115 mL) under $N_2$ was added PCC (3.73 g, 17.3 mmol). The reaction flask was fitted with a reflux condenser, and the reaction mixture was stirred under $N_2$ for 90 min. Anhydrous $Et_2O$ (120 mL) was added to the reaction mixture, and a brown solid precipitated out. The resulting slurry was filtered through a pad of silica gel to remove the solid. The brown gum left in the reaction flask washed with $Et_2O$ (3×50 mL). The combined filtrate was concentrated to give a yellow oil (1.54 g, 65% crude yield) that was carried on to the next step without further purification. TLC $R_f$=0.50 (Hex/EtOAc, v/v, 7:3). $^1H$ NMR (300 MHz, CDCl3): 9.82 (t, J=1.5 Hz, 1H), 7.08 (m, 2H), 6.91 (m, 2H), 2.92 (t, J=7.5 Hz, 2H), 2.77 (t, J=7.5 Hz, 2H), 1.32 (s, 9H), FIG. 71. $^{13}C$ NMR (75 MHz, CDCl3): 201.9, 154.0, 135.3, 128.8, 124.5, 45.6, 29.0, 27.7, FIG. 72. TOF-MS-ESI: [2M+Na]$^+$ calculated 435.55 found 435.6.

Example 47

(S)-β-4-tert-Butoxyphenyl-γ-(S)—N-benzyl-α-methylbenzylamino alcohol (11b)

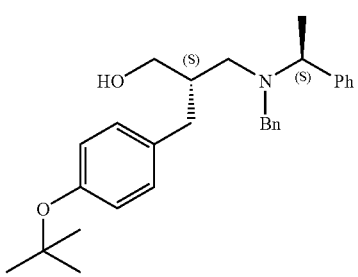

11b (S)-β-4-tert-Butoxyphenyl-γ-(S)—N-benzyl-α-methylbenzylamino alcohol (11b): A suspension of L-proline (357 mg, 3.1 mmol) in HPLC grade DMF (50 mL) was stirred at room temperature under $N_2$ for 12 h. The mixture was cooled to −25° C. under $N_2$ and aldehyde 10b (2.49 g, 12.1 mmol)

was added. N,O-acetal 3 (2.37 g, 9.3 mmol) was then added to the cooled solution, and the reaction mixture was stirred at −25° C. under N$_2$. The reaction was monitored by NMR for conversion of the starting aldehyde. If the reaction proceeds too long, elimination of the dibenzylamine to give the α,β-unsaturated aldehyde (retro-Michael reaction of the Mannich product) occurs. When the reaction was complete, the reaction mixture was warmed to 0° C., and NaBH$_4$ (1.06 g, 27.9 mmol) and MeOH (10 mL) were added. The reaction mixture was stirred for 2 h at 0° C. The mixture was poured slowly into saturated aqueous NH$_4$Cl (25 mL), and the resulting milky mixture was extracted with Et$_2$O (3×50 mL; the extraction was monitored by TLC). The organic layers were combined, dried and concentrated to give a crude mixture, from which the major diastereomer was isolated via chromatography eluting with 10:1 Hexanes:EtOAc. After column chromatography, the pure major diastereomer contained a small amount of the chiral dibenzylamine that is a byproduct from the retro-Michael reaction of the Mannich product. This amine streaks through the column, and it can be eliminated with repeated chromatography, but this causes the yield to suffer. This small impurity does not affect the next step of the synthesis. Isolated yield=43% (desired diastereomer). TLC R$_f$=0.48 (Hex/EtOAc, v/v, 7:3). $^1$H NMR (300 MHz, CDCl$_3$): 7.36-7.26 (m, 10H), 6.96 (m, 2H), 6.89 (m, 2H), 4.00 (q, J=6.9 Hz, 1H), 3.84 (d, J=13 Hz, 1H), 3.56 (m, 1H), 3.32 (d, J=13 Hz, 1H), 3.05 (dd, J=10.5, 8 Hz, 1H), 2.43 (m, 2H), 2.28 (d, J=7.4 Hz, 2H), 2.16 (m, 1H), 1.32 (s, 9H), 1.29 (d, J=6.7 Hz, 3H). $^{13}$C NMR (75 MHz, CDCl3): 153.7, 142.9, 139.1, 135.2, 129.5, 128.7, 128.5, 128.4, 127.6, 127.4, 127.2, 127.1, 127.0, 124.4, 78.4, 67.3, 66.1, 56.8, 55.2, 53.9, 39.2, 36.0, 29.1, 15.5, 10.2. TOF-MS-ESI: [M+H]$^+$ calculated 432.6, found 432.3. [α]$^{rt}_D$=+16.50° (c=9.2, MeOH).

Example 48

(S)-β-4-tert-Butoxylphenyl-γ-Fmoc-amino alcohol (12b)

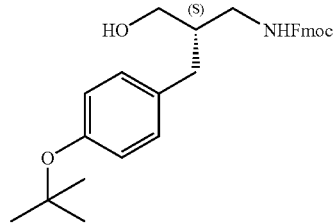

(S)-β-4-tert-Butoxylphenyl-γ-Fmoc-amino alcohol (12b): Benzyl amino alcohol (11b) (1.5 g, 3.48 mmol) was dissolved in MeOH (35 mL). Ammonium formate (4.52 g, 69.6 mmol), HOAc (199 μL, 3.48 mmol) and Pearlman's catalyst (0.75 g, 50% by mass) were added (gas began to evolve from the reaction mixture upon addition of Pearlman's catalyst). The reaction mixture was heated to reflux under N$_2$ and stirred at reflux for 12 h. Debenzylation was monitored by NMR because completely debenzylated material and mono-debenzylated material could not be resolved by TLC. The reaction mixture was filtered through celite to remove the solid catalyst after complete debenzylation. The filtrate was concentrated and was carried on to the next step without further purification. $^1$H NMR (300 MHz, CD$_3$OD): 7.15 (m, 2H), 6.94 (m, 2H), 3.17 (dd, J=10.6, 3.9 Hz, 1H), 3.52 (dd, J=10.8, 7.4 Hz, 1H), 2.99 (m, 2H), 2.60 (m, 2H), 2.15 (m, 1H), 1.31 (s, 9H). $^{13}$C NMR (75 MHz, CD$_3$OD): 154.0, 134.1, 129.4, 124.2, 78.3, 63.3, 42.4, 40.6, 34.2, 28.0. TOF-MS-ESI: [M+H]$^+$ calculated 238.4, found 238.1; [2M+H]$^+$ calculated 475.7, found 475.3.

The amino alcohol crude product dissolved in anhydrous CH$_2$Cl$_2$ (30 mL) was cooled to 0° C. Fmoc-OSu (1.17 g, 3.48 mmol) and DIEA (6.1 mL, 34.8 mmol) were added to the solution. The mixture was stirred at 0° C. for 2 h (TLC indicated complete reaction). The reaction mixture was transferred to a separation funnel and washed with water. The organic layer was collected, dried over MgSO$_4$, filtered and concentrated. The product was isolated via chromatography (EtOAc/Hexanes, 7:3) as a white solid. The product co-elutes with and cannot be easily purified from Fmoc-OH. The mixture was taken into the next step, and the Fmoc-OH was easily separable from the final amino acid. Estimated yield of the two step transformation is about 45%. TLC R$_f$=0.29 (Hex/EtOAc, v/v, 1:1). $^1$H NMR (300 MHz, CDCl$_3$): 7.77 (m, 2H), 7.58 (m, 2H), 7.43-7.29 (m, 4H), 7.04 (m, 2H), 6.91 (m, 2H), 4.94 (t, J=5.9 Hz, 1H), 4.47 (d, J=6.1 Hz, 2H), 4.21 (t, J=6.5 Hz, 1H), 3.54 (m, 1H), 3.41-3.3.13 (m, 3H), 3.05 (t, J=6.5 Hz), 2.58 (m, 1H), 2.47 (m, 1H), 1.61 (m, 1H), 1.32 (s, 9H), $^{13}$C NMR (75 MHz, CDCl3): 158.0, 157.0, 144.1, 141.6, 134.8, 129.5, 127.9, 127.3, 125.2, 125.1, 124.5, 120.2, 78.5, 67.1, 67.0, 62.3, 47.5, 47.3, 43.6, 41.4, 34.9, 29.1. TOF-MS-ESI: [M+Na]$^+$ calculated 482.6, found 482.2; [2M+Na]$^+$ calculated 942.1, found 941.4.

Example 49

(S)-Fmoc-β$^2$-Homotyrosine (13b)

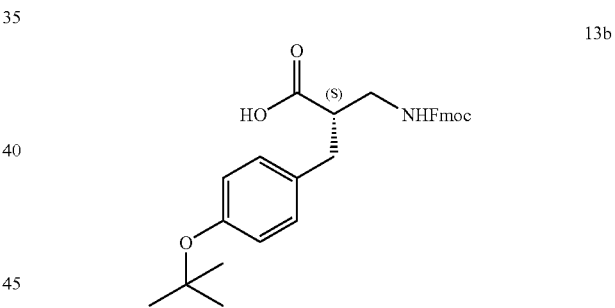

(S)-Fmoc-β$^2$-Homotyrosine (13b): A solution of 12b (170 mg, crude product from above containing Fmoc-OH) in acetone (3.7 mL) was cooled to 0° C. Jones's reagent (1.11 mL of 0.5 M H$_2$Cr$_2$O$_7$, 0.56 mmol) was added, and the reaction mixture was stirred for ~12 h, during which time it warmed to room temperature. Excess $^i$PrOH (4 mL) was added, and the reaction mixture was stirred until it turned green. The solution was diluted with H$_2$O (3 mL), and the acetone and $^i$PrOH were removed via rotary evaporation. The remaining aqueous mixture was extracted with Et$_2$O (3×4 mL, the extraction was monitored by TLC), and the combined organic layers were dried over MgSO$_4$, filtered and concentrated. The crude product was purified on a Biotage Flash Chromatography system with a gradient of 12%-100% EtOAc in Hexanes. The product (73 mg, 62% yield) was obtained as a clear, foamy solid after concentrating the flash chromatography fractions, re-dissolving in CHCl$_3$, concentrating, and drying under vacuum. TLC R$_f$=0.24 (EtOAc/Hex, v/v, 1:1), mp 48-57° C. $^1$H NMR (300 MHz, CDCl$_3$): 7.74 (m, 2H), 7.56-7.35 (m, 4H), 7.29-7.26 (m, 2H), 7.07-7.03 (m, 2H), 7.00-6.84 (m, 2H), 5.22 (br, 1H), 4.37 (m, 2H), 4.17 (m, 1H), 3.38-2.74 (br, 5H), 1.31-1.24 (m, 9H). $^{13}$C NMR (75 MHz, CDCl$_3$): 158.1, 156.8, 154.2, 152.9, 144.0, 143.7, 141.4, 133.1, 129.5, 127.9, 127.2, 125.3, 124.5, 120.2, 78.6, 77.4, 67.1, 47.3, 42.4, 41.8, 35.2, 29.0. TOF-MS-ESI: [M−H]-calculated 472.6, found 472.2; [2M−H]$^-$ calculated 946.11, found 945.3. $[\alpha]^{rt}_D$=−2.32° (c=9.26, CH$_2$Cl$_2$).

$\beta^2$-Homolysine (13c): The aldehyde precursor 10c used for the synthesis of $\beta^2$-Homolysine (13c) was prepared from 6-aminohexanol as outlined below.

Example 50

6-(di-Boc)-aminohexanol (S5)

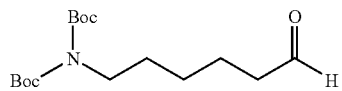

10c 6-(di-Boc)-aminohexanol (S5): 6-amino-hexanol (1.10 g, 9.4 mmol) was dissolved in 115 mL of THF and cooled to −10° C. n-BuLi (12.5 ml, 2.5 M hexane solution) was then added dropwise producing a white precipitate. The reaction mixture was left to stir for 5 min followed by addition of Boc$_2$O (7.0 g, 32.0 mmol). After 45 min, the reaction was quenched with saturated aqueous NH$_4$Cl, and the mixture was extracted with EtOAc. The combined organic fractions were washed with saturated aqueous NaHCO$_3$ and then brine, dried over MgSO$_4$, filtered, and concentrated to give a yellow oil. The yellow oil was dissolved in 180 mL of MeOH, followed by addition of 90 mL of 1 N NaOH, and left to stir for 15.5 h. The reaction mixture was diluted with water, and extracted with EtOAc. The combined organic fractions were washed with brine, dried over MgSO$_4$, filtered, and concentrated. Chromatography (EtOAc/Hexanes; 1:3) afforded 1.39 g (47% yield) S5 as a yellow oil. TLC R$_f$=0.23 (EtOAc/Hexanes, v/v, 1:3). $^1$H NMR (300 MHz, CDCl$_3$): δ 3.64 (t, J=6.4 Hz, 2H), 3.56 (t, J=7.3 Hz, 2H) 1.60-1.55 (m, 4H), 1.50 (s, 18H), 1.44-1.26 (m, 5H). $^{13}$C NMR (75 MHz, CDCl$_3$): δ 153.0, 82.2, 62.9, 46.5, 32.8, 29.1, 28.3, 26.7, 25.6. TOF-MS-ESI: [M+Na]$^+$ calculated 340.3, found 340.5.

Example 51

(S)-β-(1-(Di-Boc)-4-Butyl-γ-(S)—N-Benzyl-α-Methylbenzylamino Alcohol (11c)

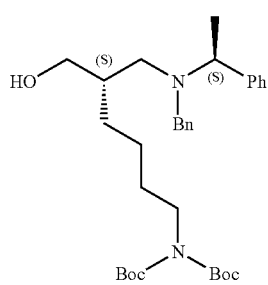

11c (S)-β-(1-(Di-Boc)-4-butyl-γ-(S)—N-benzyl-α-methylbenzylamino alcohol (11c) L-proline (0.18 g 0.7045 mmol) was suspended in 26 mL of DMF and stirred over night followed by cooling to −30° C. Aldehyde 10c (3.67 g, 11.6 mmol) dissolved in 3 mL of DMF was added to the reaction mixture via a syringe, followed by drop-wise addition of N,O-acetal 3 (2.0 g, 7.8 mmol). The reaction mixture was left to stir for 4.5 h at −25° C., and NMR analysis of a small aliquot of solution indicated completion of the reaction. NaBH$_4$ (0.59 g, 15.6 mmol) was added to the reaction mixture with 4 mL of MeOH, and the reaction mixture was left to stir at 0° C. for 20 min. The reaction mixture was then slowly poured to an aqueous solution of saturated NH$_4$Cl followed by extraction with Et$_2$O. The organic fractions were combined, washed with brine, dried over MgSO$_4$, filtered and concentrated to give an oil, from which the major diastereomer was isolated by column chromatography, eluting with 1:4 EtOAc:hexanes, to yield a clear oil, (2.4 g, 54% yield). TLC R$_f$=0.26 (EtOAc/Hexanes, v/v, 1:4). $^1$H NMR (300 MHz, CDCl$_3$) δ 7.36-7.22 (m, 10H), 4.82 (br s, 1H), 4.02 (q, J=6.9 Hz, 1H) 3.91, (d, J=13 Hz, 1H), 3.58-3.50 (m, 3H), 3.36 (d, J=13 Hz, 1H) 3.00 (m, J=8.7 Hz, 1H) 2.55 (m, J=12 Hz, 1H), 2.43 (m, J=12 Hz, 1H), 1.94-1.84 (m, 1H), 1.56-1.46, (m, 2H), 1.49 (s, 18H) 1.35, (d, J=6.8, Hz, 2H) 1.30-1.20 (m, 2H) 1.05-0.98, (m, 2H). $^{13}$C NMR (75 MHz, CDCl$_3$): δ 153.0, 142.7, 138.9, 129.4, 128.7, 128.39, 128.3, 127.5, 127.3, 82.3, 68.1, 56.4, 55.1, 54.6, 46.3, 36.9, 29.9, 29.5, 28.3, 24.7, 9.5. TOF-MS-ESI: [M+H]$^+$ calculated 541.7, found 541.8. Optical rotation: $[\alpha]^{rt}_D$=+5.6° (c=7.1, MeOH).

Example 52

(S)-β-(1-(di-Boc)-amino-4-butyl-γ-Fmoc-amino alcohol (12c)

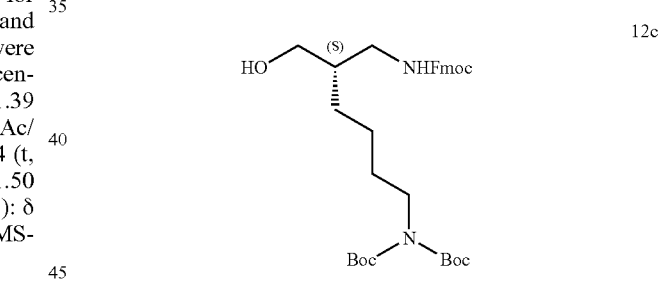

12c (S)-β-(1-(di-Boc)-amino-4-butyl-γ-Fmoc-amino alcohol (12c): Compound 11c (0.32 g, 0.53 mmol) was dissolved in 20 mL of MeOH followed by addition of ammonium formate (0.34 g, 5.3 mmol) and 0.32 g of wet 10% Pd/C. The reaction mixture was heated to reflux and stirred under nitrogen for 7 h. The reaction mixture was cooled to room temperature and filtered through celite with an excess of MeOH. Evaporation of solvent yielded a clear oil. The oil was dissolved in 10 mL of CH$_2$Cl$_2$, DIEA (300 μL, 1.72 mmol) and Fmoc-OSu (0.20 g, 0.59 mmol) were added and the reaction mixture was left to stir for 10 h. The reaction mixture was diluted with EtOAc and washed with saturated NaHSO$_4$, saturated NaHCO$_3$, brine, dried over MgSO$_4$, filtered and concentrated. Evaporation of solvent produced an oil, which was purified via column chromatography, eluting with 1:1 EtOAc:hexanes, to yield a clear oil (0.24 g, 81% yield), 81%. TLC R$_f$=0.11 (EtOAc/Hexanes, v/v, 1:1). $^1$HNMR (300 MHz, CDCl$_3$) δ 7.74 (d, J=7.5 Hz, 2H), 7.59 (d, J=7.4 Hz, 2H), 7.38 (t, J=7.4 Hz 2H), 7.27 (t, 7.4 Hz 2H), 5.58 (t, J=6.4 Hz, 1H), 4.396, (d, 7.2 Hz, 2H) 4.19 (t, J=6.8 Hz, 1H), 3.61-3.35 (m, 6H) 3.16-3.08 (m, 1H) 1.61-1.56 (m, 3H) 1.50 (s, 18H) 1.35-1.22 (m, 4H). $^{13}$C NMR (75

MHz, CDCl$_3$): δ 158.10, 153.26, 144.10, 141.56, 127.91, 127.26, 125.24, 120.19, 82.45, 67.05, 62.83, 47.54, 45.85, 41.57, 41.11, 29.27, 28.33, 27.96, 24.10. TOF-MS-ESI: [M+Na]$^+$ calculated 591.7, found 591.8. Optical rotation: [α]$^{rt}_D$=+7.2° (c=8.1, CH$_2$Cl$_2$).

Example 53

(S)-β$^2$-Homolysine(diBoc)-OH (13c)

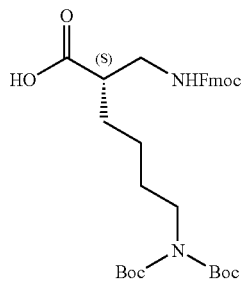

13c (S)-β$^2$-Homolysine(diBoc)-OH (13c): 12c (0.23 g, 0.41 mmol) was dissolved in 9 mL of acetone and cooled to 0° C. followed by drop-wise addition of a 1.3 ml Jones reagent (0.5 M H$_2$Cr$_2$O$_7$ solution in water). The reaction mixture was left to stir for 4 h while gradually warming to room temperature followed by quenching with an excess of isopropanol. After stirring for an additional 3 h the reaction mixture was diluted with water and a small amount of ether, and then carefully acidified to pH 2 with 10% aqueous NaHSO$_4$. The aqueous layer was extracted with ether and the combined organic fractions were washed with brine and dried (MgSO$_4$). Evaporation of solvent produced an oil that was purified by column chromatography eluting with 1:2 EtOAc:hexanes and 1% AcOH to produce a white foam upon evaporation of solvent (0.18 g, 77% yield). TLC R$_f$=0.24 (EtOAc/Hexanes, v/v, 1:2). $^1$H NMR (300 MHz, CDCl$_3$) δ 8.99 (br s 1H), 7.74 (d, J=7.0 Hz, 2H), 7.57 (d, J=7.3 Hz, 2H), 7.38 (t, J=7.0 Hz, 2H), 7.29 (t, J=7.3 Hz, 2H), rotamers 6.57, 6.26, 5.42 (t, J=6.0 Hz) rotamers 4.52, 4.35 (m, 2H), 4.22 (m, 1H), 3.56 (m, 2H) rotamers 3.47-3.05 (m, 2H), rotamers 2.66, 2.33, (m, 1H) 1.70-1.36, (m, 5H) 1.49 (s, 18H), 1.28-1.20 (m, 1H) $^{13}$C NMR (75 MHz, CDCl$_3$): δ rotamers 179.5 and 178.5, rotamers 157.8 and 156.8, rotamers 144.1 and 143.8, 141.4, 127.8, 127.2, rotamers 125.2 and 124.9, 120.1, 82.4, rotamers 67.3 and 67.0, rotamers 50.7 and 47.3, rotamers 46.2 and 45.7, rotamers 42.8 and 42.1, rotamers 29.8 and 29.3 rotamers 29.7 and 29.1, rotamers 28.2 and 24.3. TOF-MS-ESI: [M+Na]$^+$ calculated 582.7, found 582.0. Optical rotation: [α]$^{rt}_D$=+2.3° (c=11.3, CH$_2$Cl$_2$).

Example 54

Synthesis of β$^2$-Homotryptophan via Organocatalytic Mannich Reaction Between Aldehydes and Diallylamine-Derived Iminium

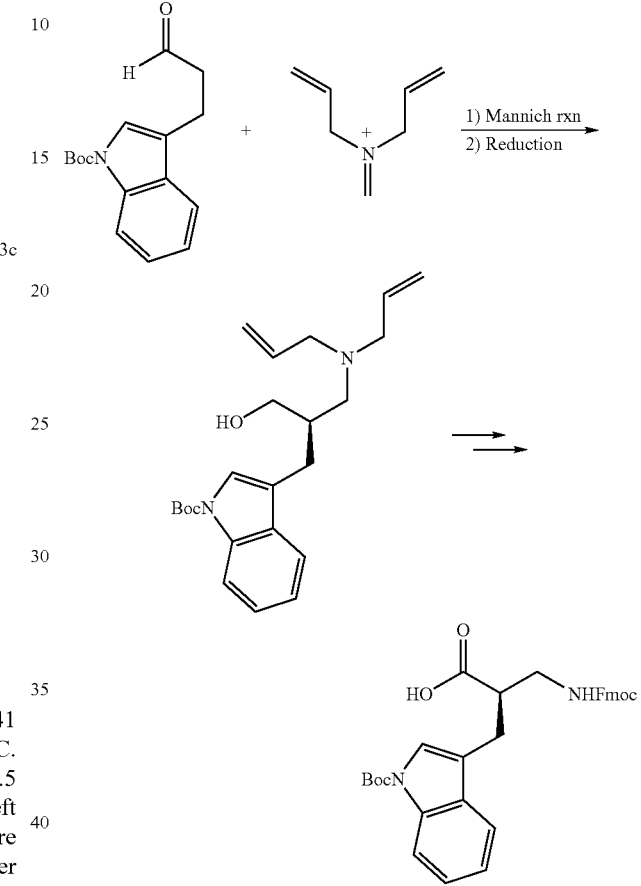

Organocatalytic Mannich reaction between aldehydes and diallylamine-derived iminium precursor followed by in situ reduction provides β-substituted γ-diallylamino alcohols. The allyl groups can be removed using Pd(PPh$_3$)$_4$ as catalyst and N,N'-dimethylbarbituric acid as allyl trapping agent, at which condition functional groups (e.g. indole) that are sensitive to hydrogenolysis are intact. This Mannich reaction was applied to prepare β$^2$-homotryptophan, an important β$^2$-amino acid that is difficult to prepared using other methods.

β$^2$-Amino acids, 3-aminopropanoic acids bearing a single substituent adjacent to the carboxylic acid group, can be found embedded within natural products that exhibit interesting biological activities. In addition, recent research has established that β$^2$-residues are essential for the formation of specific β-peptide and hybrid non-natural peptide secondary structures (e.g., 12/10-helix, β$^2$/β$^3$ reverse turn). Designed peptides containing β$^2$-residues display useful functions including mimicry of somatostatin signaling and inhibition of viral infection. Despite of the increasing interests in β$^2$-amino acids, the preparative synthetic methods for β²-amino acids are not available. Most of the reported routes involve tedious chromatographic purifications (e.g., isolation of diastereomers from alkylation of chiral enolates), and few of these synthetic approaches are amenable to large-scale synthesis or diversity in side chain functionality.

The inventors describe herein a very practical method for making β²-amino acids with both hydrophobic and polar side chains, such as β²-homoglutamic acid, β²-homotyrosine and β²-homolysine. The inventors' approach involved organocatalytic Mannich reactions between aldehydes and dibenzyliminium ions to provide β-substituted-γ-amino alcohols as the key intermediates. Our method using hydrogenolysis to remove the benzyl protecting groups are proved to be clean and efficient in the synthesis of most β²-amino acids. However, it may be problematic in making β²-residues with side chain groups that are sensitive to hydrogenolysis (e.g., 5-8). On the other hand, β²-residues such as 5-8 can be very useful for foldamers designs and other studies. For instance, β²-amino acids with alkyne or azide side chains can participate in Huisgen cycloaddition (click chemistry), and therefore serve the purpose of post-peptide modifications. The inventors are particularly interested in β²-homotryptophan at this moment since it is an important non-natural amino acid residue in current foldamers studies. Tryptophan plays very important roles in structures and functions of proteins due to the special structural features of its side chain, such as hydrophobicity and lipophilicity, and its ability for hydrogen bonding interactions and aromatic interactions. In addition, the fluorescence properties of the indole ring make tryptophan a good probe in studying peptides and proteins. The β³-homotryptophan derivative can be prepared via homologation of the corresponding α-amino acid. However the synthesis of the β²-analog remains a challenge. Preparative scale synthesis of β²-tryptophan using the reported method is still illusive. In addition, introducing structural diversity to the indole ring can be very difficult using current methods.

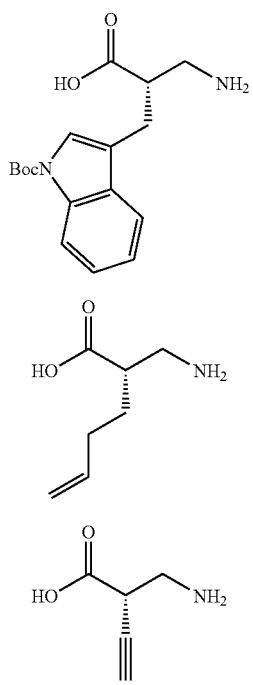

-continued

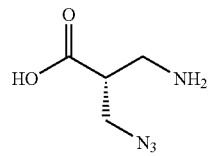

18 examples of beta2-amino acids with unsaturated functional groups

Here the inventors report a new method of making β²-homotryptophan that uses organocatalytic Mannich reaction between proper aldehyde and diallylamine-derived iminium ion, a straightforward modification of the reaction with dibenzylamine-derived iminium ions as electrophiles as disclosed above. The allyl groups in the resulting Mannich product in the present studies can be cleaved under conditions at which sensitive functional groups such as indole are intact as shown in SCHEME XXI below.

SCHEME XXI

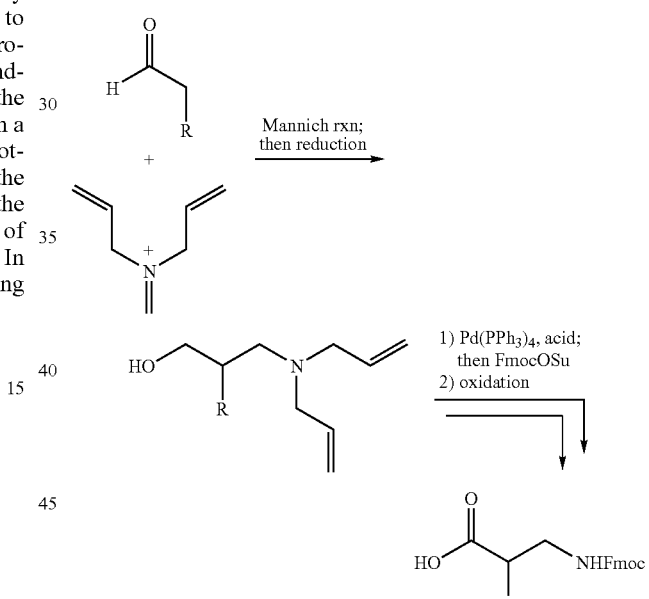

The diallyliminium precursor, N,O-acetal 20, was prepared in large quantities by reacting diallylamine and paraformaldehyde in MeOH using procedures analogous to those for the synthesis of dibenzyliminium precursors (ref). The inventors initially investigated the Mannich reaction between hydrocinnamaldehyde 19 and iminium precursor 20 (SCHEME XXII). The Mannich reaction gave comparable yield and enantioselectivity as above reported Mannich reactions with dibenzyliminium ions as electrophiles at similar conditions. For example, the Mannich reaction shown in SCHEME XXII with 20 mol % 22 as catalyst in 1M LiCl-DMF at −25° C. gave the Mannich product (after in situ reduction) with 88-90% ee. The effect of salt (LiCl) on the product ee using either 22 or L-proline as catalyst is consistent with the inventor's previous studies.

SCHEME XXII

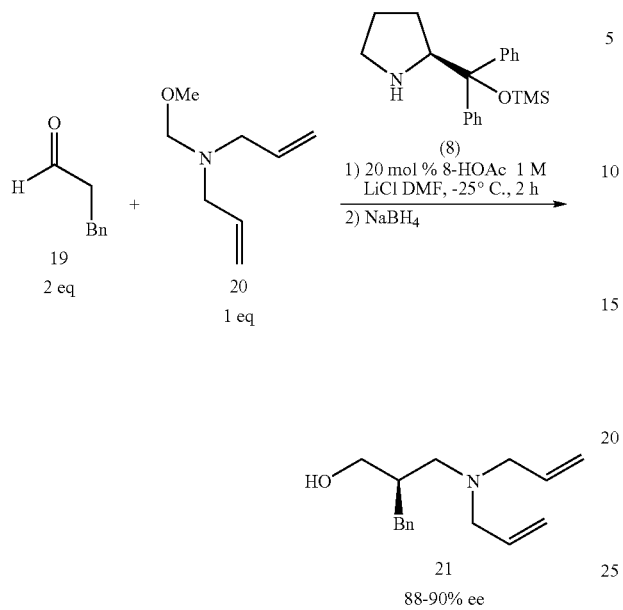

If the above Mannich reaction is to be useful for making β²-amino acids, then the removal of the allyl protecting groups must be achieved at mild conditions. With de-allylation conditions reported by Knochel and others (ref: Synthesis, 2000, 941-948), preliminary studies using 21 as substrate indicated that the allyl groups can be removed effectively at mild condition. The inventors then turned their attention to the synthesis of β²-tryptophan.

The aldehyde reactant for the Mannich reaction was prepared in a few steps starting from Fisher indole synthesis that follows a literature method (SCHEME XXIII). This synthesis was chosen for the preparation of the aldehyde starting materials because it allows access to aldehydes with functional indole rings, and therefore likely to result in a diverse set of β²-tryptophan derivatives.

SCHEME XXIII

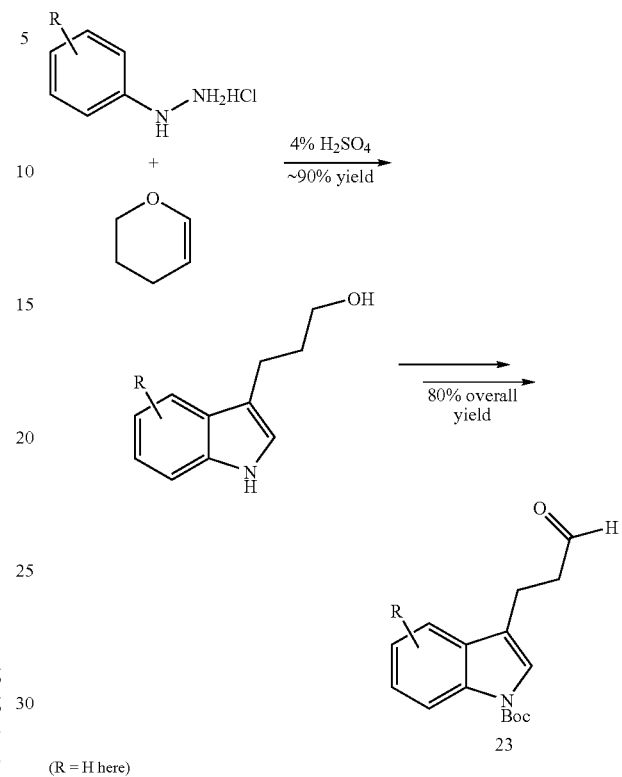

(R = H here)

Shown in SCHEME XXIV is the synthesis of β²-homotryptophan. Mannich reaction followed by reduction gave diallylamino alcohol 24 in 87% yield. The inventors' attempt to determine ee of 24 by chiral phase HPLC was not successful. Instead, the ee of 24 was estimated to be 83% via ¹H NMR analysis of its ester derivative. Recrystallization of 24 to improve its ee is in progress. Deallylation of 24, followed by Fmoc protection of the resulting primary amine in a one-pot operation gave 25 with 89% yield. Jones oxidation of 24 finishes the synthesis of β²-homotryptophan, with ~50% overall yield starting from 23.

SCHEME XXIV

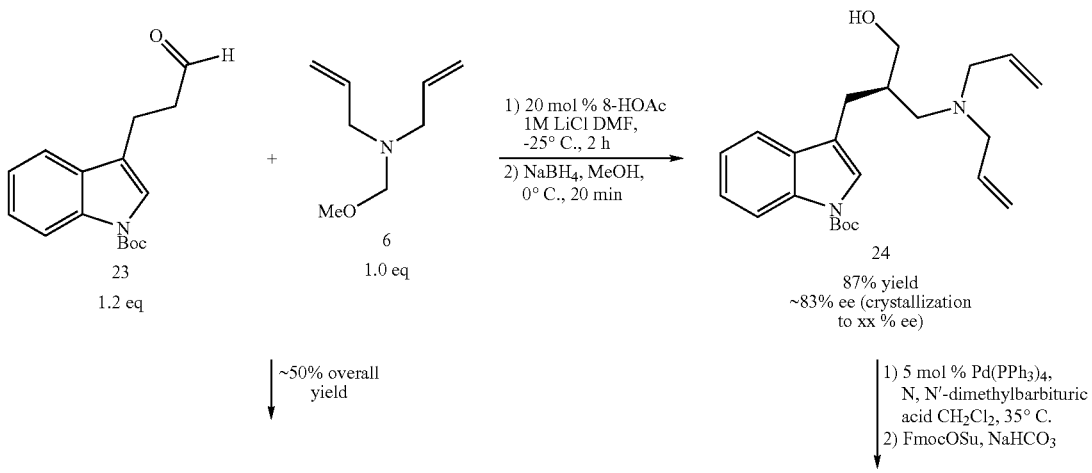

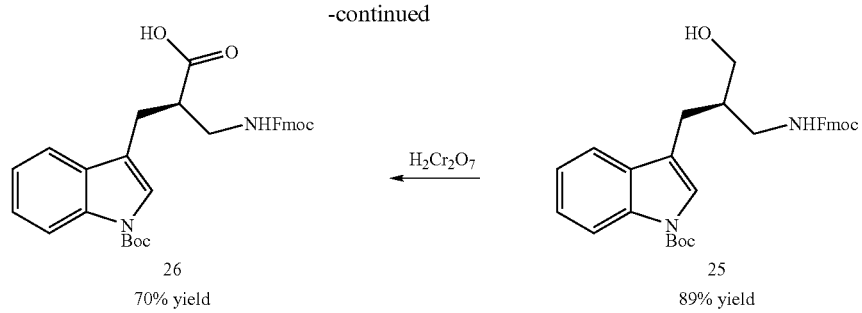

26
70% yield 25
89% yield

In summary, the inventors have introduced organocatalytic Mannich reactions between aldehydes and diallyliminium, a modification of herein disclosed Mannich reactions. The new Mannich reaction gives comparable yield and enantioselectivity as reactions previously reported at similar conditions. The inventors have applied this reaction to develop a new route for the synthesis of $\beta^2$-tryptophan, an important type of $\beta^2$-amino acid that is difficult to prepare. This method may be extended by only routine experimentation to make other $\beta^2$-amino acids such as those with alkenes and alkynes in the side chain; and the synthesis of these residues are in progress.

Example 55

Non-Asymmetric Racemic Synthesis

In addition to the asymmetric syntheses described in the above examples, non-asymmetric synthesis can be achieved via equation (1) or (2) shown in the below scheme:

Reacting of aldehydes (A) with N,O-acetal (B) in the presence of catalytic amount (e.g. 20 mol %) of acids (e.g. acetic acid) in DMF can give the racemic amino aldehyde products (C) (equation 1). Alternatively, a three-component reaction between aldehydes (A), dibenzyl amine (E), paraformaldehyde or formaldehyde aqueous solution (F) in the presence of catalytic amount (e.g. 20 mol %) of acid (e.g. acetic acid) in DMF can gave racemic amino aldehydes C (equation 2). in situ reduction of C gave the racemic amino alcohol D; from D racemic amino acids and their derivatives can be prepared using analogous methods described in the asymmetric synthesis.

It should be noted that N,O-acetal other than B (such as G below), and amine other than E (such as H below) also gave similar reactions.

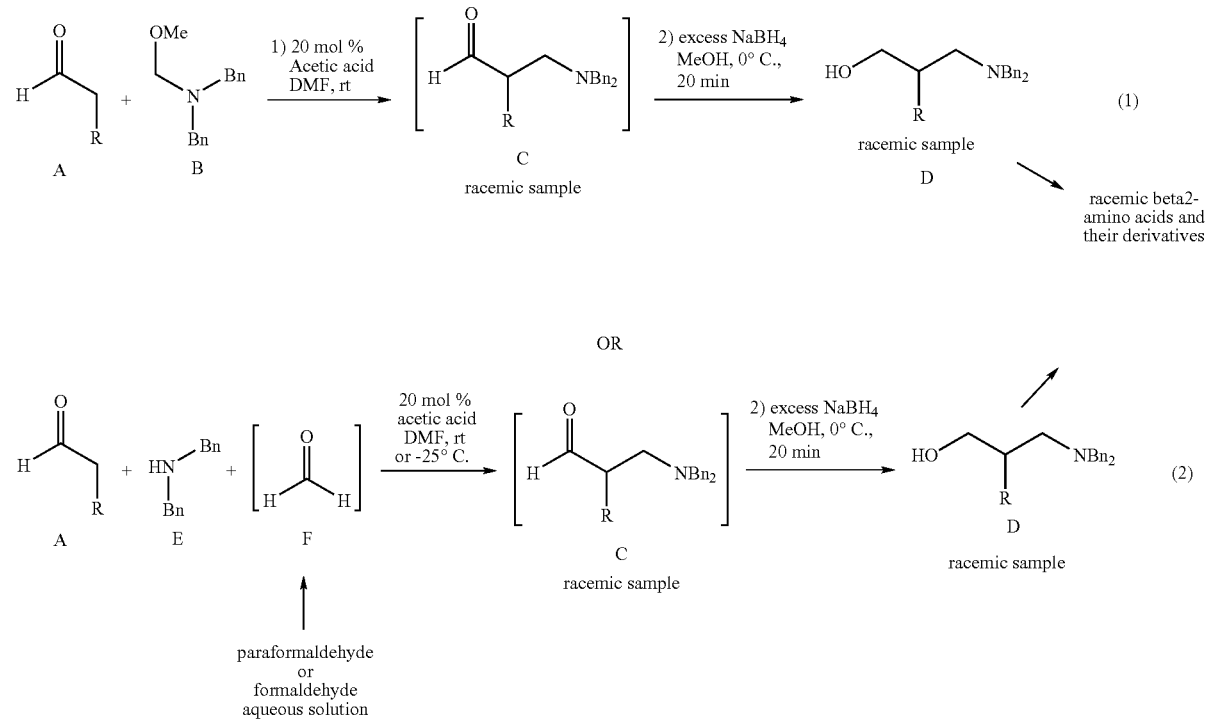

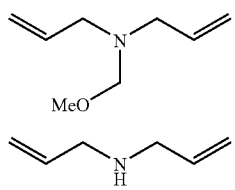

Accordingly, the present invention is not limited to the asymmetric syntheses and may certainly be extended to the generation of racemic mixtures by no more than routine experimentation.

As described herein, various exemplary embodiments of methods according to this invention can be used produce $\beta^2$ amino acids and $\beta^2$ amino peptides that can be used pharmacologically, prophylactically or medically in situations where degradation compounds by native enzymes is deleterious. In other embodiments, the invention can be used clinically to identify peptido-mimics useful in pharmacological treatments.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A method of synthesizing a $\beta^2$ amino acid by aldehyde aminomethylation, comprising steps of:
    (a) reacting an aldehyde with an iminium ion via a Mannich reaction to yield an α-substituted β-amino aldehyde;
    (b) reducing the α-substituted β-amino aldehyde in situ to a corresponding β-substituted γ-amino alcohol; and
    (c) oxidizing the β-substituted γ-amino alcohol to provide a corresponding $\beta^2$ amino acid.

2. The method of claim 1, wherein the method is stereoselective in the synthesis of the $\beta^2$ amino acid.

3. The method of claim 1, wherein the method is diastereoselective in the synthesis of the $\beta^2$ amino acid.

4. The method of claim 1, wherein the method is enantioselective in the synthesis of the $\beta^2$ amino acid.

5. The method of claim 1, wherein the method yields a racemic mixture of the $\beta^2$ amino acid.

6. The method of claim 1, wherein the method includes an additional step of protecting the corresponding β-substituted γ-amino alcohol to provide a protected β-substituted γ-amino alcohol that is then oxidized in step (c) to the corresponding $\beta^2$ amino acid in protected form.

7. The method of claim 1 wherein said iminium ion is chiral.

8. The method of claim 1, wherein the Mannich reaction takes place in the presence of L-proline, L-alpha-m-proline, L-Pro-NH$_2$, L-Pro-NHMe, L-Pro-NMe$_2$, L-Pro-OMe, or a pyrrolidine catalyst.

9. The method of claim 1, wherein the aldehyde has the structure

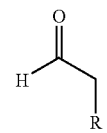

wherein R is Et, Pr, i-Pr, Bn, MeO$_2$CCH$_2$, n-Hex, CH$_2$-iPr, CH$_2$C$_6$H$_{12}$, (CH$_2$)$_4$NHBoc, (Boc)$_2$N(CH$_2$)$_3$, MeO$_2$CCH$_2$,

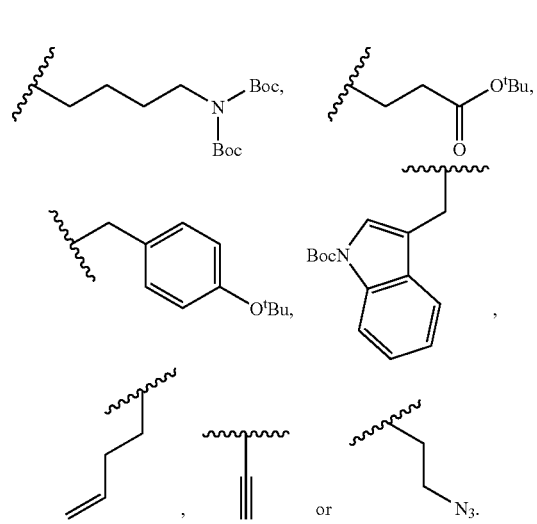

10. The method of claim 1, wherein the iminium ion is generated in situ from a formaldehyde derived N,O-acetal having the structure:

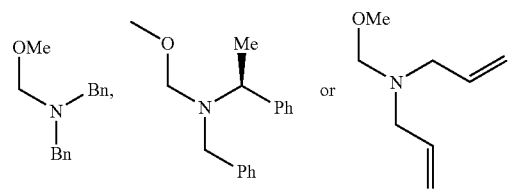

11. A method of synthesizing a β-substituted γ-amino alcohol by aldehyde aminomethylation, comprising steps of:
    (a) reacting an aldehyde with an iminium ion via a Mannich reaction to yield an α-substituted β-amino aldehyde; and
    (b) reducing the α-substituted β-amino aldehyde in situ to a corresponding β-substituted γ-amino alcohol.

12. The method of claim 11, wherein the method is stereoselective in the synthesis of the β-substituted γ-amino alcohol.

13. The method of claim 11, wherein the method is diastereoselective in the synthesis of the β-substituted γ-amino alcohol.

14. The method of claim 11, wherein the method is enantioselective in the synthesis of the β-substituted γ-amino alcohol.

15. The method of claim 11, wherein the method yields a racemic mixture of the β-substituted γ-amino alcohol.

16. The method of claim 11, wherein the method includes an additional step of protecting the corresponding β-substituted γ-amino alcohol to provide said β-substituted γ-amino alcohol in protected form.

17. The method of claim 11, wherein said iminium ion is chiral.

18. The method of claim 11, wherein the Mannich reaction takes place in the presence of L-proline, L-alpha-m-proline, L-Pro-NH$_2$, L-Pro-NHMe, L-Pro-NMe$_2$, L-Pro-OMe, or a pyrrolidine catalyst.

19. The method of claim 11, wherein the aldehyde has the structure

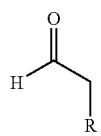

wherein R is Et, Pr, i-Pr, Bn, MeO$_2$CCH$_2$, n-Hex, Ch$_2$-iPr, CH$_2$C$_6$H$_{12}$, (CH$_2$)$_4$NHBoc,

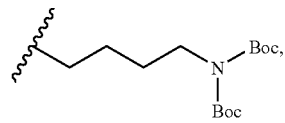 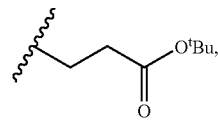

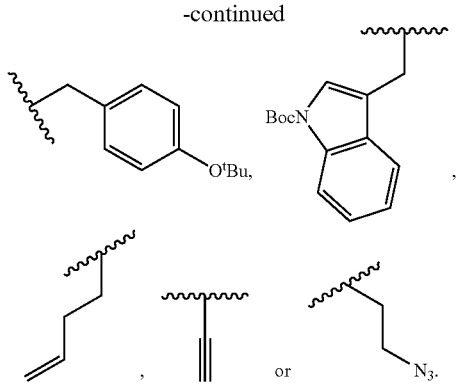

20. The method of claim 11, wherein the iminium ion is generated in situ from a formaldehyde derived N,O-acetal having the structure:

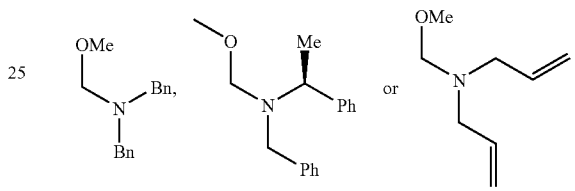

* * * * *